United States Patent [19] [11] Patent Number: 5,004,741
Evans et al. [45] Date of Patent: Apr. 2, 1991

[54] METHODS OF ANTAGONIZING CCK OR GASTRIN WITH BENZODIAZEPINE ANALOGS

[75] Inventors: Ben E. Evans, Lansdale; Mark G. Bock; Roger M. Freidinger, both of Hatfield, all of Pa.

[73] Assignee: Merck & Co., Inc., Rahway, N.J.

[21] Appl. No.: 269,212

[22] Filed: Nov. 9, 1988

Related U.S. Application Data

[60] Division of Ser. No. 26,420, Mar. 16, 1987, Pat. No. 4,820,834, which is a continuation-in-part of Ser. No. 741,972, Jun. 10, 1985, abandoned, which is a continuation-in-part of Ser. No. 705,272, Feb. 25, 1985, abandoned, which is a continuation-in-part of Ser. No. 624,854, Jun. 26, 1984, abandoned.

[51] Int. Cl.$^5$ ............................................... A61K 31/55
[52] U.S. Cl. ..................................... 514/221; 514/925; 514/926; 514/927
[58] Field of Search ................ 514/221, 925, 926, 927

[56] References Cited

PUBLICATIONS

*Chemical Abstracts*, vol. 87 5923j (1977).

Primary Examiner—Stanley J. Friedman
Assistant Examiner—Raymond J. Henley, III
Attorney, Agent, or Firm—Roy D. Meredith; Charles M. Caruso

[57] ABSTRACT

Methods of antagonizing gastrin and/or cholecystokinin (CCK) with benzodiazepine analogs are disclosed, as well as related pharmaceutical compositions, which are useful in treating disorders of the gastrointestinal tract, central nervous system, and of the appetite.

15 Claims, No Drawings

METHODS OF ANTAGONIZING CCK OR GASTRIN WITH BENZODIAZEPINE ANALOGS

CROSS REFERENCE

This is a division of application Ser. No. 07/026,420, filed Mar. 16, 1987, now U.S. Pat. No. 4,820,834, which is a continuation-in-part of U.S. application Ser. No. 06/741,972 filed June 10, 1985, now abandoned, which is a continuation-in-part of U.S. application Ser. No. 06/705,272 filed Feb. 25, 1985, now abandoned, which in turn is a continuation-in-part of U.S. application Ser. No. 06/624,854, filed June 26, 1984, now abandoned.

Starting materials for the compounds of Formula I are described in U.S. application Ser. No. 942,131, filed Dec. 16, 1986, now pending which is a continuation-in-part of U.S. application Ser. No. 624,853, filed June 26, 1984, now abandoned entitled "Acylaminophenylketones and Amines" which is incorporated herein by reference.

BACKGROUND OF THE INVENTION

Cholecystokinins (CCK) and gastrin are structurally-related neuropeptides which exist in gastrointestinal tissue and in the the central nervous system (see, V. Mutt, *Gastrointestinal Hormones*, G. B. J. Glass, Ed., Raven Press, N.Y., p. 169 and G. Nisson, ibid, p. 127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (a naturally-occurring neuropeptide, also, and the minimum fully active sequence), and 39- and 12-amino acid forms, while gastrin occurs in 34-, 17- and 14-amino acid forms, with the minimum active sequence being the C-terminal pentpeptide, Gly-Trp-Met-Asp-Phe-NH$_2$ which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", Ann. Repts. Med. Chem. 17, 31, 33 [1982] and references cited therein; J. A. Williams, *Biomed. Res.* 3 107 [1982]); and J. E. Morley, *Life Sci.* 30, 479, [1982]).

The primary role of gastrin, on the other hand, appears to be stimulation of the secretion of water and electrolytes from the stomach, and, as such, it is involved in control of gastric acid and pepsin secretion. Other physiological effects of gastrin then include increased mucosal blood flow and increased antral motility, with rat studies having shown that gastrin has a positive trophic effect on the gastric mucosa, as evidenced by increased DNA, RNA and protein synthesis.

Antagonists to CCK and to gastrin have been useful for preventing and treating CCK-related and/or gastrin-related disorders of the gastrointestinal (GI) and central nervous (CNS) systems of animals, especially of humans. Just as there is some overlap in the biological activities of CCK and gastrin, antagonists also tend to have affinity for both receptors. In a practical sense, however, there is enough selectivity to the different receptors that greater activity against specific CCK- or gastrin-related disorders can often also be identified.

Selective CCK antagonists are themselves useful in treating CCK-related disorders of the appetite regulatory systems of animals as well as in potentiating and prolonging opiate-mediated analgesia, thus having utility in the treatment of pain [see P. L. Faris et al., Science 226, 1215 (1984)], while selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value.

Also, since CCK and gastrin also have trophic effects on certain tumors [K. Okyama, *Hokkaido J. Med. Sci.*, 60, 206–216 (1985)], antagonists of CCK and gastrin are useful in treating these tumors [see, R. D. Beauchamp et al., *Ann. Surg.*, 202,303 (1985)].

Four distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol.*, 242, G 161 (1982) and P. Robberecht et al., *Mol., Pharmacol.*, 17, 268 (1980)).

The second class comprises peptide antagonists which are C-terminal fragments and analogs of CCK, of which both shorter (Boc-Met-Asp-Phe-NH$_2$, Met-Asp-Phe-NH$_2$), and longer (Cbz-Tyr(SO$_3$H)-Met-Gly-Trp-Met-Asp-NH$_2$) C-terminal fragments of CCK can function as CCK antagonists, according to recent structure-function studies (see, R. T. Jensen et al., *Biochem. Biophys. Acta.*, 757, 250 (1983), and M. Spanarkel et al., *J. Biol. Chem.*, 258, 6746 (1983)). The latter compound was recently reported to be a partial agonist [see, J. M. Howard et al., *Gastroenterology* 86(5) Part 2, 1118 (1984)].

Then, the third class of CCK-receptor antagonists comprises the amino acid derivatives: proglumide, a derivative of glutaramic acid, and the N-acyl tryptophans including para-chlorobenzoyl-L-tryptophan (benzotript), [see, W. F. Hahne et al., *Proc. Natl. Acad. Sci. U.S.A.*, 78, 6304 (1981), R. T. Jensen et al., *Biochem. BiophYs. Acta.*, 761, 269 (1983)]. All of these compounds, however, are relatively weak antagonists of CCK IC$_{50}$: generally 10$^{-4}$M [although more potent analogs of proglumide have been recently reported in F. Makovec et al., *Arzneim-Forsch Drug Res.*, 35 (II), 1048 (1985) and in German Patent Application DE 3522506A1], but down to 10$^{-6}$M in the case of peptides), and the peptide CCK-antagonists have substantial stability and absorption problems.

In addition, a fourth class consists of improved CCK-antagonists comprising a nonpeptide of novel structure from fermentation sources [R. S. L. Chang et al., *Science*, 230, 177–179 (1985)] and 3-substituted benzodiazepines based on this structure [published European Patent Applications 167 919, 167 920 and 169 392, B. E. Evans et al, *Proc. Natl. Acad. Sci. U.S.A.*, 83, p. 4918–4922 (1986) and R. S. L. Chang et al, ibid, p. 4923–4926] have also been reported.

No really effective receptor antagonists of the in vivo effects of gastrin have been reported (J. S. Morley, *Gut*

*Pept. Ulcer Proc.*, Hiroshima Symp. 2nd, 1983, p. 1), and very weak in vitro antagonists, such as proglumide and certain peptides have been described [(J. Martinez, *J. Med. Chem.* 27, 1597 (1984)]. Recently, however, pseudopeptide analogs of tetragastrin have been reported to be more effective gastrin antagonists than previous agents [J. Martinez et al., *J. Med. Chem.*, 28, 1874–1879 (1985)].

The benzodiazepine (BZD) structure class, which has been widely exploited as therapeutic agents, especially as central nervous system (CNS) drugs, such as anxiolytics, and which exhibits strong binding to "benzodiazepine receptors" in vitro, has not in the past been reported to bind to CCK or gastrin receptors. Benzodiazepines have been shown to antagonize CCK-induced activation of rat hippocampal neurones but this effect is mediated by the benzodiazepine receptor, not the CCK receptor [see J. Bradwejn et al., *Nature*, 312, 363 (1984)]. Of these reported BZD's, additionally, the large majority do not contain substituents attached to the 3-position of the seven membered ring, as it is well known in the art that 3-substituents result in decreasing anxiolytic activity, especially as these substituents increase in size.

It was, therefore, an object of this invention to identify substances which more effectively antagonize the function of cholecystokinins and gastrin in disease states in animals, preferably mammals, especially in humans. It was another object of this invention to prepare novel compounds which more selectively inhibit cholecystokinins or inhibit gastrin. It was still another object of this invention to develop a method of antagonizing the functions of cholecystokinin and gastrin in disease states in mammals. It is also an object of this invention to develop a method of preventing or treating disorders of the gastrointestinal, central nervous and appetite regulatory systems of mammals, especially of humans, or of increasing food intake of animals.

SUMMARY OF THE INVENTION

It has now been found that compounds of Formula I are antagonists of gastrin and cholecystokinin (CCK) and bind to the gastrin and CCK receptors. These compounds are useful in the treatment and prevention of CCK-related disorders of the gastrointestinal, central nervous and appetite regulatory systems of animals, preferably mammals and especially humans. They are also useful in the treatment and prevention of gastrin related disorders, gastrointestinal ulcers, Zollinger-Ellison syndrome, antral G cell hyperplasia, and other conditions in which reduced gastrin activity is of therapeutic value.

Also within the invention are those compounds of Formula I that are novel.

DETAILED DESCRIPTION OF THE INVENTION

The compounds of formula I are useful in a method of antagonizing the binding of cholecystokinins to cholecystokinin receptors or antagonizing the binding of gastrin to gastrin receptors which comprises contacting said cholecystokinin receptors or said gastrin receptors, respectively, with a compound represented by the

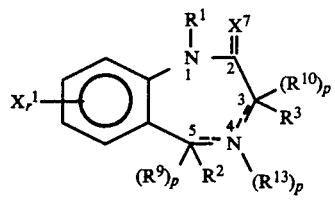

wherein $R^1$ is H, $C_1$-$C_6$ linear or branched alkyl, loweralkenyl, lower alkynyl, —$X^{12}COOR^6$, —$X^{11}$-cycloloweralkyl, —$X^{12}NR^4R^5$, —$X^{12}CONR^4R^5$, —$X^{12}CN$, or —$X^{11}CX_3^{10}$;

$R^2$ is H, loweralkyl, substituted or unsubstituted phenyl (wherein the substitutents may be 1 or 2 of halo, loweralkyl, loweralkoxy, loweralkylthio, carboxyl, carboxyloweralkyl, nitro, —$CF_3$, or hydroxy), 2-, 3-, 4-pyridyl,

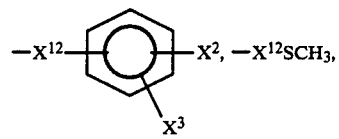

—$X^{12}SOCH_3$, —$X^{12}SO_2CH_3$, or —$X^{12}COOR^6$;

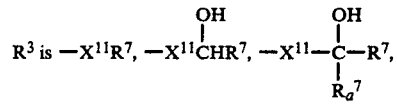

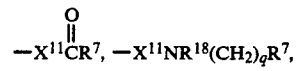

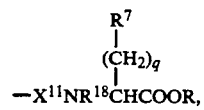

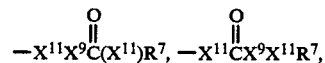

$NH(CH_2)_{2-3}NHR^7$, —$NH(CH_2)_{2-3}NHCOR^7$,

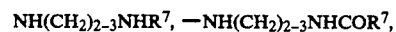

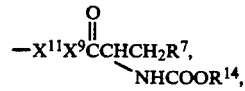

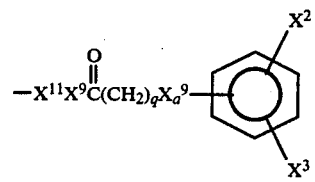

—$X^{11}NR^{18}SO_2(CH_2)_qR^7$ or

R⁴ and R⁵ are independently R⁶ or in combination with the N of the NR⁴R⁵ group form an unsubstituted or mono or disubstituted, saturated or unsaturated, 4–7 membered hetrocyclic ring or benzofused 4–7 membered heterocyclic ring, or said heterocyclic ring or said benzofused heterocyclic ring which further comprises a second heteroatom selected from O and NCH₃ and the substituent(s) is/are independently selected from $C_{1-4}$ alkyl;

R⁶ is H, loweralkyl, cycloloweralkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or CF₃;

R⁷ and R⁷ₐ are independently α- or β-naphthyl, substituted or unsubstituted phenyl (wherein the substituents may be 1 or 2 of halo, —NO₂, —OH, —X¹¹NR⁴R⁵, loweralkyl, CF₃, CN, SCF₃, C≡CH, CH₂SCF₃,

OCHF₂, SH, SPh, PO₃H, loweralkoxy, or loweralkylthio, COOH); 2-, 3-, 4-pyridyl,

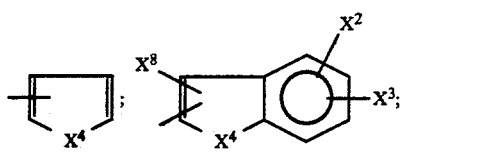

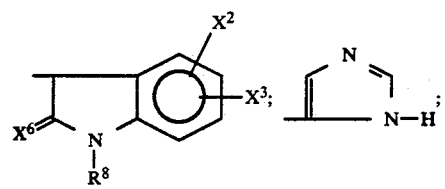

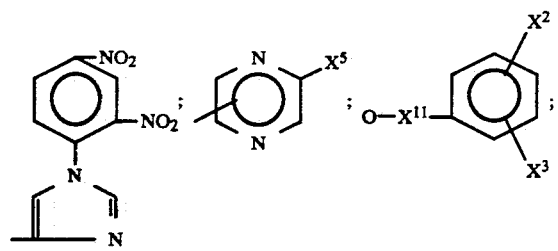

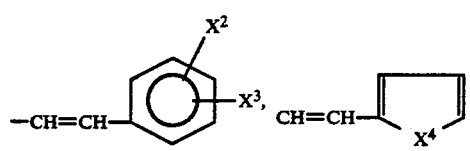

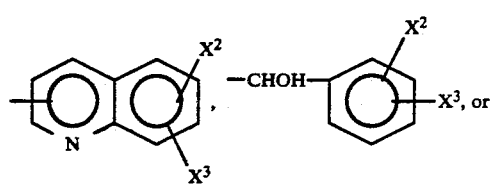

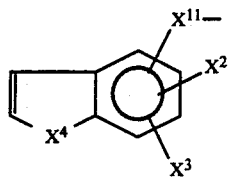

R⁸ is H, loweralkyl, cycloloweralkyl, —X¹²CONH₂, —X¹²COOR⁶, —X¹²-cycloloweralkyl, —X¹²NR⁴R⁵,

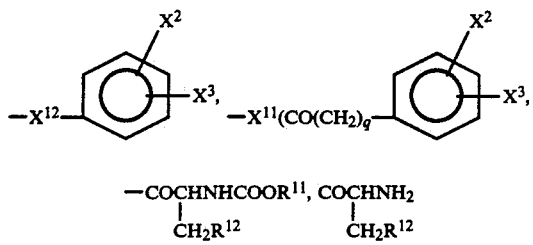

R⁹ and R¹⁰ are independently H, —OH, or —CH₃;
R¹¹ and R¹² are independently loweralkyl or cycloloweralkyl;
R¹³ is H, loweralkyl, acyl, O, or cycloloweralkyl;
R¹⁴ is loweralkyl or phenylloweralkyl;
R¹⁵ is H, loweralkyl,

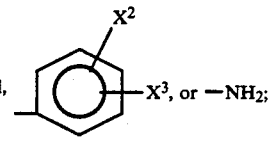

R¹⁸ is H, loweralkyl, or acyl;
o is 0 when its adjacent ≡ is unsaturated and 1 when its adjacent ≡ is saturated except that when R¹³ is O, p—1 and ≡ is unsaturated;
q is 0–4;
r is 1 or 2;
X¹ is H, —NO₂, CF₃, CN, OH, loweralkyl, halo, loweralkylthio, loweralkoxy, —X¹¹COOR⁶, or —X¹¹NR⁴R⁵;
X² and X³ are independently H, —OH, —NO₂, halo, loweralkylthio, loweralkyl, or loweralkoxy;
X⁴ is S, O, CH₂, NR¹⁸ or NR⁸;
X⁵ is H, CF₃, CN, —COOR⁶, NO₂, or halo;
X⁶ is O or HH;
X⁷ is O, S, HH, or NR¹⁵ with the proviso that X⁷ can be NR¹⁵ only when R¹ is not H;
X⁸ is H, loweralkyl;
X⁹ and X⁹ₐ are independently NR¹⁸ or O;
X¹⁰ is F, Cl, or Br;
X¹¹ is absent or $C_{1-4}$ linear or branched alkylidene;
X¹² is $C_{1-4}$ linear or branched alkylidene;
≡ is a saturated or unsaturated bond and the pharmaceutically acceptable salts thereof.

Also within the invention are the novel compounds of Formula II:

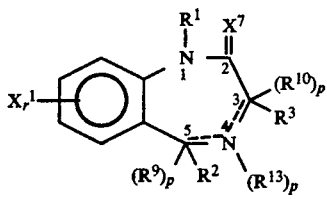

wherein $R^1$ is H, $C_1$—$C_6$ linear or branched alkyl, loweralkenyl, lower alkynyl, —$X^{12}COOR^6$, —$X^{11}$-cycloloweralkyl, —$X^{12}NR^4R^5$, —$X^{12}CONR^4R^5$, —$X^{12}CN$, or —$X^{11}CX^{10}_3$;

$R^2$ is H, loweralkyl, substituted or unsubstituted phenyl (wherein the substitutents may be 1 or 2 or halo, lower alkyl, loweralkoxy, loweralkylthio, carboxyl, carboxyloweralkyl, nitro, —$CF_3$, or hydroxy), 2-, 3-, 4-pryidyl,

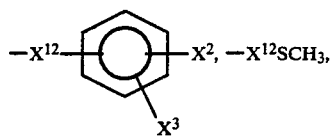

—$x^{12}SOCH_3$, —$X^{12}SO_2CH_3$, or —$X^{12}COOR^6$;

$R^3$ is —$X^{11}NR^{18}(CH_2)_qR^{16}$

—$NH(CH_2)_{2-3}NHR^7$, —$NH(CH_2)_{2-3}NHCOR^7$,

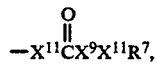

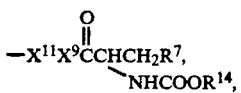

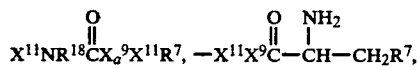

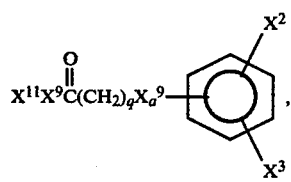

$X^{11}NR^{18}SO_2(CH_2)_qR^7$ or $X^{11}\overset{O}{\overset{\|}{C}}R^7$, with the proviso that $R^{10}$ is not H or —$CH_3$ when $R^3$ is $X^{11}\overset{O}{\overset{\|}{C}}R^7$;

$R^4$ and $R^5$ are independently $R^6$ or in combination with the N of the $NR^4R^5$ group form an unsubstituted or mono or disubstituted, saturated or unsaturated, 4–7 membered heterocyclic ring, or benzofused 4–7 membered heterocyclic ring or said heterocyclic ring or said benzofused heterocyclic ring which further comprises a second heteroatom selected from O and $NCH_3$ and the substituent(s) is/are independently selected from $C_{1-4}$ alkyl;

$R^6$ is H, loweralkyl, cycloloweralkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or $CF_3$;

$R^7$ is α- or β-naphthyl, substituted or unsubstituted phenyl (wherein the substituents may be 1 to 2 of halo, —$NO_2$, —OH, —$X^{11}NR^4R^5$, loweralkyl, $CF_3$, CN, $SCF_3$, C=CH, $CH_2SCF_3$,

$OCHF_2$, SH, SPh, $PO_3H$, loweralkoxy, loweralkylthio or COOH), 2-, 3-, 4- pyridyl,

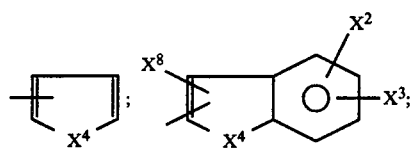

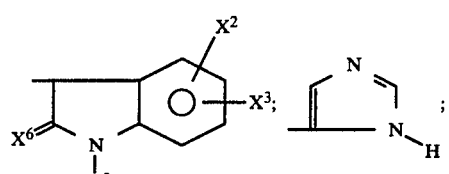

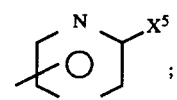

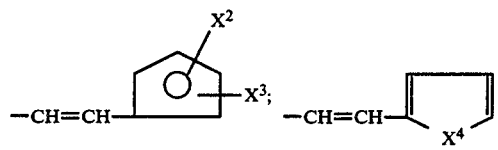

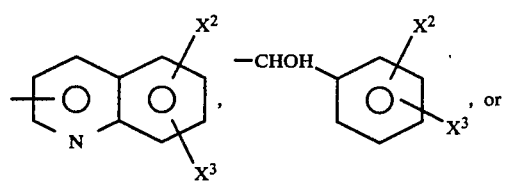

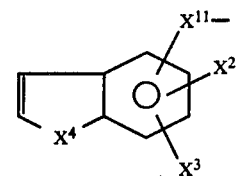

$R^8$ is H, loweralkyl, cycloloweralkyl, —$X^{12}CONH_2$, —$X^{12}COOR^6$, —$X^{12}$-cycloloweralkyl, —$X^{12}NR^4R^5$,

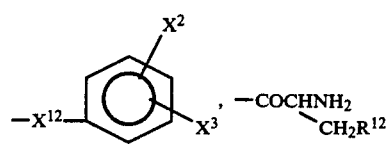

-continued

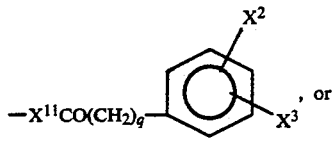, or

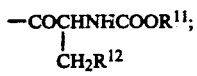

$R^9$ and $R^{10}$ are independently H, —OH, or —CH$_3$;
$R^{11}$ and $R^{12}$ are independently loweralkyl or cycloloweralkyl;
$R^{13}$ is H, loweralkyl, acyl, O, or cycloloweralkyl; is loweralkyl or phenylloweralkyl;
$R^{14}$ is loweralkyl or phenylloweralkyl;
$R^{15}$ is H, loweralkyl,

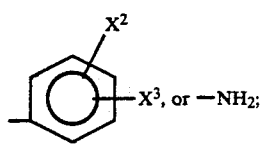

$R^{16}$ is alpha or beta naphthyl or 2-indolyl;
$R^{18}$ is H or loweralkyl;
p is 0 when its adjacent = is unsaturated and 1 when its adjacent = is saturated except that when $R^{13}$ is O, p=1 and = is unsaturated;
q is 0–4;
r is 1 or 2;
$X^1$ is H, —NO$_2$, CF$_3$, CN, OH, loweralkyl, halo, loweralkylthio, loweralkoxy, —X$^{11}$COOR$^6$, or —X$^{11}$NR$^4$R$^5$;
$X^2$ and $X^3$ are independently H, —OH,—NO$_2$, halo, loweralkylthio, loweralkyl, or loweralkoxy;
$X^4$ is S, O, CH$_2$, or NR$^8$;
$X^5$ is H, CF$_3$, CN, —COOR$^6$, NO$_2$, or halo;
$X^6$ is O or HH;
$X^7$ is O, S, HH, or NR$^{15}$ with the proviso that $X^7$ can be NR$^{15}$ only when $R^1$ is not H;
$X^8$ is H, loweralkyl;
$X^9$ and $X^9$ are independently NR$^{18}$, O;
$X^{10}$ is F, Cl, or Br;
$X^{11}$ is absent or C$_{1-4}$ linear or branched alkylidene;
$X^{12}$ is C$_{1-4}$ linear or branched alkylidene; = is a saturated or unsaturated bond; with the proviso that when $X^1$, is Cl in the seven position, $R^1$ is H and $R^2$ is unsubstituted phenyl, then $R^3$ is not NHCO(CH$_2$)$_2$C$_6$H$_5$ or NHCOC$_6$H$_5$; and the pharmaceutically acceptable salts thereof.

As used herein, the definition of each expression, e.g. m, n, p, loweralkyl, etc., when it occurs more than once in any structure, is intended to be independent of its definition elsewhere in the same structure. Thus, the ring fragment

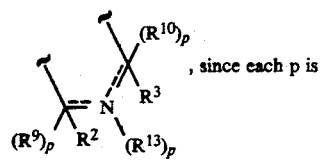, since each p is independently 1 or 0, represents the three structures

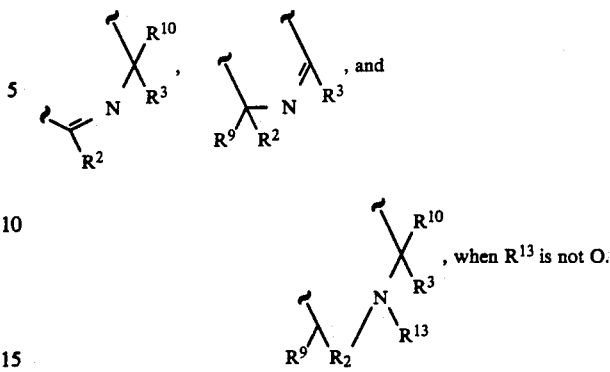

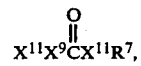, when $R^{13}$ is not O.

In the compounds of Formula I, the preferred stereochemistry for CCK antagonism relates to D-tryptophan, where C$^2$ and N$^4$ of Formula I correspond to the carbonyl carbon and α-amino N of D-tryptophan and $R^3$ occupies the position of the indolylmethyl side chain.

In the compounds of Formula I, the preferred stereochemistry for gastrin antagonism can be either D or L depending on the nature of $R^3$. For example, when $R^3=X^{11}R^7$ or $$X^{11}X^9\overset{O}{\underset{\|}{C}}X^{11}R^7,$$

the preferred stereochemistry corresponds to D-tryptophan, as above. When $$R^3 = X^9\overset{O}{\underset{\|}{C}}X_a^9X^{11}R^7,$$

the preferred stereochemistry corresponds to L-tryptophan.

As used herein, halo is F, Cl, Br or I; loweralkyl is 1-7 carbon straight or branched chain alkyl and includes methyl, ethyl, propyl, isopropyl, butyl, isobutyl, and t-butyl, pentyl, hexyl, and heptyl; in loweralkoxy and loweralkylthio, the alkyl portion is loweralkyl as previously defined; cycloloweralkyl is cycloalkyl of 3-7 carbons; loweralkenyl is 1-5 carbon straight or branched chain alkenyl; acyl is formyl, acetyl, propionyl, benzoyl or butyryl; loweralkynyl is 1-5 carbon straight or branched chain alkynyl.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the comPounds of Formula I which contain a basic or acidic moiety by conventional chemical methods. Generally, the salts are prepared by reacting the free base or acid with stoichiometric amounts or with an excess of the desired saltforming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

An embodiment of this invention is the preparation of compounds of Formula II.

The ability of the compounds of Formula I to antagonize CCK and gastrin makes these compounds useful as pharmaceutical agents for mammals, especially for humans, for the treatment and prevention of disorders wherein CCK and/or gastrin may be involved. Examples of such disease states include gastrointestinal disorders, especially such as irritable bowel syndrome, gastroesophageal reflux disease or ulcers, excess pancreatic or gastric secretion, acute pancreatitis, or motility disorders; central nervous system disorders, caused by CCK interactions with dopamine, such as neuroleptic disorders, tardive dyskinesia, Parkinson's disease, psychosis or Gilles de la Tourette Syndrome; disorders of appetite regulatory systems; Zollinger-Ellison syndrome, antral G cell hyperplasia, or pain (potentiation of opiate analgesia); as well as certain tumors of the lower esophagus, stomach, intestines and colon.

The compounds of Formula I thereof, may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. P/1023A - 22 - 17119IC For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 50 mg/kg of body weight, and preferably, of from 0.5 mg/kg to about 20 mg/kg of body weight, administered in single or divided doses. In some cases, however, it may be necessary to use dosages outside these limits.

In the treatment of irritable bowel syndrome, for instance, 0.1 to 10 mg/kg of a CCK antagonist might be administered orally (p.o.), divided into two doses per day (b.i.d.). In treating delayed gastric emptying, the dosage range would probably be the same, although the drug might be administered either intravenously (I.V.) or orally, with the I.V. dose probably tending to be slightly lower due to better availability. Acute pancreatitis might be treated preferentially in an I.V. form, whereas spasm and/or reflex esophageal, chronic Pancreatitis, post vagotomy diarrhea, anorexia or pain associated with biliary dyskinesia might indicate p.o. form administration.

In the use of a gastrin antagonist as a tumor palliative for gastrointestinal neoplasms with gastrin receptors, as a modulator of central nervous system activity, treatment of Zollinger-Ellison syndrome, or in the treatment of peptic ulcer disease, a dosage of 0.1 to 10 mg/kg administered one-to-four times daily might be indicated.

Because these compounds antagonize the function of CCK in animals, they may also be used as feed additives to increase the food intake of animals in daily dosage of approximately 0.05 to 50 mg/kg of body weight.

The compounds of Formula I are prepared according to the following schemes.

REACTION SCHEME I

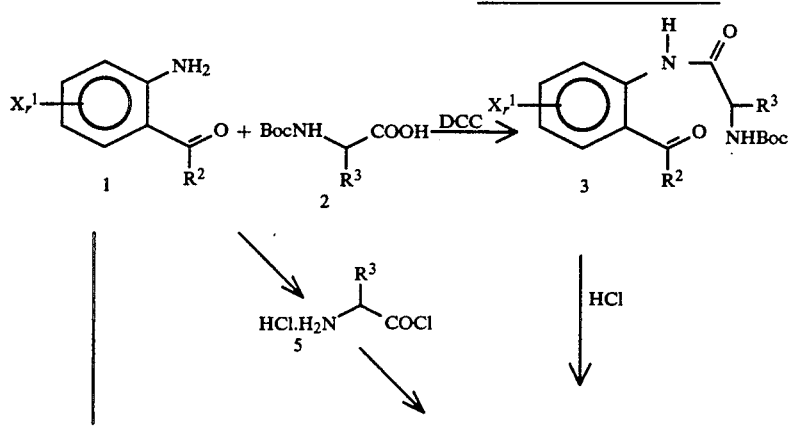

-continued
REACTION SCHEME I
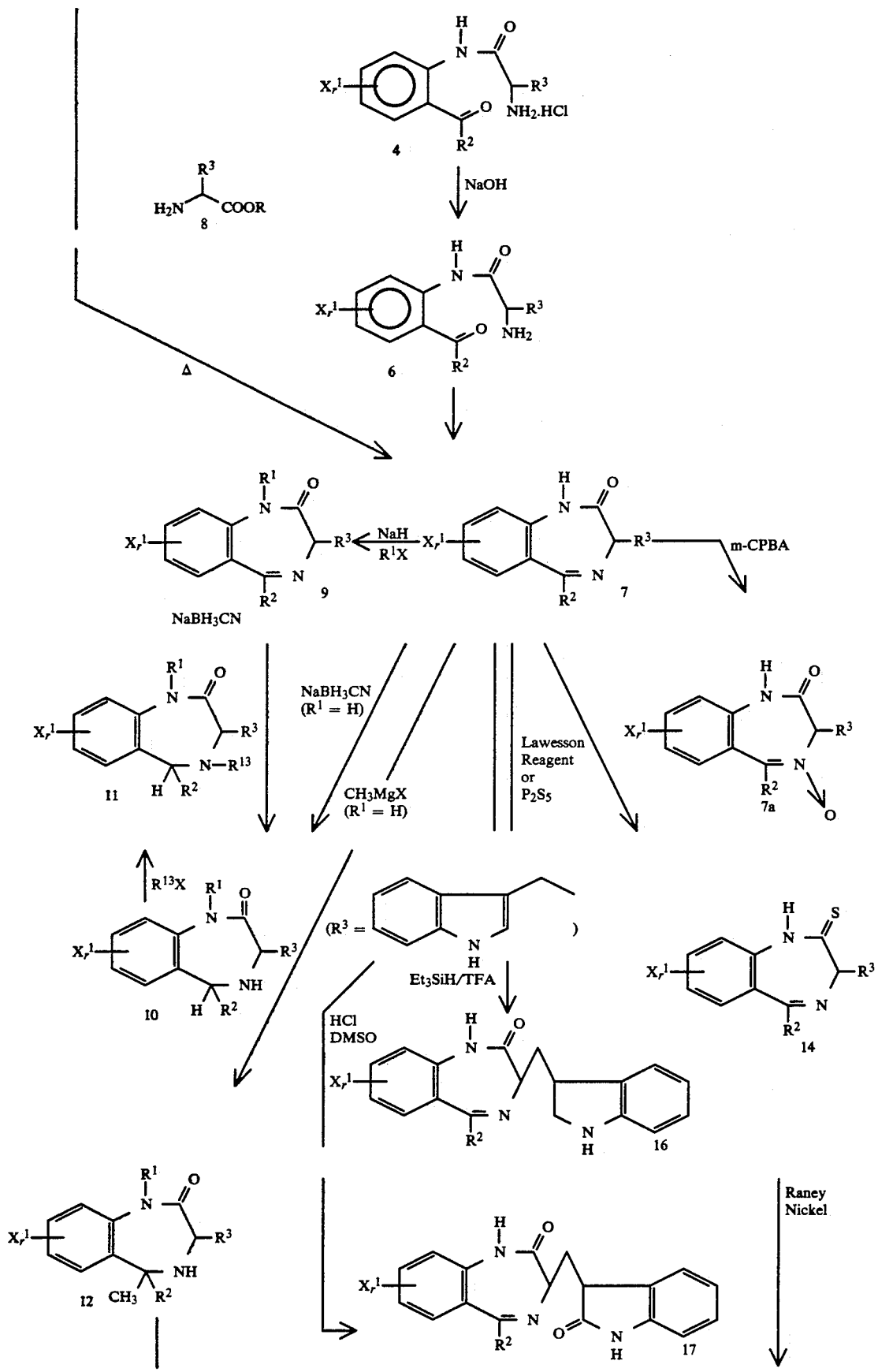

-continued
REACTION SCHEME I
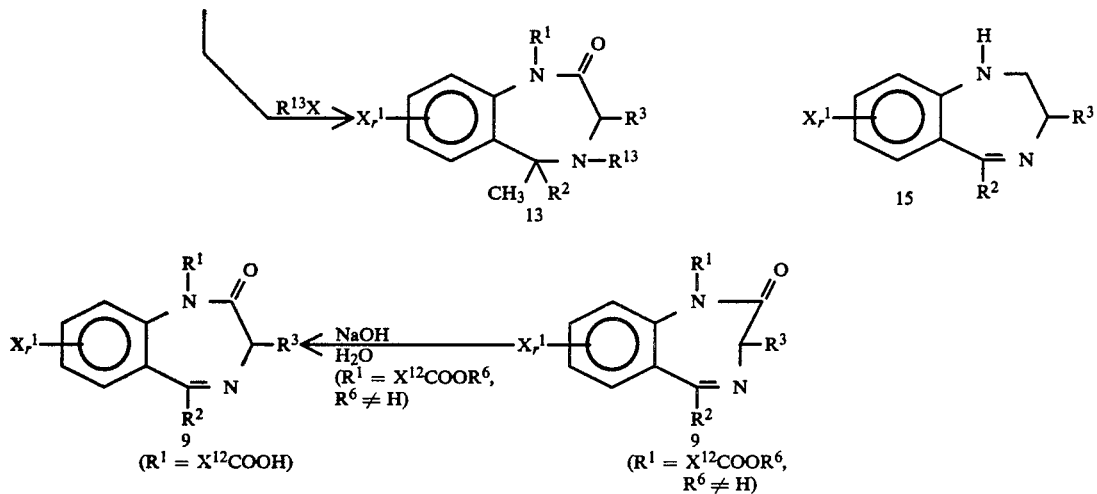

REACTION SCHEME II
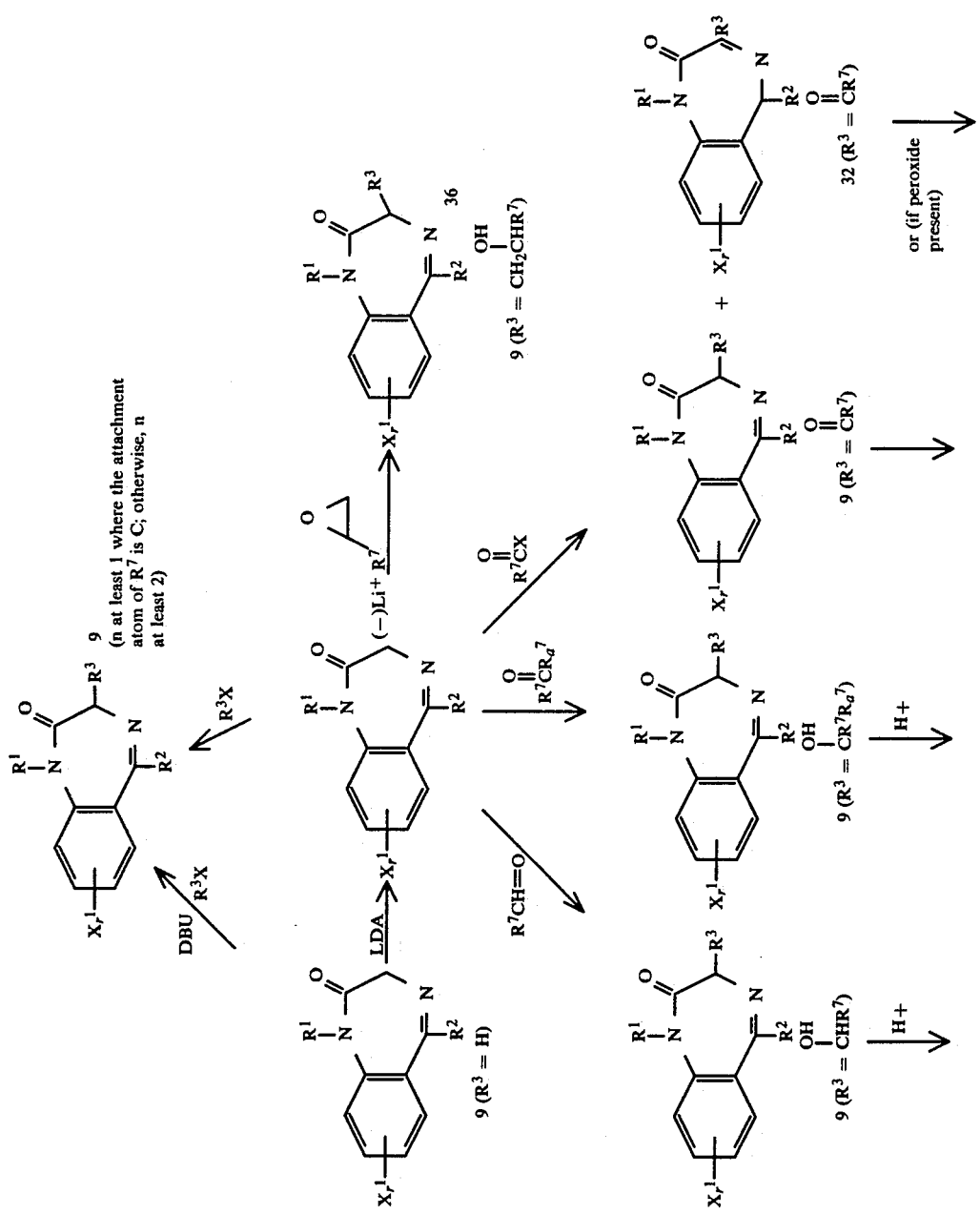

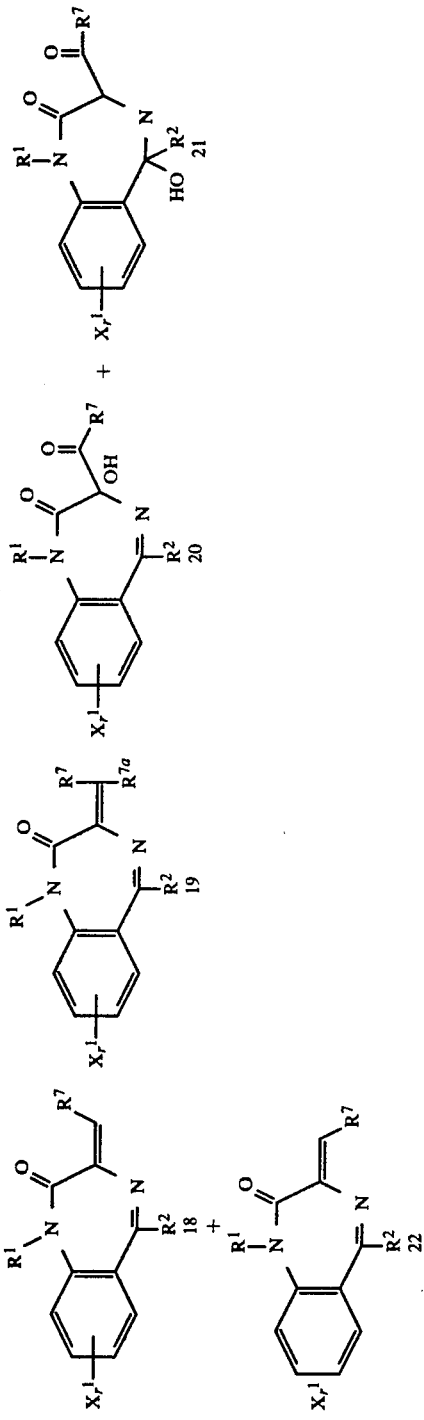
REACTION SCHEME II -continued

REACTION SCHEME III
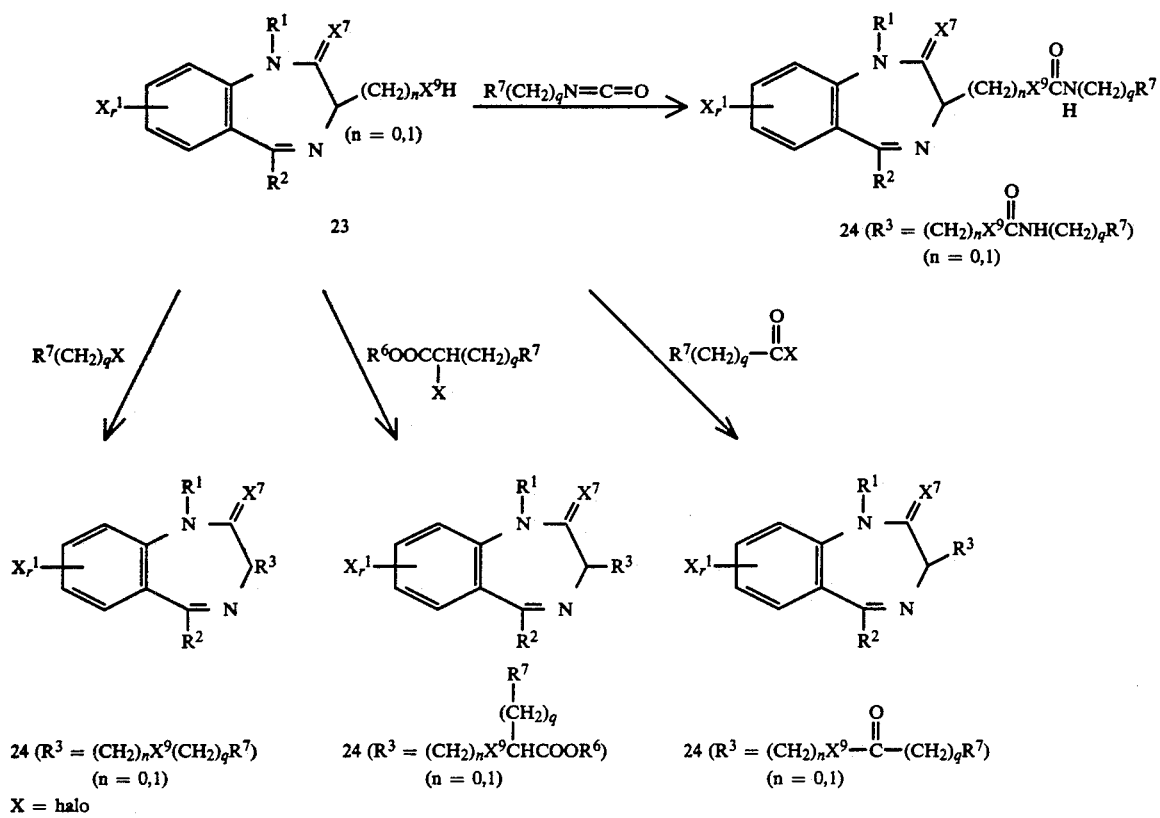
REACTION SCHEME IIIa
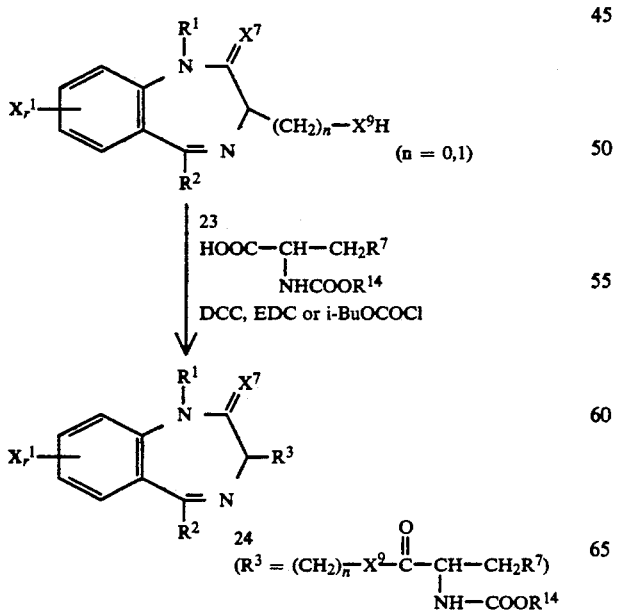
REACTION SCHEME IIIb
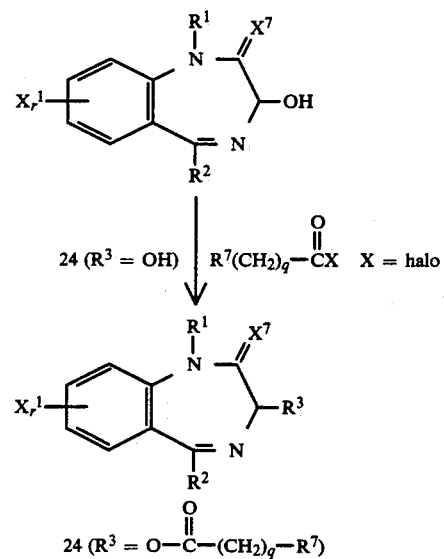

REACTION SCHEME IIIc
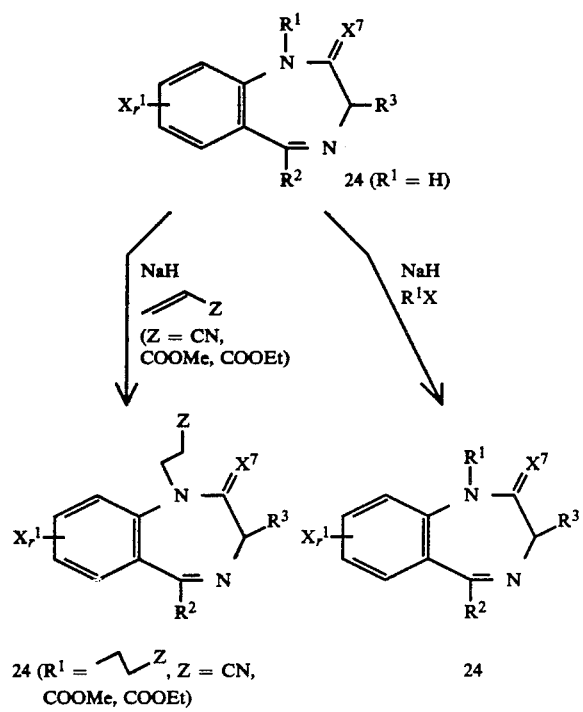
REACTION SCHEME IIId
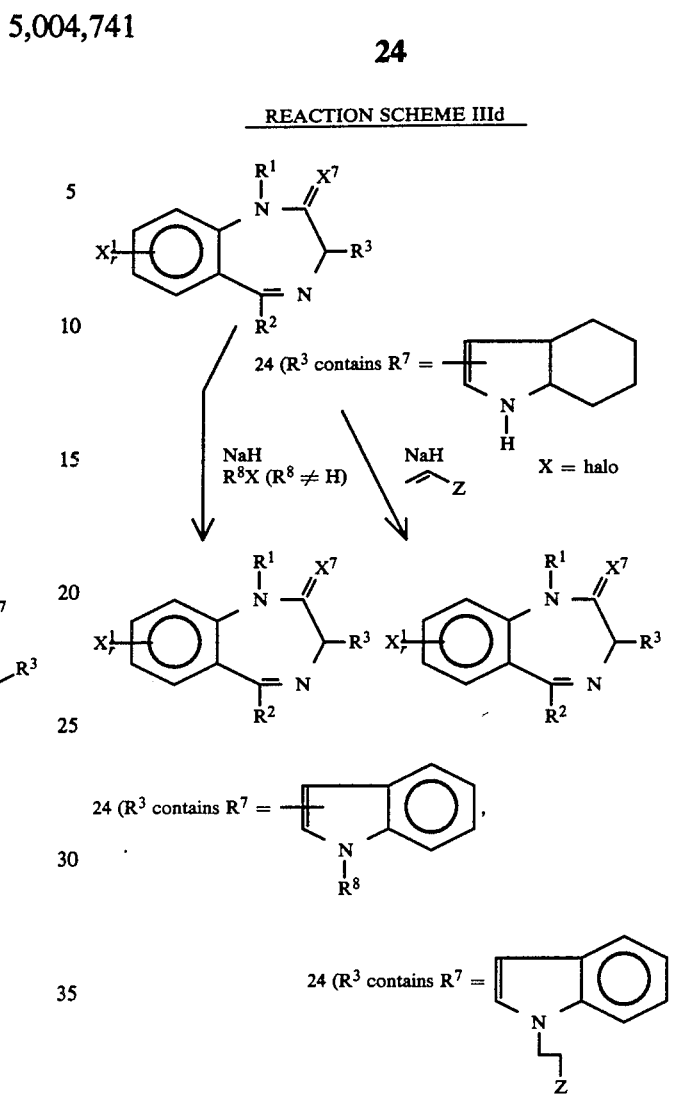
Where, in the 24 compound, $R^1$ and/or $R^8$ is an ester [$(X^{12})COO$-$C_1$-$C_3$ alkyl] moiety, this group can be conventionally hydrolyzed to obtain the corresponding acid moiety or treated with $NH_3$ to obtain the corresponding amide moiety.
REACTION SCHEME IV
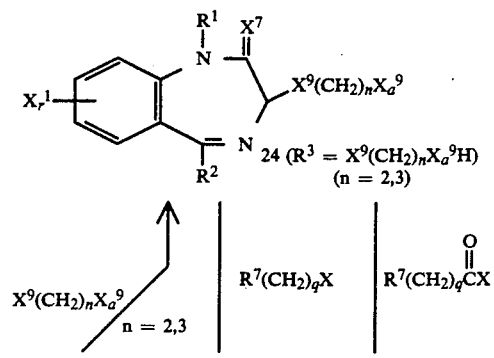

REACTION SCHEME IV
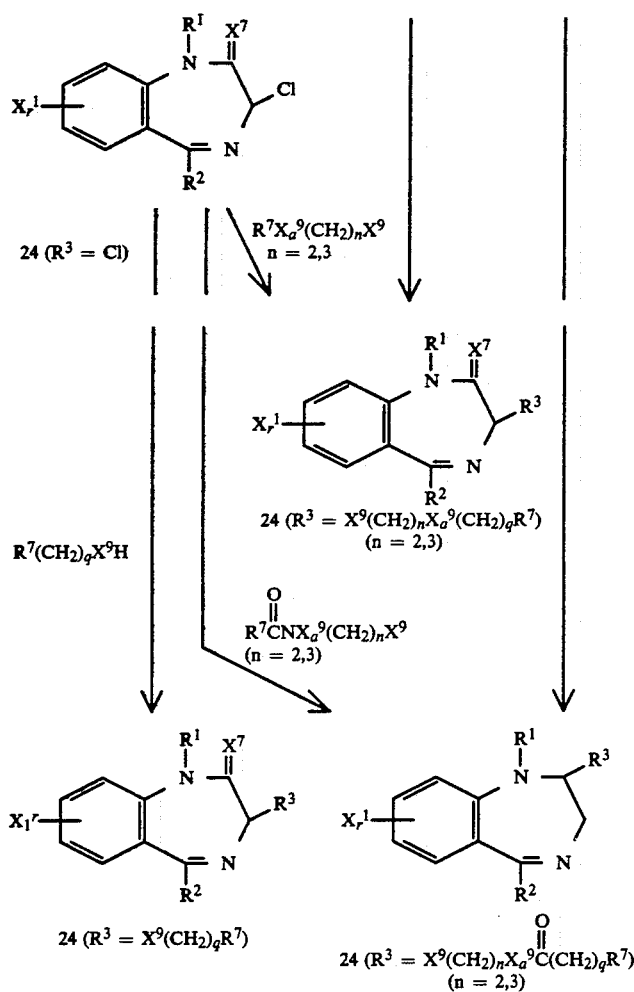
SCHEME IVa
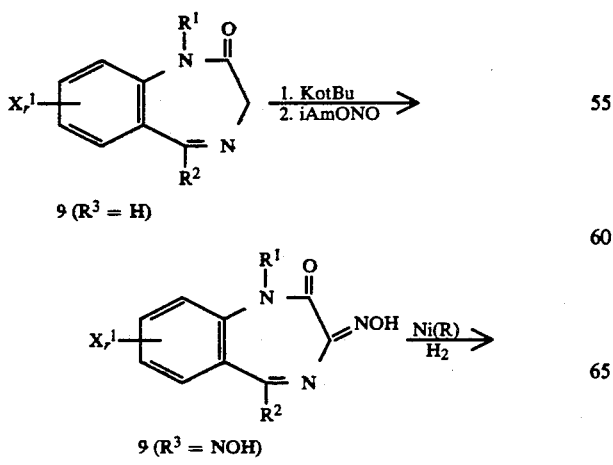
-continued
SCHEME IVa
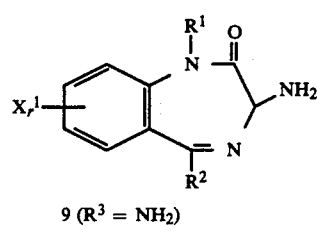

REACTION SCHEME V
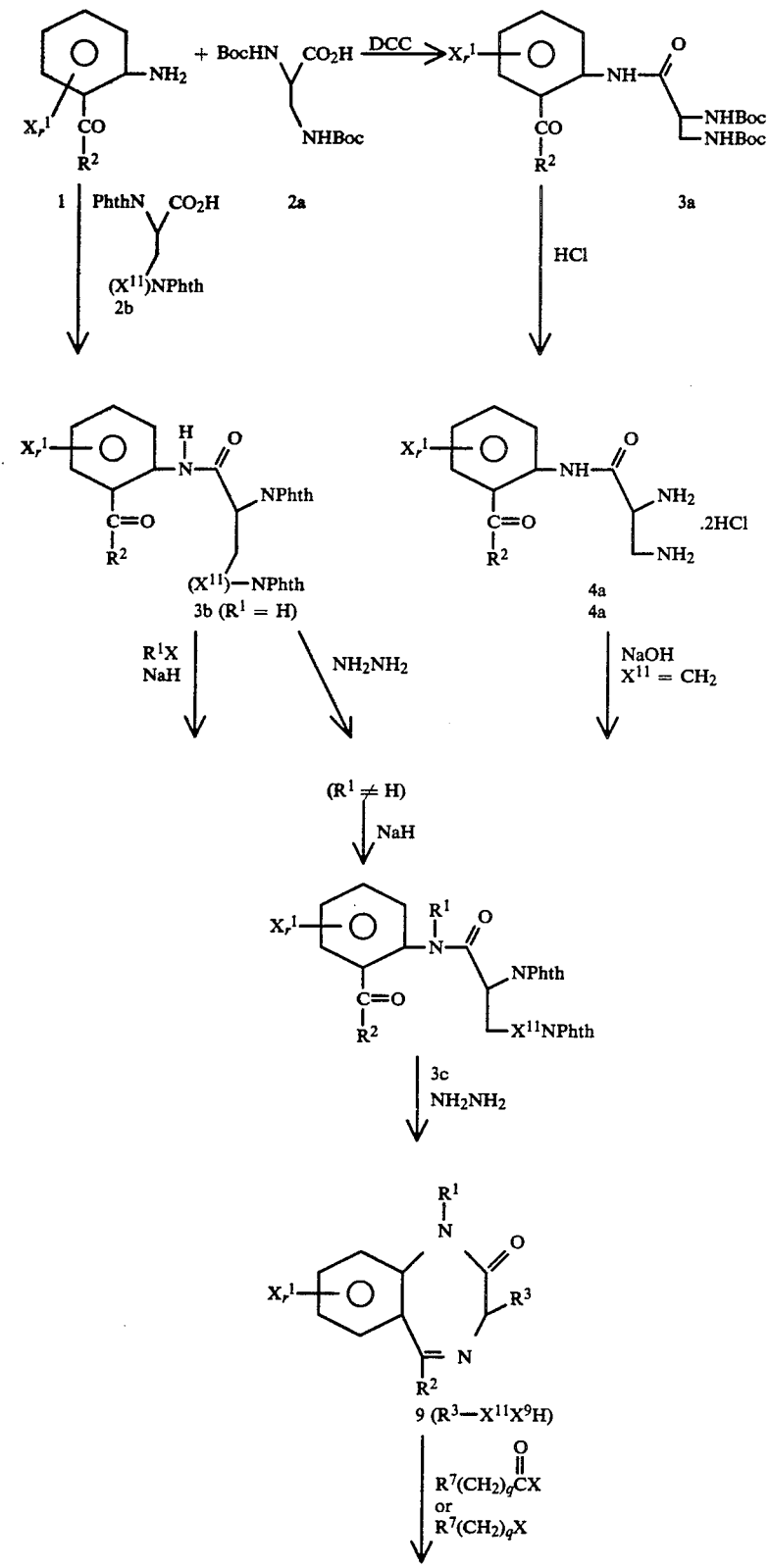

-continued
REACTION SCHEME V
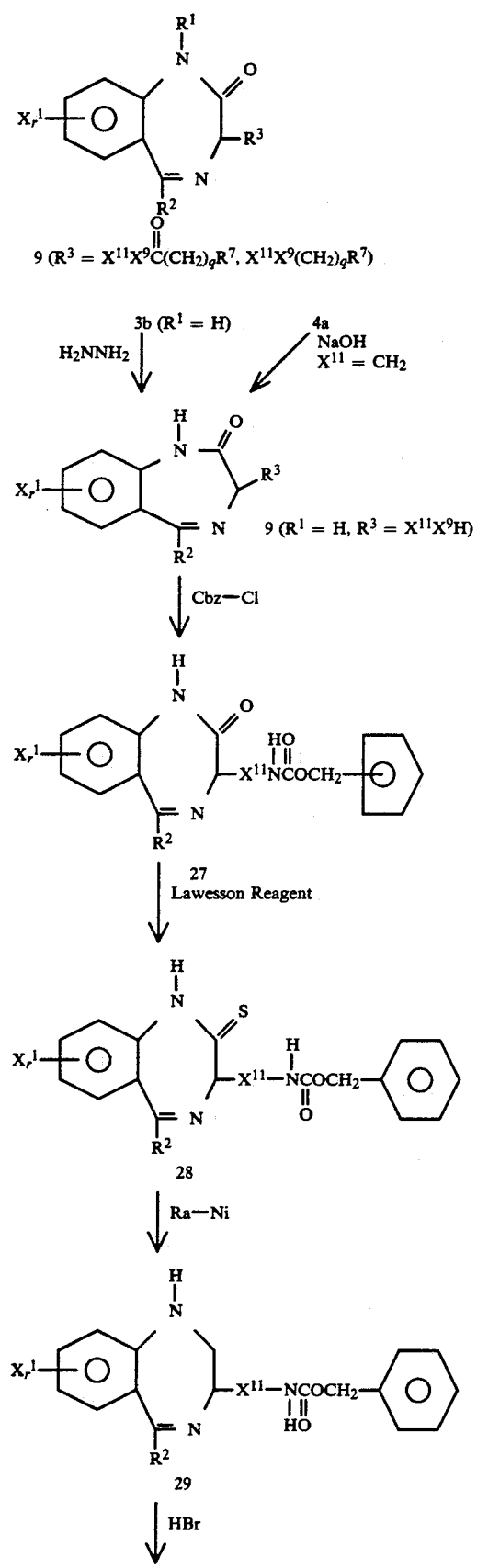

REACTION SCHEME V
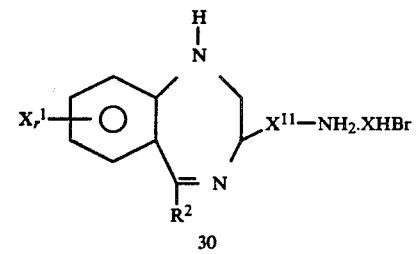
30
↓ R⁷(CH₂)qCX or
R⁷(CH₂)qX
     ∥
     O
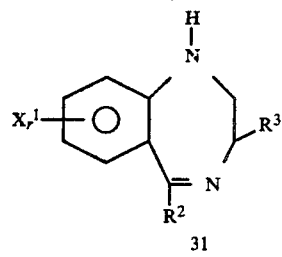
31
↓
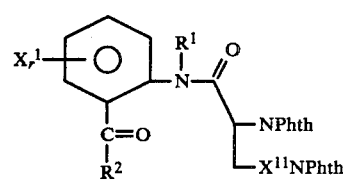
↓ 30
NH₂NH₂
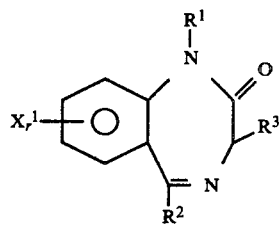
9 (R³ = —X¹¹X⁹H)
↓ R⁷(CH₂)qCX
     ∥
     O
  or
R⁷(CH₂)qX
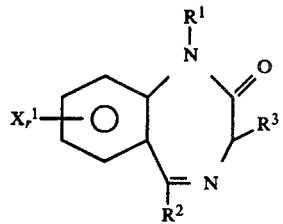
9 (R³ = X¹¹X⁹(CH₂)qR⁷
  or
        O
        ∥
   X¹¹X⁹C(CH₂)qR⁷)

REACTION SCHEME V

-continued

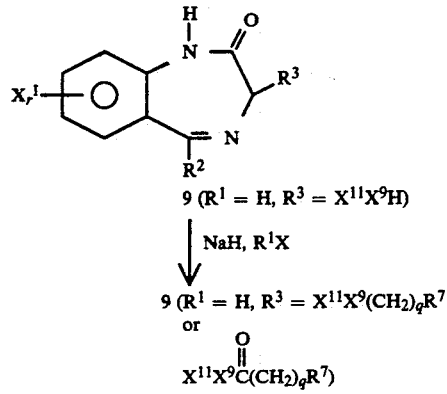

9 (R$^1$ = H, R$^3$ = X$^{11}$X$^9$H)

↓ NaH, R$^1$X 9 (R$^1$ = H, R$^3$ = X$^{11}$X$^9$(CH$_2$)$_q$R$^7$
or
X$^{11}$X$^9$$\overset{O}{\underset{\|}{C}}$(CH$_2$)$_q$R$^7$)

2-Aminoarylketones 1, (Scheme I) preferably 2-amino-benzophenones containing various substituents in the aryl rings, preferably halo substituents, are coupled to N-protected D-amino acids 2 (preferably, Boc-amino acids) using dicyclohexylcarbodiimide (DCC) or other conventional peptide coupling reagent. The product 3 is N-deprotected by treatment with acid, preferably anhydrous HCl in ethyl acetate, to give the α-aminoacyl derivative 4 of the 2-aminoarylketone. Alternatively, this same product is obtained by treatment of the 2-aminoarylketone 1 with the acid chloride hydrochloride 5 of the D-amino acid, which is prepared from the amino acid with PCl$_5$-AcCl.

Treatment of this α-aminoacyl derivative 4 with base, preferably aqueous sodium hydroxide in methanol, gives the free base 6 which is cyclized to the 3,5-disubstituted benzodiazepine 7 upon stirring in the methanolic base for 2-120 hours, preferably 48 hours. Alternatively, the 3,5-disubstituted benzodiazepine 7 is obtained by heating the 2-aminoarylketone 1 with the ester 8, preferably methyl or ethyl, of the D-amino acid, preferably in refluxing pyridine, for 2-48 hours, preferably for 18 hours.

Alternatively (Scheme V), the ketones 1 may be coupled with N-phthalylamino acids such as 2b to give the products 3b using DCC or other conventional peptide coupling reagent. 3b may be deprotected and cyclized to 9 (R$^1$=H, R$^3$=X$^{11}$X$^9$H) by treating with hydrazine. Alternatively, 3b may be first alkylated by treatment with sodium hydride followed by an alkyl halide in dimethylformamide (DMF) to give the alkyl derivative 3c. Treating this product with hydrazine gives the N$^1$-alkylbenzodiazepine, 9 (R$^3$=X$^{11}$X$^9$H).

9 (R$^3$=X$^{11}$X$^9$H) are alkylated by treatment with alkyl halide or dialkyl sulfate or acylated by treatment with acid halides or anhydrides, preferably in the presence of base such as triethyl amine. The products are the alkyl and acyl derivatives 9(R$^3$=X$^{11}$X$^9$(CH$_2$)$_q$R$^7$ and

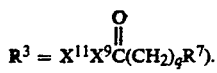

R$^3$ = X$^{11}$X$^9$$\overset{O}{\underset{\|}{C}}$(CH$_2$)$_q$R$^7$).

Alternatively, protection of the 3-amino function in 9 (R$^3$=X$^{11}$NH$_2$), preferably with benzylchloroformate affords the acyl derivative 27. Treatment of this material with P$_2$S$_5$ or Preferably with Lawesson's reagent in toluene gives the thioamide 28 which is converted to the amine 29 with Raney nickel in ethanol. Deprotection of the resulting product 29 via hydrogenolysis, or preferably by the action of hydrobromic acid, yields the corresponding amino compound 30. Alkylation of 30 by treatment with alkyl halide or dialkyl sulfonate or acylation with carboxylic acid halide or carboxylic acid anhydride in the presence of an acid binding agent such as triethylamine or preferably with a carboxylic acid in the presence of a peptide coupling reagent such as dicyclohexyl-carbodiimide gives the alkyl or acyl derivatives 31.

3,5-Disubstituted benzodiazepines 7 (Scheme I) are also treated with sodium hydride in dimethylformamide (DMF), followed by an alkyl halide, to give the 1-alkyl derivatives 9. These or the parent 1-unsubstituted compound 7 are reduced, preferably with sodium cyanoborohydride and acetic acid at 15°, to give the corresponding 4,5-dihydro compounds 10. These are alkylated on N$_4$ by treatment with alkyl halide or dialkyl sulfate. Alternatively, the 4,5-dihydro compounds are acylated on N$_4$ by treatment with acyl halides or anhydrides, Preferably in the presence of base such as triethylamine. The products are the alkyl and acyl derivatives 11. Alternatively, where R$^1$ is —X$^{12}$COOR$^6$ (R$^6$ not=H), 9 are treated with a base such as sodium hydroxide in methanol to give the acids 9 (R$^1$=Xhu 12COOH).

The 3,5-disubstituted benzodiazepines 7 are treated with alkyl- or arylmagnesium halides, preferably methylmagnesium iodide, to give the dihydro compounds 12. The products are alkylated and acylated on nitrogen, as described for the 3,5-disubstituted4,5-dihydro derivatives, to give the derivatives 13.

The 3,5-disubstituted benzodiazepines 7 are treated with P$_2$S$_5$ or Lawesson's reagent (2,4-bis(4-methoxyphenyl)-2,4-dithioxo-1,3,2,4-dithiadiphosphetane) to give the 2-thiones 14. These are reduced with Raney nickel to the 2-unsubstituted compounds 15. The latter may be alkylated with alkyl halide or sulfate, acylated with acyl halide or anhydride, reduced with sodium cyanoborohydride, or substituted with alkyl- or aryl magnesium halide as described for 7 above.

Where the 3-position in a 3,5-disubstituted benzodiazepine 7 bears a substituent containing an indole moiety, preferably 3-indolylmethyl, reduction with triethylsilane/TFA provides the corresponding indoline 16. Alternatively, oxidation with HCl-dimethylsulfoxide provides the oxindole 17. 16 and 17 may be subjected to the reactions described for 7 to obtain alkyl, acyl, and dihydro derivatives. Dialkyl, alkylacyl, and trialkyl compounds may also be made using these methods.

The 3,5-disubstituted benzodiazepines 7 may also be oxidized, preferably with m-chloroperoxybenzoic acid, to give the corresponding 4-N-oxides 7a.

Alternatively, (Scheme II) 3-unsubstituted-5-substituted-1-substituted or unsubstituted benzodiazepines 9 ($R^1$=H) (Scheme II) prepared as described in the prior art may be treated with base, preferably lithium diisopropylamide, in an inert solvent, preferably THF, according to the procedure of J. Org. Chem., 46 4945 (1981). The resulting salt may be alkylated to obtain 9 with, for example, benzyl bromide or gramine methiodide. The resulting racemates may be resolved to obtain the Preferred 3(R) enantiomers, or may be used as such.

Alternatively, the salt may be treated with an alkyl or aryl aldehyde, ketone, or acid halide or anhydride to give the 1-hydroxymethylene compounds

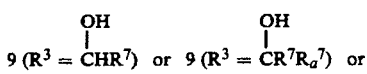

the 1-ketomethylene derivatives 9 ($R^3 = CR^7$) and

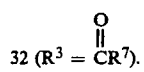

If the acid halide reaction is carried out in solvent containing peroxide, the 3- and 5-hydroxy analogs 20 and 21 (resp.) may be obtained.

The hydroxymethylene compounds

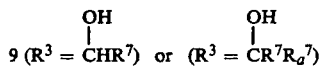

may be treated with acids, preferably trifluoroacetic acid, to obtain the olefins 18, 19, and/or 22.

Alternatively, 3-substituted benzodiazepines may be obtained by treating the 3-unsubstituted compound 9 ($R^3$=H) with 1,8-diazabicyclo[5.4.0] undec-7-ene (DBU) and alkylating agent such as alkyl halide or sulfate or, preferably, gramine methiodide. Resolution to obtain the preferred 3(R) enantiomer may be carried out as described above.

3-Amino-5-substituted-1-substituted or unsubstituted benzodiazepines 9 ($R^3$—$NH_2$) are prepared as described in the prior art. Alternatively, 9 ($R^3$=$NH_2$) are prepared as shown in Scheme IVa. Treatment of the 3-unsubstituted compound 9 ($R^3$=H) with a suitable base, preferably potassium t-butoxide, followed by a nitrosatinq agent, preferably isoamyl nitrate, provides the oxime 9 ($R^3$=NOH). Reduction, preferably with Raney nickel, gives the 3-amino compounds 9 ($R^3$=$NH_2$). Alternatively, 9 ($R^3$=$NH_2$) are prepared by the method disclosed in U.S. Pat. No. 4,628,084.

3-Amino and 3-aminomethyl-5-substituted-1substituted or unsubstituted benzodiazepines 23 Scheme III) are alkylated with alkyl halides or with α-halo acids and esters to give the alkyl derivatives

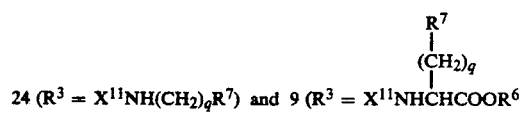

With acyl halides, the amines 23 give the corresponding amides

With isocyanates, the amines 23 give the corresponding ureas

With N-protected or unprotected α-amino acids and a coupling reagent such as DCC, EDC, or isobutyl chloroformate, the amines 23 give the amides

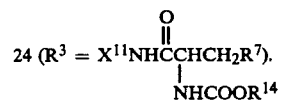

3-Hydroxy-5-substituted-7-substituted or unsubstituted-1-substituted or unsubstituted benzodiazepines 24 ($R^3$=OH) (Scheme IIIb) are acylated with acyl halides to give the esters 24

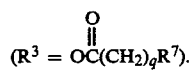

3-Chloro-5-substituted-1-substituted or unsubstituted benzodiazepines 24 ($R^3$=Cl) (Scheme IV) may be used to monoalkylate amines to give the 3-substituted amino compounds 24 ($R^3$=$NH_2$). The 3-chloro compounds 29 may also be used to monoalkylate 1,2-ethanediamine and 1,3-propanediamine to give the compounds 24 ($R^3$=NH($CH_2$)$NH_2$). These may be alkylated to provide 24 ($R^3$=NH$X^{11}$NH($CH_2$)$qR^7$) or acylated to give

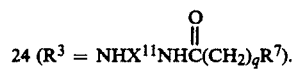

Alternatively, the latter two compounds may be obtained from the previously mono-alkylated or acylated diamine and chloro compound 24 ($R^3$=Cl).

3-Substituted-5-substituted-7-substituted or unsubstituted benzodiazepines 24 ($R^1$=H) (Scheme IIIc) may be treated with sodium hydride in a suitable solvent, such as DMF, followed by an alkyl halide to provide the 1-alkyl derivatives 24. When an acrylate such as methyl or ethyl acrylate or acylonitrile is substituted for the alkyl halide, the 1-(2-substituted)ethyl compounds,

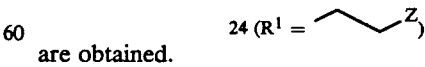

are obtained.

When $R^3$ contains $R^7$ where $R^7$ is 1-unsubstituted-2- or 3-indolyl (Scheme IIId), the compounds 24 may be further alkylated by treatment with sodium hydride followed by an alkyl halide or an acrylate, such as methyl or ethyl acrylate or acrylonitrile, or an activated amino acid such as Boc-phenylalanine anhydride to give the corresponding 1-substituted indole compounds 24 (Scheme IIId) in which $R^8$ is as defined herein and $R^8$ is other than hydrogen.

The compounds 24 wherein $R^1$ and/or $R^8$ is $X^{12}$-COOMe or $X^{12}$-COOEt may be treated with sodium hydroxide in an aqueous solvent, preferably aqueous solvent, preferably aqueous methanol, and then acidified to give the corresponding acids 24, wherein $R^1$ and/or $R^8$ is $X^{12}$COOH. Alternatively, these same compounds may be treated with aqueous or anhydrous ammonia to give the amides 24 wherein $R^1$ and/or $R^8$ is $X^{12}$CONH$_2$.

In cases where the starting materials are optically active, the chirality at $C_3$ is controlled by the synthesis. When racemic starting materials are employed, racemic products are obtained. The enantiomers may be separated by resolution.

In Vitro Activity of Compounds of Formula I

The biological activity of the compounds of Formula I have been evaluated using 1.)an $^{125}$I-CCK receptor binding assay and in vitro isolated tissue preparations and 2.) $^{125}$I-gastrin and $^3$Hpentagastrin binding assays.

Materials and Methods

1. CCK Receptor Binding (Pancreas)

CCK-33 was radiolabeled with $^{125}$I-Bolton Hunter reagent (2000 Ci/mmole) as described by Sankara et al. (*J. Biol. Chem.* 254: 9349-9351, 1979). Receptor binding was performed according to Innis and Snyder (*Proc. Natl. Acad. Sci.* 77: 6917-6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200-350 g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline). For the binding assay, 25 µl of buffer (for total binding) or unlabeled CCK-8 sulfate to give a final concentration of 1 µM (for nonspecific binding) or the compounds of Formula I (for determination of inhibition of $^{125}$I-CCK binding) and 25 µl of $^{125}$I-CCK-33 (30,000-40,000 cpm) were added to 450 µl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (*Ann. N.Y. Acad. Sci.* 51: 660, 1949), $^{125}$I-CCK-33 was progressively diluted with increasing concentrations of CCK-33.

2. CCK Receptor Binding (Brain)

CCK-33 was radiolabeled and the binding was performed according to the description for the pancreas method with modifications according to Saito et al., *J. Neurochem.* 37:483-490, 1981.

Male Hartley guinea pigs (300-500g) were sacrificed by decapitation and the brains were removed and placed in ice-cold 50 mM, Tris HCl plus 7.58 g/1 Trizma-7.4 (pH 7.4 at 25° C.). Cerebral cortex was dissected and used as a receptor source. Each gram of fresh guinea pig brain tissue was homogenized in 10 ml of Tris/Trizma buffer with a Brinkman polytron PT-10. The homogenates were centrifuged at 42,000 g for 15 minutes. Pellets were resuspended in Tris Buffer, centrifuged as above and resuspended in 200 volumes of binding assay buffer (10 mM N-2-hydroxyethyl-piperazine-N'-2-ethane 30 sulfonic acid (HEPES), 5 mM MgCl$_2$, 0.25 mg/ml bacitracin, 1 mM ethylene glycol-bis-(8-aminoethyl-ether-N,N'-tetraacetic acid) (EGTA), and 0.4% bovine serum albumin (BSA)). For the binding assay, 25 µl of buffer (for total binding) or unlabeled CCK-8 sulfate to give a final concentration of 1 µm (for nonspecific binding) or the compounds of Formula I (for determination of inhibition of $^{125}$I-CCK binding) and 25 µl of $^{125}$I-CCK-33 (30,000-40,000 cpm) were added to 450 µl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

The compounds of Formula I can be determined to be competitive antagonists of CCK according to the following assays.

3. Isolated guinea pig gall bladder

Male Hartley guinea pigs (400-600 g) are sacrificed by decapitation. The whole gall bladder is dissected free from adjacent tissues and cut into two equal halves. The gall bladder strips are suspended along the axis of the bile duct in a 5 ml organ bath under 1 g tension. The organ bath contains a Kreb's bicarbonate solution (NaCl 118 mM, KCl 4.75 mM, CaCl 2.54 mM, KH$_2$PO$_4$ 1.19 mM, Mg SO$_4$ 1.2 mM, NaHCO$_3$ 25 mM and dextrose 11 mM) maintained at 32° C. and bubbled with 95O$_2$ and 5% CO$_2$. Isometric contractions are recorded using Statham (60 g; 0.12 mm) strain gauges and a Hewlett-Packard (77588) recorder. The tissues are washed every 10 minutes for 1 hour to obtain equilibrium prior to the beginning of the study. CCK-8 is added cumulatively to the baths and EC$_{50}$'s determined using regression analysis. After washout (every 10 minutes for 1 hour), the compound of Formula I is added at least 5 minutes before the addition of CCk-8 and the EC$_{50}$ of CCK-8 in the presence of the compound of Formula I similarly determined.

4. Isolated longitudinal muscle of guinea pig ileum

Longitudinal muscle strips with attached nerve plexus are prepared as described in *Brit. J. Pharmac.* 23: ; 356-363, 1964; *J. Physiol.* 194: 13-33, 1969. Male Hartley guinea pigs are decapitated and the ileum removed (10 cm of the terminal ileum is discarded and the adjacent 20 cm piece used). A piece (10 cm) of the ileum is stretched on a glass pipette. Using a cotton applicator to stroke tangentially away from the mesentery attachment at one end, the longitudinal muscle is separated from the underlying circular muscle. The longitudinal muscle is then tied to a thread and by gently pulling, stripped away from the entire muscle. A Piece of approximately 2 cm is suspended in 5 ml organ bath containing Krebs solution and bubbled with 95% )$_2$ and 5%

$CO_2$ at 37° C. under 0.5 g tension. CCK-8 is added cumulatively to the baths and $EC_{50}$ values in the presence and absence of compounds of Formula I determined as described in the gall bladder Protocol (above).

Gastrin Antagonism

Gastrin antagonist activity of compounds of Formula I is determined using the following assay.

Gastrin Receptor Binding in Guinea Pig Gastric Glands

Preparation of quinea pig gastric mucosal glands

Guinea Pig gastric mucosal glands were prepared by the Procedure of Berglingh and Obrink Acta Physiol. Scand. 96: 150 (1976) with a slight modification according to Praissman et al. C. J. Receptor Res. 3: (1983). Gastric mucosa from guinea pigs ( 300–500 g body weight, male Hartley) were washed thoroughly and minced with fine scissors in standard buffer consisting of the following: 130 mM 15 NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at PH 7.4. The minced tissues were washed and then incubated in a 37° C. shaker bath for 40 minutes with the buffer containing 0.1% collagenase and 0.1% BSA and bubbled with 95% $O_2$ and 5% $CO_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

Binding studies

The washed guinea pig gastric glands prepared as above were resuspended in 25 ml of standard buffer containing 0.25 mg/ml of bacitracin. For binding studies, to 220 µl of gastric glands in triplicate tubes, 10 µl of buffer (for total binding) or gastrin (1 µM final concentration, for nonspecific binding) or test compound and 10 µl of $^{125}$I-gastrin (NEN, 2200 Ci/mmole, 25 PM final) or $^3$H-pentagastrin (NEN 22 Ci/mmole, 1 nM final) were added. The tubes were aerated with 95% $O_2$ and 5% $CO_2$ and capped. The reaction mixtures after incubation at 25° C. for 30 minutes were filtered under reduced pressure on glass G/F B filters (Whatman) and immediately washed further with 4×4 ml of standard buffer containing 0.1% BSA. The radioactivity on the filters was measured using a Beckman gamma 5500 for $^{125}$I-gastrin or liquid scintillation counting for $^3$H-pentagastrin.

In Vitro Results

1. Effect of The Compounds of Formula I on $^{125}$I-CCK-33 receptor binding

The preferred compounds of Formula I are those which inhibited specific $^{125}$I-CCK-33 binding in a concentration dependent manner.

Scatchard analysis of specific $^{125}$I-CCK-33 receptor binding in the absence and presence of the compounds of Formula I indicated the compound of Formula I competitively inhibited specific $^{125}$I-CCK-33 receptor binding since it increased the $K_D$ (dissociation constant) without affecting the $B_{max}$ (maximum receptor number). A $K_i$ value (dissociation constant of inhibitor) of the compounds of Formula I. was estimated.

The data of Table 1 were obtained for compounds of Formula I.

TABLE I

| | CCK Receptor Binding Results | | |
|---|---|---|---|
| | $IC_{50}$ (uM) | | |
| Compound of Example | $^{125}$I-CCK Pancreas | $^{125}$I-CCK Brain | $^{125}$I-Gastrin Gastric Glands |
| 1 | 67 | >100 | 167 |
| 2 & 3 | 04 | 81.5 | 40 |
| 4a & 44 | 0.36 | 16. | 49 |
| 4b | 0.27 | 18 | 8 |
| 5 | 3.4 | 100 | 30 |
| 6 | 1.2 | 50 | 100 |
| 7 | >100 | 100 | >100 |
| 8 | 100 | 100 | 27 |
| 9 | 10.7 | 48 | 78 |
| 10 | 16.7 | >100 | 47 |
| 12 | 4 | >100 | 28 |
| 13 | 80 | 100 | >100 |
| 14 | 42 | 60 | 12 |
| 15 | 60 | 80 | 38 |
| 16 | >100 | >100 | 128 |
| 17 | 23 | 100 | 200 |
| 18 | 49 | 61 | 62 |
| 19 | 33 | >100 | 14 |
| 20 | >100 | >100 | >100 |
| 21 | 100 | >100 | 200 |
| 22 | 21 | >100 | 161 |
| 23 | 10 | >100 | 200 |
| 24 | 11 | >100 | 161 |
| 25 | 12 | >100 | 139 |
| 26 | 75 | >100 | 100 |
| 27a | >100 | >100 | >1000 |
| 27b | 100 | >100 | >1000 |
| 28 | 5 | >100 | 200 |
| 29 | 48 | >100 | 80 |
| 31 | 1.4 | >100 | 200 |
| 32 | 10.6 | 36 | >100 |
| 33 | >100 | >100 | 238 |
| 34 | 4.5 | >100 | 167 |
| 35 | 10 | 15 | >100 |
| 36 | 0.3 | 30 | >100 |
| 37 | 2.2 | 30 | 58 |
| 38 | 100 | >100 | >100 |
| 39 | 100 | 30 | 23 |
| 40 | 3.6 | >100 | >100 |
| 41 | 100 | >100 | 25 |
| 42 | 8.3 | >100 | 24 |
| 43 | 0.3 | 23 | 5 |
| 45 | 10.6 | >100 | >1000 |
| 46 | >100 | >100 | >1000 |
| 47 | 24 | 40 | 24 |
| 48 | 54 | 33 | 8.4 |
| 49 | >100 | 100 | 34 |
| 50a | 15 | 2.6 | 1.2 |
| 50b | 100 | 40 | 61 |
| 51 | >100 | 32 | 25 |
| 52 | >100 | 33 | 26 |
| 53a | 100 | 4.2 | 0.85 |
| 53b | 19 | 100 | >100 |
| 55 | 7.6 | 38.6 | 76 |
| 57 | 2.9 | 100 | 700 |
| 58 | 18 | 12 | 24 |
| 59 | 1.4 | >100 | >100 |
| 60 | 1.3 | 100 | 12 |
| 62 | >100 | >100 | >1000 |
| 63 | >100 | >100 | >1000 |
| 65 | >100 | >100 | >1000 |
| 66 | 22 | 100 | 7.4 |
| 67 | 22 | 100 | 47 |
| 68 | 7 | 30 | >100 |
| 69 | 14 | >100 | 350 |
| 70 | 15 | 100 | 200 |
| 73 | 0.0047 | 8 | 4 |
| 74 | 3 | 100 | >100 |
| 75 | 4.8 | 100 | 4.7 |
| 76 | 1 | 11 | 32 |
| 77 | 6 | 20 | 250 |
| 78 | 0.0014 | 5.5 | 0.65 |
| 79a | 0.0008 | 0.77 | 0.72 |
| 79b | 0.0014 | 15 | >2 |
| 80 | 0.0023 | 3.4 | 2.9 |
| 81a | 0.0014 | 0.3 | 0.19 |
| 81b | 0.0013 | 1 | 1.6 |

TABLE I-continued

CCK Receptor Binding Results

| Compound of Example | IC$_{50}$ (uM) | | $^{125}$I-Gastrin Gastric Glands |
|---|---|---|---|
| | $^{125}$I-CCK Pancreas | $^{125}$I-CCK Brain | |
| 82 | 2.7 | 12 | >100 |
| 83 | 0.7 | 13 | 26 |
| 84a | 1.9 | >40 | >40 |
| 84b | 100 | >100 | 55 |
| 85a | 100 | >100 | >100 |
| 85b | >100 | >100 | >100 |
| 87 | 0.0008 | 0.27 | 0.17 |
| 88 | 0.0006 | 0.3 | 0.027 |
| 89 | 0.019 | 1.1 | 0.24 |
| 90 | 0.049 | 11 | 5.2 |
| 91 | 0.0025 | 2.9 | 0.8 |
| 92 | 0.0043 | 1.6 | 0.62 |
| 93 | 0.7 | 2.9 | 2 |
| 94 | 0.053 | 3.8 | 3.8 |
| 95 Z | 100 | 34 | >100 |
| 95 E | 25 | 33 | >100 |
| 96 | 17 | >100 | 500 |
| 97 | 20 | >100 | 200 |
| 98 | 28 | 100 | 86 |
| 99 | 10 | 74 | 80 |
| 100 | 4 | 34 | 22 |
| 102 | 0.7 | 30 | 12.8 |
| 103 | 1.4 | 11 | 5.8 |
| 104 | 0.3 | >100 | >100 |
| 105 | 0.0021 | 3 | 4.6 |
| 106 | 0.11 | >50 | >10 |
| 107 | 0.049 | 50 | >10 |
| 108 | 0.15 | >50 | >10 |
| 109 | 1.1 | 8.4 | 18 |
| 110 | 1 | 3.3 | 3.9 |
| 111 | 0.007 | 40 | 8.4 |
| 112 | 24 | >50 | >10 |
| 113 | 0.0015 | 5.6 | 0.39 |
| 114 | 0.005 | 12 | 4.8 |
| 115 | 0.022 | 3.5 | >10 |
| 116 | 0.3 | 80 | >10 |
| 118 | 0.071 | 38 | >10 |
| 119 | 13 | 33 | >10 |
| 120 | 0.12 | 50 | >10 |
| 121 | 0.011 | 5.5 | 3.8 |
| 122 | 0.071 | 16 | 29 |
| 123 | 2.1 | 66 | >10 |
| 124 | 0.25 | 100 | >10 |
| 125 | 0.9 | 100 | >10 |
| 126 | 0.2 | 29 | >10 |
| 127 | 0.0047 | 7 | 6.3 |
| 128 | 0.009 | 32 | 11 |
| 129 | 0.11 | 1.9 | 0.69 |
| 130 | 0.041 | >40 | 8.2 |
| 131 | 0.0083 | 40 | 6.7 |
| 132 | 0.032 | >100 | 8.2 |
| 133 | 0.9 | >40 | 110 |
| 134 | 0.015 | 40 | 9.5 |
| 135 | 0.021 | >40 | 5 |
| 136 | 0.096 | >40 | 5.4 |
| 137 | 7.5 | >40 | 52 |
| 138 | 58 | 100 | >100 |
| 139 | 3.4 | >100 | 30 |
| 140 | 0.081 | 75 | 4.3 |
| 141 | 0.029 | >40 | 25 |
| 142 | 0.066 | 18 | 2.4 |
| 143 | 0.22 | 23 | 8 |
| 144 | 0.48 | 43 | 9.4 |
| 145 | 0.24 | 65 | 36 |
| 146 | 1.4 | 100 | 40 |
| 147 | 0.5 | >100 | 180 |
| 148 | 1.8 | 100 | 31 |
| 149 | 0.73 | >100 | 22 |
| 150 | 1.7 | 83 | 130 |
| 151 | 11 | 22 | 7.5 |
| 152 | 0.27 | >100 | >100 |
| 153 | 1.7 | >40 | >40 |
| 154 | 0.0035 | 3.5 | 0.5 |
| 155 | 1.5 | >100 | 128 |
| 156 | 0.0035 | 4 | 0.68 |
| 157 | 0.019 | 8 | 2.4 |
| 158 | 0.11 | 100 | 25 |
| 159 | 0.0034 | 3 | 0.53 |
| 160 | 0.020 | 12 | 14 |
| 161 | 6.2 | 70 | 19 |
| 162 | 0.043 | 31 | 9 |
| 163 | 3.6 | 12 | 80 |
| 164 | 100 | 18 | >100 |
| 165 | 27 | 8 | >100 |
| 166 | 1.6 | 12 | 29 |
| 167 | 0.00075 | 1.7 | 0.39 |
| 168 | 0.015 | 2.4 | 2 |
| 169 | 58 | 3.8 | 4.4 |
| 170 | 0.8 | 45 | 11 |
| 171 | 9 | 5.6 | 5.8 |
| 172 | 3.4 | 16 | 3.7 |
| 173 | 0.15 | >40 | 28 |
| 174 | 5.5 | >40 | 18 |
| 175 | 0.7 | 15 | 8 |
| 176 | 1.0 | 10 | 3.2 |
| 177 | 0.018 | 3.7 | 0.55 |
| 178 | 4.9 | >100 | >100 |
| 179 | 4.4 | 3.6 | 18 |
| 180 | 0.016 | >100 | 11 |
| 181 | 0.002 | 9.3 | 4.4 |
| 182 | 0.11 | 0.3 | 0.26 |
| 185 | 0.73 | >100 | 22 |
| 186 | 3.1 | >100 | >100 |
| 187 | 0.003 | 1.3 | 5.3 |
| 188 | >30 | 3.2 | 1.3 |
| 189 | 1.1 | >100 | 73 |
| 190 | 0.78 | >100 | 130 |
| 191 | 0.80 | >100 | >100 |
| 192 | 0.0003 | 0.64 | 0.18 |
| 193 | 1.6 | >100 | 13 |
| 194 | 0.22 | 0.0012 | 0.004 |
| 195 | 4.8 | >0.1 | 0.4 |
| 196 | 0.0009 | 2.4 | 1.9 |
| 197 | 1.9 | 5.9 | 10 |
| 198 | >10 | 18 | 1.5 |
| 199 | 3.2 | 54 | 100 |
| 200 | 0.1 | 63 | 67 |
| 201 | 0.25 | >100 | >100 |
| 202 | 0.056 | 0.072 | 0.12 |
| 203 | 0.0013 | 4.6 | 6.2 |
| 204 | 0.37 | 0.001 | 0.0033 |
| 205 | 35 | >0.3 | 33 |
| 206 | 12 | >100 | >100 |
| 207 | 115 | 3.3 | 4.2 |
| 208 | 1.3 | 0.044 | 0.14 |
| 209 | 2.2 | 0.3 | 0.3 |
| 210 | 0.3 | 10 | 21 |
| 211 | 13 | 93 | 6.7 |
| 212 | 1.9 | 0.4 | 0.6 |
| 213 | 2.1 | 0.38 | 0.28 |
| 214 | 0.003 | 0.22 | 0.12 |
| 215 | 4.8 | 1.8 | 0.56 |
| 216 | 0.001 | 2.4 | 1.7 |
| 217 | 0.051 | 0.023 | 0.022 |
| 218 | 0.0026 | 1.8 | 1.8 |
| 219 | 0.0005 | 1.4 | 0.44 |
| 220 | 2.4 | 0.10 | 0.15 |
| 221 | 0.4 | 0.0006 | 0.002 |
| 222 | 2.2 | 0.15 | 0.23 |
| 223 | 0.14 | >100 | >100 |
| 224 | 2.1 | 0.011 | 0.025 |
| 225 | 4.7 | >100 | 130 |
| 226 | <0.1 | 2.3 | 6.4 |
| 227 | 6.6 | 50 | >100 |
| 228 | 0.049 | 100 | 60 |
| 229 | 1.2 | 0.44 | 0.26 |
| 230 | 0.49 | 0.0051 | 0.035 |
| 231 | 0.58 | 2.7 | 2.9 |
| 232 | 0.34 | 1.0 | 1.2 |
| 233 | 0.026 | 0.41 | 0.58 |
| 234 | 1.1 | 0.0055 | 0.12 |
| 235 | 29 | 1.7 | 1.4 |
| 236 | 0.52 | 0.00028 | 0.0005 |
| 237 | 1.2 | 0.008 | 0.0026 |

TABLE I-continued

| Compound of Example | CCK Receptor Binding Results IC$_{50}$ (uM) | | |
|---|---|---|---|
| | $^{125}$I-CCK Pancreas | $^{125}$I-CCK Brain | $^{125}$I-Gastrin Gastric Glands |
| 238 | 0.028 | 26 | 11 |
| 239 | 1.7 | 0.038 | 0.0045 |
| 240 | 1.3 | 2.9 | 7 |
| 241 | 0.93 | 1.4 | 0.95 |
| 242 | 0.9 | 2.3 | 0.87 |
| 243 | 0.68 | 2.8 | 3.6 |
| 244 | 0.95 | 0.74 | 0.5 |
| 245 | 7.2 | 92 | 12 |
| 246 | 0.0019 | 0.002 | 0.0024 |
| 247 | 0.0062 | 0.003 | 0.0016 |
| 248 | 20 | 5.3 | 2.2 |
| 249 | 0.41 | 0.022 | 0.012 |
| 250 | 0.0083 | 0.032 | 0.009 |
| 251 | 0.49 | 0.86 | 0.42 |
| 252 | 0.057 | 0.006 | 0.0035 |
| 253 | 0.16 | 0.02 | 0.45 |
| 254 | 0.0009 | 0.32 | 0.11 |
| 255 | 0.13 | 0.48 | 0.032 |
| 256 | 0.21 | 0.046 | 0.0098 |
| 257 | 0.026 | 0.067 | 0.048 |
| 258 | 0.003 | 0.22 | 0.06 |
| 259 | 0.046 | 0.066 | 0.014 |
| 260 | 6.8 | 38 | >1 |
| 261 | 0.43 | 11 | 3.2 |
| 262 | 2.4 | 3 | 0.39 |
| 263 | 0.0081 | 0.0071 | 0.0031 |
| 264 | 0.034 | 0.011 | 0.006 |
| 265 | 0.0082 | 0.0098 | 0.0031 |
| 266 | 0.60 | 0.0022 | 0.0013 |
| 267 | 0.0013 | 0.29 | 0.19 |
| 268 | 0.33 | 2.1 | 0.42 |
| 269 | 45 | 0.69 | 0.45 |
| 270 | 0.003 | 1.2 | 0.5 |
| 271 | 0.01 | 0.054 | 0.01 |
| 272 | 0.0044 | 0.005 | 0.0028 |
| 273 | 0.0086 | 0.079 | 0.057 |
| 274 | 0.31 | 2.3 | 1.6 |
| 275 | 0.020 | 0.11 | 0.12 |
| 276 | 0.00039 | 0.28 | 0.24 |
| 277 | 0.018 | 0.86 | 2.6 |
| 278 | 0.6 | 1.2 | 1 |
| 279 | 0.011 | 0.31 | 0.6 |
| 280 | 0.015 | 0.97 | 0.25 |
| 281 | 1.4 | 0.003 | 0.00066 |
| 282 | 0.84 | 0.0038 | 0.0016 |
| 283 | 1.1 | 71 | 66 |
| 284 | 0.017 | 0.00034 | 0.0005 |
| 285 | >0.1 | 0.00022 | 0.00026 |
| 286 | >0.1 | 0.0038 | 0.0015 |
| 287 | 0.00074 | 1.0 | 0.95 |
| 288 | 0.075 | 0.042 | 0.054 |
| 289 | 0.0001 | 0.089 | 0.66 |
| 290 | 0.002 | 0.015 | 0.0087 |
| 291 | 0.00008 | 0.38 | 0.71 |
| 292 | 0.001 | 0.0035 | 0.0115 |
| 293 | 3.1 | 0.0065 | 0.0025 |
| 294 | 0.0001 | 0.038 | 0.04 |
| 295 | 0.003 | 0.015 | 0.034 |
| 296 | 0.29 | 0.0075 | 0.0022 |
| 297 | 1.8 | 3.7 | 5.2 |

Preferred compounds of Formula I are those compounds wherein:

$R^1$ is H, $C_1$-$C_6$ linear or branched alkyl, —X$^{12}$COOR$^6$, —X$^{11}$-cycloloweralkyl, X$^{12}$NR$^4$R$^5$ or —X$^{12}$CONR$^4$R$^5$;

$R^2$ is substituted or unsubstituted phenyl (wherein the substitutents may be 1 or 2 of halo, loweralkyl, loweralkoxy, loweralkylthio, carboxyl, carboxyloweralkyl, nitro, —CF$_3$, or hydroxy), 2-, 3-, or 4- pyridyl,

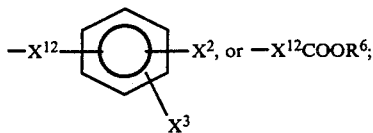

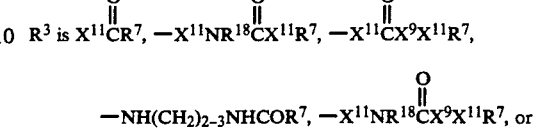

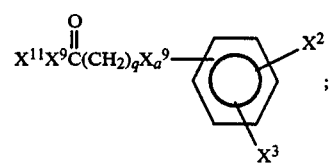

$R^4$ and $R^5$ are independently $R^6$ or in combination with the N of the 5 group form an unsubstituted or mono or disubstituted, saturated or unsaturated, 4–7 membered heterocyclic ring, of benzofused 4–7 membered heterocyclic ring or said heterocyclic ring or said benzofused heterocyclic ring which further comprises a second heteroatom selected from O and NCH$_3$ and the substituent(s) is/are independently selected from $C_{1-4}$alkyl;

$R^6$ is H, $C_1$-$C_4$ straight or branched-chain alkyl or $C_3$-$C_6$-cycloalkyl α- or β-naphthyl, substituted or unsubstituted phenyl (wherein the substituents may be 1 to 2 of halo, —NO$_2$, —OH, —X$^{11}$NR$^4$R$^5$, loweralkyl, CF$_3$, CN, SCF$_3$,

SH, SPh, loweralkoxy, loweralkylthio, or carboxy), 2-, 3-, 4-pyridyl,

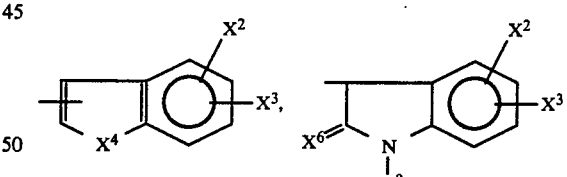

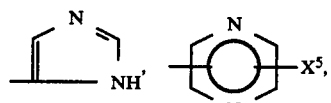

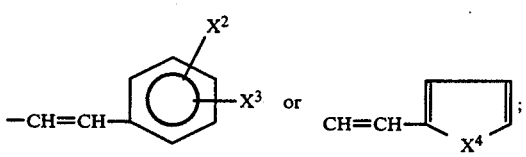

$R^8$ is H, loweralkyl or cycloloweralkyl;
$R^9$ and $R^{10}$ are independently H, —OH, or —CH$_3$;
$R^{13}$ is H, loweralkyl, acyl, O, or cycloloweralkyl;
$R^{18}$ is H or loweralkyl;

p is 0 when its adjacent ═ is unsaturated and 1 when its adjacent ═ is saturated except that when $R^{13}$ is O, p=1 and ═ is unsaturated;

q is 0-2;

r is 1 or 2;

$X^1$ is H, —$NO_2$, $CF_3$, CN, loweralkyl halo, loweralkylthio or —$X^{11}COOR^6$;

$X^2$ and $X^3$ are independently H, —$NO_2$, halo, loweralkylthio, loweralkyl, or loweralkoxy;

$X^4$ is S, O, or $NR^8$;

$X^5$ is H, $CF_3$, CN, —$COOR^6$, $NO_2$, or halo;

$X^6$ is O or HH;

$X^7$ is O, S;

$X^9$ and $X^9_a$ are independently $NR^{18}$, or O;

$X^{11}$ is absent or $C_{1-4}$ linear alkylidene;

$X^{12}$ is $C_{1-4}$ linear or branched alkylidene; ═ is a saturated or unsaturated bond and the pharmaceutically acceptable salts thereof.

More preferred compounds of Formula I are $R^1$ is H, $C_1$-$C_3$ linear or branched alkyl, —$X^{12}COOR^6$, —$X^{12}CONR^4R^5$, $R^2$ is substituted or unsubstituted phenyl (wherein the substitutents may be 1 or 2 of halo, loweralkyl, carboxyl, nitro or —$CF_3$); —$X^{12}COOR^6$; 2-, 3-, 4-pyridyl;

$R^4$ and $R^5$ are independently $R^6$ or in combination with the N of the $NR^4R^5$ group form an unsubstituted or mono or disubstituted, saturated or unsaturated, 4-7 membered heterocyclic ring, or benzofused 4-7 membered heterocyclic ring or said heterocyclic ring or said benzofused heterocyclic ring which further comprises a second heteroatom selected from O and $NCH_3$ and the substituent(s) is/are independently selected from $C_{1-4}$alkyl;

$R^6$ is H, $C_1$-$C_4$ straight or branched-chain alkyl;

$R^7$ is α- or β-naphthyl, substituted or unsubstituted phenyl (wherein the substituents may be 1 to 2 of halo, —$NO_2$, —OH, —$NR^4R^5$, loweralkyl, $CF_3$, CN, or loweralkoxy), 2-, 3-, 4- pyridyl,

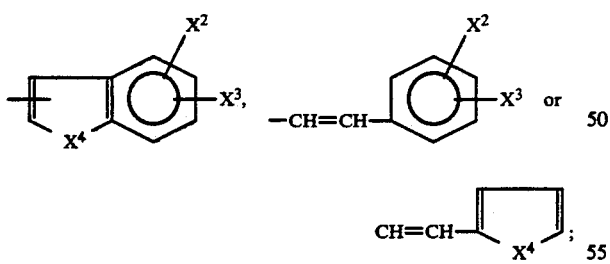

$R^9$ and $R^{10}$ are independently H, or —OH; p is 0 when its adjacent ═ is unsaturated and 1 when its adjacent ═ is saturated, the p of is $(R^{13})_p$ is 0;

r is 1 or 2;

$X^1$ is H, —$NO_2$, $CF_3$, loweralkyl or halo;

$X^2$ and $X^3$ are independently H, —$NO_2$, halo, loweralkyl, or loweralkoxy;

$X^4$ is O or $NR^8$;

$X^7$ is O or S, $X^{12}$ is $C_{1-2}$ linear or branched alkylidene;

═ is a saturated or unsaturated bond;

and the pharmaceutically acceptable salts thereof.

Even more preferred compounds of Formula I are wherein:

$R^1$ is H, $C_1$-$C_2$ linear alkyl, —$X^{12}COOR^6$, —$X^{12}CONR^4R^5$;

$R^2$ is substituted or unsubstituted phenyl (wherein the substitutent may be halo, loweralkyl, nitro, —$CF_3$), 2-, 3-, 4- pyridyl, or $X^{12}COOR^6$;

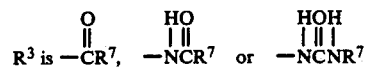

$R^4$ and $R^5$ are independently $R^6$ or in combination with the N of the $NR^4R^5$ group form an unsubstituted or mono or disubstituted, saturated or unsaturated, 4-7 membered heterocyclic ring, or benzofused 4-7 membered heterocyclic ring or said heterocyclic ring or said benzofused heterocyclic ring which further comprises a second heteroatom selected from O and $NCH_3$ and the substituent(s) is/are independently selected from $C_{1-4}$alkyl;

$R^6$ is H, $C_1$-$C_3$ straight chain alkyl;

$R^7$ is α- or β-naphthyl, substituted or unsubstituted phenyl (wherein the substituents may be 1 to 2 of halo, —$NO_2$, $NH_2$, methyl, ethyl, $CF_3$, CN, or loweralkoxy), 2-, 3-, 4- pyridyl,

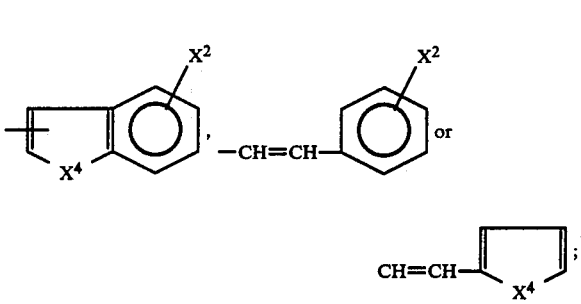

$R^{10}$ is H, or OH;

p is 1 of $(R^{10})_p$ and 0 of $(R^9)_p$ and $(R^{13})_p$, ═ at 4,5 is unsaturated and ═ at 3,4 is saturated;

r is 1 or 2;

$X^1$ is H, —$NO_2$, $CF_3$, loweralkyl or halo;

$X^2$ is H, —$NO_2$, halo or loweralkyl;

$X^3$ is H;

$X^4$ is O, NH, $NCH_3$;

$X^7$ is O or S;

$X^{12}$ is $C_{1-2}$ linear alkylidene; and the pharmaceutically acceptable salts thereof.

Yet even more preferred compounds of Formula I are wherein:

$R^1$ is H, $CH_3$, $CH_2CH_3$, $CH_2COOH$, $CH_2COOEt$, $CH_2CON(Et)_2$,

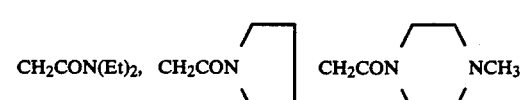

or $CH_2CH_2COOEt$;

$R^2$ is phenyl, 2-F-phenyl, 4-CH -phenyl, 2-, 3-, or 4- pyridyl;

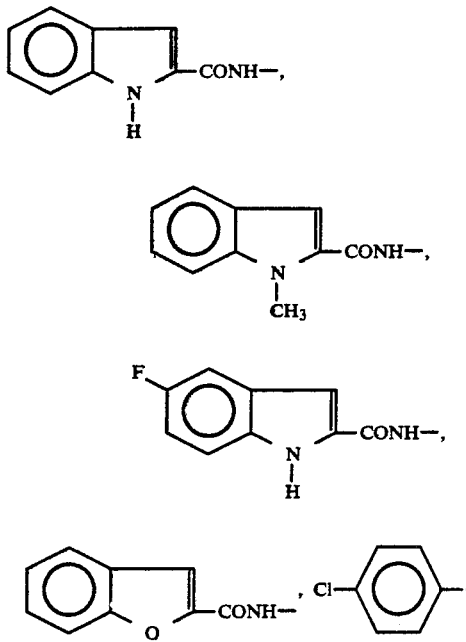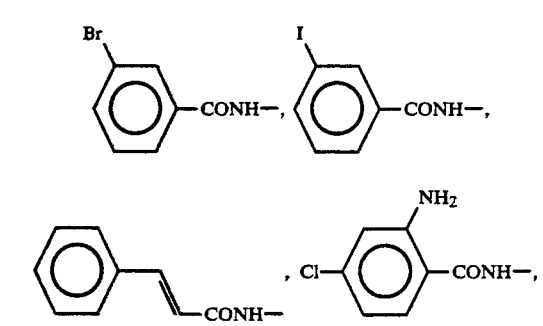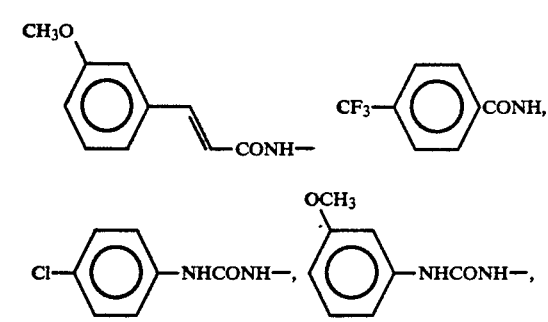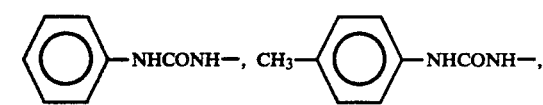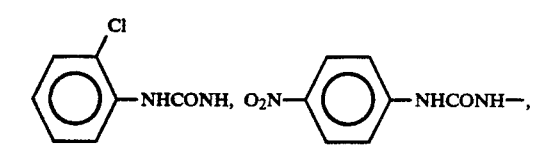

$R^{10}$ is H or -OH;
p is 1 of $(R^{10})_p$ and o of $(R^9_p)$ and $(R^{13})_p$; ═ at 4, 5 is unsaturated and ═ at 3, 4 is saturated;
r is 1;
$X^1$ is H, 7-Cl, 8-$CH_3$, 9-$CH_3$;
$X^7$ is O or S; and the pharmaceutically acceptable salts thereof.

The most preferred compounds of Formula I are:
(R)-N-(4-Chlorophenyl)-N'-(2,3-dihydro-1-methyl-5-phenyl-2-oxo-1H-1,4-benzodiazepin-3-yl)urea,
3-Benzoyl-1,3-dihydro-3-hydroxy-1-methyl-5-phenyl-2H-1,4-benzodiazepin-2-one,
5-(2-Fluorophenyl)-1,3-dihydro-3-hydroxy-3-(4-methoxy-benzoyl)-1-methyl-2H-1,4-benzodiazepin-2-one,
N-(2,3-Dihydro-1-methyl-2-oxo-5(3-methylphenyl)-1H-1,4-benzodiazepin-3-yl)-N'-(phenylmethyl)urea,
N-(2,3-Dihydro-1-ethyl-2-oxo-5-phenyl-1H-1,4-benzodia-zepin-3-yl)-N'-(3-methoxyphenyl)urea,
3-(S)-N-(2,3-Dihydro-1-methyl-2-oxo-5-phenyl-1H-1,4-benzodiazepin-3-yl)-3-(3-methoxyphenyl)-2-propenamide,
3-((((4-Chlorophenyl)amino)carbonyl)amino-2,3-dihydro-2-oxo-5-phenyl-1H-1 4-benzodiazepine-1-propanoic acid ethyl ester,
3(RS)-1,3-dihydro(2-indolecarbonylamino)-5-phenyl-2H-1,4-benzodiazepin-2-one,
1 -Carboxymethyl-1,3-dihydro-3(RS)-(2-indolecarbonylamino)-5-phenyl-2H-1,4-benzodiazepin-2-one,
1,3-Dihydro-3(RS)-(2-indolecarbonylamino)-1-methyl-5-phenyl-2H-1,4-benzodiazepin-2-one,
1,3-dihydro-1-methyl-3(RS)-[2-(1-methylindole)carbonylamino]-5-phenyl-2H-1,4-benzodiazepin-2-one,
1,3-Dihydro-1-methyl-3(RS)-(4-chlorophenylcarbonyl)amino-5-(2-fluorophenyl)-2H-1,4-benzodiazepin-2-one, 1,3-Dihydro-5-(2-fluorophenyl)-3(RS)-(2-indole carbonylamino)-1-methyl-2H-1,4-benzodiazepin-2-one, 1,3-Dihydro-5-(2-fluorophenyl)-1-methyl-3(RS)-[2'(1'-methylindole)carbonylamino]-2H-1,4-benzodiazepin-2-one, (3)(S)-(−)-1,3-Dihydro-3-(2-indolecarbonylamino)-1-methyl-5-phenyl-2H-1,4-benzodiazepin-2-one, 3(S)-(+)-1,3-Dihydro-5-(2-fluorophenyl)-3-(2-indolecarbonylamino)-1-methyl-2H-1,4-benzodiazepin-2-one, 3(S)-(+)-1,3-Dihydro-3-(4-chlorobenzoylamino)-5-(2-fluorophenyl)-1-methyl-2H-1,4-benzodiazepin-2-one, 3(S)-(−)-1,3-Dihydro-3-(4-bromobenzoylamino)-1-methyl-5-phenyl-2H-1,4-benzodiazepin-2-one, 1,3-Dihydro-5-(2-fluorophenyl)-3-(RS)-(2-indolecarbonyl amino)-2H-1,4-benzodiazepin-2-one, 1,3-Dihydro-3-(RS)-(4-chlorophenylcarbonyl)amino-5-(2-fluorophenyl)-2H-1,4-benzodiazepin-2-one, 1-Carboxymethyl-1,3-dihydro-5-(2-fluorophenyl)-3(RS)-(2-indolecarbonylamino)-2H-1,4-benzodiazepin-2-one, 1,3-Dihydro-3-(RS)-(5-fluoroindole-2-carbonylamino)-5-(2-fluorophenyl)-2H-1,4-benzodiazepin-2-one, 1,3-Dihydro-3-(RS)-(1-methylindole-2-carbonylamino)-5-(2-fluorophenyl)-2H-1,4-benzodiazepine-2-one, 1,3-Dihydro-5-(2-fluorophenyl)-3-(RS)-(2-benzofurancarbonylamino)-2H-1,4-benzodiazepin-2-one, 1,3-Dihydro-1-methyl-3-(RS)-(4-chlorophenylcarbonyl)amino-5-phenyl-2H-1,4-benzodiazePin-2-one, 3(S)-(+)-3-(3-Bromobenzoylamino)-1,3-dihydro-5-(2-fluorophenyl)-1-methyl-2H-1,4-benzodiazepin-2-one, 3(S)-(+)-3-(4-Bromobenzoylamino)-1,3-dihydro-5-(2-fluorophenyl)-1-methyl-2H-1,4-benzodiazepin-2-one, 3(S)-(+)-1,3-Dihydro-5-(2-fluorophenyl)-3-(4-iodobenzoylamino)-1-methyl-2H-1,4-benzodiazepin-2-one, 3(S)-(+)-1,3-Dihydro-5-(2-fluorophenyl)-3-(3-iodobenzoylamino)-1-methyl-2H-1,4-benzodiazepin-2-one, 1,3-Dihydro-5-(2-fluorophenyl)-3-(RS)-(2-indole) carbonylamino-2H-1,4-benzodiazepin-2-thione, 3(S)-(2-Indolecarbonyl)amino-1,3-dihydro-5-phenyl-2H1,4,-benzodiazepin-2-one.

(S)-N-(2.3-Dihydro-1-methyl-2-oxo-5-phenyl-1H-1,4benzodiazepin-3-yl)-3-phenyl-2-propenamide, 3-((((4-Chlorophenyl)amino)carbonyl)amino)-5-(2-fluorophenyl)-2,3-dihydro-2-oxo-1H-1,4-benzodiazepine-1-acetic acid ethyl ester, 3-N-(2,3-Dihydro-1-methyl-2-oxo-5-phenyl-1H-1,4-benzodiazepin-3-yl)-2-amino-4-chlorobenzamide (S)-N-(2,3-Dihydro-1-methyl-2-oxo-5-phenyl-1H-1,4-benzodiazepin-3-yl)-4-(trifluoromethyl)-benzamide, 3-((((4-Chlorophenyl)amino)carbonyl)amino)-2,3-dihydro-2-oxo-5-phenyl-1H-1,4-benzodiazepine-1acetic acid ethyl ester, 5-(2-Fluorophenyl)-2,3-dihydro-3-((1H-indol-2ylcarbonyl)amino)-2-oxo-1H-1,4-benzodiazepine-1acetic acid ethyl ester, 4-Bromo-N-(2,3-dihydro-1-methyl-2-oxo-5-phenyl-1H-1,4-benzodiazepin-3-yl)-benzamide, N-(5-(2-Fluorophenyl)-2,3-dihydro-1-methyl-2-oxo-1H-1,4-benzodiazepin-3-yl)-4-(trifluoromethyl)-benzamide, (S)-N-(5-(2-Fluorophenyl)-2,3-dihydro-1-methyl-2-oxo-1H-1,4-benzodiazepin-3-yl)-4-(trifluoromethyl)benzamide, 3-((((4-Chlorophenyl)amino)carbonyl)amino)-N,N-diethyl-2,3-dihydro-2-oxo-5-phenyl-1H-1,4benzodiazepine-1-acetamide, 1-((3-((((4-Chlorophenyl)amino)carbonyl)amino)-2,3-dihydro-2-oxo-5-phenyl-1H-1,4-benzodiazepin-1-yl)acetyl)pyrrolidine, 1-((3-((((4-Chlorophenyl)amino)carbonyl)amino)-2,3-dihydro-2-oxo-5-phenyl-1H-1,4-benzodiazepin-1-yl)acetyl)-4-methylpiperazine, 3-((((4-Chlorophenyl)acetyl)amino)-2,3-dihydro-2-oxo-5-phenyl-1H-1,4-benzodiazepine-1-acetic acid ethyl ester, N-(5-(2-Fluorophenyl)-2,3-dihydro-1-methyl-2-oxo-1H-1,4-benzodiazepin-3-yl)-N.-(3-methoxyphenyl)-urea, N-(2,3-Dihydro-1-methyl-2-oxo-5-phenyl-1H-1,4-benzodiazepin-3-yl)-N'-(3-methoxyphenyl)-urea, N-(2,3-Dihydro-1-methyl-2-oxo-5-phenyl-1H-1,4-benzodiazePin-3-yl)-N'-phenylurea, N-(2,3-Dihydro-1-methyl-2-oxo-5-phenyl-1H-1,4-benzodiazepin-3-yl)-N'-(4-methylphenyl)-urea, N-(2-Chlorophenyl)-N'-(2,3-dihydro-1-methyl-2-oxo-5-phenyl-1H-1,4-benzodiazepin-3-yl)-urea, N-(4-Nitrophenyl)-N'-(2,3-dihydro-1-methyl-2-oxo-5-phenyl-1H-1,4-benzodiazepin-3-yl)-urea, N-(2,4-Dichlorophenyl)-N'-(2,3-dihydro-1-methyl-2-oxo-5-phenyl-1H-1,4-benzodiazepin-3-yl)-urea, N-(2,3-Dihydro-1-methyl-2-oxo-5-phenyl-1H-1,4-benzodiazepin-3-yl)-N'-(3-methylphenyl)-urea, N-(2,3-Dihydro-1-methyl-2-oxo-5-phenyl-1H-1,4-benzodiazepin-3-yl)-N.-(3-nitrophenyl)-urea, N-(3-Chlorophenyl)-N'-(2,3-dihydro-1-methyl-2-oxo5-phenyl-1H-1,4-benzodiazepin-3-yl)urea, (R)-N-(2,3-Dihydro-1-methyl-2-oxo-5-phenyl-1H-1,4-benzodiazepin-3-yl)-N.-(3-methoxyphenyl)-urea, (S)-N-(2,3-Dihydro-1-methyl-2-oxo-5-phenyl-1H-1,4-benzodiazepin-3-yl)-N'-(3-methoxyphenyl)-urea, N-(2,3-Dihydro-1-methyl-2-oxo-5-phenyl-1H-1,4-benzodiazepin-3-yl)-N'-(2-nitrophenyl)-urea, N-(2,3-Dihydro-1-methyl-2-oxo-5-phenyl-1H-1,4-benzodiazepin-3-yl)-N'-(3-fluorophenyl)-urea, N-(3-Bromophenyl)-N'-(2,3-dihydro-1-methyl-2-oxo-5-phenyl-1H-1,4-benzodiazepin-3-yl)-urea, N-(2,3-Dihydro-1-methyl-2-oxo-5-phenyl-1H-1,4-benzodiazepin-3-yl)-N'-1-naphthalenyl-urea, (S)-N-(2,3-Dihydro-1-methyl-2-oxo-5-phenyl-1H-1,4-benzodiazepin-3-yl)-N'-(2-chlorophenyl)-urea, (R)-N-(2,3-Dihydro-1-methyl-2-oxo-5-phenyl-1H-1,4-benzodiazepin-3-yl)-N'-(3-methylphenyl)-urea, (R)-N-(2,3-Dihydro-1-methyl-2-oxo-5-phenyl-1H-1,4-benzodiazePin-3-yl)-N'-(3-bromophenyl)-urea, 1-{[3-[(((3-Methoxyphenyl)amino)carbonyl)amino]-2,3-dihydro-2-oxo-5-phenyl-1H-1,4-benzodiazepin-1-yl] acetyl}pyrrolidine, 3{[[(((3-Methoxyphenyl)amino)carbonyl)amino]-N,N-diethyl-2,3-dihydro-2-oxo-5-phenyl-1H-1,4-benzodiazepin-1-acetamide, 3-{[(((2-Chlorophenyl)amino)carbonyl]amino}-N,N-diethyl-2,3-dihydro-2-oxo-5-phenyl-1H-1,4-benzodiazepine-1-acetamide, 3-N-(2,3-Dihydro-9-methyl-2-oxo-5-phenyl-1H-1,4-benzodiazepin-3-yl)-1H-indole-2-carboxamide, 3-N-(2,3-Dihydro-1,9-dimethyl-2-oxo-5-phenyl-1H-1,4-benzodiazepin-3-yl)-1H-indole-2-carboxamide, N-(3-Methoxyphenyl)-N'-(2.3-dihydro-1,9-dimethyl-2-oxo-5-phenyl-1H-1 4-benzodiazepin-3-yl)-urea, 3-N-(2,3-Dihydro-1-methyl-2-oxo-5-(p-tolyl)-1H-1,4-benzodiazepin-3-yl)-1H-indole-2-carboxamide N-(3-Methoxyphenyl)-N'-(2.3-dihydro-1-methyl-2-oxo-5-(p-tolyl)-1H-1.4-benzodiazepin-3-yl)-urea, (R)-N-(2.3-Dihydro-1-methyl-2-oxo-5-phenyl-1H-1,4-benzodiazepin-3-yl)-N'-(4-methylphenyl)-urea.

3-N-(2.3-Dihydro-1 8-dimethyl-2-oxo-5-phenyl-1H-1,4-benzodiazepin-3-yl)-1H-indole-2-carboxamide,
N-(3-Methoxyphenyl)-N'-(2.3-dihydro-1.B-dimethyl-2-oxo-5-phenyl-1H-1,4-benzodiazepin-3-yl)-urea or
(R)-N-(2.3-Dihydro-1-methyl-2-oxo-5-phenyl-1H-1,4-benzodiazepin-3-yl)-N'-(3-chlorophenyl)-urea.

In another aspect of the invention is that some of the compounds of Formula I are specific for CCK as compared to gastrin and vice-versa. What is meant by a compound that is "specific" for CCK is that such compound is at least ten times more potent as an antagonist of CCK as compared to gastrin and vice-versa for a compound that is specific for gastrin. Such specificity is highly desirable because CCK specific compound can be utilized with little interference with gastrin receptors. Similarly, a gastrin specific compound can be utilized with essentially no interference with the CCK receptors.

Examples of CCK specific compounds of Formula I are:
3(RS)-1,3-Dihydro(2-indolecarbonylamino)-5-phenyl-2H-1,4-benzodiazepin-2-one,
1-Carboxymethyl-1,3-dihydro-3(RS)-(2-indolecarbonylamino)-5-phenyl-2H-1,4-benzodiazepin-2-one,
1,3-Dihydro-3(RS)-(2-indolecarbonylamino)-1-methyl-5-phenyl-2H-1,4-benzodiazepin-2-one,
1,3-dihydro-1-methyl-3(RS)-[2-(1-methylindole)carbonylamino]-5-phenyl-2H-1,4-benzodiazepin-2-one,
1,3-Dihydro-1-methyl-3(RS)-(4-chlorophenylcarbonyl)amino-5-(2-fluorophenyl)-2H-1,4-benzodiazepin-2-one,
1,3-Dihydro-5-(2-fluorophenyl)-3(RS)-(2-indolecarbonylamino)-1-methyl-2H-1,4-benzodiazepin-2-one,
1,3-Dihydro-5-(2-fluorophenyl)-1-methyl-3(RS)-[2'-(1'-methylindole)carbonylamino]-2H-1,4-benzodiazepin-2-one,
3(S)-(−)-1,3-Dihydro-3-(2-indolecarbonylamino)-1-methyl-5-phenyl-2H-1,4-benzodiazepin-2-one,
3(S)-(+)-1,3-Dihydro-5-(2-fluorophenyl)-3-(2-indolecarbonylamino)-1-methyl-2H-1,4-benzodiazepin-2-one,
3(S)-(+)-1,3-Dihydro-3-(4-chlorobenzoylamino)-5-(2-fluorophenyl)-1-methyl-2H-1,4-benzodiazepin-2-one,
(S)-(−)-1,3-Dihydro-3-(4-bromobenzoylamino)-1-methyl-5-phenyl-2H-1,4-benzodiazepin-2-one,
1,3-Dihydro-5-(2-fluorophenyl)-3-(RS)-(2-indolecarbonyl amino)-2H-1,4-benzodiazepin-2-one,
1,3-Dihydro-3-(RS)-(4-chlorophenylcarbonyl)amino-5-(2-fluorophenyl)-2H-1,4-benzodiazepin-2-one,
1-Carboxymethyl-1,3-dihydro-5-(2-fluorophenyl)-3(RS)-2-indolecarbonylamino)-2H-1,4-benzodiazepin-2-one,
1,3-Dihydro-3-(RS)-(5-fluoroindole-2-carbonylamino)-5-(2-fluorophenyl)-2H-1,4-benzodiazepin-2-one,
1,3-Dihydro-3-(RS)-(1-methylindole-2-carbonylamino)-5-(2-fluorophenyl)-2H-1,4-benzodiazepine-2-one,
1,3-Dihydro-5-(2-fluorophenyl)-3-(RS)-(2-benzofurancarbonylamino)-2H-1,4-benzodiazepin-2-one,
1,3-Dihydro-1-methyl-3-(RS)-(4-chlorophenylcarbonyl)amino-5-phenyl-2H-1,4-benzodiazepin-2-one,
3(S)-(+)-3-(3-Bromobenzoylamino)-1,3-dihydro-5-(2-fluorophenyl)-1-methyl-2H-1,4-benzodiazepin-2-one,
3(S)-(+)-3-(4-Bromobenzoylamino)-1,3-dihydro-5-(2-fluorophenyl)-1-methyl-2H-1,4-benzodiazepin-2-one,
3(S)-(+)-1,3-Dihydro-5-(2-fluorophenyl)-3-(4-iodobenzoylamino)-1-methyl-2H-1,4-benzodiazepin-2-one,
3(S)-(+)-1,3-Dihydro-5-(2-fluorophenyl)-3-(3-iodobenzoylamino)-1-methyl-2H-1,4-benzodiazepin-2-one,
1,3-Dihydro-5-(2-fluorophenyl)-3-(RS)-(2-indole) carbonylamino-2H-1,4-benzodiazepin-2-thione,
3(S)-(2-Indolecarbonyl)amino-1,3-dihydro-5-phenyl-2H-1,4,-benzodiazepin-2-one,
(S)-N-(2,3-Dihydro-1-methyl-2-oxo-5-phenyl-1H-1,4-benzodiazepin-3-yl)-3-phenyl-2-propenamide,
3N-(2,3-Dihydro-1-methyl-2-oxo-5-phenyl-1H-1,4-benzodiazepin-3-yl)-2-amino-4-chlorobenzamide
(S)-N-(2,3-Dihydro-1-methyl-2-oxo-5-phenyl-1H-1,4-benzodiazepin-3-yl)-4-(trifluoromethyl)-benzamide,
5-(2-Fluorophenyl)-2,3-dihydro-3-((1H-indol-2-ylcarbonyl)amino)-2-oxo-1H-1,4-benzodiazepine-1acetic acid ethyl ester,
4-Bromo-N-(2,3-dihydro-1-methyl-2-oxo-5-phenyl-1H-1,4-benzodiazepin-3-yl)-benzamide,
N-(5-(2-Fluorophenyl)-2,3-dihydro-1-methyl-2-oxo-1H-1,4-benzodiazepin-3-yl)-4-(trifluoromethyl)-benzamide,
(S)-N-(5-(2-Fluorophenyl)-2,3-dihydro-1-methyl-2-oxo-1H-1,4-benzodiazepin-3-yl)-4-(trifluoromethyl)benzamide,
N-(2-Chlorophenyl)-N'-(2,3-dihydro-1-methyl-2-oxo-5-phenyl-1H-1,4-benzodiazepin-3-yl)-urea,
N-(2,4-Dichlorophenyl)-N'-(2,3-dihydro-1-methyl-2-oxo-5-phenyl-1H-1,4-benzodiazepin-3-yl)-urea,
(S)-N-(2,3-Dihydro-1-methyl-2-oxo-5-phenyl-1H-1,4-benzodiazepin-3-yl)-N'-(3-methoxyphenyl)-urea,
N-(2,3-Dihydro-1-methyl-2-oxo-5-phenyl-1H-1,4-benzodiazepin-3-yl)-N'-(2-nitrophenyl)-urea,
(S)-N-(2,3-Dihydro-1-methyl-2-oxo-5-phenyl-1H-1,4-benzodiazepin-3-yl)-N'-(2-chlorophenyl)-urea
3-N-(2,3-Dihydro-9-methyl-2-oxo-5-phenyl-1H-1,4-benzodiazepin-3-yl)-1H-indole-2-carboxamide,
3-N-(2,3-Dihydro-1,9-dimethyl-2-oxo-5-phenyl-1H-1,4-benzodiazepin-3-yl)-1H-indole-2-carboxamide,
3-N-(2,3-Dihydro-1-methyl-2-oxo-5-(p-tolyl)-1H-1,4-benzodiazepin-3-yl)-1H-indole-2-carboxamide,
N-(3-Methoxyphenyl)-N'-(2,3-dihydro-1-methyl-2-oxo-5-(p-tolyl)-1H-1,4-benzodiazepin-3-yl)-urea,
3-N-(2,3-Dihydro-1,8-dimethyl-2-oxo-5-phenyl-1H-1,4-benzodiazepin-3-yl)-1H-indole-2-carboxamide and
N-(3-Methoxyphenyl)-N'-(2,3-dihydro-1,8-dimethyl-2-oxo-5-phenyl-1H-1,4-benzodiazepin-3-yl)-urea.

Examples of gastrin specific compounds of Formula I are:
3-((((4-Chlorophenyl)amino)carbonyl)amino)-5-(2-fluorophenyl)-2,3-dihydro-2-oxo-1H-1,4-benzodiazepine-1-acetic acid ethyl ester,
3-((((4-Chlorophenyl)amino)carbonyl)amino)-2,3-dihydro-2-oxo-5-phenyl-1H-1,4-benzodiazepine-1acetic acid ethyl ester,
3-((((4-Chlorophenyl)amino)carbonyl)amino)-N,N-diethyl-2,3-dihydro-2-oxo-5-phenyl-1H-1,4-benzodiazepine-1-acetamide,
1-((3-((((4-Chlorophenyl)amino)carbonyl)amino)-2,3-dihydro-2-oxo-5-phenyl-1H-1,4-benzodiazepin-1-yl)acetyl)pyrrolidine,
1-((3-((((4-Chlorophenyl)amino)carbonyl)amino)-2,3-dihydro-2-oxo-5-phenyl-1H-1,4-benzodiazepin-1-yl)acetyl)-4-methylpiperazine,
3-(((4-Chlorophenyl)acetyl)amino)-2,3-dihydro-2-oxo-5-phenyl-1H-1,4-benzodiazepine-1-acetic acid ethyl ester,
N-(2,3-Dihydro-1-methyl-2-oxo-5-phenyl-1H-1,4-benzodiazepin-3-yl)-N'-phenylurea,
N-(4-Nitrophenyl)-N'-(2,3-dihydro-1-methyl-2-oxo-5-phenyl-1H-1,4-benzodiazepin-3-yl)-urea, (R)-N-(2,3-Dihydro-1-methyl-2-oxo-5-phenyl-1H-1,4-benzodiazepin-3-yl)N'-(3-methoxyphenyl)-urea,
(R)-N-(2,3-Dihydro-1-methyl-2-oxo-5-phenyl-1H-1,4-benzodiazepin-3-yl)-N'-(3-methylphenyl)-urea,
(R)-N-(2,3-Dihydro-1-methyl-2-oxo-5-phenyl-1H 1,4-benzodiazepin-3-yl)-N'-(3-bromophenyl)-urea,
1-{[3-[(((3-Methoxyphenyl)amino)carbonyl)amino]-2,3-dihydro-2-oxo-5-phenyl-1H-1,4-benzodiazepin-1-yl]acetyl}pyrrolidine,
3-{[((3-Methoxyphenyl)amino)carbonyl)amino]-N,N-diethyl-2,3-dihydro-2-oxo-5-phenyl-1H-1,4-benzodiazepin-1-acetamide,
3-{[((2-Chlorophenyl)amino)carbonyl]amino}-N,N-diethyl-2,3-dihydro-2-oxo-5-phenyl-1H-1,4-benzodiazepine-1-acetamide,
(R)-N-(2,3-Dihydro-1-methyl-2-oxo-5-phenyl-1H-1,4-benzodiazepin-3-yl)-N'-(4-methylphenyl)-urea,
(R)-N-(2,3-Dihydro-1-methyl-2-oxo-5-phenyl-1H-1,4-benzodiazepin-3-yl)-N'-(3-chlorophenyl)-urea.

Examples of Compounds of Formula I are listed in Table 2.

TABLE 2

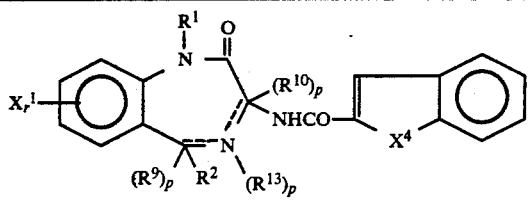

$X^4$ = NH, N—CH$_3$, O, or S

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| CF$_3$ | 1 | H | — | Ph | — | H |
| OH | 1 | H | — | Ph | — | H |
| NO$_2$ | 1 | H | — | Ph | — | H |
| H | 1 | CH$_3$ | — | Ph | — | H |
| Cl | 1 | CH$_3$ | — | Ph | — | H |
| F | 1 | CH$_3$ | — | Ph | — | H |
| CF$_3$ | 1 | CH$_3$ | — | Ph | — | H |
| OH | 1 | CH$_3$ | — | Ph | — | H |
| NO$_2$ | 1 | CH$_3$ | — | Ph | — | H |
| H | 1 | CH$_2$COOH | — | Ph | — | H |
| Cl | 1 | CH$_2$COOH | — | Ph | — | H |
| F | 1 | CH$_2$COOH | — | Ph | — | H |
| CF$_3$ | 1 | CH$_2$COOH | — | Ph | — | H |
| OH | 1 | CH$_2$COOH | — | Ph | — | H |
| NO$_2$ | 1 | CH$_2$COOH | — | Ph | — | H |
| H | 1 | CH$_2$CH$_3$ | — | Ph | — | H |
| OH | 1 | CH$_2$CH$_3$ | — | Ph | — | H |
| H | 1 | CH$_2$COOEt | — | Ph | — | H |
| OH | 1 | CH$_2$COOEt | — | Ph | — | H |
| H | 1 | CH$_2$CH$_2$COOH | — | Ph | — | H |
| OH | 1 | CH$_2$CH$_2$COOH | — | Ph | — | H |
| H | 1 | H | — | o-F-Ph | — | H |
| Cl | 1 | H | — | o-F-Ph | — | H |
| F | 1 | H | — | o-F-Ph | — | H |
| CF$_3$ | 1 | H | — | o-F-Ph | — | H |
| OH | 1 | H | — | o-F-Ph | — | H |
| NO$_2$ | 1 | H | — | o-F-Ph | — | H |
| H | 1 | CH$_3$ | — | o-F-Ph | — | H |
| Cl | 1 | CH$_3$ | — | o-F-Ph | — | H |
| F | 1 | CH$_3$ | — | o-F-Ph | — | H |
| CF$_3$ | 1 | CH$_3$ | — | o-F-Ph | — | H |
| OH | 1 | CH$_3$ | — | o-F-Ph | — | H |
| NO$_2$ | 1 | CH$_3$ | — | o-F-Ph | — | H |
| H | 1 | CH$_2$COOH | — | o-F-Ph | — | H |
| Cl | 1 | CH$_2$COOH | — | o-F-Ph | — | H |
| F | 1 | CH$_2$COOH | — | o-F-Ph | — | H |
| CF$_3$ | 1 | CH$_2$COOH | — | o-F-Ph | — | H |
| OH | 1 | CH$_2$COOH | — | o-F-Ph | — | H |
| NO$_2$ | 1 | CH$_2$COOH | — | o-F-Ph | — | H |
| H | 1 | CH$_2$CH$_3$ | — | o-F-Ph | — | H |

TABLE 2-continued

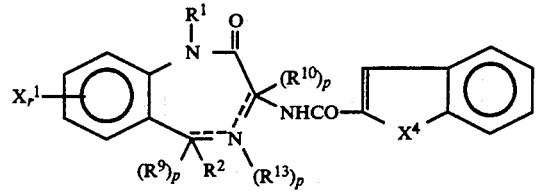

$X^4$ = NH, N—CH$_3$, O, or S

| $X^1$ | r | $R^1$ | $(R^9)_p$ | $R^2$ | $(R^{13})_p$ | $(R^{10})_p$ |
|---|---|---|---|---|---|---|
| OH | 1 | CH$_2$CH$_3$ | — | o-F-Ph | — | H |
| H | 1 | CH$_2$COOEt | — | o-F-Ph | — | H |
| OH | 1 | CH$_2$COOEt | — | o-F-Ph | — | H |
| H | 1 | CH$_2$CH$_2$COOH | — | o-F-Ph | — | H |
| OH | 1 | CH$_2$CH$_2$COOH | — | o-F-Ph | — | H |
| H | 1 | H | — | p-Cl-Ph | — | H |
| F | 1 | H | — | p-Cl-Ph | — | H |
| CF$_3$ | 1 | H | — | p-Cl-Ph | — | H |
| OH | 1 | H | — | p-Cl-Ph | — | H |
| H | 1 | CH$_3$ | — | p-Cl-Ph | — | H |
| F | 1 | CH$_3$ | — | p-Cl-Ph | — | H |
| CF$_3$ | 1 | CH$_3$ | — | p-Cl-Ph | — | H |
| OH | 1 | CH$_3$ | — | p-Cl-Ph | — | H |
| H | 1 | CH$_2$COOH | — | p-Cl-Ph | — | H |
| F | 1 | CH$_2$COOH | — | p-Cl-Ph | — | H |
| CF$_3$ | 1 | CH$_2$COOH | — | p-Cl-Ph | — | H |
| OH | 1 | CH$_2$COOH | — | p-Cl-Ph | — | H |
| H | 1 | CH$_2$CH$_3$ | — | p-Cl-Ph | — | H |
| H | 1 | CH$_2$COOEt | — | p-Cl-Ph | — | H |
| H | 1 | CH$_2$CH$_2$COOH | — | p-Cl-Ph | — | H |
| H | 1 | H | — | CH$_2$COOt-Bu | — | H |
| Cl | 1 | H | — | CH$_2$COOt-Bu | — | H |
| F | 1 | H | — | CH$_2$COOt-Bu | — | H |
| CF$_3$ | 1 | H | — | CH$_2$COOt-Bu | — | H |
| OH | 1 | H | — | CH$_2$COOt-Bu | — | H |
| NO$_2$ | 1 | H | — | CH$_2$COOt-Bu | — | H |
| H | 1 | CH$_3$ | — | CH$_2$COOt-Bu | — | H |
| Cl | 1 | CH$_3$ | — | CH$_2$COOt-Bu | — | H |
| F | 1 | CH$_3$ | — | CH$_2$COOt-Bu | — | H |
| CF$_3$ | 1 | CH$_3$ | — | CH$_2$COOt-Bu | — | H |
| OH | 1 | CH$_3$ | — | CH$_2$COOt-Bu | — | H |
| NO$_2$ | 1 | CH$_3$ | — | CH$_2$COOt-Bu | — | H |
| H | 1 | CH$_2$COOH | — | CH$_2$COOt-Bu | — | H |
| Cl | 1 | CH$_2$COOH | — | CH$_2$COOt-Bu | — | H |
| F | 1 | CH$_2$COOH | — | CH$_2$COOt-Bu | — | H |
| CF$_2$ | 1 | CH$_2$COOH | — | CH$_2$COOt-Bu | — | H |
| OH | 1 | CH$_2$COOH | — | CH$_2$COOt-Bu | — | H |
| NO$_2$ | 1 | CH$_2$COOH | — | CH$_2$COOt-Bu | — | H |
| H | 1 | CH$_2$CH$_3$ | — | CH$_2$COOt-Bu | — | H |
| OH | 1 | CH$_2$CH$_3$ | — | CH$_2$COOt-Bu | — | H |
| H | 1 | CH$_2$COOEt | — | CH$_2$COOt-Bu | — | H |
| OH | 1 | CH$_2$COOEt | — | CH$_2$COOt-Bu | — | H |
| H | 1 | CH$_2$CH$_2$COOH | — | CH$_2$COOt-Bu | — | H |
| OH | 1 | CH$_2$CH$_2$COOH | — | CH$_2$COOt-Bu | — | H |
| H | 1 | H | — | CH$_2$COOEt | — | H |
| Cl | 1 | H | — | CH$_2$COOEt | — | H |
| F | 1 | H | — | CH$_2$COOEt | — | H |
| CF$_3$ | 1 | H | — | CH$_2$COOEt | — | H |
| OH | 1 | H | — | CH$_2$COOEt | — | H |
| NO$_2$ | 1 | H | — | CH$_2$COOEt | — | H |
| H | 1 | CH$_3$ | — | CH$_2$COOEt | — | H |
| Cl | 1 | CH$_3$ | — | CH$_2$COOEt | — | H |
| F | 1 | CH$_3$ | — | CH$_2$COOEt | — | H |
| CF$_3$ | 1 | CH$_3$ | — | CH$_2$COOEt | — | H |
| OH | 1 | CH$_3$ | — | CH$_2$COOEt | — | H |
| NO$_2$ | 1 | CH$_3$ | — | CH$_2$COOEt | — | H |
| H | 1 | CH$_2$COOH | — | CH$_2$COOEt | — | H |
| Cl | 1 | CH$_2$COOH | — | CH$_2$COOEt | — | H |
| F | 1 | CH$_2$COOH | — | CH$_2$COOEt | — | H |
| CF$_3$ | 1 | CH$_2$COOH | — | CH$_2$COOEt | — | H |
| OH | 1 | CH$_2$COOH | — | CH$_2$COOEt | — | H |
| NO$_2$ | 1 | CH$_2$COOH | — | CH$_2$COOEt | — | H |
| H | 1 | CH$_2$CH$_3$ | — | CH$_2$COOEt | — | H |
| OH | 1 | CH$_2$CH$_3$ | — | CH$_2$COOEt | — | H |
| H | 1 | CH$_2$COOEt | — | CH$_2$COOEt | — | H |
| OH | 1 | CH$_2$COOEt | — | CH$_2$COOEt | — | H |
| H | 1 | CH$_2$CH$_2$COOH | — | CH$_2$COOEt | — | H |

TABLE 2-continued

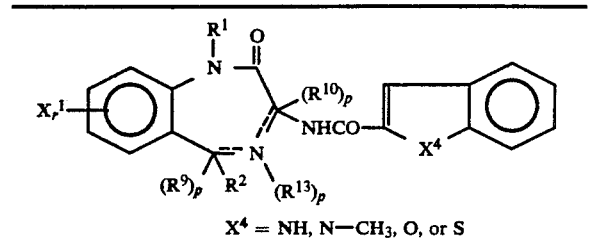

$X^4$ = NH, N—$CH_3$, O, or S

| $X^1$ | r | $R^1$ | $(R^9)_p$ $R^2$ | $(R^{13})_p$ | $(R^{10})_p$ |
|---|---|---|---|---|---|
| OH | 1 | $CH_2CH_2COOH$ | — $CH_2COOEt$ | — | H |

TABLE 3

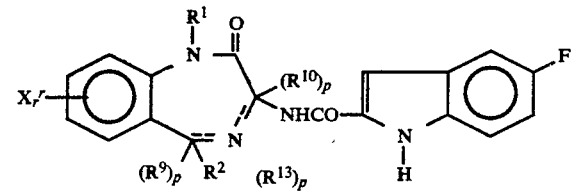

| $X^1$ | r | $R^1$ | $(R^9)_p$ $R^2$ | $(R^{13})_p$ | $(R^{10})_p$ |
|---|---|---|---|---|---|
| H | 1 | H | — Ph | — | H |
| Cl | 1 | H | — Ph | — | H |
| F | 1 | H | — Ph | — | H |
| $CF_3$ | 1 | H | — Ph | — | H |
| OH | 1 | H | — Ph | — | H |
| $NO_2$ | 1 | H | — Ph | — | H |
| H | 1 | $CH_3$ | — Ph | — | H |
| Cl | 1 | $CH_3$ | — Ph | — | H |
| F | 1 | $CH_3$ | — Ph | — | H |
| $CF_3$ | 1 | $CH_3$ | — Ph | — | H |
| OH | 1 | $CH_3$ | — Ph | — | H |
| $NO_2$ | 1 | $CH_3$ | — Ph | — | H |
| H | 1 | $CH_2COOH$ | — Ph | — | H |
| Cl | 1 | $CH_2COOH$ | — Ph | — | H |
| F | 1 | $CH_2COOH$ | — Ph | — | H |
| $CF_3$ | 1 | $CH_2COOH$ | — Ph | — | H |
| OH | 1 | $CH_2COOH$ | — Ph | — | H |
| $NO_2$ | 1 | $CH_2COOH$ | — Ph | — | H |
| H | 1 | $CH_2CH_3$ | — Ph | — | H |
| OH | 1 | $CH_2CH_3$ | — Ph | — | H |
| H | 1 | $CH_2COOEt$ | — Ph | — | H |
| OH | 1 | $CH_2COOEt$ | — Ph | — | H |
| H | 1 | $CH_2CH_2COOH$ | — Ph | — | H |
| OH | 1 | $CH_2CH_2COOH$ | — Ph | — | H |
| H | 1 | H | — o-F-Ph | — | H |
| Cl | 1 | H | — o-F-Ph | — | H |
| F | 1 | H | — o-F-Ph | — | H |
| $CF_3$ | 1 | H | — o-F-Ph | — | H |
| OH | 1 | H | — o-F-Ph | — | H |
| $NO_2$ | 1 | H | — o-F-Ph | — | H |
| H | 1 | $CH_3$ | — o-F-Ph | — | H |
| Cl | 1 | $CH_3$ | — o-F-Ph | — | H |
| F | 1 | $CH_3$ | — o-F-Ph | — | H |
| $CF_3$ | 1 | $CH_3$ | — o-F-Ph | — | H |
| OH | 1 | $CH_3$ | — o-F-Ph | — | H |
| $NO_2$ | 1 | $CH_3$ | — o-F-Ph | — | H |
| H | 1 | $CH_2COOH$ | — o-F-Ph | — | H |
| Cl | 1 | $CH_2COOH$ | — o-F-Ph | — | H |
| F | 1 | $CH_2COOH$ | — o-F-Ph | — | H |
| $CF_3$ | 1 | $CH_2COOH$ | — o-F-Ph | — | H |
| OH | 1 | $CH_2COOH$ | — o-F-Ph | — | H |
| $NO_2$ | 1 | $CH_2COOH$ | — o-F-Ph | — | H |
| H | 1 | $CH_2CH_3$ | — o-F-Ph | — | H |
| OH | 1 | $CH_2CH_3$ | — o-F-Ph | — | H |
| H | 1 | $CH_2COOEt$ | — o-F-Ph | — | H |
| OH | 1 | $CH_2COOEt$ | — o-F-Ph | — | H |
| H | 1 | $CH_2CH_2COOH$ | — o-F-Ph | — | H |
| OH | 1 | $CH_2CH_2COOH$ | — o-F-Ph | — | H |
| H | 1 | H | — p-Cl-Ph | — | H |
| F | 1 | H | — p-Cl-Ph | — | H |
| $CF_3$ | 1 | H | — p-Cl-Ph | — | H |
| OH | 1 | H | — p-Cl-Ph | — | H |
| H | 1 | $CH_3$ | — p-Cl-Ph | — | H |

TABLE 3-continued

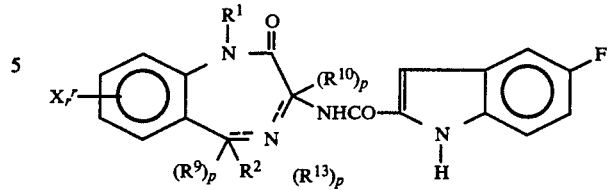

| $X^1$ | r | $R^1$ | $(R^9)_p$ $R^2$ | $(R^{13})_p$ | $(R^{10})_p$ |
|---|---|---|---|---|---|
| F | 1 | $CH_3$ | — p-Cl-Ph | — | H |
| $CF_3$ | 1 | $CH_3$ | — p-Cl-Ph | — | H |
| OH | 1 | $CH_3$ | — p-Cl-Ph | — | H |
| H | 1 | $CH_2COOH$ | — p-Cl-Ph | — | H |
| F | 1 | $CH_2COOH$ | — p-Cl-Ph | — | H |
| $CF_3$ | 1 | $CH_2COOH$ | — p-Cl-Ph | — | H |
| OH | 1 | $CH_2COOH$ | — p-Cl-Ph | — | H |
| H | 1 | $CH_2CH_3$ | — p-Cl-Ph | — | H |
| H | 1 | $CH_2COOEt$ | — p-Cl-Ph | — | H |
| H | 1 | $CH_2CH_2COOH$ | — p-Cl-Ph | — | H |
| H | 1 | H | — $CH_2COOt$-Bu | — | H |
| Cl | 1 | H | — $CH_2COOt$-Bu | — | H |
| F | 1 | H | — $CH_2COOt$-Bu | — | H |
| $CF_3$ | 1 | H | — $CH_2COOt$-Bu | — | H |
| OH | 1 | H | — $CH_2COOt$-Bu | — | H |
| $NO_2$ | 1 | H | — $CH_2COOt$-Bu | — | H |
| H | 1 | $CH_3$ | — $CH_2COOt$-Bu | — | H |
| Cl | 1 | $CH_3$ | — $CH_2COOt$-Bu | — | H |
| F | 1 | $CH_3$ | — $CH_2COOt$-Bu | — | H |
| $CF_3$ | 1 | $CH_3$ | — $CH_2COOt$-Bu | — | H |
| OH | 1 | $CH_3$ | — $CH_2COOt$-Bu | — | H |
| $NO_2$ | 1 | $CH_3$ | — $CH_2COOt$-Bu | — | H |
| H | 1 | $CH_2COOH$ | — $CH_2COOt$-Bu | — | H |
| Cl | 1 | $CH_2COOH$ | — $CH_2COOt$-Bu | — | H |
| F | 1 | $CH_2COOH$ | — $CH_2COOt$-Bu | — | H |
| $CF_3$ | 1 | $CH_2COOH$ | — $CH_2COOt$-Bu | — | H |
| OH | 1 | $CH_2COOH$ | — $CH_2COOt$-Bu | — | H |
| $NO_2$ | 1 | $CH_2COOH$ | — $CH_2COOt$-Bu | — | H |
| H | 1 | $CH_2CH_3$ | — $CH_2COOt$-Bu | — | H |
| OH | 1 | $CH_2CH_3$ | — $CH_2COOt$-Bu | — | H |
| H | 1 | $CH_2COOEt$ | — $CH_2COOt$-Bu | — | H |
| OH | 1 | $CH_2COOEt$ | — $CH_2COOt$-Bu | — | H |
| H | 1 | $CH_2CH_2COOH$ | — $CH_2COOt$-Bu | — | H |
| OH | 1 | $CH_2CH_2COOH$ | — $CH_2COOt$-Bu | — | H |
| H | 1 | H | — $CH_2COOEt$ | — | H |
| Cl | 1 | H | — $CH_2COOEt$ | — | H |
| F | 1 | H | — $CH_2COOEt$ | — | H |
| $CF_3$ | 1 | H | — $CH_2COOEt$ | — | H |
| OH | 1 | H | — $CH_2COOEt$ | — | H |
| $NO_2$ | 1 | H | — $CH_2COOEt$ | — | H |
| H | 1 | $CH_3$ | — $CH_2COOEt$ | — | H |
| Cl | 1 | $CH_3$ | — $CH_2COOEt$ | — | H |
| F | 1 | $CH_3$ | — $CH_2COOEt$ | — | H |
| $CF_3$ | 1 | $CH_3$ | — $CH_2COOEt$ | — | H |
| OH | 1 | $CH_3$ | — $CH_2COOEt$ | — | H |
| $NO_2$ | 1 | $CH_3$ | — $CH_2COOEt$ | — | H |
| H | 1 | $CH_2COOH$ | — $CH_2COOEt$ | — | H |
| Cl | 1 | $CH_2COOH$ | — $CH_2COOEt$ | — | H |
| F | 1 | $CH_2COOH$ | — $CH_2COOEt$ | — | H |
| $CF_3$ | 1 | $CH_2COOH$ | — $CH_2COOEt$ | — | H |
| OH | 1 | $CH_2COOH$ | — $CH_2COOEt$ | — | H |
| $NO_2$ | 1 | $CH_2COOH$ | — $CH_2COOEt$ | — | H |
| H | 1 | $CH_2CH_3$ | — $CH_2COOEt$ | — | H |
| OH | 1 | $CH_2CH_3$ | — $CH_2COOEt$ | — | H |
| H | 1 | $CH_2COOEt$ | — $CH_2COOEt$ | — | H |
| OH | 1 | $CH_2COOEt$ | — $CH_2COOEt$ | — | H |
| H | 1 | $CH_2CH_2COOH$ | — $CH_2COOEt$ | — | H |
| OH | 1 | $CH_2CH_2COOH$ | — $CH_2COOEt$ | — | H |

TABLE 4

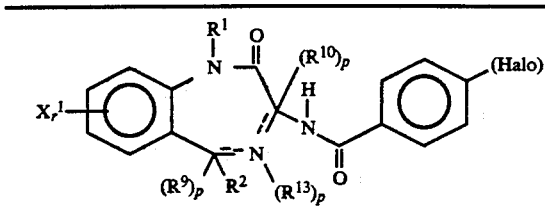

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |
| $NO_2$ | 1 | H | — | Ph | — | H |
| H | 1 | $CH_3$ | — | Ph | — | H |
| Cl | 1 | $CH_3$ | — | Ph | — | H |
| F | 1 | $CH_3$ | — | Ph | — | H |
| $CF_3$ | 1 | $CH_3$ | — | Ph | — | H |
| OH | 1 | $CH_3$ | — | Ph | — | H |
| $NO_2$ | 1 | $CH_3$ | — | Ph | — | H |
| H | 1 | $CH_2COOH$ | — | Ph | — | H |
| Cl | 1 | $CH_2COOH$ | — | Ph | — | H |
| F | 1 | $CH_2COOH$ | — | Ph | — | H |
| $CF_3$ | 1 | $CH_2COOH$ | — | Ph | — | H |
| OH | 1 | $CH_2COOH$ | — | Ph | — | H |
| $NO_2$ | 1 | $CH_2COOH$ | — | Ph | — | H |
| H | 1 | $CH_2CH_3$ | — | Ph | — | H |
| OH | 1 | $CH_2CH_3$ | — | Ph | — | H |
| H | 1 | $CH_2COOEt$ | — | Ph | — | H |
| OH | 1 | $CH_2COOEt$ | — | Ph | — | H |
| H | 1 | $CH_2CH_2COOH$ | — | Ph | — | H |
| OH | 1 | $CH_2CH_2COOH$ | — | Ph | — | H |
| H | 1 | H | — | o-F-Ph | — | H |
| Cl | 1 | H | — | o-F-Ph | — | H |
| F | 1 | H | — | o-F-Ph | — | H |
| $CF_3$ | 1 | H | — | o-F-Ph | — | H |
| OH | 1 | H | — | o-F-Ph | — | H |
| $NO_2$ | 1 | H | — | o-F-Ph | — | H |
| H | 1 | $CH_3$ | — | o-F-Ph | — | H |
| Cl | 1 | $CH_3$ | — | o-F-Ph | — | H |
| F | 1 | $CH_3$ | — | o-F-Ph | — | H |
| $CF_3$ | 1 | $CH_3$ | — | o-F-Ph | — | H |
| OH | 1 | $CH_3$ | — | o-F-Ph | — | H |
| $NO_2$ | 1 | $CH_3$ | — | o-F-Ph | — | H |
| H | 1 | $CH_2COOH$ | — | o-F-Ph | — | H |
| Cl | 1 | $CH_2COOH$ | — | o-F-Ph | — | H |
| F | 1 | $CH_2COOH$ | — | o-F-Ph | — | H |
| $CF_3$ | 1 | $CH_2COOH$ | — | o-F-Ph | — | H |
| OH | 1 | $CH_2COOH$ | — | o-F-Ph | — | H |
| $NO_2$ | 1 | $CH_2COOH$ | — | o-F-Ph | — | H |
| H | 1 | $CH_2CH_3$ | — | o-F-Ph | — | H |
| OH | 1 | $CH_2CH_3$ | — | o-F-Ph | — | H |
| H | 1 | $CH_2COOEt$ | — | o-F-Ph | — | H |
| OH | 1 | $CH_2COOEt$ | — | o-F-Ph | — | H |
| H | 1 | $CH_2CH_2COOH$ | — | o-F-Ph | — | H |
| OH | 1 | $CH_2CH_2COOH$ | — | o-F-Ph | — | H |
| H | 1 | H | — | p-Cl-Ph | — | H |
| F | 1 | H | — | p-Cl-Ph | — | H |
| $CF_3$ | 1 | H | — | p-Cl-Ph | — | H |
| OH | 1 | H | — | p-Cl-Ph | — | H |
| H | 1 | $CH_3$ | — | p-Cl-Ph | — | H |
| F | 1 | $CH_3$ | — | p-Cl-Ph | — | H |
| $CF_3$ | 1 | $CH_3$ | — | p-Cl-Ph | — | H |
| OH | 1 | $CH_3$ | — | p-Cl-Ph | — | H |
| H | 1 | $CH_2COOH$ | — | p-Cl-Ph | — | H |
| F | 1 | $CH_2COOH$ | — | p-Cl-Ph | — | H |
| $CF_3$ | 1 | $CH_2COOH$ | — | p-Cl-Ph | — | H |
| OH | 1 | $CH_2COOH$ | — | p-Cl-Ph | — | H |
| H | 1 | $CH_2CH_3$ | — | p-Cl-Ph | — | H |
| H | 1 | $CH_2COOEt$ | — | p-Cl-Ph | — | H |
| H | 1 | $CH_2CH_2COOH$ | — | p-Cl-Ph | — | H |
| H | 1 | H | — | $CH_2COOt\text{-}Bu$ | — | H |
| Cl | 1 | H | — | $CH_2COOt\text{-}Bu$ | — | H |
| F | 1 | H | — | $CH_2COOt\text{-}Bu$ | — | H |
| $CF_3$ | 1 | H | — | $CH_2COOt\text{-}Bu$ | — | H |
| OH | 1 | H | — | $CH_2COOt\text{-}Bu$ | — | H |
| $NO_2$ | 1 | H | — | $CH_2COOt\text{-}Bu$ | — | H |
| H | 1 | $CH_3$ | — | $CH_2COOt\text{-}Bu$ | — | H |
| Cl | 1 | $CH_3$ | — | $CH_2COOt\text{-}Bu$ | — | H |
| F | 1 | $CH_3$ | — | $CH_2COOt\text{-}Bu$ | — | H |
| $CF_3$ | 1 | $CH_3$ | — | $CH_2COOt\text{-}Bu$ | — | H |
| OH | 1 | $CH_3$ | — | $CH_2COOt\text{-}Bu$ | — | H |
| $NO_2$ | 1 | $CH_3$ | — | $CH_2COOt\text{-}Bu$ | — | H |
| H | 1 | $CH_2COOH$ | — | $CH_2COOt\text{-}Bu$ | — | H |
| Cl | 1 | $CH_2COOH$ | — | $CH_2COOt\text{-}Bu$ | — | H |
| F | 1 | $CH_2COOH$ | — | $CH_2COOt\text{-}Bu$ | — | H |
| $CF_3$ | 1 | $CH_2COOH$ | — | $CH_2COOt\text{-}Bu$ | — | H |
| OH | 1 | $CH_2COOH$ | — | $CH_2COOt\text{-}Bu$ | — | H |
| $NO_2$ | 1 | $CH_2COOH$ | — | $CH_2COOt\text{-}Bu$ | — | H |
| H | 1 | $CH_2CH_3$ | — | $CH_2COOt\text{-}Bu$ | — | H |
| OH | 1 | $CH_2CH_3$ | — | $CH_2COOt\text{-}Bu$ | — | H |
| H | 1 | $CH_2COOEt$ | — | $CH_2COOt\text{-}Bu$ | — | H |
| OH | 1 | $CH_2COOEt$ | — | $CH_2COOt\text{-}Bu$ | — | H |
| H | 1 | $CH_2CH_2COOH$ | — | $CH_2COOt\text{-}Bu$ | — | H |
| OH | 1 | $CH_2CH_2COOH$ | — | $CH_2COOt\text{-}Bu$ | — | H |
| H | 1 | H | — | $CH_2COOEt$ | — | H |
| Cl | 1 | H | — | $CH_2COOEt$ | — | H |
| F | 1 | H | — | $CH_2COOEt$ | — | H |
| $CF_3$ | 1 | H | — | $CH_2COOEt$ | — | H |
| OH | 1 | H | — | $CH_2COOEt$ | — | H |
| $NO_2$ | 1 | H | — | $CH_2COOEt$ | — | H |
| H | 1 | $CH_3$ | — | $CH_2COOEt$ | — | H |
| Cl | 1 | $CH_3$ | — | $CH_2COOEt$ | — | H |
| F | 1 | $CH_3$ | — | $CH_2COOEt$ | — | H |
| $CF_3$ | 1 | $CH_3$ | — | $CH_2COOEt$ | — | H |
| OH | 1 | $CH_3$ | — | $CH_2COOEt$ | — | H |
| $NO_2$ | 1 | $CH_3$ | — | $CH_2COOEt$ | — | H |
| H | 1 | $CH_2COOH$ | — | $CH_2COOEt$ | — | H |
| Cl | 1 | $CH_2COOH$ | — | $CH_2COOEt$ | — | H |
| F | 1 | $CH_2COOH$ | — | $CH_2COOEt$ | — | H |
| $CF_3$ | 1 | $CH_2COOH$ | — | $CH_2COOEt$ | — | H |
| OH | 1 | $CH_2COOH$ | — | $CH_2COOEt$ | — | H |
| $NO_2$ | 1 | $CH_2COOH$ | — | $CH_2COOEt$ | — | H |
| H | 1 | $CH_2CH_3$ | — | $CH_2COOEt$ | — | H |
| OH | 1 | $CH_2CH_3$ | — | $CH_2COOEt$ | — | H |
| H | 1 | $CH_2COOEt$ | — | $CH_2COOEt$ | — | H |
| OH | 1 | $CH_2COOEt$ | — | $CH_2COOEt$ | — | H |
| H | 1 | $CH_2CH_2COOH$ | — | $CH_2COOEt$ | — | H |
| OH | 1 | $CH_2CH_2COOH$ | — | $CH_2COOEt$ | — | H |

TABLE 5

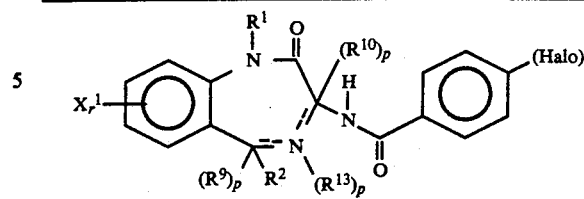

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |
| $NO_2$ | 1 | H | — | Ph | — | H |
| H | 1 | $CH_3$ | — | Ph | — | H |
| Cl | 1 | $CH_3$ | — | Ph | — | H |
| F | 1 | $CH_3$ | — | Ph | — | H |
| $CF_3$ | 1 | $CH_3$ | — | Ph | — | H |
| OH | 1 | $CH_3$ | — | Ph | — | H |
| $NO_2$ | 1 | $CH_3$ | — | Ph | — | H |
| H | 1 | $CH_2COOH$ | — | Ph | — | H |
| Cl | 1 | $CH_2COOH$ | — | Ph | — | H |
| F | 1 | $CH_2COOH$ | — | Ph | — | H |

TABLE 5-continued

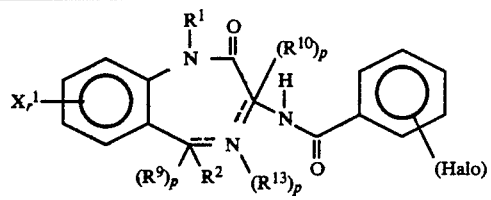

| X¹ | r | R¹ | (R⁹)ₚ | R² | (R¹³)ₚ | (R¹⁰)ₚ |
|---|---|---|---|---|---|---|
| CF₃ | 1 | CH₂COOH | — | Ph | — | H |
| OH | 1 | CH₂COOH | — | Ph | — | H |
| NO₂ | 1 | CH₂COOH | — | Ph | — | H |
| H | 1 | CH₂CH₃ | — | Ph | — | H |
| OH | 1 | CH₂CH₃ | — | Ph | — | H |
| H | 1 | CH₂COOEt | — | Ph | — | H |
| OH | 1 | CH₂COOEt | — | Ph | — | H |
| H | 1 | CH₂CH₂COOH | — | Ph | — | H |
| OH | 1 | CH₂CH₂COOH | — | Ph | — | H |
| H | 1 | H | — | o-F-Ph | — | H |
| Cl | 1 | H | — | o-F-Ph | — | H |
| F | 1 | H | — | o-F-Ph | — | H |
| CF₃ | 1 | H | — | o-F-Ph | — | H |
| OH | 1 | H | — | o-F-Ph | — | H |
| NO₂ | 1 | H | — | o-F-Ph | — | H |
| H | 1 | CH₃ | — | o-F-Ph | — | H |
| Cl | 1 | CH₃ | — | o-F-Ph | — | H |
| F | 1 | CH₃ | — | o-F-Ph | — | H |
| CF₃ | 1 | CH₃ | — | o-F-Ph | — | H |
| OH | 1 | CH₃ | — | o-F-Ph | — | H |
| NO₂ | 1 | CH₃ | — | o-F-Ph | — | H |
| H | 1 | CH₂COOH | — | o-F-Ph | — | H |
| Cl | 1 | CH₂COOH | — | o-F-Ph | — | H |
| F | 1 | CH₂COOH | — | o-F-Ph | — | H |
| CF₃ | 1 | CH₂COOH | — | o-F-Ph | — | H |
| OH | 1 | CH₂COOH | — | o-F-Ph | — | H |
| NO₂ | 1 | CH₂COOH | — | o-F-Ph | — | H |
| H | 1 | CH₂CH₃ | — | o-F-Ph | — | H |
| OH | 1 | CH₂CH₃ | — | o-F-Ph | — | H |
| H | 1 | CH₂COOEt | — | o-F-Ph | — | H |
| OH | 1 | CH₂COOEt | — | o-F-Ph | — | H |
| H | 1 | CH₂CH₂COOH | — | o-F-Ph | — | H |
| OH | 1 | CH₂CH₂COOH | — | o-F-Ph | — | H |
| H | 1 | H | — | o-Cl-Ph | — | H |
| F | 1 | H | — | p-Cl-Ph | — | H |
| CF₃ | 1 | H | — | p-Cl-Ph | — | H |
| OH | 1 | H | — | p-Cl-Ph | — | H |
| H | 1 | CH₃ | — | p-Cl-Ph | — | H |
| F | 1 | CH₃ | — | p-Cl-Ph | — | H |
| CF₃ | 1 | CH₃ | — | p-Cl-Ph | — | H |
| OH | 1 | CH₃ | — | p-Cl-Ph | — | H |
| H | 1 | CH₂COOH | — | p-Cl-Ph | — | H |
| F | 1 | CH₂COOH | — | p-Cl-Ph | — | H |
| CF₃ | 1 | CH₂COOH | — | p-Cl-Ph | — | H |
| OH | 1 | CH₂COOH | — | p-Cl-Ph | — | H |
| H | 1 | CH₂CH₃ | — | p-Cl-Ph | — | H |
| H | 1 | CH₂COOEt | — | p-Cl-Ph | — | H |
| H | 1 | CH₂CH₂COOH | — | p-Cl-Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | CH₂COOH | — | CH₂COOt-Bu | — | H |
| Cl | 1 | CH₂COOH | — | CH₂COOt-Bu | — | H |
| F | 1 | CH₂COOH | — | CH₂COOt-Bu | — | H |
| CF₃ | 1 | CH₂COOH | — | CH₂COOt-Bu | — | H |
| OH | 1 | CH₂COOH | — | CH₂COOt-Bu | — | H |
| NO₂ | 1 | CH₂COOH | — | CH₂COOt-Bu | — | H |
| H | 1 | CH₂CH₃ | — | CH₂COOt-Bu | — | H |
| OH | 1 | CH₂CH₃ | — | CH₂COOt-Bu | — | H |
| H | 1 | CH₂COOEt | — | CH₂COOt-Bu | — | H |
| OH | 1 | CH₂COOEt | — | CH₂COOt-Bu | — | H |
| H | 1 | CH₂CH₂COOH | — | CH₂COOt-Bu | — | H |

TABLE 5-continued

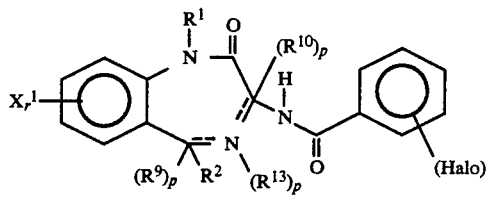

| X¹ | r | R¹ | (R⁹)ₚ | R² | (R¹³)ₚ | (R¹⁰)ₚ |
|---|---|---|---|---|---|---|
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | CH₂COOH | — | CH₂COOEt | — | H |
| Cl | 1 | CH₂COOH | — | CH₂COOEt | — | H |
| F | 1 | CH₂COOH | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | CH₂COOH | — | CH₂COOEt | — | H |
| Cl | 1 | CH₂COOH | — | CH₂COOEt | — | H |
| F | 1 | CH₂COOH | — | CH₂COOEt | — | H |
| CF₃ | 1 | CH₂COOH | — | CH₂COOEt | — | H |
| OH | 1 | CH₂COOH | — | CH₂COOEt | — | H |
| NO₂ | 1 | CH₂COOH | — | CH₂COOEt | — | H |
| H | 1 | CH₂CH₃ | — | CH₂COOEt | — | H |
| OH | 1 | CH₂CH₃ | — | CH₂COOEt | — | H |
| H | 1 | CH₂COOEt | — | CH₂COOEt | — | H |
| OH | 1 | CH₂COOEt | — | CH₂COOEt | — | H |
| H | 1 | CH₂CH₂COOH | — | CH₂COOEt | — | H |
| OH | 1 | CH₂CH₂COOH | — | CH₂COOEt | — | H |
| OH | 1 | CH₂COOEt | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 6

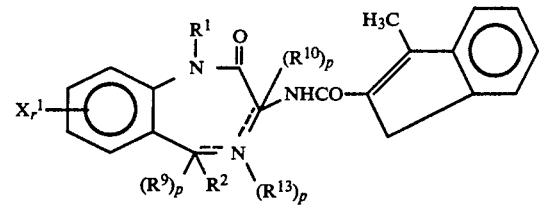

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | CH₂COOH | — | Ph | — | H |
| Cl | 1 | CH₂COOH | — | Ph | — | H |
| F | 1 | CH₂COOH | — | Ph | — | H |
| CF₃ | 1 | CH₂COOH | — | Ph | — | H |
| OH | 1 | CH₂COOH | — | Ph | — | H |
| NO₂ | 1 | CH₂COOH | — | Ph | — | H |
| H | 1 | CH₂CH₃ | — | Ph | — | H |
| OH | 1 | CH₂CH₃ | — | Ph | — | H |

TABLE 6-continued

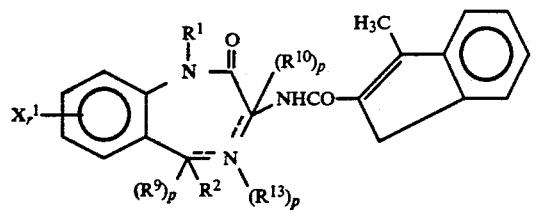

| $X^1$ | r | $R^1$ | $(R^9)_p$ | $R^2$ | $(R^{13})_p$ | $(R^{10})_p$ |
|---|---|---|---|---|---|---|
| H | 1 | CH₂COOEt | — | Ph | — | H |
| OH | 1 | CH₂COOEt | — | Ph | — | H |
| H | 1 | CH₂CH₂COOH | — | Ph | — | H |
| OH | 1 | CH₂CH₂COOH | — | Ph | — | H |
| H | 1 | H | — | o-F-Ph | — | H |
| Cl | 1 | H | — | o-F-Ph | — | H |
| F | 1 | H | — | o-F-Ph | — | H |
| CF₃ | 1 | H | — | o-F-Ph | — | H |
| OH | 1 | H | — | o-F-Ph | — | H |
| NO₂ | 1 | H | — | o-F-Ph | — | H |
| H | 1 | CH₃ | — | o-F-Ph | — | H |
| Cl | 1 | CH₃ | — | o-F-Ph | — | H |
| F | 1 | CH₃ | — | o-F-Ph | — | H |
| CF₃ | 1 | CH₃ | — | o-F-Ph | — | H |
| OH | 1 | CH₃ | — | o-F-PH | — | H |
| NO₂ | 1 | CH₃ | — | o-F-Ph | — | H |
| H | 1 | CH₂COOH | — | o-F-Ph | — | H |
| Cl | 1 | CH₂COOH | — | o-F-Ph | — | H |
| F | 1 | CH₂COOH | — | o-F-Ph | — | H |
| CF₃ | 1 | CH₂COOH | — | o-F-Ph | — | H |
| OH | 1 | CH₂COOH | — | o-F-Ph | — | H |
| NO₂ | 1 | CH₂COOH | — | o-F-Ph | — | H |
| H | 1 | CH₂CH₃ | — | o-F-Ph | — | H |
| OH | 1 | CH₂CH₃ | — | o-F-Ph | — | H |
| H | 1 | CH₂COOEt | — | o-F-Ph | — | H |
| OH | 1 | CH₂COOEt | — | o-F-Ph | — | H |
| H | 1 | CH₂CH₂COOH | — | o-F-Ph | — | H |
| OH | 1 | CH₂CH₂COOH | — | o-F-Ph | — | H |
| H | 1 | H | — | p-Cl-Ph | — | H |
| F | 1 | H | — | p-Cl-Ph | — | H |
| CF₃ | 1 | H | — | p-Cl-Ph | — | H |
| OH | 1 | H | — | p-Cl-Ph | — | H |
| H | 1 | CH₃ | — | p-Cl-Ph | — | H |
| F | 1 | CH₃ | — | p-Cl-Ph | — | H |
| CF₃ | 1 | CH₃ | — | p-Cl-Ph | — | H |
| OH | 1 | CH₃ | — | p-Cl-Ph | — | H |
| H | 1 | CH₂COOH | — | p-Cl-Ph | — | H |
| F | 1 | CH₂COOH | — | p-Cl-Ph | — | H |
| CF₃ | 1 | CH₂COOH | — | p-Cl-Ph | — | H |
| OH | 1 | CH₂COOH | — | p-Cl-Ph | — | H |
| H | 1 | CH₂CH₃ | — | p-Cl-Ph | — | H |
| H | 1 | CH₂COOEt | — | p-Cl-Ph | — | H |
| H | 1 | CH₂CH₂COOH | — | p-Cl-Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | CH₂COOH | — | CH₂COOt-Bu | — | H |
| Cl | 1 | CH₂COOH | — | CH₂COOt-Bu | — | H |
| F | 1 | CH₂COOH | — | CH₂COOt-Bu | — | H |
| CF₃ | 1 | CH₂COOH | — | CH₂COOt-Bu | — | H |
| OH | 1 | CH₂COOH | — | CH₂COOt-Bu | — | H |
| NO₂ | 1 | CH₂COOH | — | CH₂COOt-Bu | — | H |
| H | 1 | CH₂CH₃ | — | CH₂COOt-Bu | — | H |
| OH | 1 | CH₂CH₃ | — | CH₂COOt-Bu | — | H |
| H | 1 | CH₂COOEt | — | CH₂COOt-Bu | — | H |
| OH | 1 | CH₂COOEt | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |

TABLE 6-continued

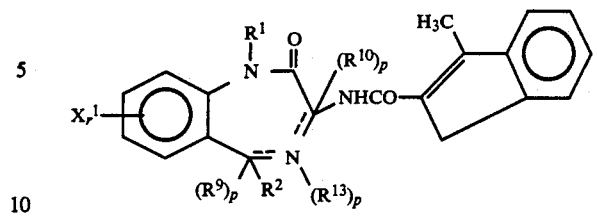

| $X^1$ | r | $R^1$ | $(R^9)_p$ | $R^2$ | $(R^{13})_p$ | $(R^{10})_p$ |
|---|---|---|---|---|---|---|
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | CH₂COOH | — | CH₂COOEt | — | H |
| Cl | 1 | CH₂COOH | — | CH₂COOEt | — | H |
| F | 1 | CH₂COOH | — | CH₂COOEt | — | H |
| CF₃ | 1 | CH₂COOH | — | CH₂COOEt | — | H |
| OH | 1 | CH₂COOH | — | CH₂COOEt | — | H |
| NO₂ | 1 | CH₂COOH | — | CH₂COOEt | — | H |
| H | 1 | CH₂CH₃ | — | CH₂COOEt | — | H |
| OH | 1 | CH₂CH₃ | — | CH₂COOEt | — | H |
| H | 1 | CH₂COOEt | — | CH₂COOEt | — | H |
| OH | 1 | CH₂COOEt | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 7

| $X^1$ | r | $R^1$ | $(R^9)_p$ | $R^2$ | $(R^{13})_p$ | $(R_{10})_p$ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | CH₂COOH | — | Ph | — | H |
| Cl | 1 | CH₂COOH | — | Ph | — | H |
| F | 1 | CH₂COOH | — | Ph | — | H |
| CF₃ | 1 | CH₂COOH | — | Ph | — | H |
| OH | 1 | CH₂COOH | — | Ph | — | H |
| NO₂ | 1 | CH₂COOH | — | Ph | — | H |
| H | 1 | CH₂CH₃ | — | Ph | — | H |
| OH | 1 | CH₂CH₃ | — | Ph | — | H |
| H | 1 | CH₂COOEt | — | Ph | — | H |
| OH | 1 | CH₂COOEt | — | Ph | — | H |
| H | 1 | CH₂CH₂COOH | — | Ph | — | H |
| OH | 1 | CH₂CH₂COOH | — | Ph | — | H |
| H | 1 | H | — | o-F-Ph | — | H |
| Cl | 1 | H | — | o-F-Ph | — | H |
| F | 1 | H | — | o-F-Ph | — | H |
| CF₃ | 1 | H | — | o-F-Ph | — | H |
| OH | 1 | H | — | o-F-Ph | — | H |
| NO₂ | 1 | H | — | o-F-Ph | — | H |
| H | 1 | CH₃ | — | o-F-Ph | — | H |
| Cl | 1 | CH₃ | — | o-F-Ph | — | H |
| F | 1 | CH₃ | — | o-F-Ph | — | H |

TABLE 7-continued

Structure: R¹-N on benzene ring with X¹ᵣ substituent, carbonyl, (R¹⁰)ₚ, thiophene (S); (R⁹)ₚ R² and N(R¹³)ₚ with =O

| X¹ | r | R¹ | (R⁹)ₚ | R² | (R¹³)ₚ | (R¹⁰)ₚ |
|---|---|---|---|---|---|---|
| CF₃ | 1 | CH₃ | — | o-F-Ph | — | H |
| OH | 1 | CH₃ | — | o-F-Ph | — | H |
| NO₂ | 1 | CH₃ | — | o-F-Ph | — | H |
| H | 1 | CH₂COOH | — | o-F-Ph | — | H |
| Cl | 1 | CH₂COOH | — | o-F-Ph | — | H |
| F | 1 | CH₂COOH | — | o-F-Ph | — | H |
| CF₃ | 1 | CH₂COOH | — | o-F-Ph | — | H |
| OH | 1 | CH₂COOH | — | o-F-Ph | — | H |
| NO₂ | 1 | CH₂COOH | — | o-F-Ph | — | H |
| H | 1 | CH₂CH₃ | — | o-F-Ph | — | H |
| OH | 1 | CH₂CH₃ | — | o-F-Ph | — | H |
| H | 1 | CH₂COOEt | — | o-F-Ph | — | H |
| OH | 1 | CH₂COOEt | — | o-F-Ph | — | H |
| H | 1 | CH₂CH₂COOH | — | o-F-Ph | — | H |
| OH | 1 | CH₂CH₂COOH | — | o-F-Ph | — | H |
| H | 1 | H | — | p-Cl-Ph | — | H |
| F | 1 | H | — | p-Cl-Ph | — | H |
| CF₃ | 1 | H | — | p-Cl-Ph | — | H |
| OH | 1 | H | — | p-Cl-Ph | — | H |
| H | 1 | CH₃ | — | p-Cl-Ph | — | H |
| F | 1 | CH₃ | — | p-Cl-Ph | — | H |
| CF₃ | 1 | CH₃ | — | p-Cl-Ph | — | H |
| OH | 1 | CH₃ | — | p-Cl-Ph | — | H |
| H | 1 | CH₂COOH | — | p-Cl-Ph | — | H |
| F | 1 | CH₂COOH | — | p-Cl-Ph | — | H |
| CF₃ | 1 | CH₂COOH | — | p-Cl-Ph | — | H |
| OH | 1 | CH₂COOH | — | p-Cl-Ph | — | H |
| H | 1 | CH₂CH₃ | — | p-Cl-Ph | — | H |
| H | 1 | CH₂COOEt | — | p-Cl-Ph | — | H |
| H | 1 | CH₂CH₂COOH | — | p-Cl-Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | CH₂COOH | — | CH₂COOt-Bu | — | H |
| Cl | 1 | CH₂COOH | — | CH₂COOt-Bu | — | H |
| F | 1 | CH₂COOH | — | CH₂COOt-Bu | — | H |
| CF₃ | 1 | CH₂COOH | — | CH₂COOt-Bu | — | H |
| OH | 1 | CH₂COOH | — | CH₂COOt-Bu | — | H |
| NO₂ | 1 | CH₂COOH | — | CH₂COOt-Bu | — | H |
| H | 1 | CH₂CH₃ | — | CH₂COOt-Bu | — | H |
| OH | 1 | CH₂CH₃ | — | CH₂COOt-Bu | — | H |
| H | 1 | CH₂COOEt | — | CH₂COOt-Bu | — | H |
| OH | 1 | CH₂COOEt | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | CH₂COOH | — | CH₂COOEt | — | H |
| Cl | 1 | CH₂COOH | — | CH₂COOEt | — | H |
| F | 1 | CH₂COOH | — | CH₂COOEt | — | H |
| CF₃ | 1 | CH₂COOH | — | CH₂COOEt | — | H |
| OH | 1 | CH₂COOH | — | CH₂COOEt | — | H |
| NO₂ | 1 | CH₂COOH | — | CH₂COOEt | — | H |
| H | 1 | CH₂CH₃ | — | CH₂COOEt | — | H |
| OH | 1 | CH₂CH₃ | — | CH₂COOEt | — | H |
| H | 1 | CH₂COOEt | — | CH₂COOEt | — | H |
| OH | 1 | CH₂COOEt | — | CH₂COOEt | — | H |
| H | 1 | CH₂CH₂COOH | — | CH₂COOEt | — | H |
| OH | 1 | CH₂CH₂COOH | — | CH₂COOEt | — | H |
| H | 1 | CH₃ | — | Ph | — | OH |
| H | 1 | CH₂CH₃ | — | Ph | — | OH |
| H | 1 | CH₂COOEt | — | Ph | — | OH |
| H | 1 | CH₃ | — | o-F-Ph | — | OH |
| H | 1 | CH₂CH₃ | — | o-F-Ph | — | OH |
| H | 1 | CH₂COOEt | — | o-F-Ph | — | OH |
| H | 1 | CH₃ | — | CH₂COOt-Bu | — | OH |
| H | 1 | CH₂CH₃ | — | CH₂COOt-Bu | — | OH |
| H | 1 | CH₂COOEt | — | CH₂COOt-Bu | — | OH |

TABLE 8

Structure: R¹-N on benzene ring with X¹ᵣ substituent, carbonyl, (R¹⁰)ₚ, NHCO-CH=CH-Ph; (R⁹)ₚ R² and N(R¹³)ₚ

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | CH₂COOH | — | Ph | — | H |
| Cl | 1 | CH₂COOH | — | Ph | — | H |
| F | 1 | CH₂COOH | — | Ph | — | H |
| CF₃ | 1 | CH₂COOH | — | Ph | — | H |
| OH | 1 | CH₂COOH | — | Ph | — | H |
| NO₂ | 1 | CH₂COOH | — | Ph | — | H |
| H | 1 | CH₂CH₃ | — | Ph | — | H |
| OH | 1 | CH₂CH₃ | — | Ph | — | H |
| H | 1 | CH₂COOEt | — | Ph | — | H |
| OH | 1 | CH₂COOEt | — | Ph | — | H |
| H | 1 | CH₂CH₂COOH | — | Ph | — | H |
| OH | 1 | CH₂CH₂COOH | — | Ph | — | H |
| H | 1 | H | — | o-F-Ph | — | H |
| Cl | 1 | H | — | o-F-Ph | — | H |
| F | 1 | H | — | o-F-Ph | — | H |
| CF₃ | 1 | H | — | o-F-Ph | — | H |
| OH | 1 | H | — | o-F-Ph | — | H |
| NO₂ | 1 | H | — | o-F-Ph | — | H |
| H | 1 | CH₃ | — | o-F-Ph | — | H |
| Cl | 1 | CH₃ | — | o-F-Ph | — | H |
| F | 1 | CH₃ | — | o-F-Ph | — | H |
| CF₃ | 1 | CH₃ | — | o-F-Ph | — | H |
| OH | 1 | CH₃ | — | o-F-Ph | — | H |
| NO₂ | 1 | CH₃ | — | o-F-Ph | — | H |
| H | 1 | CH₂COOH | — | o-F-Ph | — | H |
| Cl | 1 | CH₂COOH | — | o-F-Ph | — | H |
| F | 1 | CH₂COOH | — | o-F-Ph | — | H |

TABLE 8-continued

Structure: benzene ring with X¹ᵣ substituent, fused to a 7-membered ring containing N-R¹, C=O, C(R¹⁰)ₚ-NHCO-CH=CH-Ph, C(R²)(R⁹)ₚ=N-(R¹³)ₚ

| X¹ | r | R¹ | (R⁹)ₚ | R² | (R¹³)ₚ | (R¹⁰)ₚ |
|---|---|---|---|---|---|---|
| CF₃ | 1 | CH₂COOH | — | o-F-Ph | — | H |
| OH | 1 | CH₂COOH | — | o-F-Ph | — | H |
| NO₂ | 1 | CH₂COOH | — | o-F-Ph | — | H |
| H | 1 | CH₂CH₃ | — | o-F-Ph | — | H |
| OH | 1 | CH₂CH₃ | — | o-F-Ph | — | H |
| H | 1 | CH₂COOEt | — | o-F-Ph | — | H |
| OH | 1 | CH₂COOEt | — | o-F-Ph | — | H |
| H | 1 | CH₂CH₂COOH | — | o-F-Ph | — | H |
| OH | 1 | CH₂CH₂COOH | — | o-F-Ph | — | H |
| H | 1 | H | — | p-Cl-Ph | — | H |
| F | 1 | H | — | p-Cl-Ph | — | H |
| CF₃ | 1 | H | — | p-Cl-Ph | — | H |
| OH | 1 | H | — | p-Cl-Ph | — | H |
| H | 1 | CH₃ | — | p-Cl-Ph | — | H |
| F | 1 | CH₃ | — | p-Cl-Ph | — | H |
| CF₃ | 1 | CH₃ | — | p-Cl-Ph | — | H |
| OH | 1 | CH₃ | — | p-Cl-Ph | — | H |
| H | 1 | CH₂COOH | — | p-Cl-Ph | — | H |
| F | 1 | CH₂COOH | — | p-Cl-Ph | — | H |
| CF₃ | 1 | CH₂COOH | — | p-Cl-Ph | — | H |
| OH | 1 | CH₂COOH | — | p-Cl-Ph | — | H |
| H | 1 | CH₂CH₃ | — | p-Cl-Ph | — | H |
| H | 1 | CH₂COOEt | — | p-Cl-Ph | — | H |
| H | 1 | CH₂CH₂COOH | — | p-Cl-Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | CH₂COOH | — | CH₂COOt-Bu | — | H |
| Cl | 1 | CH₂COOH | — | CH₂COOt-Bu | — | H |
| F | 1 | CH₂COOH | — | CH₂COOt-Bu | — | H |
| CF₃ | 1 | CH₂COOH | — | CH₂COOt-Bu | — | H |
| OH | 1 | CH₂COOH | — | CH₂COOt-Bu | — | H |
| NO₂ | 1 | CH₂COOH | — | CH₂COOt-Bu | — | H |
| H | 1 | CH₂CH₃ | — | CH₂COOt-Bu | — | H |
| OH | 1 | CH₂CH₃ | — | CH₂COOt-Bu | — | H |
| H | 1 | CH₂COOEt | — | CH₂COOt-Bu | — | H |
| OH | 1 | CH₂COOEt | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | CH₂OOH | — | CH₂COOEt | — | H |
| Cl | 1 | CH₂COOH | — | CH₂COOEt | — | H |
| F | 1 | CH₂COOH | — | CH₂COOEt | — | H |
| CF₃ | 1 | CH₂COOH | — | CH₂COOEt | — | H |
| OH | 1 | CH₂COOH | — | CH₂COOEt | — | H |
| NO₂ | 1 | CH₂COOH | — | CH₂COOEt | — | H |
| H | 1 | CH₂CH₃ | — | CH₂COOEt | — | H |
| OH | 1 | CH₂CH₃ | — | CH₂COOEt | — | H |
| H | 1 | CH₂COOEt | — | CH₂COOEt | — | H |
| OH | 1 | CH₂COOEt | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 9

Structure: benzene ring with X¹ᵣ, fused to 7-membered ring containing N-R¹, C=O, C(R¹⁰)ₚ-NHCONH-(Halo-phenyl), C(R²)(R⁹)ₚ=N-(R¹³)ₚ

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | CH₂COOH | — | Ph | — | H |
| Cl | 1 | CH₂COOH | — | Ph | — | H |
| F | 1 | CH₂COOH | — | Ph | — | H |
| CF | 1 | CH₂COOH | — | Ph | — | H |
| OH | 1 | CH₂COOH | — | Ph | — | H |
| NO₂ | 1 | CH₂COOH | — | Ph | — | H |
| H | 1 | CH₂CH₃ | — | Ph | — | H |
| OH | 1 | CH₂CH₃ | — | Ph | — | H |
| H | 1 | CH₂COOEt | — | Ph | — | H |
| OH | 1 | CH₂COOEt | — | Ph | — | H |
| H | 1 | CH₂CH₂COOH | — | Ph | — | H |
| OH | 1 | CH₂CH₂COOH | — | Ph | — | H |
| H | 1 | H | — | o-F-Ph | — | H |
| Cl | 1 | H | — | o-F-Ph | — | H |
| F | 1 | H | — | o-F-Ph | — | H |
| CF₃ | 1 | H | — | o-F-Ph | — | H |
| OH | 1 | H | — | o-F-Ph | — | H |
| NO₂ | 1 | H | — | o-F-Ph | — | H |
| H | 1 | CH₃ | — | o-F-Ph | — | H |
| Cl | 1 | CH₃ | — | o-F-Ph | — | H |
| F | 1 | CH₃ | — | o-F-Ph | — | H |
| CF₃ | 1 | CH₃ | — | o-F-Ph | — | H |
| OH | 1 | CH₃ | — | o-F-Ph | — | H |
| NO₂ | 1 | CH₃ | — | o-F-Ph | — | H |
| H | 1 | CH₂COOH | — | o-F-Ph | — | H |
| Cl | 1 | CH₂COOH | — | o-F-Ph | — | H |
| F | 1 | CH₂COOH | — | o-F-Ph | — | H |
| CF₃ | 1 | CH₂COOH | — | o-F-Ph | — | H |
| OH | 1 | CH₂COOH | — | o-F-Ph | — | H |
| NO₂ | 1 | CH₂COOH | — | o-F-Ph | — | H |
| H | 1 | CH₂CH₃ | — | o-F-Ph | — | H |
| OH | 1 | CH₂CH₃ | — | o-F-Ph | — | H |
| H | 1 | CH₂COOEt | — | o-F-Ph | — | H |
| OH | 1 | CH₂COOEt | — | o-F-Ph | — | H |
| H | 1 | CH₂CH₂COOH | — | o-F-Ph | — | H |
| OH | 1 | CH₂CH₂COOH | — | o-F-Ph | — | H |
| H | 1 | H | — | p-Cl-Ph | — | H |
| F | 1 | H | — | p-Cl-Ph | — | H |
| CF₃ | 1 | H | — | p-Cl-Ph | — | H |
| OH | 1 | H | — | p-Cl-Ph | — | H |
| H | 1 | CH₃ | — | p-Cl-Ph | — | H |
| F | 1 | CH₃ | — | p-Cl-Ph | — | H |

Continuation of Table 8 (top right):

| X¹ | r | R¹ | (R⁹)ₚ | R² | (R¹³)ₚ | (R¹⁰)ₚ |
|---|---|---|---|---|---|---|
| OH | 1 | CH₂CH₂COOH | — | CH₂COOEt | — | H |

TABLE 9-continued

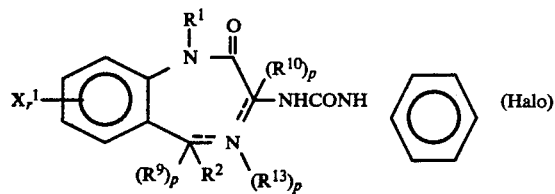

| $X^1$ | r | $R^1$ | $(R^9)_p$ | $R^2$ | $(R^{13})_p$ | $(R^{10})_p$ |
|---|---|---|---|---|---|---|
| $CF_3$ | 1 | $CH_3$ | — | p-Cl-Ph | — | H |
| OH | 1 | $CH_3$ | — | p-Cl-Ph | — | H |
| H | 1 | $CH_2COOH$ | — | p-Cl-Ph | — | H |
| F | 1 | $CH_2COOH$ | — | p-Cl-Ph | — | H |
| $CF_3$ | 1 | $CH_2COOH$ | — | p-Cl-Ph | — | H |
| OH | 1 | $CH_2COOH$ | — | p-Cl-Ph | — | H |
| H | 1 | $CH_2CH_3$ | — | p-Cl-Ph | — | H |
| H | 1 | $CH_2COOEt$ | — | p-Cl-Ph | — | H |
| H | 1 | $CH_2CH_2COOH$ | — | p-Cl-Ph | — | H |
| H | 1 | H | — | $CH_2COOt$-Bu | — | H |
| Cl | 1 | H | — | $CH_2COOt$-Bu | — | H |
| F | 1 | H | — | $CH_2COOt$-Bu | — | H |
| $CF_3$ | 1 | H | — | $CH_2COOt$-Bu | — | H |
| OH | 1 | H | — | $CH_2COOt$-Bu | — | H |
| $NO_2$ | 1 | H | — | $CH_2COOt$-Bu | — | H |
| H | 1 | $CH_3$ | — | $CH_2COOt$-Bu | — | H |
| Cl | 1 | $CH_3$ | — | $CH_2COOt$-Bu | — | H |
| F | 1 | $CH_3$ | — | $CH_2COOt$-Bu | — | H |
| $CF_3$ | 1 | $CH_3$ | — | $CH_2COOt$-Bu | — | H |
| OH | 1 | $CH_3$ | — | $CH_2COOt$-Bu | — | H |
| $NO_2$ | 1 | $CH_3$ | — | $CH_2COOt$-Bu | — | H |
| H | 1 | $CH_2COOH$ | — | $CH_2COOt$-Bu | — | H |
| Cl | 1 | $CH_2COOH$ | — | $CH_2COOt$-Bu | — | H |
| F | 1 | $CH_2COOH$ | — | $CH_2COOt$-Bu | — | H |
| $CF_3$ | 1 | $CH_2COOH$ | — | $CH_2COOt$-Bu | — | H |
| OH | 1 | $CH_2COOH$ | — | $CH_2COOt$-Bu | — | H |
| $NO_2$ | 1 | $CH_2COOH$ | — | $CH_2COOt$-Bu | — | H |
| H | 1 | $CH_2CH_3$ | — | $CH_2COOt$-Bu | — | H |
| OH | 1 | $CH_2CH_3$ | — | $CH_2COOt$-Bu | — | H |
| H | 1 | $CH_2COOEt$ | — | $CH_2COOt$-Bu | — | H |
| OH | 1 | $CH_2COOEt$ | — | $CH_2COOt$-Bu | — | H |
| H | 1 | $CH_2CH_2COOH$ | — | $CH_2COOt$-Bu | — | H |
| OH | 1 | $CH_2CH_2COOH$ | — | $CH_2COOt$-Bu | — | H |
| H | 1 | H | — | $CH_2COOEt$ | — | H |
| Cl | 1 | H | — | $CH_2COOEt$ | — | H |
| F | 1 | H | — | $CH_2COOEt$ | — | H |
| $CF_3$ | 1 | H | — | $CH_2COOEt$ | — | H |
| OH | 1 | H | — | $CH_2COOEt$ | — | H |
| $NO_2$ | 1 | H | — | $CH_2COOEt$ | — | H |
| H | 1 | $CH_3$ | — | $CH_2COOEt$ | — | H |
| Cl | 1 | $CH_3$ | — | $CH_2COOEt$ | — | H |
| F | 1 | $CH_3$ | — | $CH_2COOEt$ | — | H |
| $CF_3$ | 1 | $CH_3$ | — | $CH_2COOEt$ | — | H |
| OH | 1 | $CH_3$ | — | $CH_2COOEt$ | — | H |
| $NO_2$ | 1 | $CH_3$ | — | $CH_2COOEt$ | — | H |
| H | 1 | $CH_2COOH$ | — | $CH_2COOEt$ | — | H |
| Cl | 1 | $CH_2COOH$ | — | $CH_2COOEt$ | — | H |
| F | 1 | $CH_2COOH$ | — | $CH_2COOEt$ | — | H |
| $CF_3$ | 1 | $CH_2COOH$ | — | $CH_2COOEt$ | — | H |
| OH | 1 | $CH_2COOH$ | — | $CH_2COOEt$ | — | H |
| $NO_2$ | 1 | $CH_2COOH$ | — | $CH_2COOEt$ | — | H |
| H | 1 | $CH_2CH_3$ | — | $CH_2COOEt$ | — | H |
| OH | 1 | $CH_2CH_3$ | — | $CH_2COOEt$ | — | H |
| H | 1 | $CH_2COOEt$ | — | $CH_2COOEt$ | — | H |
| OH | 1 | $CH_2COOEt$ | — | $CH_2COOEt$ | — | H |
| H | 1 | $CH_2CH_2COOH$ | — | $CH_2COOEt$ | — | H |
| OH | 1 | $CH_2CH_2COOH$ | — | $CH_2COOEt$ | — | H |

TABLE 10

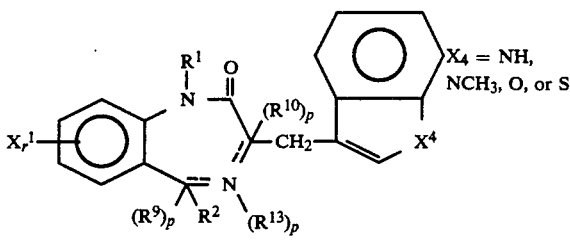

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |
| $NO_2$ | 1 | H | — | Ph | — | H |
| H | 1 | $CH_3$ | — | Ph | — | H |
| Cl | 1 | $CH_3$ | — | Ph | — | H |
| F | 1 | $CH_3$ | — | Ph | — | H |
| $CF_3$ | 1 | $CH_3$ | — | Ph | — | H |
| OH | 1 | $CH_3$ | — | Ph | — | H |
| $NO_2$ | 1 | $CH_3$ | — | Ph | — | H |
| H | 1 | $CH_2COOH$ | — | Ph | — | H |
| Cl | 1 | $CH_2COOH$ | — | Ph | — | H |
| F | 1 | $CH_2COOH$ | — | Ph | — | H |
| $CF_3$ | 1 | $CH_2COOH$ | — | Ph | — | H |
| OH | 1 | $CH_2COOH$ | — | Ph | — | H |
| $NO_2$ | 1 | $CH_2COOH$ | — | Ph | — | H |
| H | 1 | $CH_2CH_3$ | — | Ph | — | H |
| OH | 1 | $CH_2CH_3$ | — | Ph | — | H |
| H | 1 | $CH_2COOEt$ | — | Ph | — | H |
| OH | 1 | $CH_2COOEt$ | — | Ph | — | H |
| H | 1 | $CH_2CH_2COOH$ | — | Ph | — | H |
| OH | 1 | $CH_2CH_2COOH$ | — | Ph | — | H |
| H | 1 | H | — | o-F-Ph | — | H |
| Cl | 1 | H | — | o-F-Ph | — | H |
| F | 1 | H | — | o-F-Ph | — | H |
| $CF_3$ | 1 | H | — | o-F-Ph | — | H |
| OH | 1 | H | — | o-F-Ph | — | H |
| $NO_2$ | 1 | H | — | o-F-Ph | — | H |
| H | 1 | $CH_3$ | — | o-F-Ph | — | H |
| Cl | 1 | $CH_3$ | — | o-F-Ph | — | H |
| F | 1 | $CH_3$ | — | o-F-Ph | — | H |
| $CF_3$ | 1 | $CH_3$ | — | o-F-Ph | — | H |
| OH | 1 | $CH_3$ | — | o-F-Ph | — | H |
| $NO_2$ | 1 | $CH_3$ | — | o-F-Ph | — | H |
| H | 1 | $CH_2COOH$ | — | o-F-Ph | — | H |
| Cl | 1 | $CH_2COOH$ | — | o-F-Ph | — | H |
| F | 1 | $CH_2COOH$ | — | o-F-Ph | — | H |
| $CF_3$ | 1 | $CH_2COOH$ | — | o-F-Ph | — | H |
| OH | 1 | $CH_2COOH$ | — | o-F-Ph | — | H |
| $NO_2$ | 1 | $CH_2COOH$ | — | o-F-Ph | — | H |
| H | 1 | $CH_2CH_3$ | — | o-F-Ph | — | H |
| OH | 1 | $CH_2CH_3$ | — | o-F-Ph | — | H |
| H | 1 | $CH_2COOEt$ | — | o-F-Ph | — | H |
| OH | 1 | $CH_2COOEt$ | — | o-F-Ph | — | H |
| H | 1 | $CH_2CH_2COOH$ | — | o-F-Ph | — | H |
| OH | 1 | $CH_2CH_2COOH$ | — | o-F-Ph | — | H |
| H | 1 | H | — | p-Cl-Ph | — | H |
| F | 1 | H | — | p-Cl-Ph | — | H |
| $CF_3$ | 1 | H | — | p-Cl-Ph | — | H |
| OH | 1 | H | — | p-Cl-Ph | — | H |
| H | 1 | $CH_3$ | — | p-Cl-Ph | — | H |
| F | 1 | $CH_3$ | — | p-Cl-Ph | — | H |
| $CF_3$ | 1 | $CH_3$ | — | p-Cl-Ph | — | H |
| OH | 1 | $CH_3$ | — | p-Cl-Ph | — | H |
| H | 1 | $CH_2COOH$ | — | p-Cl-Ph | — | H |
| F | 1 | $CH_2COOH$ | — | p-Cl-Ph | — | H |
| $CF_3$ | 1 | $CH_2COOH$ | — | p-Cl-Ph | — | H |
| OH | 1 | $CH_2COOH$ | — | p-Cl-Ph | — | H |
| H | 1 | $CH_2CH_3$ | — | p-Cl-Ph | — | H |
| H | 1 | $CH_2COOEt$ | — | p-Cl-Ph | — | H |
| H | 1 | $CH_2CH_2COOH$ | — | p-Cl-Ph | — | H |
| H | 1 | H | — | $CH_2COOt$-Bu | — | H |
| Cl | 1 | H | — | $CH_2COOt$-Bu | — | H |
| F | 1 | H | — | $CH_2COOt$-Bu | — | H |
| $CF_3$ | 1 | H | — | $CH_2COOt$-Bu | — | H |
| OH | 1 | H | — | $CH_2COOt$-Bu | — | H |
| $NO_2$ | 1 | H | — | $CH_2COOt$-Bu | — | H |

TABLE 10-continued

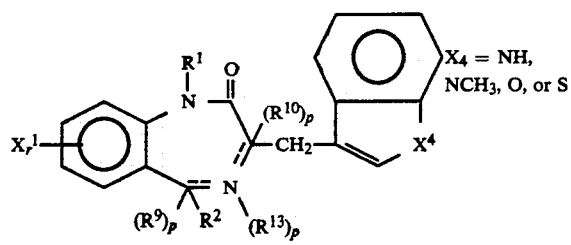

X₄ = NH, NCH₃, O, or S

| X¹ | r | R¹ | (R⁹)p | R² | (R¹³)p | (R¹⁰)p |
|---|---|---|---|---|---|---|
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | CH₂COOH | — | CH₂COOt-Bu | — | H |
| Cl | 1 | CH₂COOH | — | CH₂COOt-Bu | — | H |
| F | 1 | CH₂COOH | — | CH₂COOt-Bu | — | H |
| CF₃ | 1 | CH₂COOH | — | CH₂COOt-Bu | — | H |
| OH | 1 | CH₂COOH | — | CH₂COOt-Bu | — | H |
| NO₂ | 1 | CH₂COOH | — | CH₂COOt-Bu | — | H |
| H | 1 | CH₂CH₃ | — | CH₂COOt-Bu | — | H |
| OH | 1 | CH₂CH₃ | — | CH₂COOt-Bu | — | H |
| H | 1 | CH₂COOEt | — | CH₂COOt-Bu | — | H |
| OH | 1 | CH₂COOEt | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | CH₂COOH | — | CH₂COOEt | — | H |
| Cl | 1 | CH₂COOH | — | CH₂COOEt | — | H |
| F | 1 | CH₂COOH | — | CH₂COOEt | — | H |
| CF₃ | 1 | CH₂COOH | — | CH₂COOEt | — | H |
| OH | 1 | CH₂COOH | — | CH₂COOEt | — | H |
| NO₂ | 1 | CH₂COOH | — | CH₂COOEt | — | H |
| H | 1 | CH₂CH₃ | — | CH₂COOEt | — | H |
| OH | 1 | CH₂CH₃ | — | CH₂COOEt | — | H |
| H | 1 | CH₂COOEt | — | CH₂COOEt | — | H |
| OH | 1 | CH₂COOEt | — | CH₂COOEt | — | H |
| H | 1 | CH₂CH₂COOH | — | CH₂COOEt | — | H |
| OH | 1 | CH₂CH₂COOH | — | CH₂COOEt | — | H |
| H | 1 | CH₃ | — | Ph | — | OH |
| H | 1 | CH₂CH₃ | — | Ph | — | OH |
| H | 1 | CH₂COOEt | — | Ph | — | OH |
| H | 1 | CH₃ | — | o-F-Ph | — | OH |
| H | 1 | CH₂CH₃ | — | o-F-Ph | — | OH |
| H | 1 | CH₂COOEt | — | o-F-Ph | — | OH |
| H | 1 | CH₃ | — | CH₂COOt-Bu | — | OH |
| H | 1 | CH₂CH₃ | — | CH₂COOt-Bu | — | OH |
| H | 1 | CH₂COOEt | — | CH₂COOt-Bu | — | OH |

TABLE 11

| X¹ | r | R¹ | (R⁹)p | R² | (R¹³)p | (R¹⁰)p |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | CH₂COOH | — | Ph | — | H |
| Cl | 1 | CH₂COOH | — | Ph | — | H |
| F | 1 | CH₂COOH | — | Ph | — | H |
| CF₃ | 1 | CH₂COOH | — | Ph | — | H |
| OH | 1 | CH₂COOH | — | Ph | — | H |
| NO₂ | 1 | CH₂COOH | — | Ph | — | H |
| H | 1 | CH₂CH₃ | — | Ph | — | H |
| OH | 1 | CH₂CH₃ | — | Ph | — | H |
| H | 1 | CH₂COOEt | — | Ph | — | H |
| OH | 1 | CH₂COOEt | — | Ph | — | H |
| H | 1 | CH₂CH₂COOH | — | Ph | — | H |
| OH | 1 | CH₂CH₂COOH | — | Ph | — | H |
| H | 1 | H | — | o-F-Ph | — | H |
| Cl | 1 | H | — | o-F-Ph | — | H |
| F | 1 | H | — | o-F-Ph | — | H |
| CF₃ | 1 | H | — | o-F-Ph | — | H |
| OH | 1 | H | — | o-F-Ph | — | H |
| NO₂ | 1 | H | — | o-F-Ph | — | H |
| H | 1 | CH₃ | — | o-F-Ph | — | H |
| Cl | 1 | CH₃ | — | o-F-Ph | — | H |
| F | 1 | CH₃ | — | o-F-Ph | — | H |
| CF₃ | 1 | CH₃ | — | o-F-Ph | — | H |
| OH | 1 | CH₃ | — | o-F-Ph | — | H |
| NO₂ | 1 | CH₃ | — | o-F-Ph | — | H |
| H | 1 | CH₂COOH | — | o-F-Ph | — | H |
| Cl | 1 | CH₂COOH | — | o-F-Ph | — | H |
| F | 1 | CH₂COOH | — | o-F-Ph | — | H |
| CF₃ | 1 | CH₂COOH | — | o-F-Ph | — | H |
| OH | 1 | CH₂COOH | — | o-F-Ph | — | H |
| NO₂ | 1 | CH₂COOH | — | o-F-Ph | — | H |
| H | 1 | CH₂CH₃ | — | o-F-Ph | — | H |
| OH | 1 | CH₂CH₃ | — | o-F-Ph | — | H |
| H | 1 | CH₂COOEt | — | o-F-Ph | — | H |
| OH | 1 | CH₂COOEt | — | o-F-Ph | — | H |
| H | 1 | CH₂CH₂COOH | — | o-F-Ph | — | H |
| OH | 1 | CH₂CH₂COOH | — | o-F-Ph | — | H |
| H | 1 | H | — | p-Cl-Ph | — | H |
| F | 1 | H | — | p-Cl-Ph | — | H |
| CF₃ | 1 | H | — | p-Cl-Ph | — | H |
| OH | 1 | H | — | p-Cl-Ph | — | H |
| H | 1 | CH₃ | — | p-Cl-Ph | — | H |
| F | 1 | CH₃ | — | p-Cl-Ph | — | H |
| CF₃ | 1 | CH₃ | — | p-Cl-Ph | — | H |
| OH | 1 | CH₃ | — | p-Cl-Ph | — | H |
| H | 1 | CH₂COOH | — | p-Cl-Ph | — | H |
| F | 1 | CH₂COOH | — | p-Cl-Ph | — | H |
| CF₃ | 1 | CH₂COOH | — | p-Cl-Ph | — | H |
| OH | 1 | CH₂COOH | — | p-Cl-Ph | — | H |
| H | 1 | CH₂CH₃ | — | p-Cl-Ph | — | H |
| H | 1 | CH₂COOEt | — | p-Cl-Ph | — | H |
| H | 1 | CH₂CH₂COOH | — | p-Cl-Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |

TABLE 11-continued

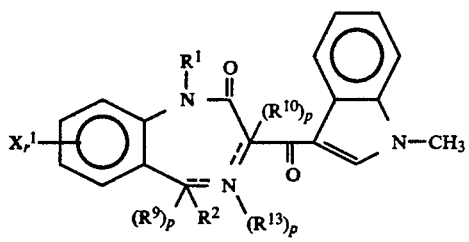

| X¹ | r | R¹ | (R⁹)ₚ | R² | (R¹³)ₚ | (R¹⁰)ₚ |
|---|---|---|---|---|---|---|
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | CH₂COOH | — | CH₂COOt-Bu | — | H |
| Cl | 1 | CH₂COOH | — | CH₂COOt-Bu | — | H |
| F | 1 | CH₂COOH | — | CH₂COOt-Bu | — | H |
| CF₃ | 1 | CH₂COOH | — | CH₂COOt-Bu | — | H |
| OH | 1 | CH₂COOH | — | CH₂COOt-Bu | — | H |
| NO₂ | 1 | CH₂COOH | — | CH₂COOt-Bu | — | H |
| H | 1 | CH₂CH₃ | — | CH₂COOt-Bu | — | H |
| OH | 1 | CH₂CH₃ | — | CH₂COOt-Bu | — | H |
| H | 1 | CH₂COOEt | — | CH₂COOt-Bu | — | H |
| OH | 1 | CH₂COOEt | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | CH₂COOH | — | CH₂COOEt | — | H |
| Cl | 1 | CH₂COOH | — | CH₂COOEt | — | H |
| F | 1 | CH₂COOH | — | CH₂COOEt | — | H |
| CF₃ | 1 | CH₂COOH | — | CH₂COOEt | — | H |
| OH | 1 | CH₂COOH | — | CH₂COOEt | — | H |
| NO₂ | 1 | CH₂COOH | — | CH₂COOEt | — | H |
| H | 1 | CH₂CH₃ | — | CH₂COOEt | — | H |
| OH | 1 | CH₂CH₃ | — | CH₂COOEt | — | H |
| H | 1 | CH₂COOEt | — | CH₂COOEt | — | H |
| OH | 1 | CH₂COOEt | — | CH₂COOEt | — | H |
| H | 1 | CH₂CH₂COOH | — | CH₂COOEt | — | H |
| OH | 1 | CH₂CH₂COOH | — | CH₂COOEt | — | H |
| H | 1 | CH₃ | — | Ph | — | OH |
| H | 1 | CH₂CH₃ | — | Ph | — | OH |
| H | 1 | CH₂COOEt | — | Ph | — | OH |
| H | 1 | CH₃ | — | o-F-Ph | — | OH |
| H | 1 | CH₂CH₃ | — | o-F-Ph | — | OH |
| H | 1 | CH₂COOEt | — | o-F-Ph | — | OH |
| H | 1 | CH₃ | — | CH₂COOt-Bu | — | OH |
| H | 1 | CH₂CH₃ | — | CH₂COOt-Bu | — | OH |
| H | 1 | CH₂COOEt | — | CH₂COOt-Bu | — | OH |

TABLE 12

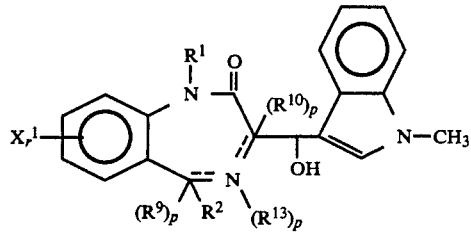

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | CH₂COOH | — | Ph | — | H |
| Cl | 1 | CH₂COOH | — | Ph | — | H |
| F | 1 | CH₂COOH | — | Ph | — | H |
| CF₃ | 1 | CH₂COOH | — | Ph | — | H |
| OH | 1 | CH₂COOH | — | Ph | — | H |
| NO₂ | 1 | CH₂COOH | — | Ph | — | H |
| H | 1 | CH₂CH₃ | — | Ph | — | H |
| OH | 1 | CH₂CH₃ | — | Ph | — | H |
| H | 1 | CH₂COOEt | — | Ph | — | H |
| OH | 1 | CH₂COOEt | — | Ph | — | H |
| H | 1 | CH₂CH₂COOH | — | Ph | — | H |
| OH | 1 | CH₂CH₂COOH | — | Ph | — | H |
| H | 1 | H | — | o-F-Ph | — | H |
| Cl | 1 | H | — | o-F-Ph | — | H |
| F | 1 | H | — | o-F-Ph | — | H |
| CF₃ | 1 | H | — | o-F-Ph | — | H |
| OH | 1 | H | — | o-F-Ph | — | H |
| NO₂ | 1 | H | — | o-F-Ph | — | H |
| H | 1 | CH₃ | — | o-F-Ph | — | H |
| Cl | 1 | CH₃ | — | o-F-Ph | — | H |
| F | 1 | CH₃ | — | o-F-Ph | — | H |
| CF₃ | 1 | CH₃ | — | o-F-Ph | — | H |
| OH | 1 | CH₃ | — | o-F-Ph | — | H |
| NO₂ | 1 | CH₃ | — | o-F-Ph | — | H |
| H | 1 | CH₂COOH | — | o-F-Ph | — | H |
| Cl | 1 | CH₂COOH | — | o-F-Ph | — | H |
| F | 1 | CH₂COOH | — | o-F-Ph | — | H |
| CF₃ | 1 | CH₂COOH | — | o-F-Ph | — | H |
| OH | 1 | CH₂COOH | — | o-F-Ph | — | H |
| NO₂ | 1 | CH₂COOH | — | o-F-Ph | — | H |
| H | 1 | CH₂CH₃ | — | o-F-Ph | — | H |
| OH | 1 | CH₂CH₃ | — | o-F-Ph | — | H |
| H | 1 | CH₂COOEt | — | o-F-Ph | — | H |
| OH | 1 | CH₂COOEt | — | o-F-Ph | — | H |
| H | 1 | CH₂CH₂COOH | — | o-F-Ph | — | H |
| OH | 1 | CH₂CH₂COOH | — | o-F-Ph | — | H |
| H | 1 | H | — | p-Cl-Ph | — | H |
| F | 1 | H | — | p-Cl-Ph | — | H |
| CF₃ | 1 | H | — | p-Cl-Ph | — | H |
| OH | 1 | H | — | p-Cl-Ph | — | H |
| H | 1 | CH₃ | — | p-Cl-Ph | — | H |
| F | 1 | CH₃ | — | p-Cl-Ph | — | H |
| CF₃ | 1 | CH₃ | — | p-Cl-Ph | — | H |
| OH | 1 | CH₃ | — | p-Cl-Ph | — | H |
| H | 1 | CH₂COOH | — | p-Cl-Ph | — | H |
| F | 1 | CH₂COOH | — | p-Cl-Ph | — | H |
| CF₃ | 1 | CH₂COOH | — | p-Cl-Ph | — | H |
| OH | 1 | CH₂COOH | — | p-Cl-Ph | — | H |
| H | 1 | CH₂CH₃ | — | p-Cl-Ph | — | H |
| H | 1 | CH₂COOEt | — | p-Cl-Ph | — | H |
| H | 1 | CH₂CH₂COOH | — | p-Cl-Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |

TABLE 12-continued

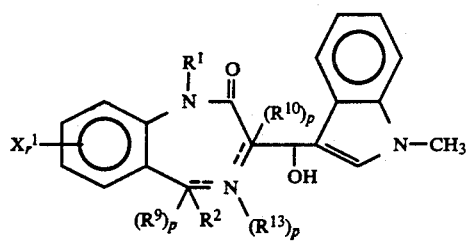

| X¹ | r | R¹ | (R⁹)ₚ | R² | (R¹³)ₚ | (R¹⁰)ₚ |
|---|---|---|---|---|---|---|
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | CH₂COOH | — | CH₂COOt-Bu | — | H |
| Cl | 1 | CH₂COOH | — | CH₂COOt-Bu | — | H |
| F | 1 | CH₂COOH | — | CH₂COOt-Bu | — | H |
| CF₃ | 1 | CH₂COOH | — | CH₂COOt-Bu | — | H |
| OH | 1 | CH₂COOH | — | CH₂COOt-Bu | — | H |
| NO₂ | 1 | CH₂COOH | — | CH₂COOt-Bu | — | H |
| H | 1 | CH₂CH₃ | — | CH₂COOt-Bu | — | H |
| OH | 1 | CH₂CH₃ | — | CH₂COOt-Bu | — | H |
| H | 1 | CH₂COOEt | — | CH₂COOt-Bu | — | H |
| OH | 1 | CH₂COOEt | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |

TABLE 12-continued

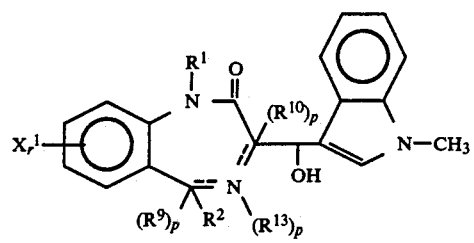

| X¹ | r | R¹ | (R⁹)ₚ | R² | (R¹³)ₚ | (R¹⁰)ₚ |
|---|---|---|---|---|---|---|
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | CH₂COOH | — | CH₂COOEt | — | H |
| Cl | 1 | CH₂COOH | — | CH₂COOEt | — | H |
| F | 1 | CH₂COOH | — | CH₂COOEt | — | H |
| CF₃ | 1 | CH₂COOH | — | CH₂COOEt | — | H |
| OH | 1 | CH₂COOH | — | CH₂COOEt | — | H |
| NO₂ | 1 | CH₂COOH | — | CH₂COOEt | — | H |
| H | 1 | CH₂CH₃ | — | CH₂COOEt | — | H |
| OH | 1 | CH₂CH₃ | — | CH₂COOEt | — | H |
| H | 1 | CH₂COOEt | — | CH₂COOEt | — | H |
| OH | 1 | CH₂COOEt | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 13

Compounds of the Formula

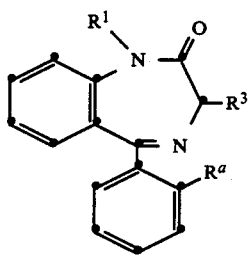

| No. | Rᵃ | R¹ | R³ |
|---|---|---|---|
| 577 | F | —CH₂—CF₃ | ![indole-CH2] |
| 586 | F | H | ![thiophene] |
| 625 | H | H | —NH—CO—CH₂—[indole] |
| 643 | F | —(CH₂)₂—CN | —CH₂—[azaindole] |

TABLE 13-continued
Compounds of the Formula
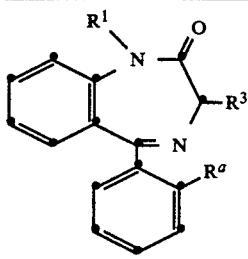
| No. | $R^a$ | $R^1$ | $R^3$ |
|---|---|---|---|
| 648 | F | H | —NH—CO-(1H-indol-2-yl) |
| 651 | F | H | —NH—CO-(4-nitrophenyl) |
| 652 | H | H | —O—CO-(1H-indol-2-yl) |
| 659 | F | H | —NH—CO-(2-methylthien-3-yl) |
| 665 | H | H | —NH—CO-(1H-indol-2-yl) |
| 666 | F | H | —NH—CO-(1H-indol-2-yl) |
| 668 | F | H | —NH—CO—CH$_2$-(benzothien-3-yl) |
| 676 | F | H | —NH—CO-(quinolin-2-yl) |
| 677 | F | H | —NH—CO—CHOH-phenyl |

TABLE 13-continued
Compounds of the Formula
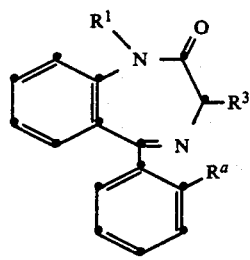
| No. | $R^a$ | $R^1$ | $R^3$ |
|---|---|---|---|
| 678 | F | H | —NH—CO—(5-chloro-indol-2-yl) |
| 679 | H | H | —N(CH₃)—CO—(indol-2-yl) |
| 686 | F | H | —NH—CO—(5-bromo-indol-2-yl) |
| 688 | F | H | —NH—CO—(5-hydroxy-indol-2-yl) |
| 690 | F | —CH₂—CO—NH₂ | —CH₂—(indol-2-yl) |
| 691 | F | H | —NH—CH₂—(indol-2-yl) |
| 692 | F | H | —NH—CO—CH₂—NH—phenyl |
| 694 | F | H | —NH—CO—(5-methoxy-indol-2-yl) |

TABLE 13-continued
Compounds of the Formula
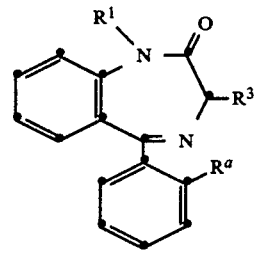
| No. | $R^a$ | $R^1$ | $R^3$ |
|---|---|---|---|
| 695 | F | H | —NH—CO—(1-methylindol-2-yl) |
| 716 | H | H | —NH—CO—phenyl |
| 720 | F | H | —NH—CO—(2-chlorophenyl) |
| 722 | H | H | —NH—CO—(indolin-2-yl) |
| 724 | H | H | —NH—CO—(2-chlorophenyl) |
| 725 | H | CH$_3$ | —NH—CO—(2-chlorophenyl) [(−)-enantiomer] |
| 726 | H | CH$_3$ | —NH—CO—(2-chlorophenyl) [(+)-enantiomer] |
| 736 | F | H | —NH—CO—(4-trifluoromethylphenyl) |
| 737 | F | H | —NH—CO—(4-methylphenyl) |

TABLE 13-continued
Compounds of the Formula
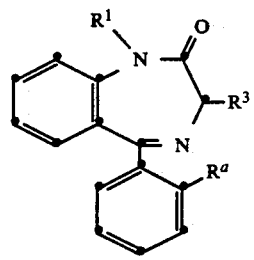
| No. | $R^a$ | $R^1$ | $R^3$ |
|---|---|---|---|
| 727 | H | CH$_3$ | —N(CH$_3$)—CO—(2-Cl-phenyl) |
| 728 | H | CH$_3$ | —NH—CO—(2-Cl-phenyl) |
| 740 | H | H | —NH—CO—(4-Cl-phenyl) |
| 745 | F | H | —NH—CO—(4-OCH$_3$-phenyl) |
| 752 | F | H | —NH—CO—(3,4-(OCH$_3$)$_2$-phenyl) |
| 753 | F | H | —NH—CO—(pentafluorophenyl) |
| 755 | H | H | —NH—CO—(3,4-Cl$_2$-phenyl) |
| 761 | F | CH$_3$ | —NH—CO—(4-Cl-phenyl) (N$^4$-oxide) |
| 763 | F | H | —NH—COO—CH$_2$—phenyl |

TABLE 13-continued
Compounds of the Formula
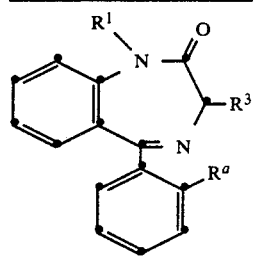
| No. | $R^a$ | $R^1$ | $R^3$ |
|---|---|---|---|
| 772 | H | H | —NH—CO—C6H4—SCH3 (para) |
| 779 | F | —CO—C6H4—Cl (para) | —NH—CO—C6H4—Cl (para) |
| 781 | H | H | —NH—CO—C6H4—SCF3 (meta) |
| 782 | H | H | —NH—CO—C6H4—CF3 (para) |
| 786 | F | —NH—CO—C6H4—SCF3 (para) | —O—CO—C6H4—Cl (para) |
| 787 | F | H | —O—CO—C6H4—Cl (para) |
| 790 | F | CH3 | —NH—CO—C6H4—C(CH3)3 (para) (+)enantiomer |
| 791 | F | H | —NH—CO—(pyrrole-2-yl) |
| 793 | H | H | —NH—CO—(2-naphthyl) |
| 794 | F | CH3 | —NH—CO—C6H4—Br (meta) (−)enantiomer |

TABLE 13-continued
Compounds of the Formula
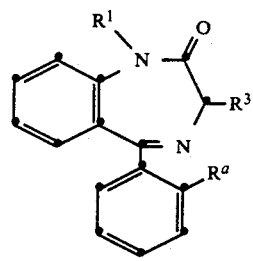
| No. | $R^a$ | $R^1$ | $R^3$ |
|---|---|---|---|
| 795 | F | CH$_3$ | 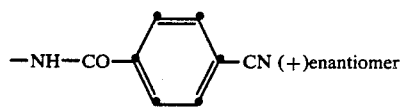 —NH—CO—⟨⟩—CN (+)enantiomer |
| 796 | H | H | 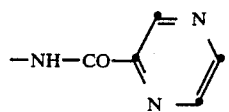 |
| 799 | H | H |  |
| 800 | H | H | 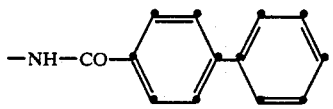 |
| 801 | H | H | 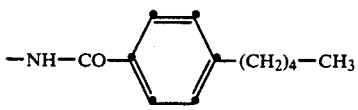 |
| 802 | H | H |  |
| 803 | H | H | 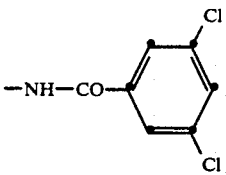 |
| 804 | H | H | 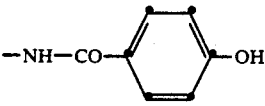 |
| 805 | H | H | 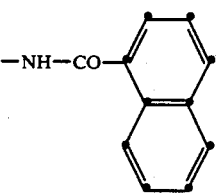 |

TABLE 13-continued

Compounds of the Formula

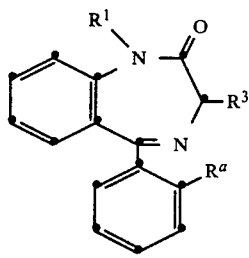

| No. | $R^a$ | $R^1$ | $R^3$ |
|---|---|---|---|
| 816 | H | H | —NH—CO—C₆H₄—CN |
| 825 | F | CH₃ | —NH—CO—(iodophenyl) (+)enantiomer |
| 827 | F | CH₃ | —NH—CO—(iodophenyl) (−)enantiomer |
| 829 | F | CH₃ | —NH—CO—(bromophenyl) (+)enantiomer |
| 830 | F | CH₃ | —NH—CO—(chlorophenyl) (+)enantiomer |

Other compounds of Formula I are listed on the following table.

TABLE 14

| No. | Compound |
|---|---|
| 632 | [structure: benzodiazepine with —CH₂—NH—COO—CH₂—phenyl and 2-F phenyl] |

TABLE 14-continued
| No. | Compound |
|-----|----------|
| 633 | 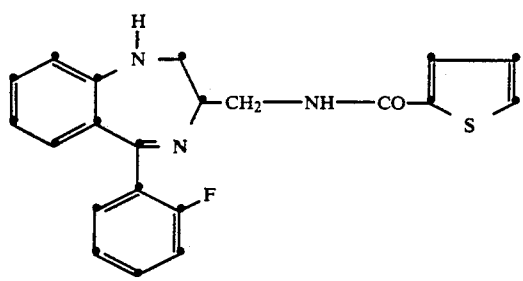 |
| 636 | 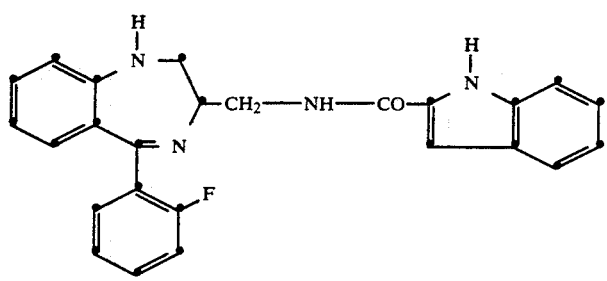 |
| 638 | 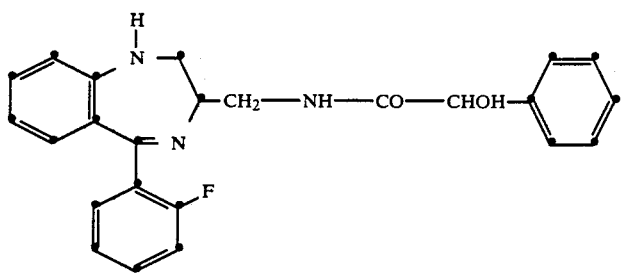 |
| 646 | 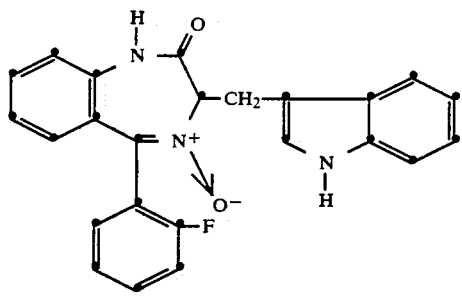 |
| 732 | 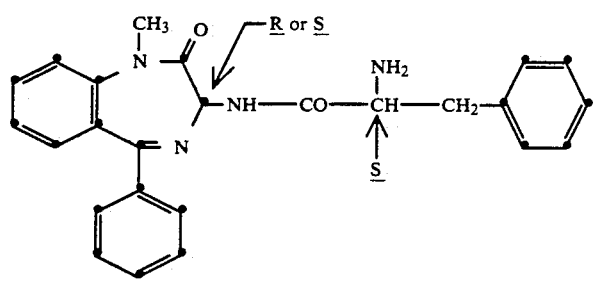 |

TABLE 14-continued
| No. | Compound |
|---|---|
| 733 | 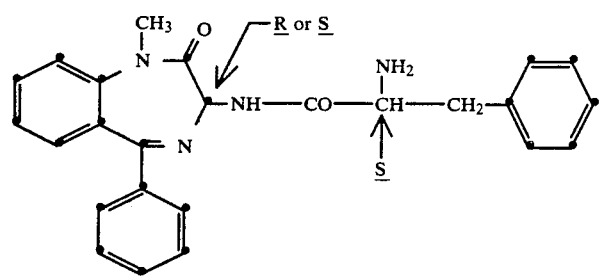 |
| 777 | 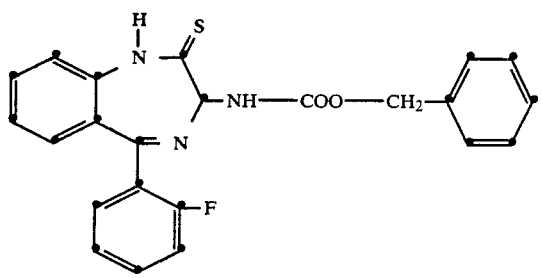 |
| 808 | 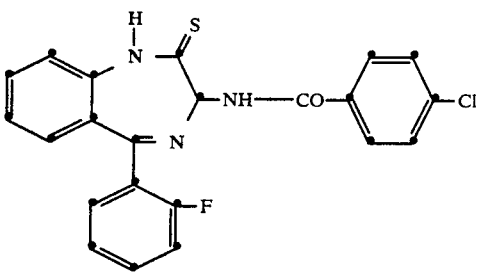 |
| 809 | 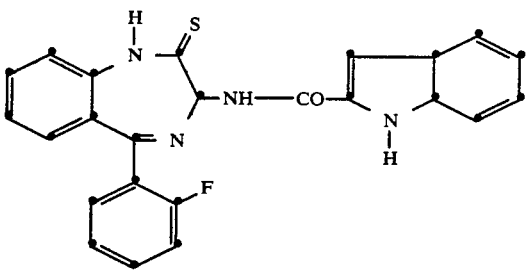 |
| 826 | 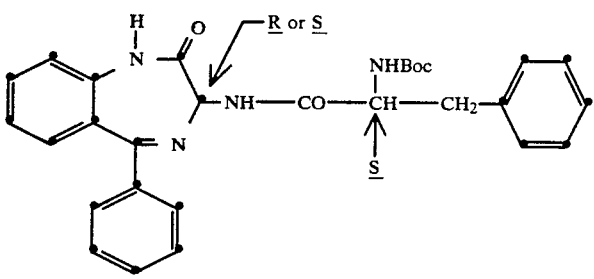 |

TABLE 14-continued

| No. | Compound |
| --- | --- |
| 828 | 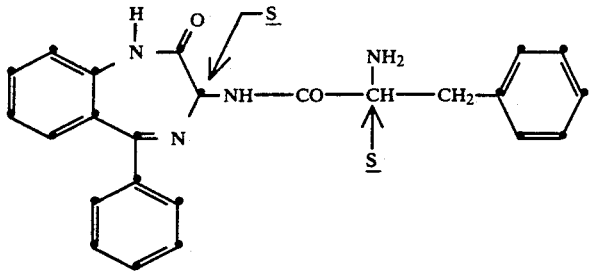 |

The invention is further defined by reference to the following preparations and examples, which are intended to be illustrative and not limiting.

All temperatures are in degrees Celsius.

EXAMPLE 1

2-N-(Nα-Boc-D-tryptophanyl)amino-2'-fluorobenzophenone

2-Amino-2'-fluorobenzophenone (4 g, 18.6 mmole), Boc-D-tryptophan (5.65 g, 18.6 mmole) and dicyclohexylcarbodiimide (DCC) (18.6 ml of a 1M solution in methylene chloride, 18.6 mmole) were combined in 28 ml of dry tetrahydrofuran stirred in an ice bath. The mixture was allowed to warm to room temperature and stirred overnight. The solids were removed by filtration and the filtrate evaporated in vacuo. The residue was chromatographed on 9" (23 cm) of silica gel (230–400 mesh) in a 55 mm diameter column using 1 L of each of methylene chloride and 2% and 3% (v/v) diethyl ether in methylene chloride.

The product fractions were combined and evaporated in vacuo. The residue was crystallized from diethyl ether and the resulting solid dried in vacuo at 40° for 20 hours: (m.p. 64°-67°).

The compound showed a single component by thin layer chromatography (TLC) ($R_f$=0.36, silica gel plate eluted with 6% (v/v) diethyl ether in methylene chloride). The NMR spectrum was consistent with the title structure and verified the presence of $Et_2O$.

Anal. Calc'd for $C_{29}H_{28}FN_3O_4 \cdot Et_2O$: C, 68.85; H, 6.65; N, 7.30. Found: C, 69.25; H, 6.75; N, 7.30.

EXAMPLE 2

1,3-Dihydro-5-(2-fluorophenyl)-3(R)-(3'-indolyl)methyl-2H-1,4-benzodiazepin-2-one 2-N-(Nα-Boc-D-tryptophanyl)amino-2'-fluorobenzophenone (4.0 g=8.0 mmole) in 37 ml of ethyl acetate was stirred in an ice bath and saturated with hydrogen chloride gas for 20 minutes. The mixture was evaporated to dryness in vacuo to give 2-N-(D-tryptophanyl)amino-2'-fluorobenzophenonehydrochloride. The residue in 125 ml of methanol was treated with 30 ml of water and the pH of the mixture adjusted to 8.5–9.0 with 10% sodium hydroxide solution. The mixture was stirred at room temperature for three days.

The suspension was filtered and the resulting white solid dried in vacuo at 40° overnight: (m.p. 251°-254°).

The compound showed a single component by thin layer chromatography (TLC) ($R_f$=0.59, silica gel plate eluted with 1:1 (v/v) diethyl ether/methylene chloride) and by HPLC (greater than 99%). The NMR spectrum was consistent with the title structure. The mass spectrum showed a molecular ion at m/e=383.

Anal. Calcd. for $C_{24}H_{18}FN_3O$: C, 75.18; H, 4.73; N, 10.96. Found: C, 74.88; H, 4.70, N, 10.65.

EXAMPLE 3

1,3-Dihydro-5-(2-fluorophenyl)-3(R)-(3'-indolyl)methyl-2H-1,4-benzodiazepin-2-one 2-Amino-2'-fluorobenzophenone (12.5 g=58 mmole) was stirred in 100 ml of dry tetrahydrofuran in an ice bath. D-Tryptophan acid chloride hydrochloride (16 g=62 mmole), slurried in 50 ml of tetrahydrofuran, was added over 10 minutes, and the mixture stirred 2 hours in the ice bath. The resulting solid was filtered, then added to 200 ml of methanol containing 200 ml of water. The pH was adjusted to 8.5-9.0 with 10% sodium hydroxide, the mixture was stirred for three days, then filtered. The solid was dried in vacuo at 40°.

EXAMPLE 4

1,3-Dihydro-5-(2-fluorophenyl)-3(R)-[3'-(1'-methylindolyl)-methyl]-1-methyl-2H-1,4-benzodiazepin-2-one (A) and 1,3-dihydro-5-(2-fluorophenyl)-3(R)-(3'-indolyl)methyl-1-methyl-2H-1,4-benzodiazepin-2-one (B)

A 1,3-Dihydro-5-(2-fluorophenyl)-3(R)-(3'-indolyl)-methyl-2H-1,4-benzodiazepin-2-one (0.85 g, 2.2 mmole) and sodium hydride (0.11 g of a 50% suspension in mineral oil, 2.3 mmole) were stirred in 10 ml of dry, degassed dimethylformamide under nitrogen in an ice bath. After 40 minutes, methyl iodide (0.14 mL=2.25 mmole) was added in one portion. The mixture was stirred for 1.5 hours at room temperature, then poured into 100 ml of water and extracted with methylene chloride ($CH_2Cl_2$) (3×30 mL). The $CH_2Cl_2$ layers were washed with water, dried over potassium carbonate, filtered and evaporated in vacuo. The residue was chromatographed on 9" (23 cm) of silica gel (250–400 mesh) in a 55 mm diameter column eluted with 4% (v/v) diethyl ether in $CH_2Cl_2$. The first product eluted was A which was obtained as a glass upon evaporation. The solid was dried in vacuo at room temperature: (m.p. 97°-100° ( )).

The compound showed a single component by thin layer chromatography ($R_f$=0.57, silica gel plate eluted with 10% (v/v) diethyl ether in $CH_2Cl_2$) and by HPLC (98%). The NMR spectrum was consistent with the title structure and verified the presence of $CH_2Cl_2$. The mass spectrum showed a molecular ion at m/e=411.

Anal. Calc'd. for $C_{26}H_{22}FN_3O \cdot 0.1CH_2Cl_2$ C, 74.64; H, 5.33, N, 10.01. Found: C, 74.69; H, 5.32; N, 9.63.

B The second component eluted was the monomethyl compound B which was obtained as a foam (0.66 g) upon evaporation. Crystallization from hexane/CH$_2$Cl$_2$ gave analytical material; (m.p. 80°–85° (↑)).

The compound showed a single component by thin layer chromatography (silica gel plates eluted with 4% (v/v) diethyl ether in CH$_2$Cl$_2$) and by HPLC (99%). The NMR spectrum was consistent with the title structure and verified the presence of CH$_2$Cl$_2$.

Anal. Calc'd for C$_{25}$H$_{20}$FN$_3$O.0.75CH$_2$Cl$_2$: C, 67.06, H, 4.70; N, 9.11. Found: C, 67.04; H, 4.81; N, 9.14.

EXAMPLE 5

7-Chloro-1,3-dihydro-3(R)-(3'-indolyl)methyl-5-phenyl-2H-1,4-benzodiazepin-2-one 2-Amino-5-chlorobenzophenone (1.2 g, 5.2 mmole) and D-tryptophan methyl ester hydrochloride (1.3 g, 5.1 mmole) were combined in dry pyridine (25 mL) and heated at reflux under nitrogen for 5 hrs. The mixture was evaporated in vacuo and the residue washed twice with pH 6 buffer and dissolved in ethyl acetate (50 mL). The ethyl acetate solution was dried over sodium sulfate, filtered, and evaporated in vacuo to give an oil which was chromatographed on a 13 inch (33 cm) column of silica gel (230–400 mesh) in a 25 mm diameter column eluted with 20% (v/v) ether methylene chloride. The product fractions were evaporated in vacuo to give the title compound as a white solid which was dried in vacuo at 100°: (m.p. 130°–155° (↑)).

The compound showed a single spot by thin layer chromatography (R$_f$=0.36, silica gel plate eluted with 4:1 CH$_2$Cl$_2$/ether) The NMR spectrum was consistent with the title structure and verified the presence of ether. The compound was 99.8% pure by HPLC. The mass spectrum showed a molecular ion at m/e=399.

Anal. Calc'd for C$_{24}$H$_{18}$ClN$_3$O.0.5C$_4$H$_{10}$O: C, 71.47; H, 5.31; N, 9.62; Cl, 8.12. Found C, 71.62; H, 5.83; N, 9.47; Cl, 8.24.

EXAMPLE 6

1,3-Dihydro-3(R)-(3'-indolyl)methyl-5-phenyl-2H-1,4-benzodiazepin-2-one

The procedure of Example 1 was carried out using 2-aminobenzophenone (1.97 g, 0.01 mole), Boc-D-tryptophan (3.04 g, 0.01 mole) and DCC (10 mL of 1M solution in methylene chloride (CH$_2$Cl$_2$) in THF (15 mL). The crude product obtained after filtration and evaporation of the mixture was deprotected and cyclized by the procedure of Example 2. The mixture was evaporated in vacuo, combined with water (50 mL) and extracted with chloroform (250 mL). The chloroform solution was hired over potassium carbonate, filtered, and evaporated to dryness in vacuo. Recrystallization from a mixture of acetone (50 mL) and ether (50 mL) gave a white solid which was dried in vacuo at 100°: (m.p. 260°–263° (d)).

The compound showed a single spot by TLC (R$_f$=0.53, silica gel plate eluted with 1:1 CH$_2$Cl$_2$/ether). The NMR spectrum was consistent with the title structure and verified the presence of acetone. The compound was 99.6% pure by HPLC. The mass spectrum showed a molecular ion at m/e=365.

Anal. Calc'd for C$_{24}$H$_{19}$N$_3$O.0.5C$_3$H$_6$O: C, 77.64, H, 5.62, N, 10.65. Found: C, 77.34, H, 5.44, N, 10.87.

EXAMPLE 7

1,3-Dihydro-3(S)-[3'-(1'-methylindolyl)methyl]-1-methyl-5-methylthio-2H-1,4-benzodiazepin-2-one 1,3-Dihydro-3(S)-(3'-indolyl)methyl-2H-1,4-benzodiazepin-2-one-5-thione (450 mg, 1.4 mmole) was suspended in 30 ml of toluene, 8 ml of tetrahydrofuran, and 15 ml of 40% sodium hydroxide solution. This mixture was treated with 203 mg (0.6 mmole) of tetra-n-butylammonium sulfate and 0.25 ml (4.0 mmole) of iodomethane and stirred rapidly at room temperature. After four hours the phases were separated and the aqueous layer extracted once with ethyl acetate. The combined organic extracts were washed with water (2×50 ml) and brine, then dried (MgSO$_4$) and concentrated in vacuo to afford a yellow oil. Preparative thick layer chromatography (hexane-ethyl acetate 2:1 v/v) afforded the title compound as a white solid. R$_f$=0.45 (2:1 hexane-ethyl acetate). The analytical sample was recrystallized from ethyl acetate-ether, m.p. 170° C.; TLC, HPLC: 99% pure. Pmr (CDCl$_3$) according to theory (methyl proton resonate 2.46 ppm, 3.39 ppm, and 3.72 ppm respectively). MS (20 ev.): 363 (M+), 184, 144.

Elemental Analysis: C$_{21}$H$_{21}$N$_3$OS Calc'd.: N, 11.56; C, 69.39; H, 5.82. Found: N, 11.47; C, 69.22; H, 6.04.

EXAMPLE 8

1,3-Dihydro-3(S)-(3'-indolyl)methyl-1-methyl-5-methylthio-2H-1,4-benzodiazepin-2-one 1,3-Dihydro-3(S)-(3'-indolyl)methyl-2H-1,4-benzodiazepin-2-one-5-thione (450 mg, 1.4 mmole) was suspended in 30 ml of toluene, 8 ml of tetrahydrofuran, and 15 ml of 40% sodium hydroxide solution. The mixture was treated with 203 mg (0.6 mmole) of tetra-n-butylammonium sulfate and 0.25 ml (4.0 mmole) of iodomethane and stirred rapidly at room temperature. After four hours the phases were separated and the aqueous layer extracted once with ethyl acetate. The combined organic extracts were washed with water (2×50 ml) and brine, then dried (MgSO$_4$) and concentrated in vacuo to afford a yellow oil. Preparative thick layer chromatography (hexane-ethyl acetate 2:1 v/v) afforded the title compound as a white solid. R$_f$=0.40 (2:1 hexane-ethyl acetate). The analytical sample was recrystallized from ethyl acetate-ether, m.p. 90°–91° C. TLC, HPLC: 99% pure. Pmr (CDCl$_3$): according to theory (methyl protons resonate at 2.45 ppm and 3.40 ppm, respectively): MS (20 ev): 349 (M+), 302, 220, 130.

Elemental Analysis: C$_{20}$H$_{19}$N$_3$OS. Calc'd.: N, 12.02; C, 68.74; H, 5.48. Found: N, 12.10; C, 68.58; H, 5.71.

EXAMPLE 9

1,3-Dihydro-5-(2-fluorophenyl)-3(R)-(3'-α-indolenyl)-methyl-2H-1,4-benzodiazepin-2-one 1,3-Dihydro-5-(2-fluorophenyl)-3(R)-(3'-indolyl)-methyl-2H-1,4-benzodiazepin-2-one (120 mg, 0.31 mmole) was dissolved in 2 ml of trifluoroacetic acid. The resulting orange solution was treated with 0.5 ml (3.1 mmole) of triethylsilane and stirred rapidly at room temperature. After two hours, the reaction mixture was rotoevaporated to dryness and the residue was partitioned between water/ethyl acetate. The organic phase was washed with sodium bicarbonate solution (sat.), and brine, then dried (MgSO$_4$) and concentrated. The analytical sample was obtain via preparative thick layer chromatography on silica gel (1:1 hexane-ethyl acetate v/v, multiple elutions).

$R_f$=0.38 (2:1 ethyl acetate-hexane). Pmr (CDCl$_3$): in accord with theory. MS (FAB): 386 (M+H). Elemental Analysis: C$_{24}$H$_{20}$FN$_3$O.0.4H$_2$O Calc'd.: N, 10.70, C, 73.41, H, 5.34. Found: N, 10.50, C, 73.62, H, 5.45.

EXAMPLE 10

1,3-Dihydro-5-(2-fluorophenyl)-3(R)-(3'-β-indolenyl)-methyl-2H-1,4-benzodiazepin-2-one 1,3-Dihydro-5-(2-fluorophenyl)-3(R)-(3'-indolyl)-methyl-2H-1,4-benzodiazepin-2-one (120 mg, 0.31 mmole) was dissolved in 2 ml of trifluoroacetic acid. The resulting orange solution was treated with 0.5 ml (3.1 mmole) of triethylsilane and stirred rapidly at room temperature. After two hours, the reaction mixture was rotoevaporated to dryness and the residue was partitioned between water/ethyl acetate. The organic phase was washed with sodium bicarbonate solution (sat.), and brine, then dried (MgSO$_4$) and concentrated. The analytical sample was obtained via preparative thick layer chromatography on silica gel (1:1 hexane-ethyl acetate v/v, multiple elutions). $R_f$=0.30 (2:1 ethyl acetate-hexane). Pmr (CDCl$_3$) : in accord with theory. MS (FAB): 386 (M+H).

Elemental Analysis: C$_{24}$H$_{20}$FN$_3$O.0.3H$_2$O Calc'd.: N, 10.75; C, 73.75; H, 5.31. Found: N, 10.57; C, 73.86; H, 5.38.

EXAMPLE 11

1,3-Dihydro-5-(2-fluorophenyl)-3(R)-(3'-indolyl)methyl-2H-1,4-benzodiazepin-2-thione 1,3-Dihydro-5-(2-fluorophenyl)-3(R)-(3'-indolyl)-methyl-2H-1,4-benzodiazepin-2-one (6.98 g, 18.20 mmole) was refluxed with 4.41 g (10.92 mmole) of 2,4-bis-(4-methoxyphenyl)-2,4-dithioxo-1,3,2,4-dithiadiphosphetane in 100 ml of toluene for 1.5 hours. The solvent was removed in vacuo and the residue partitioned between ethylacetate and 10% sodium hydroxide solution. The organic phase was washed with 10% sodium hydroxide (3×50 ml) and brine, then dried (MgSO$_4$) and rotoevaporated to give an orange oil (10 g). Plug filtration of the crude product through silica gel (100 g) afforded a solid which was recrystallized from ether to afford the analytical sample. m.p. 147°–148° C. Pmr: according to theory.

EXAMPLE 12

1,3-Dihydro-5-(2-fluorophenyl)-3(R)-(3'-indolyl)methyl-2H-1,4-benzodiazepine To a solution of 1,3-dihydro-5-(2-fluorophenyl)-3(R)-(3'-indolyl)methyl-2H-1,4-benzodiazepin-2-thione (178 mg, 0.44 mmole) in 20 ml of absolute ethanol was added at room temperature one spatula of moist (ethanol) Raney-nickel catalyst (freshly prepared according to Fieser and Fieser, "Reagents for Organic Synthesis", Vol. I, p. 729, John Wiley & Sons., Inc. N.Y., 1967). The resulting suspension was protected from moisture and stirred rapidly for one hour. The reaction mixture was filtered and the filtrate concentrated to give 150 mg of a yellow oil. Purification via silica gel chromatography (chloroform-methanol-ammonia 95:5:0.5 v/v) afforded the analytical sample.

TLC, HPLC: confirmed purity. MS (20 ev): 369 (M+), 239, 212, 130, 83. Pmr (CDCl$_3$): according to theory. Elemental Analysis: C$_{24}$H$_{20}$FN$_3$.0.07 CHCl$_3$. Calc'd.: N, 11.12; C, 76.52; H, 5.35. Found: N, 10.90; C, 76.66; H, 5.59.

EXAMPLE 13

7-Chloro-1,3-dihydro-3(R)-benzyl-5-phenyl-2H-1,4-benzodiazepin-2-one

The procedure of Example 1 was carried out using 2-amino-5-chlorobenzophenone (2.32 gm, 0.01 mol), Boc-D-Phenylalanine (2.65 gm, 0.01 mol), and DCC (10 ml of 1.0M solution in CH$_2$Cl$_2$) in CH$_2$Cl$_2$ (10 ml). After filtration and evaporation, the crude solid was deprotected and cyclized by the procedure of Example 2. After stirring 5 days, the mixture was evaporated in vacuo, treated with H$_2$O (50 ml), and extracted with EtOAc (2×100 ml). The combined organic extracts were washed with brine (50 ml), dried over MgSO$_4$, filtered and evaporated to dryness in vacuo. Chromatography on silica gel eluted with 7.5% (v/v) Et$_2$O in CH$_2$Cl$_2$ gave a white foam which was crystallized from Et$_2$O. The solid was dried in vacuo at 65° C.: (m.p. 154°–7° C.).

The compound showed a single spot by TLC ($R_f$=0.32, silica gel plate eluted with 10% (v/v) Et$_2$O in CH$_2$Cl$_2$). The NMR spectrum was consistent with the title structure. The compound was 100% pure by HPLC.

Anal. Calc'd for C$_{22}$H$_{17}$ClN$_2$O: C, 73.23; H, 4.75; N, 7.76; Cl, 9.83. Found: C, 73.59; H, 4.78; N, 7.95; Cl, 10.03.

EXAMPLE 14

7-Chloro-1,3-dihydro-3(R)-(2-methyl-1-propyl)-5-phenyl-2H-1,4-benzodiazepin-2-one The procedure of Example 1 was carried out using 2-amino-5-chlorobenzophenone (2.32 gm, 0.01 ml), Boc-D-Leucine monohydrate (2.49 gm, 0.01 mol), and DCC (10 ml of 1.0M solution in CH$_2$Cl$_2$) in CH$_2$Cl$_2$ (25 ml). Filtration, concentration in vacuo and chromatography (silica gel, 5% (v/v) Et$_2$O in CH$_2$Cl$_2$) gave a yellow oil which was deprotected and cyclized by the procedure of Example 2. After stirring 48 h, the mixture was evaporated in vacuo, treated with H$_2$O (50 ml), and extracted with EtOAc (2×200 ml). The combined organic extracts were washed with brine (50 ml), dried over MgSO$_4$, filtered, and evaporated to dryness in vacuo. Chromatography (silica gel, 7.5% (v/v) Et$_2$O in CH$_2$Cl$_2$) of the crude product gave a white foam which was crystallized from Et$_2$O. The solid was dried in vacuo at 65° C.: (m.p. 156°–60° C.).

The compound showed a single spot by TLC ($R_f$=0.38, silica gel plate, 10% (v/v) Et$_2$O in CH$_2$Cl$_2$). The NMR spectrum was consistent with the title structure. The compound was 100% pure by HPLC.

Anal. Calc'd for C$_{19}$H$_{19}$ClN$_2$O: C, 69.82; H, 5.86; N, 8.57; Cl, 10.85. Found: C, 69.81; H, 5.84; N, 8.71; Cl, 11.20.

EXAMPLE 15

3(R)-Benzyloxymethyl-7-chloro-1,3-dihydro-5-phenyl-2H-1,4-benzodiazepin-2-one The procedure of Example 1 was carried out using 2-amino-5-chlorobenzophenone (2.32 gm, 0.01 mol), N-Boc-O-Benzyl-D-serine (2.95 gm, 0.01 mol), and DCC (10 ml of 1.0M solution in CH$_2$Cl$_2$) in CH$_2$Cl$_2$ (10 ml). Filtration, concentration in vacuo and chromatography (silica gel, CH$_2$Cl$_2$) gave a colorless oil which was deprotected and cyclized by the procedure of Example 2. After stirring 5 days, the mixture was evaporated in vacuo, treated with H$_2$O (50 ml), and extracted with EtOAc (2×100 ml). The combined organic extracts were washed with brine (50 ml), dried over MgSO$_4$, filtered, and evaporated to dryness in vacuo. Chromatography (silica gel, 75% (v/v) Et$_2$O in CH$_2$Cl$_2$) of the crude product gave a white foam which was crystallized from Et$_2$O. The solid was dried in vacuo at 65° C.: (m.p 113°–5° C.)

The compound showed a single spot by TLC (R$_f$=0.27, silica gel plate, 10% (v/v) Et$_2$O in CH$_2$Cl$_2$). The NMR spectrum was consistent with the title structure and verified the presence of Et$_2$O and H$_2$O. The compound was 100% pure by HPLC.

Anal. Calc'd for C$_{23}$H$_{19}$ClN$_2$O$_2$.0.1 C$_4$H$_{10}$O.0.25-H$_2$O: C, 69.78; H, 5.13; N, 6.96; Cl, 8.80. Found: C, 69.53; H, 5.17; N, 6.99; Cl, 8.98.

EXAMPLE 16

7-Chloro-1,3-dihydro-3(R)-(4-benzyloxybenzyl)-5-phenyl-2H-1,4-benzodiazepin-2-one The procedure of Example 1 was carried out using 2-amino-5-chlorobenzophenone (2.32 gm, 0.01 mol), N-Boc-O-Benzyl-D-Tyrosine (3.71 gm, 0.01 mol), and DCC (10 ml of 1.0M solution in CH$_2$Cl$_2$) in CH$_2$Cl$_2$ (10 ml). After filtration and evaporation, the crude solid was deprotected and cyclized by the procedure of Example 2. After stirring 5 days, the mixture was evaporated in vacuo, treated with H$_2$O (75 ml), and extracted with EtOAc (2×125 ml). The combined organic extracts were washed with brine (50 ml), dried over MgSO$_4$, filtered, and evaporated to dryness in vacuo. Chromatography (silica gel, 7.5% (v/v) Et$_2$O in CH$_2$Cl$_2$) of the crude product gave a white foam which was dried at 69° C. in vacuo: (m.p. 97°–101° C.).

The compound showed a single spot by TLC (R$_f$=0.37, silica gel plate, 10% (v/v) Et$_2$O in CH$_2$Cl$_2$). The NMR spectrum was consistent with the title structure. The compound was greater than 99.5% pure by HPLC.

Anal. Calc'd for C$_{29}$H$_{23}$ClN$_2$O$_2$: C, 74.59; H, 4.97; N, 6.00. Found: C, 74.52; H, 4.78; N, 6.01.

EXAMPLE 17

7-Chloro-1,3-dihydro-3(RS)-(1-naphthyl)methyl-5-phenyl-2H-1,4-benzodiazepin-2-one The procedure of Example 1 was carried out using 2-amino-5-chlorobenzophenone (845 mg, 3.65 mmol), N-Boc-α-DL-naphthylalanine (1.15 gm, 3.65 mmol), and DCC (3.65 ml of 1.0M solution in CH$_2$Cl$_2$) in THF (5 ml). Filtration, concentration in vacuo and chromatography (silica gel, 1% (v/v) Et$_2$O in CH$_2$Cl$_2$) gave a light yellow foam which was deprotected and cyclized by the procedure of Example 2. After stirring 14 days, the mixture was evaporated in vacuo, treated with H$_2$O (25 ml), and extracted with CH$_2$Cl$_2$ (2×50 ml). The combined organic extracts were washed with brine (25 ml), dried over MgSO$_4$, filtered, and evaporated to dryness in vacuo. Chromatography (silica gel, 3% (v/v) Et$_2$O in CH$_2$Cl$_2$) of the crude product gave a white foam which was crystallized from hexane. The solid was dried in vacuo at 100° C.: (m.p. 180°–2° C.).

The compound showed a single spot by TLC (R$_f$=0.36, silica gel plate, 10% (v/v) Et$_2$O in CH$_2$Cl$_2$). The NMR spectrum was consistent with the title structure. The compound was greater than 99.9% pure by HPLC.

Anal. Calc'd for C$_{26}$H$_{19}$ClN$_2$O: C, 76.00; H, 4.66; H, 6.82; Cl, 8.63. Found: C, 75.99; H, 4.68; N, 6.65; Cl, 8.76.

EXAMPLE 18

7-Chloro-1,3-dihydro-3(RS)-(2-naphthyl)methyl-5-phenyl-2H-1,4-benzodiazepin-2-one The procedure of Example 1 was carried out using 2-amino-5-chlorobenzophenone (845 mg, 3.65 mmol), N-Boc-β-DL-naphthylalanine (1.15 gm, 3.65 mmol), and DCC (3.65 ml of 1.0M solution in CH$_2$Cl$_2$) in THF (5 ml). Filtration, concentration in vacuo and chromatography (silica gel, 1% (v/v) Et$_2$O in CH$_2$Cl$_2$) gave a foam which was deprotected and cyclized by the procedure of Example 2. After stirring 24 hours, the mixture was evaporated in vacuo, treated with H$_2$O (25 ml), and extracted with EtOAc (2×50 ml). The combined organic extracts were washed with brine (25 ml), dried over MgSO$_4$, filtered, and evaporated to dryness in vacuo. Chromatography (silica gel, 5% (v/v) Et$_2$O in CH$_2$Cl$_2$) of the crude product gave a foam which was crystallized from Et$_2$O/hexane. The solid was dried in vacuo at 100° C.: (m.p. 140≧–2° C.).

The compound showed a single spot by TLC (R$_f$=0.38, silica gel plate, 10% (v/v) Et$_2$O in CH$_2$Cl$_2$). The NMR spectrum was consistent with the title structure. The compound was greater than 99.7% pure by HPLC.

Anal. Calc'd for C$_{26}$H$_{19}$ClN$_2$O: C, 76.00; H, 4.66; N, 6.82; Cl, 8.63. Found: C, 75.77; H, 4.68; N, 6.77; Cl, 8.87.

EXAMPLE 19

1,3-Dihydro-5-(2-fluorophenyl)-3(RS)-(2-thienyl)methyl-2H-1,4-benzodiazepin-2-one The procedure of Example 1 was carried out using 2-amino-2'-fluorobenzophenone (1.26 gm, 5.86 mmol), N-Boc-β-(2-thienyl)-DL-alanine (1.75 gm, 6.45 mmol), and DCC (6.45 ml of 1.0M solution in CH$_2$Cl$_2$) in CH$_2$Cl$_2$ (25 ml). Filtration, concentration in vacuo and flash chromatography (silica gel, 1% (v/v) Et$_2$O in CH$_2$Cl$_2$) gave a white foam which was deprotected and cyclized by the procedure of Example 2. After stirring 3 days, the mixture was evaporated in vacuo, treated with H$_2$O (50 ml) and extracted with EtOAc (2×100 ml). The combined organic extracts were washed with brine (50 ml), dried over MgSO$_4$, filtered, and evaporated to dryness in vacuo. The resulting foam was crystallized from Et$_2$O to give the title compound as a white solid. The solid was dried in vacuo at 65° C.: (m.p. 189°–91° C.).

The compound showed a single spot by TLC (R$_f$=0.54, silica gel plate, 20% (v/v) Et$_2$O in CH$_2$Cl$_2$). The NMR spectrum was consistent with the title structure. The compound was greater than 97.9% pure by HPLC.

Anal. Calc'd for C$_{20}$H$_{15}$FN$_2$OS: C, 68.55; H, 4.32; N, 8.00. Found: C, 68.74; H, 4.47; N, 8.02.

EXAMPLE 20

1,3-Dihydro-5-(2-fluorophenyl)-3(RS)-(3-thienyl)-2H-1,4-benzodiazepin-2-one

The procedure of Example 1 was carried out using 2-amino-2'-fluorobenzophenone (1.59 g, 7.40 mmol), DL-α-Boc-amino-3-thiopheneacetic acid (2.0 gm, 7.77 mmol), and DCC (7.77 ml of 1.0M solution in CH$_2$Cl$_2$)

in CH$_2$Cl$_2$ (15 ml). Filtration, concentration in vacuo and chromatography (silica gel, 3% (v/v) Et$_2$O in CH$_2$Cl$_2$) gave a white foam which was deprotected (HCl/EtOAc, 00) and cyclized by heating (70° C. oil bath) in MeOH for 48 hours. The solvent was removed in vacuo and the residue crystallized from Et$_2$O. The compound was dried in vacuo at 65° C.: (m.p. 219°–23° C.).

The compound showed a single spot by TLC (R$_f$=0.24, silica gel plate, 30% (v/v) EtOAc in hexane). The NMR spectrum was consistent with the title structure. The compound was greater than 98.5% pure by HPLC.

Anal. Calc'd for C$_{19}$H$_{13}$FN$_2$OS: C, 67.84; H, 3.90; N, 8.33. Found: C, 67.75; H, 4.13; N, 7.98.

EXAMPLE 21

1,3-Dihydro-5-(2-fluorophenyl)-3(R)-[3'-β-(1'-t-Boc-L-leucyl)-indolenyl]methyl-2H-1,4-benzodiazepin-2-one 1,3-Dihydro-5-(2-fluorophenyl)-3(R)-(3'-β-indolenyl)methyl-2H-1,4-benzodiazepin-2-one (100 mg, 0.259 mmol), N-Boc-L-Leucine monohydrate (64.7 mg, 0.259 mmol), 1-ethyl-3-(3-dimethylaminopropyl)carbodiimide hydrochloride (EDC, 49.8 mg, 0.259 mmol), and 1-hydroxybenzotriazole hydrate (HBT, 35.0 mg, 0.259 mmol) were combined in freshly degassed dimethylformamide (DMF, 2 ml) and stirred at room temperature. The pH of the solution was adjusted to 9.0–9.5 with triethylamine (0.108 ml, 0.777 mmol) and stirring was continued for 24 hours. The mixture was evaporated in vacuo, treated with 10% Na$_2$CO$_3$ (aq) (20 ml) and extracted with EtOAc (2×30 ml). The combined extracts were washed with H$_2$O (20 ml) and brine (20 ml), dried over MgSO$_4$, filtered, and evaporated to dryness in vacuo. The residue was chromatographed (silica gel, 30% (v/v) EtOAc in hexane) to give the title compound as a foam. The foam was dried in vacuo at 65° C.: (m.p. 118°–30° C.).

The compound showed a single spot by TLC (R$_f$=0.38, silica gel plate, 40% (v/v) EtOAc in hexane). The NMR spectrum was consistent with the title structure and verified the presence of hexane. The compound was greater than 97% pure by HPLC. The mass spectrum showed a molecular ion at m/e=598.

Anal. Calc'd for C$_{35}$H$_{39}$FN$_4$O$_4$.⅛C$_6$H$_{14}$: C, 70.83; H, 7.02; N, 8.93. Found: C, 70.93; H, 6.88; N, 8.94.

EXAMPLE 22

1,3-Dihydro-5-(2-fluorophenyl)-3(R)-[3'-β-(1'-t-Boc-D-leucyl)-indolenyl]methyl-2H-1,4-benzodiazepin-2-one The procedure of Example 21 was carried out using the same reagents and amounts except N-Boc-D-leucine monohydrate was substituted for N-Boc-L-leucine monohydrate. After 24 hours a second portion of Boc-D-Leucine monohydrate (32 mg, 0.129 mmol), EDC (25 mg, 0.130 mmol), and HBT (17.5 mg; 0.130 mmol) was added and the pH readjusted to 9.0–9.5 with Et$_3$N. The reaction was worked up as in Example 21, and the title compound was obtained as a foam. This was dried in vacuo at 65° C.: (m.p. 135°–48° C.).

The compound showed a single spot by TLC (R$_f$=0.37, silica gel plate, 40% (v/v) EtOAc in hexane). The NMR spectrum was consistent with the title structure. The compound was 87.5% Pure by HPLC.

Anal. Calc'd for C$_{35}$H$_{39}$FN$_4$O$_4$: C, 70.21; H, 6.57; N, 9.36. Found: C, 70.25; H, 6.89; N, 9.53.

EXAMPLE 23

1,3-Dihydro-5-(2-fluorophenyl)-3(R)-[3'-α-(1'-t-Boc-L-leucyl)-indolenyl]methyl-2H-1,4-benzodiazepin-2-one The procedure of Example 21 was carried out using the same reagents and quantities except 1,3-dihydro-5-(2-fluorophenyl)-3(R)-(3'-α-indolenyl) methyl-2H-1,4-benzodiazepin-2-one was substituted for the 3'-β isomer. After 24 hours the reaction was worked up in the same manner and the title compound was obtained as a foam. This was dried in vacuo at 65° C.: (m.p. 130°–48° C.).

The compound showed a single spot by TLC (R$_f$=0.39, silica gel plate, 40% (v/v) EtOAc in hexane). The NMR spectrum was consistent with the title compound. The compound was 91% pure by HPLC.

Anal. Calc'd for C$_{35}$H$_{39}$FN$_4$O$_4$: C, 70.21; H, 6.57; N, 9.36. Found: C, 70.54; H, 6.98; N, 9.39.

EXAMPLE 24

1,3-Dihydro-5-(2-fluorophenyl)-3(R)-[3'-α-(1'-t-Boc-D-leucyl)-indolenyl]methyl-2H-1,4-benzodiazepin-2-one The procedure of Example 23 was carried out using the same reagents and quantities except Boc-D-Leucine was substituted for Boc-L-Leucine. After 24 hours the reaction was worked up in the same manner and the title compound was obtained as a white foam. This was dried in vacuo at 65° C.: (m.p. 130°–145° C.).

The compound showed a single spot by TLC (R$_f$=0.39, silica gel plate, 40% (v/v) EtOAc in hexane). The NMR spectrum was consistent with the title structure. The compound was 95.1% pure by HPLC.

Anal. Calc'd for C$_{35}$H$_{39}$FN$_4$O$_4$: C, 70.21; H, 6.57; N, 9.36. Found: C, 70.31; H, 6.81; N, 9.67.

EXAMPLE 25

7-Chloro-1,3,4,5-tetrahydro-3(R)-(3'-indolyl)methyl-5-phenyl-2H-1,4-benzodiazepin-2-one 7-Chloro-1,3,dihydro-3(R)-(3'-indolyl)methyl-5-phenyl-2H-1,4-benzodiazepin-2-one etherate (240 mg, 0.506 mmol) was dissolved in acetic acid (10 ml) and cooled to 10° C. To the yellow solution was added sodium cyanoborohydride (63.6 mg, 1.01 mmol) all at once. After stirring 15 minutes at 10° C., the reaction was diluted with H$_2$O (10 ml), basified with sat'd Na$_2$CO$_3$ (aq.), and extracted with EtOAc (2×25 ml). The combined organic extracts were washed with brine, dried over MgSO$_4$, filtered, and evaporated to dryness in vacuo. The residue was chromatographed (silica gel, 900/10/1/1 (v/v/v/v) of CH$_2$Cl$_2$/MeOH/H$_2$O/HoAc) and the product fractions evaporated to dryness in vacuo. The residue was dissolved in absolute ethanol, filtered, and treated with 5.37M HCl in ethanol until the solution was acidic. The product crystallized as fine white needles which were dried in vacuo at 82° C.: (m.p. 198°–204° C.).

The compound showed a single spot by TLC (R$_f$=0.35, silica gel plate, 300/10/1/1 (v/v/v/v) CH$_2$Cl$_2$/MeOH/H$_2$O/HoAc). The NMR spectrum was consistent with the title structure and verified the presence of H$_2$O. The mass spectrum showed a molecular ion at m/e=401.

Anal. Calc'd for C$_{24}$H$_{20}$ClN$_3$O.HCl.0.75H$_2$O: C, 63.79; H, 5.02; N, 9.30; Cl, 15.69. Found: C, 63.59; H, 4.94; N, 9.39; Cl, 15.32.

EXAMPLE 26

7-Chloro-1,3,4,5-tetrahydro-3(S)-(3'-indolyl)methyl-5-phenyl-2H-1,4-benzodiazepin-2-one 7-Chloro-1,3-dihydro-3(S)-(3'-indolyl)methyl-5-phenyl-2H-1,4-benzodiazepin-2-one (300 mg, 0.750 mmol) was dissolved in acetic acid (10 ml) and cooled to 10° C. To the yellow solution was added sodium cyanoborohydride (63.6 mg, 1.01 mmol) all at once. After stirring 15 minutes at 10° C., the reaction was diluted with $H_2O$ (10 ml), basified with sat'd $Na_2CO_3$ (aq.), and extracted with EtOAc (2×25 ml). The combined organic extracts were washed with brine (10 ml), dried over $MgSO_4$, filtered, and evaporated to dryness in vacuo. The crude residue was dissolved in absolute ethanol (3 ml), filtered, and treated with 5.37M ethanolic HCl until the solution was acidic. The product crystallized as fine white needles which were dried in vacuo at 82° C.: (m.p. 198°-204° C).

The compound showed a single spot by TLC ($R_f$=0.30, silica gel plate, 300/10/1/1 (v/v/v/v) of $CH_2Cl_2$/MeOH/$H_2O$/HoAc). The NMR spectrum was consistent with the title structure and verified the presence of $H_2O$ and ethanol.

Anal. Calc'd for $C_{24}H_{20}ClN_3O.HCl.0.5H_2O.0.25C_2H_5OH$: C, 64.12; H, 5.16; N, 9.16; Cl, 15.45. Found: C, 63.91; H, 5.02; N, 9.01; Cl, 15.36.

EXAMPLE 27

4-(p-Chlorobenzoyl)-5-(2-fluorophenyl)-3(R)-[3'-(1'-methylindolyl)-methyl]-1-methyl-1,3,4,5-tetrahydro-2H-1,4-benzodiazepin-2-one (A) and 4-acetyl-5-(2-fluorophenyl)-3(R)-[3'-(1'-methylindolyl)-methyl]-1-methyl-1,3,4,5-tetrahydro-2H-1,4-benzodiazepin-2-one (B)

The procedure of Example 25 was carried out using 1,3-dihydro-5-(2-fluorophenyl)-3(R)-[3'-(1'-methylindolyl)-methyl]-1-methyl-2H-1,4-benzodiazepin-2-one (1.0 gm, 2.43 mmol) and sodium cyanoborohydride (305 mg, 4.86 mmol) in glacial acetic acid (4 ml). The crude reduction product obtained upon evaporation of the EtOAc extracts was used without further purification.

A The crude reduction product (200 mg, 0.484 mmol) was partitioned between $CH_2Cl_2$ (6 ml) and $H_2O$ (5 ml) and cooled to 0° C. 1N NaOH (0.73 ml) was added, followed by p-chlorobenzoyl chloride (0.092 ml, 0.726 mmol). After 24 hours at ambient temperature, a second portion of 1N NaOH (0.50 ml) and p-chlorobenzoyl chloride (0.045 ml, 0.354 mmol) was added, and after 24 hours a third portion of 1N NaOH (50 ml) and p-chlorobenzoylchloride (0.045 ml, 0.354 mmol) was added. After another 24 hours, the mixture was extracted with $CH_2Cl_2$ (3×10 ml). The combined organic layers were washed with 10% $NaHCO_3$ (10 ml), $H_2O$ (10 ml), and brine (10 ml), dried over $MgSO_4$, filtered, and evaporated in vacuo. Chromatography (silica gel, 5% (v/v) $Et_2O$ in $CH_2Cl_2$) of the crude residue gave a foam which was crystallized from $Et_2O$. The compound was dried in vacuo at 78° C.: (m.p. 237°-43° C.).

Anal. Calc'd for $C_{33}H_{27}FClN_3O_2.0.05Et_2O$: C, 71.75; H, 4.99; N, 7.56; Cl, 6.38. Found: C, 71.84; H, 5.28; N, 7.92; Cl, 6.63.

The compound showed a single spot by TLC ($R_f$=0.50, silica gel plate, 4% (v/v) $Et_2O$ in $CH_2Cl_2$). The NMR spectrum was consistent with the title structure and verified the presence of $Et_2O$. The compound was greater than 99% pure by HPLC.

B: The crude reduction product (200 mg, 0.484 mmol) was dissolved in $CH_2Cl_2$ (10 ml) and 3 portions of acetyl chloride (each 0.026 ml, 0.363 mmol) and triethylamine (0.35 ml, 0.363 mmol) were added at 3 hour intervals. Water (2 ml) was then added and the mixture was extracted with $CH_2Cl_2$ (3×10 ml). The combined organic layers, were washed with 10% $Na_2CO_3$ (aq.) (10 ml), $H_2O$ (10 ml) and brine (10 ml), dried over $MgSO_4$, filtered, and evaporated in vacuo. Chromatography (silica gel, 5% (v/v) $Et_2O$ in $CH_2Cl_2$) of the crude residue gave a white foam which was crystallized from $Et_2O$. The compound was dried in vacuo at 78° C.: (m.p. 214°-216.5° C.).

The compound showed a single spot by TLC ($R_f$=0.41, silica gel plate, 15% (v/v) $Et_2O$ in $CH_2Cl_2$). The NMR spectrum was consistent with the title structure. The compound was greater than 99.5% pure by HPLC. The mass spectrum showed a molecular ion at m/e=455.

Anal. Calc'd for $C_{28}H_{26}FN_3O_2$: C, 73.82; H, 5.75; N, 9.23. Found: C, 73.62; H, 5.93; N, 9.22.

EXAMPLE 28

7-Chloro-5-(2-chlorophenyl)-1,3-dihydro-3(R)-(3'-indolyl)methyl-2H-1,4-benzodiazepin-2-one The procedure of Example 1 was carried out using 2-amino-2',5-dichlorobenzophenone (2.66 g, 0.01 mole), Boc-D-tryptophan (3.04 g, 0.01 mole), and DCC (10 ml of 1M solution in methylene chloride) in THF (15 ml). The crude product obtained after filtration and evaporation of the mixture was chromatographed on silica gel (230-400 mesh, 9 inch (23 cm) column 55 mm diameter), using methylene chloride followed by 5% (v/v) ether/methylene chloride. The product fractions were evaporated in vacuo to give the product as a foam. This material was deprotected and cyclized using the procedure of Example 2. The cyclization in this case required 15 days. At the end of this time the mixture was evaporated in vacuo, treated with water (10 ml), and extracted with methylene chloride (3×50 ml). The methylene chloride layers were dried over potassium carbonate, filtered, and evaporated in vacuo to give the crude product as a foam. This material was chromatographed on silica gel (230-400 mesh, 8 inch (20 cm) column, 25 mm diameter, elution with methylene chloride followed by 10% (v/v) ether/methylene chloride). The product fractions were evaporated in vacuo and the residue crystallized from ether by addition of cyclohexane. The title compound was obtained as a white solid which was dried in vacuo at 80°: (mp 140°-170° (d)).

The compound showed a single spot by TLC ($R_f$=0.61, silica gel plate eluted with 1:1 (v/v) ether/methylene chloride). The NMR spectrum was consistent with the title structure. The mass spectrum showed a molecular ion at m/e=433. The compound was 98% pure by HPLC.

Analysis Calc'd for $C_{24}H_{17}Cl_2N_3O$: C, 66.37; H, 3.94; N, 9.68: Found: C, 66.70; H, 4.05; N, 9.61.

EXAMPLE 29

1,3-Dihydro-3(R)-(3'-indolyl)methyl-5-methyl-2H-1,4-benzodiazepin-2-one

The procedure of Example 1 was carried out using 2-aminobenzophenone (1.35 g, 0.01 mole), Boc-D-tryptophan (3.04 g, 0.01 mole) and DCC (10 ml of 1M solution in methylene chloride) in THF (15 ml). The mixture was filtered, evaporated in vacuo and the residue chromatographed on silica gel (230–400 mesh, 9 inch (23 cm) column, 55 mm diameter) eluted with methylene chloride followed by 5%, 7½% and 8% (v/v) ether/methylene chloride. The product fractions were evaporated in vacuo and the residue was deprotected and cyclized by the procedure of Example 2. The cyclization required seven days. The mixture was evaporated in vacuo and partitioned between water and methylene chloride. The methylene chloride layers were washed twice with water, dried over magnesium sulfate, filtered and evaporated in vacuo. The residue was chromatographed on silica gel (230–400 mesh, 11 inch (28 cm) column, 25 mm diameter, 1:1 and 2:1 (v/v) ether/methylene chloride elution). The product fractions were evaporated in vacuo to provide the title compound: (mp 185°–190°). The compound was dried in vacuum at 100° overnight.

The compound showed a single spot by TLC ($R_f$=0.29, silica gel plate eluted with 1:1 (v/v) ether/methylene chloride). The NMR spectrum was consistent with the title structure. The mass spectrum showed a molecular ion at m/e=303. The compound was 95.6% pure by HPLC.

Analysis Calc'd for: $C_{19}H_{17}N_3O.0.1H_2O$: C, 74.78; H, 5.68; N, 13.78; Found: C, 74.60; H, 6.06; N, 13.74.

EXAMPLE 30

1-Benzyl-7-chloro-1,3-dihydro-3(R)-(3'-indolyl)methyl-5-phenyl-2H-1,4-benzodiazepin-2-one The procedure of Example 4 was carried out using 7-chloro-1,3-dihydro-3(R)-(3'-indolyl)methyl-5-phenyl-2H-1,4-benzodiazepin-2-one etherate (0.1 g, 0.22 mmole) in place of 1,3-dihydro-5-(2-fluorophenyl)-3(R)-(3'-indolyl)methyl-2H-1,4-benzodiazepin-2-one, and 50% sodium hydride in mineral oil (0.015 g, 0.31 mmole) in dry DMF (2 ml). In place of methyl iodide, benzyl bromide (0.058 g, 0.34 mmole) was added to the mixture. Chromatography on a 6 inch (15 cm), 15 mm diameter silica gel column with 5% (v/v) ether/methylene chloride elution and evaporation of the product fractions gave a residue which was recrystallized from cyclohexane to provide the title compound which was dried in vacuo at 60°: (mp ca. 80° (indistinct)).

The compound showed a single spot by TLC ($R_f$=0.66, silica gel plate eluted with 10% (v/v) ether/methylene chloride). The NMR spectrum was consistent with the title structure and verified the presence of approximately ½ mole of cyclohexane. The compound was 100% pure by HPLC. The mass spectrum showed a molecular ion at m/e=489.

Analysis Calc'd for: $C_{31}H_{24}ClN_3O.0.5C_6H_{12}$: C, 76.74; H, 5.68; N, 7.90; Cl, 6.66; Found: C, 76.83; H, 5.71; N, 7.79; Cl, 6.72.

EXAMPLE 31

7-Chloro-1,3-Dihydro-3(R)-(3'-indolyl)methyl-1-methyl-5-phenyl-2H-1,4-benzodiazepin-2-one The procedure of Example 4 was carried out using 7-chloro-1,3-dihydro-3(R)-(3'-indolyl)methyl-5-phenyl-2H-1,4-benzodiazepin-2-one etherate (0.1 g, 0.22 mmole) in place of 1,3-dihydro-5-(2-fluorophenyl)-3(R)-(3'-indolyl)methyl-2H-1,4-benzodiazepin-2-one, 50% sodium hydride in mineral oil (0.014 g, 0.29 mmole), and methyl iodide (0.045 g, 0.32 mmole) in DMF (2 ml). Chromatography on a six inch (15 cm), 15 mm diameter silica gel column provide the title compound which, after evaporation and in vacuo, was dissolved in acetone, precipitated with water and filtered. The resulting solid was dried in vacuo at 70°: (mp 134–152 (indistinct)).

The compound showed a single spot by TLC ($R_f$=0.22, silica gel plate eluted with 5% (v/v) ether/methylene chloride. The NMR spectrum was consistent with the title structure. The compound was 98.9% pure by HPLC. The mass spectrum showed a molecular ion at m/e=413.

Analysis Calc'd for: $C_{25}H_{20}ClN_3O$: C, 72.54; H, 4.87; N, 10.15; Cl, 8.57; Found: C, 72.38; H, 4.88, N, 10.20; Cl, 8.32.

EXAMPLE 32

1,3-Dihydro-5-(2-fluorophenyl)-3(S)-(3'-indolyl)methyl-2H-1,4-benzodiazepin-2-one The procedure of Example 1 was carried out using 0.7 g (3.25 mmole) of 2-amino-2'-fluorobenzophenone, 0.99 g, (3.25 mmole) of Boc-L-tryptophan, and 3.25 ml (3.25 mmole) of 1M DCC/$CH_2Cl_2$ in 5 ml of THF. The product obtained by silica gel chromatography (10 inch (25 cm) column, 25 mm diameter, methylene chloride and 2% and 3% (v/v) ether/methylene chloride elution) was deprotected and cyclized according to the procedure of Example 2. The cyclization required three days. The resulting mixture was evaporated in vacuo, partitioned between water and methylene chloride, and separated. The aqueous layer was extracted twice with methylene chloride, and the combined methylene chloride layers were washed with water, dried over sodium sulfate, filtered, and evaporated in vacuo. The residue was recrystallized from acetone/ether, and the resulting solid dried in vacuo at 100°: (mp 255°–257°).

The compound showed a single component by TLC ($R_f$=0.59, silica gel plate eluted with 1:1 (v/v) methylene chloride/ether. The NMR spectrum was consistent with the title structure. The mass spectrum showed a molecular ion at m/e=383. The compound was 99.3% pure by HPLC.

Analysis Calc'd for $C_{24}H_{18}FN_3O$: C, 75.18; H, 4.73; N, 10.96; Found: C, 75.45; H, 4.71; N, 11.11.

EXAMPLE 33

1-Benzyl-7-chloro-1,3-dihydro-3(S)-(3'-indolyl)methyl-5-phenyl-2H-1,4-benzodiazepin-2-one The procedure of Example 4 was carried out using 7-chloro-1,3-dihydro-3(S)-(3'-indolyl)methyl-5-phenyl-2H-1,4-benzodiazepin-2-one etherate (0.1 g, 0.22 mmole) in place of 1,3-dihydro-5-(2-fluorophenyl)-3(R)-(3'-indolyl)methyl-2H-1,4-benzodiazepin-2-one, 50% sodium hydride in mineral oil (0.014 g, 0.29 mmole), and benzyl bromide (0.058 g, 0.34 mmole) in place of methyl iodide. The reaction was run in 1.5 ml of dry DMF. Silica gel chromatography (8 inch (20 cm) column, 15 mm diameter, methylene chloride and 5% (v/v) ether/methylene chloride elution)) and evaporation of the product fractions in vacuo gave the title compound which was dried in vacuo at 60°: (mp 80°–120° (indistinct)).

The compound showed a single component by TLC ($R_f$=0.40, silica gel plate eluted with 5% (v/v) ether/methylene chloride). The NMR spectrum was consistent with the title structure and showed ½ mole of cyclohexane. The compound was 99.3% pure by HPLC. The mass spectrum showed a molecular ion at m/e=489.

Analysis Calc'd for $C_{31}H_{24}ClN_3O \cdot \frac{1}{2}C_6H_{12}$: C, 76.74; H, 5.68; N, 7.90; Cl, 6.66; Found: C, 76.56; H, 5.67; N, 7.86; Cl, 7.00.

EXAMPLE 34

7-Chloro-1,3-dihydro-3(R)-(3'-indolyl)methyl-5-phenyl-2H-1,4-benzodiazepin-2-thione 7-Chloro-1,3-dihydro-3(R)-(3'-indolyl)methyl-5-phenyl-2H-1,4-benzodiazepin-2-one etherate (1.0 g, 2.1 mmole) and $P_2S_5$ (0.51 g, 2.3 mmole) were combined in dry pyridine (16 ml) and heated at reflux for 40 minutes. Pyridine was removed by evaporation in vacuo and the residue treated with ice water and extracted with methylene chloride. The methylene chloride layers were combined, dried over potassium carbonate, filtered, and evaporated in vacuo to give a foam. This material was chromatographed on silica gel (9 inch (23 cm) column, 25 mm diameter, 15% (v/v) ether/methylene chloride elution), and the product fractions evaporated. The residue was recrystallized from acetone/ethyl acetate and the solid dried in vacuo at 90°: (mp 279°–280°).

The compound showed a single spot by thin layer chromatography ($R_f$=0.32, silica gel plate eluted with 10% (v/v) ether/methylene chloride). The NMR spectrum was consistent with the title structure. The compound was 98.6% pure by HPLC. The mass spectrum showed a molecular ion at m/e=415.

Analysis Calc'd for $C_{24}H_{18}ClN_3S$: C, 69.30; H, 4.36; N, 10.10; S, 7.71; Found: C, 69.39; H, 4.39; N, 10.14; S, 7.46.

EXAMPLE 35

1,3-Dihydro-5-(2-fluorophenyl)-3(R)-(3'-indolyl)methyl-2H-1,4-benzodiazepin-2-[N'-(3-thienoyl)]hydrazide 1,3-Dihydro-5-(2-fluorophenyl)-3(R)-(3'-indolyl)methyl-2H-1,4-benzodiazepin-2-thione (0.28 g, 0.7 mmole) and 3-thienoyl chloride (0.1 g, 0.7 mmole) were combined in ether (5 ml) and THF (1 ml) and stirred at room temperature. After one hour the mixture was filtered and evaporated in vacuo, and the residue chromatographed on silica gel (8 inch (20 cm) column, 25 mm diameter, 1½% followed by 3% (v/v) methanol/methylene chloride elution). The product fractions were evaporated in vacuo and the resulting solid dried in vacuo at 70°: (mp 207°–209° ( )).

The compound showed a single spot by TLC ($R_f$=0.4, silica gel plate eluted with 5% (v/v) methanol/methylene chloride). The NMR spectrum was consistent with the title structure. The compound was 92% pure by HPLC.

Analysis Calc'd for $C_{29}H_{22}FN_5OS \cdot 0.2H_2O$: C, 68.13; H, 4.42; N, 13.70; Found: C, 68.19; H, 4.30; N, 13.91.

EXAMPLE 36

1,3-Dihydro-1-ethyl-5-(2-fluorophenyl)-3(R)-(3'-indolyl)methyl-2H-1,4-benzodiazepin-2-one The procedure of Example 4 was carried out using ethyl iodide (0.35 g, 2.25 mmole) in place of methyl iodide. Silica gel chromatography followed by evaporation in vacuo gave the product which was dried at room temperature in vacuo (mp 95°–113°).

The compound showed a single spot by thin layer chromatography ($R_f$=0.44, silica gel plate eluted with 10% (v/v) ether/methylene chloride). The NMR spectrum was consistent with the title structure and showed the presence of approximately 0.15 mole of methylene chloride. The compound was 95.3% pure by HPLC. The mass spectrum showed a molecular ion at me=411.

Analysis Calc'd for: $C_{26}H_{22}FN_3O \cdot 0.15CH_2Cl_2$: C, 74.04; H, 5.30; N, 9.91; Found: C, 74.17; H, 5.22; N, 10.02.

EXAMPLE 37

1-Cyclopropylmethyl-1,3-dihydro-5-(2-fluorophenyl)-3(R)-(3'-indolyl)methyl-2H-1,4-benzodiazepin-2-one The procedure of Example 4 was carried out using cyclopropylmethylbromide (0.30 g, 2.25 mmole) in place of methyl iodide. The product obtained by chromatography and evaporation was recrystallized from a mixture of methylene, chloride, ether, and hexane, and the resulting solid dried in vacuo at 80°: (mp 207.5°–208.5°).

The compound showed a single component by TLC ($R_f$=0.26, silica gel plate eluted with 4% (v/v) ether/methylene chloride). The NMR spectrum was consistent with the title structure. The compound was 99.6% pure by HPLC. The mass spectrum showed a molecular ion at m/e=437.

Analysis Calc'd for $C_{28}H_{24}FN_3O \cdot 0.07CH_2Cl_2$: C, 76.02; H, 5.49; N, 9.48; Found: C, 75.96; H, 5.42; N, 9.30.

EXAMPLE 38

1,3-Dihydro-5-(2-fluorophenyl)-3(R)-(3'-indolyl)methyl-1-pentyl-2H-1,4-benzodiazepin-2-one The procedure of Example 4 was carried out using 1-bromopentane (0.34 g, 2.25 mmole) in place of methyl iodide. The product obtained after silica gel chromatography and evaporation was crystallized from ether and dried in vacuo at 80°: (mp 150°–151°).

The compound showed a single component by thin layer chromatography ($R_f$=0.37, silica gel plate eluted with 4% (v/v) ether/methylene chloride). The NMR spectrum was consistent with the title structure. The compound was 99.9% pure by HPLC. The mass spectrum showed a molecular ion at me=453.

Analysis Calc'd for: $C_{29}H_{28}FN_3O$: C, 76.79; H, 6.22; N, 9.26; Found: C, 76.64; H, 6.39; N, 8.83.

EXAMPLE 39

1,3-Dihydro-5-(2-fluorophenyl)-3(R)-(3'-indolyl)methyl-1-(3-methylbutyl)-2H-1,4-benzodiazepine-2-one The procedure of Example 4 was carried out using 1-bromo-3-methylbutane (0.34 g, 2.25 mmole) in place of methyl iodide. The product obtained after silica gel chromatography and evaporation was crystallized from ether and dried in vacuo at 80°: (mp=198°–199.5°).

The compound showed a single component by thin layer chromatography ($R_f$=0.30, silica gel plate eluted with 4% (v/v) ether/methylene chloride). The NMR spectrum was consistent with the title structure and showed the presence of 0.2 mole of ether. The compound was 99.9% pure by HPLC. The mass spectrum showed a molecular ion at m/e=453.

Analysis Calc'd for: $C_{29}H_{28}FN_3O \cdot 0.2C_4H_{10}O$: C, 76.42; H, 6.46; N, 8.97; Found: C, 76.52; H, 6.38; N, 9.01.

EXAMPLE 40

1,3-Dihydro-5-(2-fluorophenyl)-3(R)-(3'-indolyl)methyl-1-(2,2,2-trifluoroethyl)-2H-1,4-benzodiazepin-2-one The procedure of Example 4 was carried out using 2,2,2-trifluoroethyl iodide (0.47 g, 2.25 mmole) in place of methyl iodide. Following addition of the trifluoroethyl iodide, the reaction was heated for 18 hours in an oil bath thermostatted at 65°. Workup and chromatography as described in Example 4 gave a product which was recrystallized from ether and dried in vacuo at 80°: (mp 189°-192°).

The compound showed a single component by thin layer chromatography ($R_f=0.50$, silica gel plate eluted with 5% (v/v) ether/methylene chloride). The NMR spectrum was consistent with the title structure. The compound was 99.2% pure by HPLC. The mass spectrum showed a molecular ion at m/e=465.

Analysis Calc'd for: $C_{26}H_{19}F_4N_3O$: C, 67.09; H, 4.11; N, 9.03; Found: C, 67.32; H, 4.31; N, 8.98.

EXAMPLE 41

1,3-Dihydro-1-(2-dimethylaminoethyl)-5-(2-fluorophenyl) 3(R)-(3'-indolyl)methyl-2H-1,4-benzodiazepin-2-one The procedure of Example 4 was carried out using 1-chloro-2-(dimethylamino)propane (0.24 g, 2.25 mmole) in place of methyl iodide. Following addition of the chloride, the reaction was stirred at room temperature for 5 days and then worked up as described in Example 4. The chromatographed product was crystallized from methylene chloride/hexane and the resulting solid dried in vacuo at 80°: (mp 200°-201°).

The compound showed a single component by TLC ($R_f=0.30$, silica gel plate eluted with 5% (v/v) methanol/methylene chloride). The NMR spectrum was consistent with the title structure. The compound was 99.6% pure by HPLC. The mass spectrum showed a molecular ion at m/e=454.

Analysis Calc'd for: $C_{28}H_{27}FN_4O$: C, 73.98; H, 5.99; N, 12.33; Found: C, 73.92; H, 6.00; N, 11.28.

EXAMPLE 42

1,3-Dihydro-1-(ethoxycarbonylmethyl)-5-(2-fluorophenyl)-3(R)-(3'-indolyl)methyl-2H-1,4-benzodiazepin-2-one The procedure of Example 4 was carried out using ethyl bromoacetate (0.38 g, 2.25 mmole) in place of methyl iodide. The chromatographed product was evaporated and dried in vacuo at room temperature: (mp 88°-100°).

The compound showed a single component by TLC ($R_f=0.42$, silica gel plate eluted with 10% (v/v) ether/methylene chloride). The NMR spectrum was consistent with the title structure and showed the presence of 0.24 mole of methylene chloride. The compound was 92.6% pure by HPLC. The mass spectrum showed a molecular ion at m/e=469.

Analysis Calc'd for $C_{28}H_{24}FN_3O_3.0.24CH_2Cl_2$: C, 69.23; H, 5.04; N, 8.58; Found: C, 69.14; H, 5.09; N, 8.87.

EXAMPLE 43

1-Carboxymethyl-1,3-dihydro-5-(2-fluorophenyl)-3(R)-3'-indolyl)methyl-2H-1,4-benzodiazepin-2-one 1,3-Dihydro-1-(ethoxycarbonylmethylene)-5-(2-fluorophenyl)-3(R)-(3'-indolyl)methyl-2H-1,4-benzodiazepin-2-one (83.2 mg, 0.177 mmole), and 1 molar sodium hydroxide (0.18 ml, 0.18 mmole) were combined in 1 ml of methanol and stirred at room temperature for 24 hours. The solution was acidified with 1 molar hydrochloric acid, and the mixture evaporated in vacuo. The residue was taken up in methylene chloride, washed with water, dried over sodium sulfate, filtered, and evaporated in vacuo to dryness. The residue was triturated with ether followed by petroleum ether, and filtered to give the product which was dried in vacuo at 80°; (mp 175-180° ( )).

The compound showed a single component by TLC ($R_f=0.52$, silica gel plate eluted with 90:10:1:1 (v/v/v/v) methylene chloride/methanol/acetic acid/water). The NMR spectrum was consistent with the title structure and showed the presence of both ether and hexane. The compound was 97.2% pure by HPLC. The mass spectrum showed a molecular ion at m/e=441.

Analysis Calc'd for $C_{26}H_{20}FN_3O_3.0.1C_4H_{10}O.0.04C_6H_{14}.H_2O$: C, 68.02; H, 5.05; N, 8.94; Found: C, 67.91; H, 5.04; N, 8.92.

EXAMPLE 44

1,3-Dihydro-5-(2-fluorophenyl)-3(R)-[3'-(1'-methylindolyl)methyl]-1-methyl-2H-1,4-benzodiazepin-2-one The method of Example 4 was employed except that the starting material was 1,3-dihydro-5-(2-fluorophenyl)-3(R)-(3'-indolyl)methyl-1-methyl-2H-1,4-benzodiazepin-2-one (1.3 g, 3.3 mmole). Fifty percent sodium hydride in mineral oil (0.16 g, 3.3 mmole) and methyl iodide (0.47 g, 3.3 mmole) were employed in 10 ml of dry DMF. Following workup and chromatography as in Example 4, the product was obtained having physical properties identical to those reported in Example 4.

EXAMPLE 45

1,3-Dihydro-5-(2-fluorophenyl)-3(R)-[3'-(1'-p-chlorobenzyloylindolyl)methyl]-1-methyl-2H-1,4-benzodiazepin-2-one The procedure of Example 4 was carried out using 1,3-dihydro-5-(2-fluorophenyl)-3(R)-(3'-indolyl)methyl-1-methyl-2H-1,4-benzodiazepin-2-one (0.345 g, 0.87 mmole) in place of 1,3-dihydro-5-(2-fluorophenyl)-3(R)-(3'-indolyl)methyl-2H-1,4-benzodiazepin-2-one, and p-chlorobenzoyl chloride (0.26 g, 1.5 mmole) in place of methyl iodide. The reaction, employing 0.047 g (0.97 mmole) of 50% sodium hydride in mineral oil, was carried out in 10 ml of dry DMF. Silica gel chromatography as described in Example 4, followed by evaporation in vacuo and trituration with hexane, gave a solid which was dried in vacuo at 50°: (mp 75° ( )).

The compound showed a single component by TLC ($R_f=0.57$, silica gel plate eluted with 4% (v/v) ether/methylene chloride). The NMR spectrum was consistent with the title structure and verified the presence of approximately 0.3 mole of hexane. The compound was 99.3% pure by HPLC.

Analysis Calc'd for $C_{32}H_{23}FClN_3O.0.3C_6H_{14}$: C, 72.25; H, 4.88; N, 7.48; Cl, 6.31; Found: C, 72.42; H, 5.02; N, 7.50; Cl, 6.55.

EXAMPLE 46

7-Chloro-1,3-dihydro-3(R)-[3'(1'-benzylindolyl)methyl]1-methyl-5-phenyl-2H-1,4-benzodiazepin-2-one The procedure of Example 45 was carried out using 0.042 g (0.88 mmole) of 50% sodium hydride, and benzylbromide (0.16 g, 0.92 mmole) in place of p-chlorobenzoyl chloride. Reaction was conducted in 4 ml of dry DMF. Following silica gel chromatography and evaporation, the product was recrystallized from cyclohexane and dried in vacuo at 60°: (mp 77°-80° (indistinct)).

The compound showed a single component by TLC (R$_f$=0.59, silica gel plate eluted with 5% (v/v) ether/methylene chloride). The NMR spectrum was consistent with the title structure and showed the presence of ⅓ mole of cyclohexane. The compound was 98.7% pure by HPLC. The mass spectrum showed a molecular ion at m/e=503.

Analysis Calc'd for C$_{32}$H$_{26}$ClN$_3$O.⅓C$_6$H$_{12}$: C, 76.75; H, 5.68; N, 7.90; Cl, 6.66; Found: C. 76.50; H, 5.74; N, 7.59; Cl, 6.90.

EXAMPLE 47

1,3-Dihydro-3(RS)-[1-hydroxy-1-(3'-indolyl)]methyl-1-methyl-5-phenyl-2H-1,4-benzodiazepin-2-one The lithium salt of 1,3-dihydro-1-methyl-5-phenyl-2H-1,4-benzodiazepin-2-one (1.25 g, 5 mmole) was made according to the procedure of J. Org. Chem. 46, 3945 (1981) using 1.01 g (10 mmole) of diisopropylamine, and 6.7 ml of a 1.5 molar solution (10 mmole) of n-butyllithium in hexane. This anion solution was added by syringe to a solution of 0.725 g (5 mmole) of indole-3-carboxaldehyde in 15 ml of dry THF stirred under nitrogen in a dry ice-acetone bath. The mixture was warmed to room temperature, stirred for 1½ hours and then quenched by the addition of saturated sodium chloride solution. The mixture was separated and the aqueous layer extracted twice with methylene chloride (2×10 ml). The organic layers were dried over sodium sulfate, filtered and evaporated to dryness in vacuo. The residue was chromatographed on silica gel (230-400 mesh, 8 inch (20 cm) column, 25 mm diameter, 1:1 ether/methylene chloride elution). The evaporated product fractions were crystallized from ether and dried in vacuo at 70°: (mp 218°-221°).

The compound showed a single component by TLC (R$_f$=0.30, silica gel plate eluted with 1:1 (v/v) ether/methylene chloride). The NMR spectrum was consistent with the title structure. The compound was 90% pure by HPLC. The mass spectrum showed a molecular ion at me=395.

Analysis Calc'd for C$_{25}$H$_{21}$N$_3$O$_2$.0.25H$_2$O: C, 75.07; H, 5.42; N, 10.51; Found: C, 75.04; H, 5.50; N, 10.59.

EXAMPLE 48

1,3-Dihydro-1-methyl-5-phenyl-3-(RS)-(3-thienoyl)-2H-1,4-benzodiazepin-2-one

The procedure of Example 47 was carried out using thiophene-3-carbonyl chloride (730 mg, 5.0 mmol) in place of indole-3-carboxaldehyde. Following chromatography (silica gel, 5% (v/v) Et$_2$O in CH$_2$Cl$_2$), the product was evaporated to dryness and crystallized from Et$_2$O. The solid was dried in vacuo at 65° C.: (m.p. 205°-8° C.).

The compound showed a single spot by TLC (R$_f$=0.54, silica gel plate, 10% (v/v) Et$_2$O in CH$_2$Cl$_2$). The NMR spectrum was consistent with the title structure. The compound was greater than 92.4% pure by HPLC. The mass spectrum showed a molecular ion at m/e=360.

Anal. Calc'd for C$_{21}$H$_{16}$N$_2$O$_2$S: C, 69.98; H, 4.47; N, 7.77. Found: C, 70.27; H, 4.64; N, 7.69.

EXAMPLE 49

1,3-Dihydro-3-(RS)-[1-hydroxy-1-(3-thienyl)]methyl-1-methyl-5-phenyl-2H-1,4-benzodiazepin-2-one The procedure of Example 47 was carried out using thiophene-3-carboxaldehyde (560 mg, 5.0 mmol) in place of indole-3-carboxaldehyde. Following chromatography (silica gel, 15% (v/v) Et$_2$O in CH$_2$Cl$_2$), the product was evaporated to dryness and crystallized from Et$_2$O. The solid was dried in vacuo at 65° C.: (m.p. 189°-91° C.).

The compound showed a single spot by TLC (R$_f$=0.36, silica gel plate, 15% (v/v) Et$_2$O in CH$_2$Cl$_2$). The NMR spectrum was consistent with the title structure. The compound was greater than 99.0% pure by HPLC. The mass spectrum showed a molecular ion at m/e=362.

Anal. Calc'd for C$_{21}$H$_{18}$N$_2$O$_2$S: C, 69.59; H, 5.01; N, 7.73. Found: C, 69.62; H, 5.01; N, 7.57.

EXAMPLE 50

1,3-Dihydro-3(RS)-[1-hydroxy-1-[3-(1-methylindolyl)]-]methyl-1-methyl-5-phenyl-2H-1,4-benzodiazepin-2-one (two stereoisomers, A and B)

The procedure of Example 47 was carried out using 1-methylindole-3-carboxaldehyde (797 mg, 5.0 mmol) in place of indole-3-carboxaldehyde. The product diastereomers were separated by chromatography (silica gel, 10% (v/v) Et$_2$O in CH$_2$Cl$_2$) and evaporated to dryness.

A: The faster running component (TLC-R$_f$=0.41, silica gel plate, 60% (v/v) EtOAc in hexane) was crystallized from Et$_2$O. The solid was dried in vacuo at 65° C.: (m.p. 218°-21° C.).

The compound showed a single spot by TLC. The NMR spectrum was consistent with the title structure. The compound was greater than 96.7% pure by HPLC. The mass spectrum showed a molecular ion at m/e=409.

Anal. Calc'd for C$_{26}$H$_{23}$N$_3$O$_2$: C, 76.26; H, 5.66; N, 10.26. Found: C, 76.26; H, 5.84; H, 10.34.

B: The slower running component (TLC-R$_f$=0.30, silica gel plate, 60% (v/v) EtOAc in hexane) was crystallized from Et$_2$O. The solid was dried in vacuo at 65° C.: (m.p. 125°-30° C.).

The compound was a single spot by TLC. The NMR spectrum was consistent with the title structure and confirmed the presence of Et$_2$O. The compound was greater than 95.7% pure by HPLC. The mass spectrum showed a molecular ion at m/e=409).

Anal. Calc'd for C$_{26}$H$_{23}$N$_3$O$_2$.0.9C$_4$H$_{10}$O: C, 74.66; H, 6.77; N, 8.83. Found: C, 74.61; H, 6.80; N, 9.10.

EXAMPLE 51

1,3-Dihydro-3(RS)-(1-hydroxy-1-phenyl)methyl-1-methyl-5-phenyl-2H-1,4-benzodiazepin-2-one The procedure of Example 47 was carried out using benzaldehyde (0.53 g, 5 mmole) in place of indole-3-carboxaldehyde. The chromatographed product was crystallized from ether and dried in vacuo at 70°: (mp 192°-193°).

The compound showed a single component by TLC (R$_f$=0.53, silica gel plate eluted with 1:1 (v/v) ether/methylene chloride). The NMR spectrum was consistent with the title structure and showed the presence of 0.1 mole of ether. The compound was 99.9% pure by HPLC. The mass spectrum showed a molecular ion at m/e=338.

Analysis Calc'd for C$_{23}$H$_{20}$N$_2$O$_2$.0.1C$_4$H$_{10}$O: C, 77.24; H, 5.82; N, 7.70: Found: C, 77.11; H, 5.83; N, 7.93.

EXAMPLE 52

1,3-Dihydro-3(RS)-[1-hydroxy-1-(2-thienyl)]methyl-1-methyl-5-phenyl-2H-1,4-benzodiazepin-2-one The procedure of Example 47 was carried out using 2-thiophene-carboxaldehyde (0.56 g, 5 mmole) in place of indole-3-carboxaldehyde. The chromatographed and evaporated product was crystallized from ether and dried in vacuo at 70°: (mp 184°–185°).

The compound showed a single component by TLC ($R_f$=0.54, silica gel plate eluted with 1:1 (v/v) ether/methylene chloride). The NMR spectrum was consistent with the title structure. The compound was 99.8% pure by HPLC.

Analysis Calc'd for $C_{21}H_{18}N_2O_2S$: C, 69.59; H, 5.01; N, 7.73; Found: C, 69.59; H, 5.10; N, 8.06.

EXAMPLE 53

1,3-Dihydro-3-(RS)-hydroxy-1-methyl-5-phenyl-3-(3'-thienoyl)-2H-1,4-benzodiazepin-2-one (A) and
1,5-Dihydro-5-(RS)-hydroxy-1-methyl-5-phenyl-3-(3'-thienoyl)-2H-1,4-benzodiazepin-2-one (B)

The procedure of Example 47 was carried out using 0.75 g (5 mmole) of 3-thienoyl chloride in place of indole-3-carboxaldehyde. In this reaction, the THF employed was subsequently shown to contain significant quantities of organic peroxides. Workup and chromatography as in Example 47 provided two products each of which was evaporated in vacuo and crystallized from ether.

A: The first product obtained was A, which was dried in vacuo at 70°: (mp 193°–194°).

The compound showed a single component by TLC ($R_f$=0.57, silica gel plate eluted with 1:1 (v/v) methylene/chloride ether). The NMR spectrum was consistent with the title structure. The compound was 99.4% pure by HPLC. The mass spectrum showed a molecular ion at m/e=376. The infrared spectrum showed a strong absorption at 1675 cm$^{-1}$.

Analysis Calc'd for $C_{21}H_{16}N_2O_3S$: C, 67.00; H, 4.28; N, 7.44; Found: C, 67.04; H, 4.37; N, 7.49.

B: The second compound obtained was B, which was dried in vacuo at 70°: (mp 173°–175°).

The compound showed a single component by TLC ($R_f$=0.64, silica gel plate eluted with 1:1 methylene chloride/ether). The NMR spectrum was consistent with the title structure. The mass spectrum showed a molecular ion at m/e=376. The compound was 99.6% pure by HPLC. The infrared spectrum showed strong absorption at 1695 and 1720 cm$^{-1}$.

Analysis Calc'd for $C_{21}H_{16}N_2O_3S$: C, 67.00; H, 4.28; N, 7.44; Found: C, 66.91; H, 4.46; N, 7.32.

EXAMPLE 54

7-Chloro-1,3-dihydro-3(R)-[(2',3'-dihydro-2'-oxo-1'H-indol-3'-yl)methyl]-5-phenyl-2H-1,4-benzodiazepin-2-one 7-Chloro-1,3-dihydro-3(R)-indolylmethyl-5-phenyl-2H-1,4-benzodiazepin-2-one (200 mg, 0.5 mmol) was dissolved in DMSO (4.8 g, 10 mmol) followed by the addition of concentrated HCl (5 mmol). The molar ratio of DMSO to HCl was 2:1. Additional reagents were added to drive the reaction to completion. The additions were: 0.71 ml DMSO 1.54 ml DMSO 0.4 ml HCl 0.75 ml HCl When little starting material remained, the reaction was poured into an Erlenmeyer flask with water (20 ml), and 5 g of $NaHCO_3$ was added. Water (100 ml) was added and the mixture was extracted with 4×50 ml of n-butanol. The n-butanol solution was washed with water (3×100 ml). The n-butanol solution was evaporated and the residue was dissolved in ether and purified by preparative TLC.

The product was a pair of diasteriomers; the NMR spectrum was consistent with the title compound.

HPLC indicated two components: 54% and 43%.

TLC in 95/5/0.5 $CHCl_3$-MeOH-$H_2O$ $R_f$=0.3 (silica gel GF)

Mass Spec. gave a (M+1) at 416.

EXAMPLE 55

7-Chloro-1,3-dihydro-3(R)-[(3'-(2,4-dinitrophenyl)imidazol-5'-yl)-methyl]-5-phenyl-2H-1,4-benzodiazepin-2-one Boc-DNP-D-Histidine (1.7 g, 4 mmol) and 2-amino-5-chlorobenzophenone (0.9 g, 4 mmol) were combined in 1% ml of THF and stirred until a clear orange solution was obtained. 4.3 mL of DCC (1M) in THF was added and the reaction was stirred overnight. The reaction was filtered and evaporated. The residue was purified by flash chromatography on a silica gel 60 column with a 90:10 chloroform ether solvent system.

The resultant t-BOC protected compound was dissolved in 30 ml of ethyl acetate. The solution was cooled to −25° C. HCl gas was added until the solution was saturated. The temperature was allowed to rise to 0° C. When the reaction was complete by TLC, the ethyl acetate was evaporated and the residue was dissolved in methanol. The pH of the solution was adjusted with 10% aqueous sodium hydroxide to pH 9. After the reaction stirred overnight, the solvent was evaporated and the residue was chromatographed on a silica gel 60 column with chloroform, to give the title compound.

HPLC: 91%.

TLC: $R_f$=0.6 in 90/10/1 $CHCl_3$-MeOH-aqueous ammonia (silica gel GF)

Mass Spec. molecular ion at 516.

NMR agreed with the title compound.

Elemental analysis for $C_{25}H_{17}ClN_6O_5.1.8H_2O$ Calcd: C, 54.65; H, 3.82; N, 15.30. Observed: C, 54.38; H, 3.89; N, 15.31.

EXAMPLE 56

7-Chloro-1,3-dihydro-3(R)-(3'-imidazol-5'-yl)methyl-5-phenyl-2H-1,4-benzodiazepin-2-one This compound was obtained as a second product from the reaction sequence of Example 55. This material, which had a positive Sanger test for histidine, eluted from the silica column after the compound of Example 55, HPLC: 87%.

TLC: $R_f$=0.3 in 90/10/1 $CHCl_3$-MeOH-aqueous ammonia (silica gel GF).

Mass Spec. molecular ion at 350.

NMR was consistent with the title compound.

Elemental Analysis for: $C_{19}H_{15}ClN_4O$ 0.93 $H_2O$ 0.28$NH_3$ Calcd: C, 61.29; H, 4.79; N, 16.33. Found: C, 61.68; H, 5.12; N, 16.61.

EXAMPLE 57

3(RS)-[3'-(5'-Bromoindolyl)methyl]-1,3-dihydro-5-phenyl-2H-1,4-benzodiazepin-2-one The synthesis was carried out as described for Example 55 starting with Boc-5-bromo-DL-tryptophan and 2-aminobenzophenone. The crude product was purified by column chromatography (silica gel) using 90/10 chloroform-ether as the elution solvent.

HPLC: 99%.

Elemental analysis calcd: N 8.91; C, 61.15; H, 4.41 Found: N, 8.43; C, 61.43; H, 4.20. Mass Spec. molecular ion at 443. NMR: The NMR was in agreement with the title compound.

EXAMPLE 58

5-o-Carboxyphenyl-1,3-dihydro-3(R)-(3'-indolyl)methyl-2H-1,4-benzodiazepin-2-one 2-Amino-2'-carboxybenzophenone (2.41 g, 10 mmol) was suspended in THF, $CH_2Cl_2$, EtOAc and tryptophanyl chloride hydrochloride (2.59 g, 10 mmol) was added. The mixture was stirred at room temperature until reaction was complete by TLC. A solid was collected by filtration, dried, and dissolved in 40 ml of methanol. The pH of the solution was adjusted to a pH of 8–10 with 10% aqueous sodium hydroxide. After standing at room temperature for about 3 days, the solution was acidified to a pH of about 3. The solvent was evaporated and the residue was dissolved in 95/5 $CHCl_3/CH_3OH$ and flash chromatographed on a silica gel 60 column with a 95:5 and 90:10 chloroform-methanol solvent system to give the title compound.

HPLC: 96%.

Elemental analysis calcd: C, 61.73; H, 3.97; N, 8.38 Found: C, 61.70; H, 4.09; N, 8.48. Mass Spec. molecular ion observed at 409. NMR: The spectrum agreed with the title compound.

EXAMPLE 59

1,3-Dihydro-3(RS)-[3'-(5'-fluoroindolyl)methyl]-5-o-fluorophenyl-2H-1,4-benzodiazepin-2-one 5-Fluorotryptophyl chloride hydrochloride (1.38 g, 5 mmole), prepared from 5-fluoro-DL-tryptophan and $PCl_5$ in acetylchloride, was suspended in 15 ml of THF. 2-Amino-2'-fluorobenzophenone 1.07 g (5.0 mmol) was added to the stirred mixture. After stirring overnight the solvent was evaporated and the solid was dissolved in 50 ml of methanol. The pH of the solution was adjusted to 8–9 with 10% aqueous sodium hydroxide. The solution stood for 24 hours at room temperature. The solvent was evaporated and the crude reaction product was purified by flash chromatography with 98:2 chloroform/methanol to give the title compound.

TLC: $R_f$=0.3 in 97:3 $CHCl_3/CH_3OH$ (silica gel GF).

Elemental analysis calcd for $C_{24}H_{17}F_2N_3O$ .0.18$CHCl_3$ C, 68.75; H, 4.10; N, 9.94 Found: C, 68.78; H, 4.04; N, 9.85. NMR was in agreement with the title compound.

EXAMPLE 60

1,3-Dihydro-3(RS)-[3'-(6'-fluoroindolyl)methyl]-5-o-fluorophenyl-2H-1,4-benzodiazepin-2-one The compound was prepared according to the procedure of Example 59, using 6-fluorotryptophyl chloride hydrochloride in place of the 5-fluoro compound.

The final product was obtained as a solid which crystallized in pure form from chloroform.

TLC: $R_f$=0.4 in 97:3 $CHCl_3/CH_3OH$ (silica gel GF)

Elemental analysis calcd: C, 70.62; H, 4.20; N, 10.26 Found: C, 70.62; H, 4.10; N, 10.25. NMR was in agreement with the title compound.

EXAMPLE 61

2-N-[2(RS)3-bis-(Boc-amino)propanoyl]amino-2'-fluorobenzophenone

The procedure of Example 1 was carried out using 2-amino-2'-fluorobenzophenone (430 mg, 2.0 mmole), 2(R,S),3-bis-(Boc-amino)propionic acid (617 mg, 2.03 mmole), and dicyclohexylcarbodiimide (2.03 ml of a 1.0M solution in methylene chloride) in 10 ml of methylene chloride. Filtration, concentration in vacuo and flash chromatography (silica gel, 10% ethyl ether in methylene chloride) gave a foam, the PMR spectrum of which was consistent with the title compound.

EXAMPLE 62

2-N-[2(RS)-3-diphthalylaminopropanoyl]amino-2'-fluorobenzophenone

2-Amino-2'-fluorobenzophenone (2.10 g, 9.8 mmole) was reacted with 2,3-diphthalylaminopropionyl chloride (5 g, 9.8 mmole) in 100 ml of tetrahydrofuran. After 2.5 hours the reaction mixture was rotoevaporated to give 7 g of a yellow foam. The foam was heated for 30 minutes in 6N hydrochloric acid (100 ml) and the resulting off-white solid collected and dried. Recrystallization from ethyl acetate afforded the analytical sample, m.p. 210.5°–211.5°. NMR ($CD_3OD$): in agreement with title compound.

Analysis Calc'd for $C_{32}H_{20}FN_3O_6$ N, 7.48; C, 68.45; H, 3.59. Found: N, 7.46; C, 68.59; H, 3.63.

EXAMPLE 63

1,3-Dihydro-5-(2'-fluorophenyl)-3(RS)-aminomethyl-2H-1,4-benzodiazepin-2-one

The procedure of Example 2 was carried out in which 2-N-[2(RS)-((1,1-dimethylethoxy)carbonyl)-amino-3-((1,1-dimethylethoxy)carbonyl)amino-propanoyl]-amino-2'-fluorobenzophenone (600 mg, 1.2 mmole) was reacted in succession with excess HCl gas in ethyl acetate (15 ml) at 0° and then sodium hydroxide (0.1M solution) in aqueous methanol (10 ml). The pH of the reaction mixture was approximately 9.0. Work-up afforded the title compound as a solid, mp 168°–169°; in 90% yield.

NMR ($CDCl_3$): Spectrum in agreement with title compound.

MS (14 ev.): 283 (M+) 253.

Analysis Calc'd for $C_{16}H_{14}FN_3O.0.5C_6H_{14}$ N, 14.61; C, 68.07; H, 5.15. Found: N, 14.87; C, 68.21; H, 5.33.

EXAMPLE 64

1,3-Dihydro-5-(2'-fluorophenyl)-3(RS)-aminomethyl-2H-1,4-benzodiazepin-2-one

2-N-[2(RS),3-diphthalylaminopropanoyl]amino-2'-fluorobenzophenone (1.07 g, 1.90 mmole) was suspended in 55 ml of methanol and treated with 1 ml of 95% hydrazine. The reaction mixture was protected from moisture and stirred at room temperature. Within one hour, the reaction mixture became homogeneous. On further reaction, phthalhydrazide precipitated from solution. After 14 hours, the reaction was filtered and the filtrate concentrated. The residue was partitioned between methylene chloride and water; the organic phase was washed with water until it was free of hydrazine (Tollen's reagent negative), then dried and concentrated to give 480 mg of an oil which crystallized on standing. Trituration of the resulting solid with ether gave the analytical sample, m.p. 168°–169°, identical spectroscopically with the material prepared in Example 63.

EXAMPLE 65

1,3-Dihydro-5-(2'-fluorophenyl)-3(R)-(4-amino)butyl-2H-1,4-benzodiazepin-2-one

The procedure of Example 64 was followed whereby 2-N-[2(R),6-diphthalylaminohexanoyl]amino-2'-fluorobenzophenone (5.4 g) was deprotected and cyclized with 10 ml of 95% hydrazine in 150 ml of methanol. Workup afforded 1.35 g of product which was purified via silica gel chromatography (chloroform-methanol-ammonia, 80:30:4 v/v).

NMR (CDCl$_3$): in agreement with title compound.

Analysis Calc'd for $C_{19}H_{20}FN_3O \cdot 0.17 CHCl_3$ N, 12.15; C, 66.60; H, 5.88. Found: N, 12.32; C, 66.66; H, 6.05.

EXAMPLE 66

1,3-Dihydro-5-(2'-fluorophenyl)-3(RS)-(benzyloxycarbonyl)aminomethyl-2H-1,4-benzodiazepin-2-one To a solution of 50 ml of methylene chloride containing 260 mg (0.91 mmol) of 1,3-dihydro-5-(2-fluorophenyl)-3(RS)-aminomethyl-2H-1,4-benzodiazepin-2-one and 224 mg (1.83 mmol) of 4-dimethylaminopyridine was added 0.51 ml (3.57 mmol) of benzylchloroformate. The resulting reaction mixture was allowed to stand at room temperature overnight and then was diluted with methylene chloride (200 ml). The reaction was then washed in succession with saturated sodium bicarbonate solution and brine, then dried (MgSO$_4$) and concentrated. The residual oil was chromatographed on silica gel (chloroform-methanol-ammonia, 95:5:0.5 v/v elution) to afford 370 mg of the analytical product, m.p. 88° (soften), 90°–92° C.

TLC: Single component, R$_f$=0.35 (95:5:0.5, chloroform-methanol-ammonia).

NMR: Consistent with title structure.

Anal. calc'd for $C_{24}H_{20}FN_3O_3 \cdot \frac{1}{4}H_2O$ N, 9.96; C, 68.32; H, 4.89; Found: N, 9.86; C, 68.45; H, 5.15.

EXAMPLE 67

1,3-Dihydro-5-(2'-fluorophenyl)-3(RS)-(3-thiophenecarbonyl)aminomethyl-2H-1,4-benzodiazepin-2-one 1,3-Dihydro-5-(2'-fluorophenyl)-3(RS)-aminomethyl-2H-1,4-benzodiazepin-2-one (140 mg, 0.49 mmole) and 3-thiophenecarbonyl chloride (88 mg, 0.60 mmole) were dissolved in 10 ml of dry tetrahydrofuran at room temperature. To this solution was added 69 l of triethylamine. After addition was complete, stirring was continued for 15 minutes more and the reaction mixture was partitioned between ethylacetate (60 ml) and sodium bicarbonate solution (sat.). The organic phase was washed with 10% sodium hydroxide solution (1×20 ml) and then with 10% hydrochloric acid solution. From this acidic solution were deposited off-white crystals, after overnight standing. The solid was washed with water and dried to give 140 mg of the analytical product, mp 237°–240° (An additional 70 mg of product was obtained as the free base after concentration of the organic extracts.) The analytical product was greater than 98% pure by HPLC.

MS (14 ev.): 393 (M-HCl), 266.

NMR (DMSO-d$_6$): in agreement with title compound.

Analysis Calc'd for $C_{21}H_{17}ClFN_3O_2S$: N, 9.77; C, 58.67; H, 3.98. Found: N, 9.89; C, 58.75; H, 4.17.

EXAMPLE 68

1,3-dihydro-5-(2-fluorophenyl)-3(RS)-(2-indole carbonylaminomethyl)-2H-1,4-benzodiazepin-2-one 1,3-Dihydro-5-(2-fluorophenyl)-3(RS)-aminomethyl-2H-1,4-benzodiazepin-2-one (80 mg, 0.282 mmole) and indole-2-carbonyl chloride (53 mg, 0.30 mmol) were mixed in 5 ml of methylene chloride at room temperature. The homogeneous reaction mixture was protected from moisture and treated with 42 l (0.30 mmole) of triethylamine. Within five min., triethylamine hydrochloride precipitated. The reaction mixture was stirred at room temperature overnight and then partitioned between methylene chloride and saturated sodium bicarbonate solution. The resulting solid was collected, washed with water and dried over P$_2$O$_5$ at 70° C. In this way, 39 mg of the analytical product was obtained, m.p.: 315°–317° (d).

NMR(DMSO-d$_6$): Consistent with the title structure.

MS: Molecular ion at m/e=426.

Anal. calc'd for $C_{25}H_{19}FN_4O_2 \cdot 1.25 H_2O$ C, 66.88; H, 4.82; N, 12.48; Found: C, 66.76; H, 4.52. N, 12.25.

EXAMPLE 69

1,3-Dihydro-3(RS)-[3'-(RS)-(1,3-dihydro-5-(2'-fluorophenyl)-2H-1,4-benzodiazepin-2-one)-3-yl]methylaminomethyl-5-(2'-fluorophenyl)-2H-1,4-benzodiazepin-2-one 1,3-Dihydro-5-(2'-fluorophenyl)-3(RS)-aminomethyl-2H-1,4-benzodiazepin-2-one (60 mg, 0.21 mmole) was dissolved in 3 ml of isopropanol and treated with triethylamine (30 £ 1, 0.22 mmole). The resulting solution was heated to reflux for 18 hours, cooled and concentrated. The residual oil was chromatographed on silica gel (chloroform-methanol-ammonia, 90:10:1 v/v) to give 25 mg of the desired product as an off-white solid, mp 155°–158° (with gas evolution). MS (FAB): 550 (M+H), 549 (M+), 282 (base peak).

NMR (CDCl$_3$): in agreement with title compound.

Analysis Calc'd for $C_{32}H_{25}F_2N_5O_2 \cdot 0.35$ CHCl$_3$: N, 11.84; C, 65.70; H, 4.32. Found: N, 11.68; C, 65.53; H, 4.46.

EXAMPLE 70

1,3-Dihydro-5-(2'-fluorophenyl)-3-(RS)-(6'-chloropyrazin-2-yl)aminomethyl-2H-1,4-benzodiazepin-2-one 1,3-Dihydro-5-(2-fluorophenyl)-3-(RS)-aminomethyl-2H-1,4-benzodiazepin-2-one (72 mg, 0.25 mmol), 2,6-dichloropyrazine (45 mg, 0.30 mmol)and anhydrous potassium carbonate (83 mg, 0.60 mmol) were combined at room temperature with 2 ml of dry dimethylformamide. The resulting suspension was stirred rapidly for 24 hours and 37 mg more of 2,6-dichloropyrazine was added. After 72 hours total reaction time, the reaction mixture was poured into water (10 ml) and extracted with ethyl acetate (3×20 ml). The combined organic extracts were washed with water and brine, dried (MgSO$_4$) and concentrated to give 70 mg of crude product. The analytical sample was obtained by preparative thick layer chromatography (chloroform-methanol-ammonia, 95:5:0.5 v/v one elution).

R$_f$=0.25, m.p. 140° (soften), 148°–152°.

NMR (CDCl$_3$): Consistent with the title structure.
MS (14 ev): 395 (M+), 266, 254, 211.
Anal. calc'd for C$_{20}$H$_{15}$ClFN$_5$O.$\frac{1}{4}$H$_2$O: N, 17.49; C, 60.00; H, 3.90; Found: N, 16.59; C, 59.87; H, 3.90.

EXAMPLE 71

2-N-Methyl-N-[2(RS),3-diphthalylaminopropanoyl]amino-2'-fluorobenzophenone

Following the procedure of Example 4, 2-N-[2(RS),3-diphthalylaminopropanoyl]amino-2'-fluorobenzophenone (677 mg, 1.20 mmole) was converted to the title compound with sodium hydride (63 mg, 1.31 mmole) and methyliodide (81.5 µl, 1.31 mmole) in 5 ml of N,N-dimethylformamide. Work-up afforded the crude product which was purified by silica gel chromatography (ethyl acetate-hexane elution, 3:2 v/v); the analytical sample was obtained as white prisms by recrystallizing the chromatographed material from ethyl acetate, mp 252°.
MS (14 ev.): 575 (M+), 453, 429, 309.
NMR (CDCl$_3$): in agreement with title compound.
Analysis Calc'd for C$_{33}$H$_{22}$FN$_3$O$_6$.0.15 C$_4$H$_8$O$_2$: N, 7.13; C, 68.54; H, 3.94. N, 7.12; C, 68.43; H, 4.26.

EXAMPLE 72

1,3-Dihydro-5-(2'-fluorophenyl)-3(RS)-aminomethyl-1-methyl-2H-1,4-benzodiazepin-2-one Following the procedure of Example 64, 2-N-methyl-N-[2(RS),3-diphthalylaminopropanoyl]amino-2'-fluorobenzophenone (220 mg, 0.38 mmole) was converted to the title compound with 95% hydrazine (1 ml) in 40 ml of methanol. The analytical material was obtained via chromatography on silica gel (chloroform-methanol-ammonia, 90:10:1 v/v). The PMR spectrum (CDCl$_3$) confirmed the structure of the product; N-methyl proton at 3.46 ppm.

EXAMPLE 73

3(RS)-1,3-Dihydro-(2-indolecarbonylamino)-5-phenyl-2H-1,4-benzodiazepin-2-one 3-(RS)-Amino-1,3-dihydro-5-phenyl-2H-1,4-benzodiazepin-2-one (75 mg, 0.298 mmol), and indole-2-carbonyl chloride (58.8 mg, 0.327 mmol) were combined in CH$_2$Cl$_2$ (2 ml) and the pH adjusted to 9.0 with triethylamine (41 µl, 0.298 mmol). After stirring 10 min., the reaction was chromatographed on silica gel (180/10/1/1 of CH$_2$Cl$_2$/MeOH/H$_2$O/HOAc). The combined product fractions were washed with dilute NaHCO$_3$ (aq) (1X), H$_2$O (1X) and brine (1X), dried over MgSO$_4$, filtered and stripped to give the title compound as a white solid from ether: (m.p. 265°–268°).
TLC: Silica GF (10% MeOH in CH$_2$Cl$_2$), R$_f$=0.63, single homogeneous component.
NMR: Consistent with title structure and verifies the presence of 0.2 (C$_2$H$_5$)$_2$O.
HPLC: Greater than 99.2% pure.
M.S.: Mol. Ion=394 m/e (free base).
Anal. Calc'd for C$_{24}$H$_{18}$N$_4$O$_2$.0.2 (C$_2$H$_5$)$_2$O: C, 72.78; H, 4.93; N, 13.69; Found: C, 72.45; H, 4.60; N, 13.65.

EXAMPLE 74

1,3-Dihydro-3(RS)-[2-(3-indolyl)ethyl]amino-5-phenyl-2H-1,4-benzodiazepin-2-one 3-(RS)-Chloro-1,3,-dihydro-5-phenyl-2H-1,4-benzodiazepine-2-one (68 mg, 0.25 mmol), 3-(2-aminoethyl)indole (40 mg, 0.25 mmol) and sodium hydroxide (0.1 ml of 2.5N solution) were combined in methanol (4 ml) and stirred at room temperature for 18 hours. The mixture was evaporated in vacuo, and the residue was dissolved in methylene chloride and chromatographed on silica gel (5% v/v MeOH in CH$_2$Cl$_2$). The product fractions were evaporated in vacuo and the resulting solid crystallized from ether and dried in vacuo at 60°: (m.p. 196–197.5 (d)). TLC: Single spot (R$_f$=0.46, silica gel plate, 10% (v/v) MeOH in CH$_2$Cl$_2$).
NMR: The spectrum was consistent with the title structure and verified the presence of CH$_2$Cl$_2$.
HPLC: Greater than 94% pure.
MS: A molecular ion at m/e=394.
Anal calc'd. for C$_{25}$H$_{22}$N$_4$O.0.13 CH$_2$Cl$_2$: C, 74.43; H, 5.53; N, 13.82; Found: C, 74.62; H, 5.47; N, 13.62.

EXAMPLE 75

3(RS)-[3-(3-indolyl)propionylamino]-1,3-dihydro-5-phenyl-2H-1,4-benzodiazepin-2-one The procedure of Example 77 was carried out using 3-(3-indolyl)propionic acid (0.076 g, 0.4 mmol) in place of BOC-L-tryptophan. The product was chromatographed on silica gel using a gradient of 1:1 Et$_2$O/CH$_2$Cl$_2$ containing 0 to 2% CH$_2$OH. The product was crystallized from acetone and dried in vacuo at 60°: (m.p. 176°–182°).
TLC: Single spot (R$_f$=0.66, silica gel plate, 10% (v/v) MeOH in CH$_2$Cl$_2$).
NMR: The spectrum was consistent with the title structure.
HPLC: 99.7% pure.
MS: A molecular ion at m/e=422.
Anal. calc'd for C$_{26}$H$_{22}$N$_4$O$_2$.0.5 H$_2$O: C, 72.37; H, 5.37; N, 12.99; Found: C, 72.31; H, 5.57; N, 12.98.

EXAMPLE 76

3(RS)-(3-indoleacetylamino)-1,3-dihydro-5-phenyl-2H-1,4-benzodiazepin-2-one 3-(RS)-Amino-1,3-dihydro-5-phenyl-2H-1,4-benzodiazepin-2-one (75 mg, 0.298 mmol) and indole-3-acetyl chloride (57.8 mg, 0.298 mmol) were combined in CH$_2$Cl$_2$ (2 ml) and the pH adjusted to 9.0 with triethylamine (TEA) 41 µl, 0.298 mmol). After stirring 15 min., a second portion of indole-3-acetyl chloride (44 mg, 0.175 mmol) and TEA (30 µl, 0.215 mmol) were added and the reaction stirred an additional 15 min. The completed reaction was diluted with CH$_2$Cl$_2$, washed with H$_2$O (1X) and brine (1X), dried over MgSO$_4$, filtered and stripped to dryness in vacuo. The residue was chromatographed on silica gel (5% MeOH in CH$_2$Cl$_2$) to give the title compound as a pinkish solid from Et$_2$O: (m.p. 264°–265°).
TLC Silica GF (10% MeOH in CH$_2$Cl$_2$), R$_f$=0.44, single homogeneous component.
NMR: Consistent with title structure.
HPLC: Greater than 93.1% pure.
M.S.: molecular ion at m/e=408.
Anal. calc'd for C$_{25}$H$_{20}$N$_4$O$_2$: C, 73.51; H, 4.94; N, 13.72; Found: C, 73.54; H, 4.94; N, 13.32.

EXAMPLE 77

3(RS)-(Boc-L-tryptophanyl)amino-1,3-dihydro-5-phenyl-2H-1,4-benzodiazepin-2-one 3-(RS)-Amino-1,3-dihydro-5-phenyl-2H-1,4-benzodiazepin-2-one (0.1 g, 0.4 mmol), BOC-L-tryptophan (0.12 g, 0.4 mmol), and DCC (0.4 ml of a 1M solution in CH$_2$Cl$_2$, 0.4 mmol) were combined in 2 ml of THF to which were added 2 ml of DMF and 2 ml of $CH_2Cl_2$. The mixture was treated with triethylamine (0.11 ml), stoppered, and stirred at room temperature for four days. The mixture was treated with citric acid solution (10%, 3 ml) and $CH_2Cl_2$ (5 ml), shaken and separated. The aqueous phase was extracted with $CH_2Cl_2$ (2×5 ml). The combined organic layers were washed with citric acid (10%, 2×5 ml), sodium bicarbonate (10%, 2×5 ml), and $H_2O$ (10 ml), dried over sodium sulfate, filtered, and evaporated to dryness in vacuo. The residue was chromatographed on silica gel (1:1 (v/v) $Et_2O/CH_2Cl_2$) and the combined product fractions evaporated to dryness in vacuo. The residue was triturated with petroleum ether and the solid dried in vacuo at 70°: (m.p. 173°–177° (↑)).

TLC: Single spot ($R_f=0.56$, silica gel plate, 10% (v/v) $CH_3OH$ in $CH_2Cl_2$).

NMR: The spectrum was consistent with the title structure and verified the presence of two diastereomers.

HPLC: Greater than 99.7% pure (36% and 63.7%).

MS (FAB): a molecular ion at m/e=537.

Anal. calc'd for $C_{31}H_{31}N_5O_4$: C, 69.25; H, 5.81; N, 13.03; Found: C, 69.48; H, 6.18; N, 12.96.

EXAMPLE 78

1-Carboxymethyl-1,3-dihydro-3(RS)-(2-indolecarbonylamino)-5-phenyl-2H-1,4-benzodiazepin-2-one The procedure of Example 4 was carried out using 1,3-dihydro-3(RS)-(2-indolecarbonylamino)-5-phenyl-2H-1,4-benzodiazepin-2-one (0.87 g, 2.2 mmol) in place of 1,3-dihydro-5-(2-fluorophenyl)-3(R)-(3'-indolyl)-methyl-2H-1,4-benzodiazepin-2-one and ethyl bromoacetate (0.38 g, 2.25 mmole) in place of methyl iodide. The chromatographed product (7% ether in $CH_2Cl_2$) (0.073 g, 0.15 mmol) and sodium hydroxide (0.2 ml, 1N, 0.2 mmol) were stirred together in $CH_3OH$ (1 ml) at room temperature for 18 hours. The mixture was concentrated in vacuo, diluted to 3 ml with $H_2O$, made acidic with 1N HCl, and extracted with $CH_2Cl_2$ (3×5 ml). The combined organic layers were treated with methanol (1 ml) to dissolve precipitated solid, dried over $Na_2SO_4$, filtered, and evaporated to dryness in vacuo. The residue was crystallized from ether (4 ml) and the solid dried in vacuo at 80°: (m.p. 275°–278° (d) (↑)).

TLC: A single spot ($R_f=0.21$, silica gel plate, 180:10:1:1 (v/v/v/v) $CH_2Cl_2$:MeOH:HOAc: $H_2O$).

NMR: Spectrum was consistent with the title structure and verified with presence of $Et_2O$ and $CH_2Cl_2$.

HPLC: Greater than 98.5% pure.

MS: A molecular ion at m/e=452.

Anal. calc'd for $C_{26}H_{20}N_4O_4O_4.0.3$ $CH_2Cl_2.0.3$ $C_4H_{10}O$ C, 66.03; H, 4.76; N, 11.20; Found: C, 65.93; H, 4.56; N, 11.22.

EXAMPLE 79

1,3-Dihydro-3(RS)-(2-indolecarbonylamino)-1-methyl-5-phenyl-2H-1,4-benzodiazepin-2-one (A) and 1,3-dihydro-1-methyl-3(RS)-[2-(1-methylindole)carbonylamino]-5-phenyl-2H-1,4-benzodiazepin-2-one (B)

The Procedure of Example 4 was carried out using 1,3-dihydro-3(RS)-(2-indolecarbonylamino)-5-phenyl-2H-1,4-benzodiazepin-2-one (0.87 g, 2.2 mmol) in place of 1,3-dihydro-5-(2-fluorophenyl)-3(R)-(3'-indolyl)-methyl-2H-1,4-benzodiazepin-2-one. Chromatography using 7% (v/v) diethyl ether in $CH_2Cl_2$ and evaporation of the product fractions in vacuo gave A and B which were each crystallized from ether and dried in vacuo at 80°.

Compound A: (m.p. 268–270° (d))

TLC: A single spot ($R_f=0.43$, silica gel plate, 10% (v/v) $Et_2O$ in $CH_2Cl_2$).

NMR: Spectrum was consistent with the title structure and verified the presence of $Et_2O$ and $CH_2Cl_2$.

HPLC: 99% pure.

MS: A molecular ion at m/e=408.

Anal. calc'd for $C_{25}H_{20}N_4O_2.0.15$ $CH_2Cl_2.0.1$ $C_4H_{10}O$: C, 71.60; H, 5.01; N, 13.07; Found: C, 71.79; H, 5.01; N, 13.01.

Compound B: (m p. 202.5°–203°).

TLC: A single spot ($R_f=0.67$, silica gel plate, 10% (v/v) $Et_2O$ in $CH_2Cl_2$).

NMR: Spectrum was consistent with the title structure.

HPLC: Greater than 98.2% pure.

MS: A molecular ion at m/e=422.

Anal. calc'd for $C_{26}H_{22}N_4O_2$: C, 73.91; H, 5.25; N, 13.26; Found: C, 74.05; H, 5.20; N, 13.51.

EXAMPLE 80

1,3-Dihydro-1-methyl-3(RS)-(4-chlorophenylcarbonyl)amino-5-(2-fluorophenyl)-2H-1,4-benzodiazepin-2-one To a suspension of sodium hydride (50%) (84 mg, 1.82 mmole) in 4 ml of dry dimethylformamide at 0° C. was added, under nitrogen, 1,3-dihydro-3(RS)-(4-chlorophenylcarbonyl)amino-5-(2-fluorophenyl)-2H-1,4-benzodiazepin-2-one (648 mg, 1.59 mmole). The resulting reaction mixture became homogeneous over a one-hour period, was stirred one hour more at 0° C. and then treated with iodomethane (108 μl, 1.74 mmole). The reaction mixture was warmed to room temperature and after one hour was quenched with brine. The aqueous mixture was extracted with ethyl acetate and the combined organic extracts were washed with brine. Rotoevaporation of the dried extracts ($MgSO_4$) gave a semi-solid which was chromatographed on silica gel (chloroform-methanol-ammonia 95:5:0.5 v/v elution) to give 130 mg of recovered starting material and 360 mg of the analytical sample $R_f=0.78$, m.p. 171.5–172° C.

NMR ($CDCl_3$) consistent with the title structure

MS (14 ev): 421 (M+) 282, 266, 255,241.

Analysis calc'd for $C_{23}H_{17}ClFN_3O_2$ Calc'd: N, 9.96; C, 65.48; H, 4.06 Found: N, 10.08; C, 65.79; H, 4.08.

EXAMPLE 81

1,3-Dihydro-5-(2-fluorophenyl)-3(RS)-(2-indolecarbonylamino)-1-methyl-2H-1,4-benzodiazepin-2-one (A) and 1,3-Dihydro-5-(2-fluorophenyl)-1-methyl-3(RS)-[2'-(1'-methylindole)carbonylamino]-2H-1,4-benzodiazepin-2-one (B)

The procedure of Example 4 was carried out using 1,3-dihydro-5-(2-fluorophenyl)-3(RS)-(2-indolecarbonylamino)-2H-1,4-benzodiazepin-2-one (0.91 g, 2.2 mmole) in place of 1,3-dihydro-5-(2-fluorophenyl)-3(R)(3'-indolyl)methyl-2H-1,4-benzodiazepin-2-one. Chromatography using 10% (v/v) diethyl ether in $CH_2Cl_2$ and evaporation of the product fractions in vacuo gave A and B which were each crystallized from $Et_2O/CH_2Cl_2$ (2/1, v/v) and dried in vacuo at 40° C.

Compound A: (m.p. 282–283.5°).

TLC: A single spot ($R_f=0.53$, silica gel plate, 10% (v/v) $Et_2O$ in $CH_2Cl_2$).

NMR: The spectrum was consistent with the title structure and verified the presence of ether (½ mole) and CH$_2$Cl$_2$ (¾ mole).

HPLC: Greater than 97% pure.

MS: A molecular ion at m/e=426.

Anal. calc'd for C$_{25}$H$_{19}$FN$_4$O$_2$.0.5 C$_4$H$_{10}$O.0.75 CH$_2$Cl$_2$: C, 63.22; H, 4.88; N, 10.63; Found: C, 63.41; H, 4.66; N, 10.59.

Compound B: (m.p. 178–181°)

TLC: A single spot (R$_f$=0.76, silica gel plate, 10% (v/v) Et$_2$O in CH$_2$Cl$_2$).

NMR: The spectrum was consistent with the title structure.

HPLC: Greater than 89% pure.

M.S.: A molecular ion at m/e=440.

Anal. calc'd for C$_{26}$H$_{21}$FN$_4$O$_2$.0.75 H$_2$O: C, 68.78; H, 4.99; N, 12.34; Found: C, 68.76; H, 4.73; N, 12.38.

EXAMPLE 82

3(RS)-(2(S)-tert-Butoxycarbonylamino-3-phenyl-propanoylamino)-1,3-dihydro-5-phenyl-2H-1,4-benzodiazepin-2-one 3-(RS)-Amino-1,3-dihydro-5-phenyl-2H-1,4-benzodiazepin-2-one (1.3 g, 5.17 mmole), Boc-L-phenylalanine (1.37 g, 5.17 mmole), HBT (0.70 g, 5.17 mmole), and EDC (0.99 g, 5.17 mmole) were combined in DMF (30 ml) and stirred at room temperature. The pH of the mixture was adjusted to 9.5 with triethylamine. After ½ hour, the DMF was removed in vacuo and the residue treated with 10% citric acid (10 ml), neutralized with Na$_2$CO$_3$ and extracted with CH$_2$Cl$_2$ (3×15 ml). The combined organic layers were washed with water, dried over Na$_2$SO$_4$, filtered, and evaporated to dryness in vacuo. The residue was chromatographed on silica gel (90/3/0.3/0.3 CH$_2$Cl$_2$/MeOH/H$_2$O/HOAc) and the combined product fractions evaporated to dryness in vacuo. The residue was dissolved in CH$_2$Cl$_2$ (10 ml), washed with saturated Na$_2$CO$_3$ solution (2 ml), dried over Na$_2$SO$_4$, filtered and evaporated to dryness. The residue was treated with Et$_2$O and evaporated five times to give the title compound as a mixture of diastereomers (m.p. 143–153° C.). TLC: silica gel (90/10/1/1 CH$_2$Cl$_2$/MeOH/MoAc/H$_2$O), R$_f$=0.58

NMR: consistent with structure

HPLC: 97.5% pure (two diastereomers, 1:1)

M.S.: A molecular ion at m/e=498.

Anal. Calc'd for C$_{29}$H$_{30}$N$_4$O$_4$: Calcd: C, 69.86; H, 6.07; N, 11.24. Found: C, 69.58; H, 6.12; N, 11.22.

EXAMPLE 83

3(RS)-(2(S)-tert-Butoxycarbonylamino-3-phenyl-propanoylamino)-1,3-dihydro-1-methyl-5-phenyl-2H-1,4-benzodiazepin-2-one 3(RS)-(2(S)-tert-Butoxycarbonylamino-3-phenyl-propanoylamino)-1,3-dihydro-5-phenyl-2H-1,4-benzodiazepin-2-one (2.5 gm, 5.01 mmol) was dissolved in DMF (20 ml) cooled to 0° C., treated with a 50% oil dispersion of sodium hydride (241 mg, 5.01 mmol) and stirred 30 minutes. The resulting orange solution was treated with methyl iodide (711 mg, 5.01 mmol) and stirred 1 hour at 25° C. The DMF was removed in vacuo, and the resulting residue treated with dilute Na$_2$CO$_3$ (aqueous) and extracted with EtOAc (3x). The organic extracts were combined, washed with H$_2$O (1x), dried over MgSO$_4$, filtered and evaporated to dryness in vacuo to give a yellow oil (3.57 gm). Flash chromatography on silica gel (15% EtOAc in CH$_2$Cl$_2$) gave the title compound as a white foam (1.8 gm) from ether: (m.p. 117–20° C.) (soften)). TLC: Silica GF (180/10/1/1 of CH$_2$Cl$_2$/ MeOH/H$_2$O/HoAc R$_f$=0.48, clean, homogeneous component NMR: Consistent with structure HPLC: 98.5% pure (as a 1/1 mixture of diastereomers)

M.S.: Molecular ion at m/e=512.

Anal. calc'd for C$_{30}$H$_{32}$N$_4$O$_4$: C, 70.29; H, 6.29; N, 10.93; Found: C, 69.99; H, 6.32; N, 10.81.

EXAMPLE 84

3(R and S)-(2(S)-Amino-3-phenylpropanoylamino)-1,3-dihydro-1-methyl-5-phenyl-2H-1,4-benzodiazepin-2-one 3(RS)-(2(S)-tert-Butoxycarbonylamino-3-phenyl-propanoylamino)-1,3-dihydro-1,3-dihydro-1-methyl-5-phenyl-2H-1,4-benzodiazepin-2-one (1.8 gm, 3.51 mmol) was dissolved in EtOAc (25 ml), cooled to 0° C., and the solution saturated with HCl (g) over a 10 minute period. After stirring an additional 10 minutes the solvent was removed in vacuo. The solid residue was dissolved in H$_2$O, basified with saturated Na$_2$CO$_3$ (aq.) and extracted with EtOAc (3×). The organic layers were combined, washed with brine, dried over Na$_2$SO$_4$, filtered and stripped to dryness in vacuo to give a grey foam (1.46 gm). Flash chromatography on silica gel (90/10/1/1 of CH$_2$Cl$_2$/MeOH/H$_2$O/HOAc) separated the 1/1 pair of diastereomers into a clean upper (R$_f$=0.36) and clean lower (R$_f$=0.24) component. Each component was evaporated to dryness in vacuo, dissolved in CH$_2$Cl$_2$, washed with saturated Na$_2$CO$_2$(aq.) (1), brine (1), dried over Na$_2$SO$_4$ and filtered. The individual filtrates were concentrated to dryness to give the separated diastereomers as white foams (upper component, 605 mg; lower component, 570 mg).

A: Upper Component(3(S)isomer): (m.p. 92°–108° C. (shrink and soften)

TLC: Silica gel (90/10/1/1 of CH$_2$Cl$_2$/MeOH/H$_2$O/HoAc) R$_f$=0.36, single, homogeneous component NMR: Consistent with structure.

HPLC: Greater than 98.8% single component (100% diastereomerically pure).

M.S.: Molecular ion at m/e=412

Anal. calc'd for C$_{35}$H$_{24}$N$_4$O$_2$: C, 72.79; H, 5.87; N, 13.58; Found: C, 72.79; H, 5.96; N, 13.31.

B: Lower Component(3(R)isomer): (m.p. 97°–108° C. (shrink and soften))

TLC: silica gel (90/10/1/1 of CH$_2$Cl$_2$/MeOH/H$_2$O/-HoAc) R$_f$=0.24, single, homogeneous component NMR: Consistent with structure.

HPLC: Greater than 99.2% single component (containing less than 0.8% of upper component)

M.S.: Molecular ion at m/e=412

Anal. calc'd for C$_{25}$H$_{24}$N$_4$O$_2$: C, 72.79; H, 5.87; N, 13.58; Found: C, 72.44; H, 5.85; N, 13.48.

EXAMPLE 85

3(R)- and 3(S)-Amino-1,3-dihydro-1-methyl-5-phenyl-2H-1,4-benzodiazepin-2-one

A: 3(S)-(2(S)-amino-3-phenylpropanoylamino)-1,3-dihydro-1-methyl-5-phenyl-2H-1,4-benzodiazepin-2-one, (Example 84, upper component), (1.15 g, 2.79 mmole) was combined with phenylisothiocyanate (395 mg, 2.93 mmole) in CH$_2$Cl$_2$ (20 ml) and the mixture concentrated on a steam bath. The resulting oil was twice diluted with $CH_2Cl_2$ (20 ml) and both times reconcentrated on the steam bath. The oil was evaporated in vacuo to a foam which was treated with TFA (15 ml) and warmed for 18 minutes in an oil bath thermostatted at 52°. The TFA was removed in vacuo. The residue was treated twice with $CH_2Cl_2$ and with $Et_2O$, evaporated in vacuo after each treatment, and the resulting oil chromatographed on silica gel (90/10/1/1 of $CH_2Cl_2$/MeOH/$H_2O$/HoAc). The product fractions were evaporated in vacuo, and the residue was dissolved in $CH_2Cl_2$, washed with a small volume of 5% NaOH, dried over $Na_2SO_4$, filtered, and evaporated to give the levorotatory (3(S)) isomer of the title structure.

TLC: Silica gel (90/10/1/1 $CH_2Cl_2$/MeOH/$H_2O$/HoAc) $R_f = 0.31$

NMR: Consistent with structure, verifies presence of 0.15 mole of EtOAc

HPLC: Greater than 97.6% pure

M.S.: Molecular ion at m/e=265 $[\alpha]_D^{25} = -236°$ (0.0033 g/ml, $CH_2Cl_2$)

Anal. calc'd for $C_{16}H_{15}N_3O \cdot 0.15\ H_2O \cdot 0.15\ C_4H_{10}O$: C, 71.43; H, 6.07; N, 15.06; Found: C, 71.44; H, 5.95; N, 15.11.

B: 3(R)-(2(S)-amino-3-phenylpropanoylamino)-1,3-dihydro-1-methyl-5-phenyl-2H-1,4-benzodiazepin-2-one (Example 84, lower component) was converted by the same procedure to the dextrorotatory (3(R)) enantiomer of the title compound.

TLC: Silica gel (90/10/1/1 $CH_2Cl_2$/MeOH/$H_2O$/HoAc) $R_f = 0.31$

NMR: Consistent with structure, verifies presence of 0.15 mole of EtOAc

HPLC: Greater than 96.7% pure

M.S.: Molecular ion at m/e=265 $[\alpha]_D^{25} = +227°$ (0.0033 g/ml, $CH_2Cl_2$)

Anal. calc'd for $C_{16}H_{15}N_3O \cdot 0.15\ H_2O \cdot 0.15\ C_4H_{10}O$: C, 71.43; H, 6.07; N, 15.06; Found: C, 71.14; H, 5.99; N, 14.90.

EXAMPLE 86

3(R) and 3(S)-Amino-1,3-dihydro-5-(2-fluorophenyl)-1-methyl-2H-1,4-benzodiazepin-2-one The procedure of Example 82 was carried out using 3-(RS)-amino-1,3-dihydro-5-(2-fluorophenyl)-2H-1,4-benzodiazepin-2-one in place of 3-(RS)-amino-1,3-dihydro-5-phenyl-2H-1,4-benzodiazepin-2-one. The product was methylated using the procedure of Example 83 and the resulting methyl derivative was deprotected and separated using the procedure of Example 84. The separated isomers were each treated with phenyl isothiocyanate followed by TFA according to the method of Example 85 giving the 3(R) and 3(S) isomers of the title compound.

3(S) isomer:

TLC: Silica gel (90/10/1/1 $CH_2Cl_2$/MeOH/$H_2O$/HoAc), $R_f = 0.37$

NMR: Consistent with structure

HPLC: 95% pure

M.S.: Molecular ion at m/e=283 $[\alpha]_D^{25} = -86.3°$ (0.0025 g/ml, $CH_2Cl_2$)

3(R) isomer:

TLC: Silica gel (90/10/1/1 $CH_2Cl_2$/MeOH/$H_2O$/HoAc), $R_f = 0.37$

NMR: Consistent with structure

M.S.: Molecular ion at m/e=283 $[\alpha]_D^{25} = +71.4°$ (0.0028 g/ml, $CH_2Cl_2$)

EXAMPLE 87

3(S)-(−)-1,3-Dihydro-3-(2-indolecarbonylamino)-1-methyl-5-phenyl-2H-1,4-benzodiazepin-2-one 3(S)-(−)-3-Amino-1,3-dihydro-1-methyl-5-phenyl-2H-1,4-benzodiazepin-2-one (595 mg, 2.24 mmole) was dissolved in $CH_2Cl_2$ (15 ml) and treated with 2-indolecarbonyl chloride (403 mg, 2.24 mmole) followed by triethylamine (227 mg, 2.24 mmole). The mixture was stirred at room temperature for 30 minutes and concentrated in vacuo. The residue was chromatographed on silica gel (5% $Et_2O$/$CH_2Cl_2$) and the combined product fractions evaporated to dryness in vacuo. Three times, $Et_2O$ (15 ml) was added and evaporated in vacuo to give the title compound: (m.p. 168°-185°).

TLC: Silica gel (6% $Et_2O$/$CH_2Cl_2$), $R_f 0.23$

NMR: Consistent with structure

HPLC: Greater than 99% pure

M.S.: Molecular ion at m/e=408 $[\alpha]_D^{25} = -103°$ (0.0078 g/ml, $CH_2Cl_2$)

Anal. calc'd for $C_{25}H_{20}N_4O_2$ C, 73.51; H, 4.94; N, 13.72; Found: C, 73.38; H, 4.80; N, 13.66.

EXAMPLE 88

3(S)-(+)-1,3-Dihydro-5-(2-fluorophenyl)-3-(2-indolecarbonylamino)-1-methyl-2H-1,4-benzodiazepin-2-one The procedure of Example 87 was carried out using 3(S)-(−)-3-amino-1,3-dihydro-5-(2-fluorophenyl)-1-methyl-2H-1,4-benzodiazepin-2-one in place of 3(S)-(−)-3-amino-1,3-dihydro-1-methyl-5-phenyl-2H-1,4-benzodiazepin-2-one. The title compound was obtained as a foam: (m.p. 162°-187°).

TLC: Silica gel (10% $Et_2O$/$CH_2Cl_2$) $R_f = 0.30$

NMR: Consistent with structure, verifies presence of 0.2 $Et_2O$

HPLC: Greater than 99.6% pure

M.S.: Molecular ion at m/e=426 $[\alpha]_D^{25} = +5.57°$ (0.0031 g/ml, $CH_2Cl_2$)

Anal. calc'd for $C_{25}H_{19}FN_4O_2 \cdot 0.2 C_4H_{10}O$ C, 70.22; H, 4.80; N, 12.70; Found: C, 70.13; H, 4.75; N, 12.61.

EXAMPLE 89

3(R)-(−)-1,3-Dihydro-5-(2-fluorophenyl)-3-(2-indolecarbonylamino)-1-methyl-2H-1,4-benzodiazepin-2-one The procedure of Example 88 was carried out using 3(R)-(+)-3-amino-1,3-dihydro-5-(2-fluorophenyl)-1-methyl-2H-1,4-benzodiazepin-2-one in place of its 3(S)-(−) isomer. The title compound was obtained as a foam; (m.p. 162°-187°)

TLC: Silica gel (10% $Et_2O$/$CH_2Cl_2$) $R_f = 0.30$

NMR: Consistent with structure, verifies presence of 0.1 $Et_2O$

HPLC: Greater than 99.6% pure

M.S.: Molecular ion at m/e=426 $[\alpha]_D^{25} = -5.65°$ (0.0023 g/ml, $CH_2Cl_2$)

Anal. calc'd for $C_{25}H_{19}FN_4O_2 \cdot 0.1 C_4H_{10}O$ C, 70.31; H, 4.65; N, 12.92; Found: C, 70.16; H, 4.64; N, 12.86.

EXAMPLE 90

3(R)-(−)-1,3-Dihydro-3-(4-chlorobenzoylamino)-5-(2-fluorophenyl)-1-methyl-2H-1,4-benzodiazepin-2-one 3(R)-(+)-3-Amino-1,3-dihydro-5-(2-fluorophenyl)-1-phenyl)-1-methyl-2H-1,4-benzodiazepin-2-one (350 mg, 1.24 mmole) was dissolved in $CH_2Cl_2$ (4 ml) and treated with 4-chlorobenzoyl chloride (217 mg, 1.24 mmole) followed by triethylamine (125 mg, 1.24 mmole). The mixture was stirred at room temperature for 30 minutes and concentrated in vacuo. The residue was chromatographed on silica gel (4% $Et_2O/CH_2Cl_2$) and the combined product fractions evaporated to dryness in vacuo. Ether was added and removed in vacuo three times, giving the title compound as a foam; (m.p. 113°–128°).

TLC: Silica gel (10% $Et_2O/CH_2Cl_2$) $R_f=0.43$
NMR: Consistent with structure
HPLC: Greater than 99.6% pure
M.S.: Molecular ion at m/e=421 $[\alpha]_D^{25}=-12.8°$ (0.0031 g/ml, $CH_2Cl_2$)
Anal. calc'd for $C_{23}H_{17}ClFN_3O_2$ C, 65.48; H, 4.06; N, 9.96; Found: C, 65.48; H, 4.17; N, 9.93.

EXAMPLE 91

3(S)-(+)-1,3-Dihydro-3-(4-chlorobenzoylamino)-5-(2-fluorophenyl)-1-methyl-2H-1,4-benzodiazepin-2-one The procedure of Example 90 was carried out using 3(S)-(−)-3-amino-1,3-dihydro-5-(2-fluorophenyl)-1-methyl-2H-1,4-benzodiazepin-2-one in place of its 3(R)-(+)-isomer. The title compound was obtained as a foam; (m.p. 113°–128°).

TLC: Silica gel (10% $Et_2O/CH_2Cl_2$) $R_f=0.43$
NMR: Consistent with structure.
HPLC: Greater than 99.6% pure
M.S.: Molecular ion at m/e=421 $[\alpha_D^{25}=+13.2°$ (0.0032 g/ml, $CH_2Cl_2$).
Anal. calc'd for $C_{23}H_{17}ClFN_3O_2$ C, 65.48; H, 4.06; N, 9.96; Found: C, 65.43; H, 4.09; N, 9.81.

EXAMPLE 92

3(S)-(−)-1,3-Dihydro-3-(4-bromobenzoylamino)-1-methyl-5-phenyl-2H-1,4-benzodiazepin-2-one 3(S)-(−)-3-Amino-1,3-dihydro-1-methyl-5-phenyl-2H-1,4-benzodiazepin-2-one (35 mg, 0.132 mmole) was dissolved in $CH_2Cl_2$ (1 ml) and treated with 4-bromobenzoylchloride (29 mg, 0.132 mmole) followed by triethylamine (13.3 mg, 10.132 mmole). The mixture was stirred at room temperature for 30 minutes and concentrated in vacuo. The residue was chromatographed on silica gel (3% $Et_2O/CH_2Cl_2$) and the combined product fractions evaporated to dryness in vacuo. Ether was added and removed in vacuo three times, giving the title compound as a foam; (m.p. 120°–133°).

TLC: Silica gel (7% $Et_2O/CH_2Cl_2$), $R_f=0.36$
NMR: Consistent with structure
HPLC: Greater than 99.1% pure
M.S.: Molecular ion at m/e 447 $[\alpha]_D^{25}=-72.4°$ (0.0027 g/ml, $CH_2Cl_2$).
Anal. calc'd for $C_{23}H_{18}BrN_3O_2$ C, 61.62; H, 4.05; N, 9.37; Found: C, 61.94; H, 4.07; N, 9.20.

EXAMPLE 93

3(R)-(+)-1,3-Dihydro-3-(4-bromobenzoylamino)-1-methyl-5-phenyl-2H-1,4-benzodiazepin-2-one The procedure of Example 92 was carried out using 3(R)-(+)-3-amino-1,3-dihydro-1-methyl-5-phenyl-2H-1,4-benzodiazepin-2-one in place of its 3(S)-(−) isomer. The title compound was obtained as a foam; (m.p. 120°–133°)

TLC: Silica gel (7% $Et_2O/CH_2Cl_2$; $R_f=0.36$
NMR: Consistent with structure
HPLC: Greater than 99.2% pure
M.S.: Molecular ion at m/e=447 $[\alpha]_D^{25}=+75.1°$ (0.0022 g/ml, $CH_2Cl_2$).
Anal. calc'd for $C_{23}H_{18}BrN_3O_2$ C, 61.62; H, 4.05; N, 9.37; Found: C, 62.00; H, 4.12; N, 9.27.

EXAMPLE 94

3(R)-(+)-1,3-Dihydro-3-(2-indolecarbonylamino)-1-methyl-5-phenyl-2H-1,4-benzodiazepin-2-one The procedure of Example 87 was carried out using 3(R)-(+)-3-amino-1,3-dihydro-1-methyl-5-phenyl-2H-1,4-benzodiazepin-2-one in place of its 3(S)-(−) isomer. The title compound was obtained as a foam; (m.p. 168°–185°).

TLC: Silica gel (6% $EtO/CH_2Cl_2$); $R_f=0.23$
NMR: Consistent with structure
HPLC: Greater than 99.2% pure
M.S.: Molecular ion at m/e=408 $[\alpha]_D^{25}=+100°$ (0.0052 g/ml, $CH_2Cl_2$).
Anal. calc'd for $C_{25}H_{20}N_4O_2$ C, 73.51; H, 4.94; N, 13.72; Found: C, 73.16; H, 4.88; N, 13.53.

Effective daily dosages of compounds such as those of Examples 79, 83, 84, 87 and 88 can range to as low as 0.01 mg/kg.

EXAMPLE 95

Z-1,3-Dihydro-1-methyl-5-phenyl-3-(3-thienylmethylene)-2H-1,4-benzodiazepin-2-one and
E-1,3-Dihydro-1-methyl-5-phenyl-3-(3-thienylmethylene)-2H-1,4-benzodiazepin-2-one To a cooled (−60° C.) solution of diisopropylamine (0.84 ml, 6.0 mmol) in THF (10.2 ml) was added 1.5M butyllithium in hexane (4.0 ml, 6.0 mmol). The solution was stirred 10 min. at −60° C. and then warmed to 25° C. The light yellow solution was recooled to −60° C. and treated with solid 1,3-dihydro-1-methyl-5-phenyl-2H-1,4-benzodiazepin-2-one (75 mg, 3.0% mmol) portionwise (5×15 mg). The reaction was permitted to warm to 0° C. and then recooled to −60° C. A solution of thiophene-3-carboxaldehyde (336 mg, 3.0 mmol) in THF (6 ml) was added to the deep red anion solution, the cooling bath was removed, and the reaction allowed to warm to 25° C. The reaction was quenched with brine and extracted with ether (3×). The combined extracts were washed with $H_2O$ (1×), dried over $MgSO_4$, filtered, and stripped to dryness in vacuo. The crude red oil was chromatographed on silica gel (10% $Et_2O$ in $CH_2Cl_2$) to give the intermediate alcohol as a buff-colored solid: 210 mg, m.p. 188°–9° C. TLC: silica GF (10% $Et_2O$ in $CH_2Cl_2$) single homogeneous component. A portion of this product (171 mg, 0.472 mmol) was refluxed in a mixture of trifluoroacetic acid (3 ml) and trifluoroacetic anhydride (1 ml) for 12 hrs. The solvent was removed in vacuo and the residue was treated with $H_2O$, basified with 10% NaOH (aq) and extracted with ether (3×). The combined extracts were washed with $H_2O$ (1×), dried over $MgSO_4$, filtered and stripped to dryness in vacuo to give a crude oil. Chromatography on silica gel (2% $Et_2O$ in $CH_2Cl_2$) provided the title compounds which were obtained as light yellow solids from ether.

Z-isomer: (m.p. 196°–197° C.).

TLC: Silica GF (4% Et$_2$O in CH$_2$Cl$_2$), R$_f$=0.37, single homogeneous component.
PMR: Consistent with the title structure.
HPLC: Greater than 99.8% pure.
M.S.: Mol. ion=344 m/e.
Anal. calc'd for C$_{21}$H$_{16}$N$_2$OS: C, 73.23; H, 4.68; N, 8.13; Found: C, 73.37; H, 4.78; N, 7.79.
E-isomer: (m.p. 194°–196° C.).
TLC: Silica GF (4% Et$_2$O in CH$_2$Cl$_2$), R$_f$=0.28 single homogeneous component.
PMR: Consistent with the title structure.
HPLC: Greater than 99.9% pure.
M.S.: Mol. ion=344 m/e.
Anal. calc'd for C$_{21}$H$_{16}$N$_2$OS: C, 73.23; H, 4.68; N, 8.13; Found: C, 73.12; H, 4.83; N, 7.73.

EXAMPLE 96

3(RS)-(BOC-D-tryptophanyl)amino-1,3-dihydro-5-phenyl-2H-1,4-benzodiazepin-2-one

The procedure of Example 77 was carried out using BOC-D-tryptophan in place of BOC-L-tryptophan. The chromatographed product was crystallized from Et$_2$O and dried in vacuo at 80°: (m.p. 171°–174° ( )).
TLC: A single spot (R$_f$=0.56, silica gel plate, 10% (v/v) CH$_3$OH in CH$_2$Cl$_2$).
NMR: The spectrum was consistent with the title structure and verified the presence of two diastereomers.
HPLC: Greater than 98.4% pure (68.9% and 29.5%).
Anal. calc'd for C$_{31}$H$_{31}$N$_5$O$_4$: C, 69.25; H, 5.81; N, 13.03; Found: C, 69.24; H, 6.03; N, 13.04.

EXAMPLE 97

3(RS)-[4-(3-Indole)butyrylamino]-1,3-dihydro-5-phenyl-2H-1,4-benzodiazepin-2-one The procedure of Example 77 was carried out using 4-(3-indolyl)butyric acid (0.082 g, 0.4 mmol) in place of BOC-L-tyrptophan. The product was chromatographed as in Example 75, crystallized from a mixture of acetone (1 ml) and ether (3 ml), and dried in vacuo at 80°: (m.p., 258°–259°).
NMR: The spectrum was consistent with the title structure.
HPLC: 98.9% pure.
MS: A molecular ion at m/e=436.
Anal. calc'd for C$_{27}$H$_{24}$N$_4$O$_2$: C, 74.29; H, 5.54; N, 12.84; Found: C, 74.39; H, 5.65; N, 12.93.

EXAMPLE 98

1,3-Dihydro-3(RS)-(benzyloxycarbonyl)aminomethyl-5-(2-fluorophenyl)-2H-1,4-benzodiazepine To a magnetically stirred solution of 1,3-dihydro-3(RS)-benzyloxycarbonyl)aminomethyl-5-(2-fluorophenyl)-2H-1,4-benzodiazepin-2-thione (1.85 g, 4.3 mmol) in 150 ml of ethanol were added, at room temperature, three portions of freshly prepared Raney nickel (slurried in ethanol, approximately 4–5 g). The resulting reaction mixture was stirred vigorously overnight and treated with an additional equal portion of Raney nickel. After 50 hours of total reaction time, the suspension was filtered carefully; the residual Raney nickel was washed copiously with ethanol. Concentration of the filtrate under reduced pressure gave 880 mg of product essentially homogeneous by TLC (ethyl acetate-hexane 1:1 v/v). The analytical sample was obtained via silica gel chromatography (chloroform-methanol 96:4) as a foam. TLC, HPLC greater than 97% pure.
NMR (CDCl$_3$): Consistent with the title structure.
MS (14 ev): 403 (M+), 295, 253, 239, 219.
Anal. calc'd for C$_{24}$H$_{22}$FN$_3$O$_2$.0.03 CHCl$_3$: N, 10.32; C, 70.90, H, 5.45; Found: N, 10.16; C, 70.89; H, 5.60.

EXAMPLE 99

1,3-Dihydro-3(RS)-[3'-(thiophene)carbonyl]aminomethyl-5-(2-fluorophenyl)-2H-1,4-benzodiazepine 1,3-Dihydro-3(RS)-aminomethyl-5-(2-fluorophenyl)-2H-1,4-benzodiazepine hydrobromide (300 mg, 0.59 mmol) and 3-thiophenecarboxylic acid chloride (150 mg, 1.02 mmol) were combined in 50 ml of methylene chloride. The reaction mixture was immersed in an ice bath and treated with triethylamine (330 μl, 2.36 mmol). After addition was complete, stirring was continued at 0° C. for 10 min. more and then at room temperature for 15 min. The reaction mixture was partitioned between methylene chloride and saturated sodium bicarbonate solution. The phases were separated and the organic layer was washed with brine, then dried (MgSO$_4$) and product (300 mg) was purified via silica gel chromatography (chloroform - methanol - ammonia, 95:5:0.5 v/v, elution) to give the analytical sample. NMR (CDCl$_3$): Consistent with the title structure. MS (14 ev): 379 (M+)
Anal. calc'd for C$_{21}$H$_{18}$FN$_3$OS.0.1 CHCl$_3$: N, 10.74; C, 64.75; H, 4.66; Found: N, 10.45; C, 64.51; H, 4.82.

EXAMPLE 100

1,3-Dihydro-3(RS)-(2'-indolecarbonyl)aminomethyl-5-(2-fluorophenyl)-2H-1,4-benzodiazepine 1,3-Dihydro-3(RS)-aminomethyl-5-(2-fluorophenyl)-2H-1,4-benzodiazepine hydrobromide (300 mg, 0.59 mmol) and 2-indole carboxylic acid chloride (127 mg, 0.70 mmol) were combined in 30 ml of methylene chloride. The reaction mixture was immersed in an ice bath and treated with triethylamine (330 μl, 2.36 mmol). After addition was complete, stirring was continued at 0° C. for 10 min. more and then at room temperature for 15 minutes. The reaction mixture was partitioned between methylene chloride and saturated sodium bicarbonate solution. The phases were separated and the organic layer was washed with brine, then dried (MgSO$_4$) and concentrated under reduced pressure. The crude product (220 mg) was purified via silica gel chromatography (chloroform - methanol elution, 95:5 v/v) to give the analytical sample.
NMR (CDCl$_3$/CD$_3$OD): Consistent with the title structure.
MS (14 ev): 412 (M+), 252, 239.
Anal. calc'd for C$_{25}$H$_{21}$FN$_4$O.0.15 CHCl$_3$: N, 13.01; C, 70.19; H, 4.95; Found: N, 12.70; C, 70.19; H, 5.18.

EXAMPLE 101

1,3-Dihydro-3(RS)-(2-L-hydroxy-2-phenylacetyl)aminomethyl-5-(2-fluorophenyl)-2H-1,4-benzodiazepine 1,3-Dihydro-3(RS)-aminomethyl-5-(2-fluorophenyl)-2H-1,4-benzodiazepine hydrobromide (300 mg, 0.59 mmol) and L-mandelic acid (134 mg, 0.88 mmol) were combined in 5 ml of dimethylformamide and treated with 1-ethyl-3-(3-dimethylaminopropyl)carbodiimide hydrochloride (169 mg, 0.88 mmol). The pH of the resulting reaction mixture was adjusted to 8.5 with triethylamine and the reaction was stirred at room temperature overnight. The solvent was removed under reduced pressure and the residue was dissolved in ethyl acetate (60 ml). The organic phase was then washed in succession with sodium bicarbonate solution (3×50 ml) and brine. The dried (MgSO$_4$) extracts were concentrated to give 200 mg of crude product as a mixture of diastereomers. Preparative thick layer chromatography (chloroform - ethanol - ammonia elution, 90:10:1 v/v) afforded the less polar, faster moving component as a homogeneous analytical sample.

HPLC: Greater than 98% pure.

NMR (CDCl$_3$): Consistent with the title structure.

MS (14 ev): 403 (M+), 252, 239, 212.

Anal. calc'd for $C_{24}H_{22}FN_3O_2.0.5\ H_2O$ N, 10.18; C, 69.82; H, 5.62; Found: N, 9.67; C, 69.81; H, 5.55.

EXAMPLE 102

1-(2-Cyanoethyl)-1,3-dihydro-5-(2-fluorophenyl)-3(R)-3'-indolyl)methyl-2H-1,4-benzodiazepin-2-one (A, 85%) and 1-(2-cyanoethyl)-1,3-dihydro-5-(2-fluorophenyl)-3(R)-[1'-(2-cyanoethyl)-3'-indolyl]-methyl-2H-1,4-benzodiazepin-2-one (B, 15%)

The procedure of Example 4 was carried out using acrylonitrile (0.12 g, 2,3 mmol) in place of methyl iodide. The chromatographed product, a mixture of A (85%) and B (15%) was dried in vacuo at 90°: (m.p. 97°–105° (↑)).

NMR: The spectrum was consistent with the 85:15 mixture of the title structure and showed the presence of 0.9 mol of DMF.

HPLC: 96.4% (82.4% + 14.0%).

TLC: A single spot (R$_f$=0.22, silica gel plate, 5% (v/v) Et$_2$O in CH$_2$Cl$_2$).

MS: Molecular ions at m/e=436 and 489.

Anal. calc'd for 0.85 $C_{27}H_{21}FN_4O$ +0.15 $C_{30}H_{24}FN_5O.0.9\ C_3H_7NO$: C, 71.07; H, 5.35; N, 13.88; Found: C, 70.95; H, 5.18; N, 13.63.

EXAMPLE 103

1-(2-Carboxyethyl)-1,3-dihydro-5-(2-fluorophenyl)-3(R)-(3'-indolyl)methyl-2H-1,4-benzodiazepin-2-one The procedure of Example 4 was carried out using ethyl acrylate (0.22 g, 2.2 mmole) in place of methyl iodide. The chromatographed product was evaporated in vacuo, dissolved in methanol (5 ml), treated with sodium hydroxide (0.91 ml of 1M solution), and stirred at room temperature for 24 hours. The mixture was evaporated in vacuo, and the residue was dissolved in water (10 ml), washed with ether (10 ml), acidified with 1N HCl, and extracted with CH$_2$Cl$_2$ (3×10 ml). The CH$_2$Cl$_2$ layers were washed with water (1×10 ml), dried over sodium sulfate, filtered, and evaporated to dryness in vacuo. The residue was chromatographed on silica gel (180:5:1:1 followed by 180:10:1:1 (v/v/v/v) CH$_2$Cl$_2$:CH$_3$OH:HoAc:H$_2$O) and the product evaporated to dryness in vacuo. The residue was dried in vacuo at 40°: (m.p. 75°–90° foam, 130°–160° melt).

TLC: A single spot (R$_f$=0.32, silica gel plate, 180:10:1:1 (v/v/v/v) CH$_2$Cl$_2$:CH$_3$OH:HOAc:H$_2$O).

NMR: The spectrum was consistent with the title structure and verified the presence of ether.

HPLC: 99.6% pure.

MS: A molecular ion at m/e=455.

Anal. calc'd for $C_{27}H_{22}FN_3O_3.0.55\ C_4H_{10}O.0.035\ H_2O$): C, 69.78; H, 5.66; N, 8.36; Found: C, 69.72; H, 5.29; N, 8.07.

EXAMPLE 104

1,3-Dihydro-5-(2-fluorophenyl)-3-(2-formylaminobenzoylmethyl)-2H-1,4-benzodiazepin-2-one 1,3-Dihydro-3(R)-(3'-indolyl)methyl-5-(2-fluorophenyl)-2H-1,4-benzodiazepin-2-one (300 mg, 0.78 mmol) and m-chloroperoxybenzoic acid (85%) (156 mg, 0.90 mmol) were combined at room temperature in 20 ml of chloroform. The reaction mixture was allowed to stand at room temperature overnight, then was diluted with 30 ml of chloroform and washed with cold, saturated sodium bicarbonate solution. The combined organic extracts were washed with brine, dried (MgSO$_4$) and concentrated to afford 310 mg of crude product. Silica gel chromatography (hexane-ethyl acetate, 1:2 v/v) provided the analytical sample.

HPLC: 99% pure.

NMR (CDCl$_3$): Consistent with the title structure.

MS (14 ev): 415, 397, 369, 267.

Anal. calc'd. for $C_{24}H_{18}FN_3O_2.1.0\ CHCl_3$ N, 8.10; C, 57.87; H, 3.69; Found: N, 8.09; C, 58.14; H, 3.82.

EXAMPLE 105

1,3-Dihydro-5-(2-fluorophenyl)-3-(RS)-(2-indolecarbonylamino)-2H-1,4-benzodiazepin-2-one 3-(RS)-Amino-1,3-dihydro-5-(2-fluorophenyl)-2H-1,4-benzodiazepin-2-one (1.5 gm, 5.57 mmol), indole-2-carbonyl chloride (1.05 gm, 5.85 mmol) and triethylamine (0.814 ml, 5.85 mmol) were combined in CH$_2$Cl$_2$ (15 ml) and stirred 10 min. The reaction was concentrated and chromatographed on silica gel (5% MeOH in CH$_2$Cl$_2$) to give the title compound as a white solid from CH$_2$Cl$_2$: (m.p. 290°–291°).

TLC: Silica GF (5% MeOH in CH$_2$Cl$_2$), single homogeneous component.

NMR: Consistent with title structure and verifies the presence of 0.16 CH$_2$Cl$_2$.

HPLC: Greater than 99% pure.

M.S.: Mol. ion=412 m/e (free base).

Anal. calc'd for $C_{24}H_{17}FN_4O_2.0.16\ CH_2Cl_2$: C, 68.11; H, 4.10; N, 13.15; Found: C, 68.06, H, 4.12; N, 12.91.

EXAMPLE 106

1,3-Dihydro-3-(RS)-(4-nitrophenylcarbonyl)amino-5-(2-fluorophenyl)-2H-1,4-benzodiazepin-2-one 1,3-Dihydro-3-(RS)-amino-5-(2-fluorophenyl)-2H-1,4-benzodiazepin-2-one (100 mg, 0.37 mmol) and p-nitrobenzoic acid (70 mg, 0.41 mmol) were combined at room temperature in 5 ml of methylene chloride. To this reaction mixture was added 1-ethyl-3-(3-dimethylaminopropyl)carbodiimide hydrochloride (79 mg, 0.41 mmol). The pH of the reaction mixture was then adjusted to 8.5 with triethylamine and stirring was continued at room temperature overnight. The reaction mixture was partitioned between methylene chloride and 10% citric acid solution. The phases were separated and the organic layer was washed in succession with 10% citric acid solution (1×30 ml), saturated sodium bicarbonate solution (2×30 ml) and brine. The dried (MgSO$_4$) extracts were concentrated to yield 83 mg of crude product. Preparative thick layer chromatography (chloroform - methanol - ammonia, 96:4:0.4 v/v) afforded the analytical sample (70 mg).

HPLC: Greater than 96.5% pure.
NMR (CDCl$_3$): Consistent with the title structure.
MS (14 ev): 418 (M+), 268, 252.
Anal. calc'd for C$_{22}$H$_{15}$FN$_4$O$_4$.0.1 CHCl$_3$ N, 13.02; C, 61.68; H, 3.54; Found: N, 12.66; C, 61.94; H, 3.74.

EXAMPLE 107

1,3-Dihydro-3-(RS)-(2-indolecarbonyloxy)-5-phenyl-2H-1,4-benzodiazepin-2-one 1,3-Dihydro-3-(RS)-hydroxy-5-phenyl-2H-1,4-benzodiazepin-2-one (100 mg, 0.398 mmol) was dissolved in CH$_2$Cl$_2$ (10 ml), treated with indole-2-carbonyl chloride (78.6 mg, 0.438 mmol) and 4-dimethylaminopyridine (DMAP, 53.5 mg, 0.438 mmol) and stirred 16 hrs. at 25° C. A second portion of indole-2-carbonylchloride (78.6 mg, 0.438 mmol and DMAP (53.5 mg, 0.438 mmol) was added and the reaction stirred an additional 24 hrs. Chromatography of the reaction mixture on silica gel (1% MeOH in CH$_2$Cl$_2$) gave the title compound (100 mg) as a white solid from MeCN: (m.p. 271°-273°).

TLC: Silca GF (4% MeOH in CH$_2$Cl$_2$), R$_f$=0.41, single homogeneous component.
NMR: Consistent with title structure.
HPLC: Greater than 98.6% pure.
MS: Molecular ion at m/e=395.
Anal. calc'd for C$_{24}$H$_{17}$N$_3$O$_3$: C, 72.90; H, 4.33; N, 10.63; Found: C, 72.70; H, 4.31; N, 10.64.

EXAMPLE 108

1,3-Dihydro-5-(2-fluorophenyl)-3-(RS)-(3-thiophene carbonylamino)-2H-1,4-benzodiazepin-2-one 3-(RS)-Amino-1,3-dihydro-5-(2-fluorophenyl)-2H-1,4-benzodiazepin-2-one (75 mg, 0.229 mmol), thiophene-3-carbonyl chloride (44.9 mg, 0.306 mmol) and triethylamine (42.5 μl, 0.306 mmol) were combined in CH$_2$Cl$_2$ (4 ml) and stirred 10 min. at 25° C. The reaction was concentrated and chromatographed on silica gel (2% MeOH in CH$_2$Cl$_2$) to give the title compound as a white solid from Et$_2$O: (m.p. 238°-239°).

TLC: Silica GF (5% MeOH in CH$_2$Cl$_2$), R$_f$=0.36, single homogeneous component.
NMR: Consistent with title structure and verifies the presence of 0.05 (C$_2$H$_5$)$_2$O and 0.70 H$_2$O).
HPLC: Greater than 98.8% pure.
MS: Mol. ion=379 m/e (free base).
Anal. Calc'd for C$_{20}$H$_{14}$FN$_3$O$_2$S.0.05 (C$_2$H$_5$)$_2$O.0.70 H$_2$O: C, 61.30; H, 4.05; N, 10.62; Found: C, 61.24; H, 3.68; N, 10.57.

EXAMPLE 109

1,3-Dihydro-3-(RS)-(3-indolecarbonylamino)-5-phenyl-2H-1,4-benzodiazepin-2-one 3-(RS)-Amino-1,3-dihydro-5-phenyl-2H-1,4-benzodiazepin-2-one (49.2 mg, 0.196 mmol), indole-3-carboxylic acid (37.9 mg, 0.235 mmol) and 1M DCC in CH$_2$Cl$_2$ solution (0.235 ml, 0.235 mmol) were mixed in DMF (2 ml) and the pH adjusted to 9.0 with triethylamino (32.7 μl, 0.235 mmol). The reaction was stirred 18 hrs. at 25° C., the DMF removed in vacuo, and the residue chromatographed on a Waters Semi-Prep C-18 30×0.9 cm column (gradient elution of 5 to 95% CH$_3$CN in H$_2$O) to give the title compound as a white solid from MeOH/ether: (m.p. 265°-268°).

TLC: Silica GF (90/10/1/1 of CH$_2$Cl$_2$/MeOH/H$_2$O/HOAc), R$_f$=0.57, single homogeneous component.

NMR: Consistent with title structure and verifies the presence of 2.0 CH$_3$OH.
HPLC: 100% pure.
MS: Mol. ion=394 m/e (free base).
Anal. calc'd for C$_{24}$H$_{18}$N$_4$O$_2$.2CH$_3$OH: C, 68.10; H, 5.72; N, 12.22; Found: C, 68.19; H, 4.62; N, 12.50.

EXAMPLE 110

1,3-Dihydro-3-(RS)-(4-thianaphtheneacetyl)amino-5-(2-fluorophenyl)-2H-1,4-benzodiazepin-2-one 1,3-Dihydro-3-(RS)-amino-5-(2-fluorophenyl)-2H-1,4-benzodiazepin-2-one (100 mg, 0.37 mmol) and 4-thianaptheneacetic acid (79 mg, 0.41 mmol) were combined at room temperature in 5 ml of methylene chloride. To this reaction mixture was added 1-ethyl-3-(3-dimethylaminopropyl)carbodiimide hydrochloride (79 mg, 0.41 mmole). The pH of the reaction mixture was then adjusted to 8.5 with triethylamine and stirring was continued at room temperature overnight. The reaction mixture was partitioned between methylene chloride and 10% citric acid solution. The phases were separated and the organic layer was washed in succession with 10% citric acid solution (1×30 ml), saturated sodium bicarbonate solution (2×30 ml) and brine. The dried (MgSO$_4$) extracts were concentrated to yield 130 mg of crude product. Preparative thick layer chromatography (chloroform - methanol - ammonia, 95:5:0.5 v/v) afforded the analytical sample, m.p. 259°-260° C.

NMR (CDCl$_3$): consistent with the title structure.
MS (14 ev): 443 (M+), 268, 174.
Anal. calc'd for C$_{25}$H$_{18}$FN$_3$O$_2$S.0.075 CHCl$_3$ N, 9.28; C, 66.56; H, 4.02; Found: N, 9.10; C, 66.53; H, 4.11.

EXAMPLE 111

1,3-Dihydro-3-(RS)-(4-chlorophenylcarbonyl)amino-5-(2-fluorophenyl)-2H-1,4-benzodiazepin-2-one 1,3-Dihydro-3-(RS)-amino-5-(2-fluorophenyl)-2H-1,4-benzodiazepin-2-one (100 mg, 0.37 mmol) and p-chlorobenzoyl chloride (52 μl, 0.41 mmole) were combined at room temperature in 5 ml of methylene chloride. The resulting solution was protected from moisture and stirred at room temperature overnight. The reaction mixture was diluted with 70 ml of methylene chloride and washed with sodium bicarbonate solution (sat.) and brine. The organic extracts were dried (MgSO$_4$) and concentrated to give 150 mg of crude product. Chromatography on silica gel (chloroform - methanol - ammonia, 95:5:0.5 v/v) and trituration with hexane yielded the analytical product as a white powder, m.p. 258°-259° C.

HPLC: Greater than 98% pure.
NMR: (CDCl$_3$): Consistent with the title structure.
MS (14 ev): 407 (M+), 268, 252, 241.
Anal. calc'd for C$_{22}$H$_{15}$ClFN$_3$O$_2$.0.2 CHCl$_3$ N, 9.73; C, 61.76; H, 3.55; Calc'd. N, 9.34; C, 61.65; H. 3.68.

EXAMPLE 112

1,3-Dihydro-3-(RS)-(4-methylphenylsulfonyl)amino-5-(2-fluorophenyl)-2H-1,4-benzodiazepin-2-one 1,3-Dihydro-3-(RS)-amino-5-(2-fluorophenyl)-2H-1,4-benzodiazepin-2-one (116 mg, 0.43 mmole) and p-toluenesulfonyl chloride (82 mg, 0.43 mmole) were combined at room temperature in 5 ml of methylene chloride. The pH of the reaction mixture was then adjusted to 8.5 with triethylamine and stirring was continued at room temperature overnight. The reaction mixture was partitioned between methylene chloride and 10% citric acid solution. The phases were separated and the organic layer was washed in succession with 10% citric acid solution (1×30 ml), saturated sodium bicarbonate solution (2×30 ml) and brine. The dried (MgSO4) extracts were concentrated to yield 200 mg of crude product. Recrystallization from ethyl acetate afforded the analytical sample as white needles, m.p. 215°–216° C.

HPLC: Greater than 99% pure.
NMR (CDCl3): Consistent with the title structure.
MS (14 ev): 359, 316, 268, 241, 225, 212, 92.
Anal. calc'd for $C_{22}H_{18}FN_3O_3S \cdot 0.1 C_4H_8O_2$ N, 9.72; C, 62.23; H, 4.38; Found: N, 9.64; C, 61.92 H, 4.31.

EXAMPLE 113

1-Carboxymethyl-1,3-dihydro-5-(2-fluorophenyl)-3-(RS)-(2-indolecarbonylamino)-2H-1,4-benzodiazepin-2-one The procedure of Example 4 was carried out using 1,3-dihydro-5-(2-fluorophenyl)-3(RS)-(2-indolecarbonylamino)-2H-1,4-benzodiazepin-2-one (0.92 g, 2.2 mmole) in place of 1,3-dihydro-5-(2-fluorophenyl)-3-(R)-(3'-indolyl)-methyl-2H-1,4-benzodiazepin-2-one, and ethyl bromoacetate (0.38 g, 2.25 mmol) in place of methyl iodide. The chromatographed product (10% ether in $CH_2Cl_2$) (0.05 g, 0.098 mmol) and sodium hydroxide (0.14 ml, 1N, 0.14 mmol) were stirred together in $CH_3OH$ (3 ml) at room temperature for 36 hours. The mixture was concentrated in vacuo, diluted to 5 ml with $H_2O$, made acidic with 1N HCl, and extracted with $CH_2Cl_2$ (3×5 ml). The organic layers were combined, washed with water (1×5 ml), dried over $Na_2SO_4$, filtered, and evaporated to dryness in vacuo. The residue was crystallized from acetone (0.1 ml) and $Et_2O$ (2 ml) and the solid dried in vacuo at 60°; (m.p. 278°–278.5° (d)). TLC: A single spot ($R_f$=0.27, silica gel plate, 180:10:1:1 (v/v/v/v) $CH_2Cl_2$:$CH_3OH$:HOAc:$H_2O$).

NMR: The spectrum was consistent with the title structure and verified the presence of ether and acetone.
HPLC: 99.4% pure.
MS: A molecular ion at m/e=470.
Anal. calc'd for $C_{26}H_{19}FN_4O_4 \cdot 0.6 C_3H_6O \cdot 0.2 C_4H_{10}O \cdot 0.8 H_2O$: C, 64.25; H, 4.94; N, 10.48; Found: C, 64.29; H, 4.56; N, 10.23.

EXAMPLE 114

1,3-Dihydro-3-(RS)-(5-fluoroindole-2-carbonylamino)-5-(2-fluorophenyl)-2H-1,4-benzodiazepin-2-one 3-(RS)-Amino-1,3-dihydro-5-(2-fluorophenyl)-2H-1,4-benzodiazepin-2-one (100 mg, 0.398 mmol) was suspended in 2 ml of methylene chloride. 5-fluoroindole-2-carboxylic acid chloride (87 mg, 0.438 mmol) was added to the methylene chloride suspension. The pH of the stirred mixture was adjusted to 9 with 100 μl of triethylamine. The reaction mixture was stirred for 24 hours. The mixture was then diluted with 1 ml of methanol and filtered. The filtrate was pipetted onto a 2000 μ Analtech preparative TLC plate which was developed in a 95:5:0.5 chloroform, methanol, water (CMW) solvent system. The product band was collected. The silica was washed with 90:10:1 CMW. The filtrate was evaporated and the residue was dissolved in methanol and placed in a small vial. The solvent was evaporated to yield 15.2 mg of product.

HPLC: 90% pure.
MS: M+ (14 ev), m/e 430.
NMR: Consistent with title product.
Anal. calc'd for $C_{24}H_{16}F_2N_4O_2 \cdot 1.6 CH_3OH$ N, 11.63; C, 63.83; H, 4.65; Found: N, 11.66; C, 63.84; H, 3.72.

EXAMPLE 115

1,3-Dihydro-3-(RS)-(3'-methylindenyl-2-carbonyl)amino-5-(2-fluorophenyl)-2H-1,4-benzodiazepin-2-one 1,3-Dihydro-3-(RS)-amino-5-(2-fluorophenyl)-2H-1,4-benzodiazepin-2-one (100 mg, 0.37 mmol) and 3-methylindene-2-carboxylic acid (70 mg, 0.40 mmol) were combined at room temperature in 5 ml of methylene chloride. To this reaction mixture was added 1-ethyl-3-(3-dimethylaminopropyl)carbodiimide hydrochloride (80 mg, 0.41 mmol). The pH of the reaction mixture was then adjusted to 8.0 with triethylamine and stirring was continued at room temperature overnight (19 hours). The reaction mixture was partitioned between methylene chloride and 10% citric acid solution. The phases were separated and the organic layer was washed in succession with 10% citric acid solution (1×30 ml), saturated sodium bicarbonate solution (2×30 ml), and brine. The dried (MgSO4) extracts were concentrated to yield 130 mg of crude product. Preparative thick layer chromatography (hexane - ethyl acetate, 1:1 v/v) afforded the analytical sample.

HPLC: Greater than 98% pure.
NMR (CDCl3): Consistent with the title structure.
MS (14 ev): 425 (M+), 268, 199, 156.
Anal. calc'd for $C_{26}H_{20}FN_3O_2 \cdot 1.25 H_2O$ N, 9.38; C, 69.70; H, 5.06; Found: N, 8.86; C, 69.75; H, 4.85.

EXAMPLE 116

1,3-Dihydro-3-(RS)-(2-quinaldyl)amino-5-(2-fluorophenyl)-2H-1,4-benzodiazepin-2-one 1,3-Dihydro-3(RS)-amino-5-(2-fluorophenyl)-2H-1,4-benzodiazepin-2-one (100 mg, 0.37 mmol) and 2-quinoline carboxylic acid (quinaldic acid) (70 mg, 0.40 mmol) were combined at room temperature in 5 ml of methylene chloride. To this reaction mixture was added 1-ethyl-3-(3-dimethylaminopropyl)carbodiimide hydrochloride (76 mg, 0.40 mmole). The pH of the reaction mixture was then adjusted to 8.5 with triethylamine and stirring was continued at room temperature for 48 hours. The reaction mixture was partioned between methylene chloride and 10% citric acid solution. The phases were separated and the organic layer was washed in succession with 10% citric acid solution (1×30 ml), saturated sodium bicarbonate solution (2×30 ml) and brine. The dried (MgSO4) extracts were concentrated to yield 150 mg of crude product. Preparative thick layer chromatography (chloroform - methanol - ammonia, 97:3:0.3 v/v) afforded the analytical sample (60 mg).

NMR (CDCl3): Consistent with the title structure.
MS (14 ev): 424 (M+), 268, 241, 198, 184.
Anal. calc'd for $C_{25}H_{17}FN_4O_2 \cdot 0.75 H_2O$ N, 12.79; C, 68.56; H, 4.25; Found: N, 13.35; C, 68.53; H, 4.23.

EXAMPLE 117

(1,3-Dihydro-3-(RS)-(2-L-hydroxy-2-phenylacetyl)amino-5-(2-fluorophenyl)-2H-1,4-benzodiazepin-2-one 1,3-Dihydro-3-(RS)-amino-5-(2-fluorophenyl)-2H-1,4-benzodiazepin-2-one (100 mg, 0.37 mmol) and L-mandelic acid (63 mg, 0.41 mmol) were combined at room temperature in 10 ml of methylene chloride. To this reaction mixture was added 1-ethyl-3-(3-dimethylaminopropyl)carbodiimide hydrochloride (79 mg, 0.41 mmol). The pH of the reaction mixture was then adjusted to 8.5 with triethylamine and stirring was continued at room temperature for 96 hours. The reaction mixture was partitioned between methylene chloride and 10% citric acid solution. The phases were separated and the organic layer was washed in succession with 10% citric acid solution (1×30 ml), saturated sodium bicarbonate solution (2×30 ml) and brine. The dried (MgSO$_4$) extracts were concentrated to yield 130 mg of crude product as a mixture of diastereomers. Preparative thick layer chromatography (chloroform - methanol - ammonia, 95:5:0.5, v/v) afforded the analytical sample. NMR (CDCl$_3$): consistent with the title structure.

EXAMPLE 118

1,3-Dihydro-3-(RS)-(5-Chloroindole-2-carbonylamino)-5-(2-fluorophenyl)-2H-1,4-benzodiazepin-2-one 3-(RS)-Amino-1,3-dihydro-5-(2-fluorophenyl)-2H-1,4-benzodiazepin-2-one (100 mg, 0.391 mmol) was suspended in 2 ml of methylene chloride. 5-Chloroindole-2-carboxylic acid chloride (86.7 mg, 0.438 mmol) was added. The pH of the stirred mixture was adjusted to 9 with triethylamine (95 μl). The reaction mixture was stirred for 24 hours. The mixture was then diluted with 1 ml of methanol and filtered. The filtrate was pipetted onto a 2000 μ Analtech Preparative TLC plate which was developed in a 95:5:0.5 chloroform, methanol, water (CMW) solvent system. The product band was collected. The silica was washed with 90:10:1 CMW. The filtrate was evaporated and the residue was dissolved in methanol and placed in a small vial. The solvent was evaporated to yield 16.4 mg of purified product.

HPLC: 90% pure.
MS (14 ev): (M+) m/e 446.
NMR: Consistent with title product.
Anal. calc'd for $C_{24}H_{16}Cl_1FN_4O_2.0.8CH_3OH$ C, 63.04; H, 4.09; N, 11.86; Found: C, 63.03; H, 3.66; N, 11.58.

EXAMPLE 119

3-(RS)-[N-(2-indolecarbonyl)-N-methylamino]-1,3-dihydro-5-phenyl-2H-1,4-benzodiazepin-2-one 1,3-Dihydro-3-(RS)-methylamino-5-phenyl-2H-1,4-benzodiazepin-2-one (130 mg, 0.49 mmol) and indole-2-carbonyl chloride (88 mg, 0.49 mmol) were combined in CH$_2$Cl$_2$ (5 ml) and stirred 2 hours at 25° C. The reaction was concentrated and chromatographed on silica gel (3% MeOH in CH$_2$Cl$_2$) to give the title compound as a white solid from CH$_2$Cl$_2$: (m.p. 287°–288.5°).

TLC: Silca GF (5% MeOH in CH$_2$Cl$_2$), R$_f$=0.41, single homogeneous component.
NMR: Consistent with title structure and verified the presence of 0.25 H$_2$O.
HPLC: Greater than 97.2% pure.
MS: Mol. ion=408 m/e (free base).
Anal. calc'd for $C_{25}H_{20}N_4O_2.0.25H_2O$ C, 72.70; H, 5.00; N, 13.57; Found: C, 72.64; H, 4.87; N, 13.30.

EXAMPLE 120

1,3-Dihydro-3-(RS)-(5-Bromoindole-2-carbonylamino)-5-(2-fluorophenyl)-2H-1,4-benzodiazepin-2-one The procedure of Example 114 was carried out using 5-bromoindole-2-carboxylic acid chloride (0.113 g, 0.438 mmole) in place of 5-fluoroindole-2-carboxylic acid chloride.

HPLC: 82% pure.
MS: M+ (14 ev) , m/e 490.
NMR: Consistent with title product.
Anal. calc'd for $C_{24}H_{16}BrFN_4O_2.0.28CHCl_3$ N, 10.68; C, 55.57; H, 3.13; Found: N, 10.31; C, 55.98; H, 3.36.

EXAMPLE 121

3-(RS)-Cinnamoylamino-1,3-dihydro-5-(2-fluorophenyl)-2H-1,4-benzodiazepin-2-one 3-(RS)-Amino-1,3-dihydro-5-(2'-fluorophenyl)-2H-1,4-benzodiazepin-2-one (50 mg, 0.186 mmol) was suspended in methylene chloride (1 ml). Cinnamoyl chloride (34.5 mg, 0.207 mol) was added to the methylene chloride mixture. The pH of the stirred mixture was adjusted to ~9 with 50 μl of triethylamine. After stirring for 16 hours the mixture was filtered. The product in the filtrate was purified by prep TLC. The product band was collected by washing the silica containing the product, with 80:20:2 CMW. The solvent was evaporated and the residue was dissolved in methanol, placed in a small vial and evaporated. Yield 16.6 mg.

HPLC: 97% pure.
MS: M+ (14 ev) m/e 399
NMR: Consistent with title structure.
Anal. calc'd for $C_{24}H_{18}FN_3O_2.0.126CHCl_3$ N, 10.18; C, 70.24; H, 4.42; Found: N, 10.08; C, 70.07; H, 4.46.

EXAMPLE 122

1,3-Dihydro-3-(RS)-(5-hydroxy-2-indolylcarbonyl)amino-5-(2-fluorophenyl)-2H-1,4-benzodiazepin-2-one 1,3-Dihydro-3-(RS)-amino-5-(2-fluorophenyl)-2H-1,4-benzodiazepin-2-one (100 mg, 0.37 mmole) and 5-hydroxyindole-2-carboxylic acid (75 mg, 0.44 mmole) were combined at room temperature in a mixture of 1 ml of dimethylformamide and 5 ml of methylene chloride. To this reaction mixture was added 1-ethyl-3-(3-dimethylaminopropyl)carbodiimide hydrochloride (76 mg, 0.40 mmol). The pH of the reaction mixture was then adjusted to 8.5 with triethylamine and stirring was continued at room temperature for 48 hours. The solvent was removed under reduced pressure and the residue was partitioned between ethyl acetate and 10% citric acid solution. The phases were separated and the organic layer was washed in succession with 20% citric acid solution (1×30 ml), saturated sodium bicarbonate solution (2×30 ml) and brine. The dried (MgSO$_4$) extracts were concentrated to yield 200 mg of the product. Preparative thick layer chromatography (chloroform - ethanol - ammonia, 90:10:1, v/v) afforded the analytical sample (80 mg).

NMR (CD$_3$OD): Consistent with the title structure.
MS (14 ev): 428 (M+), 227, 176, 159.
Anal. calc'd. for $C_{24}H_{17}FN_4O_3.0.25 CHCl_3$ N, 12.23; C, 63.56; H, 3.79; Found: N, 12.09; C, 63.99; H, 4.09.

EXAMPLE 123

1-Carboxamidomethyl-1,3-dihydro-3R-(3-indolylmethyl)-5-(2-fluorophenyl)-2H-1,4-benzodiazepin-2-one 1,3-Dihydro-3R-(3-indolylmethyl)-(2-fluorophenyl)-2H-1,4-benzodiazepin-2-one (10 g, 16 mmol) was stirred in 120 ml of degassed DMF at 0° C. under nitrogen with sodium hydride (1.25 g, 26 mmol) until homogeneous (1 hour). Ethylbromoacetate (2.88 ml, 26 mmol) was added and the reaction mixture was stirred at room temperature for 1 hour. The reaction was quenched in 1 l of water. The aqueous solution was extracted with 3×250 ml of methylene chloride. The methylene chloride solution was washed with 250 ml water. The organic phase was separated, dried over sodium sulfate and concentrated in vacuo.

A portion of the crude ester (530 mg) was dissolved in 50 ml of methanol. The solution was stirred in a pressure bottle and saturated with ammonia at 0° C. The bottle was sealed and the solution was stirred at room temperature for 48 hours. The solution was concentrated in vacuo. This gave a solid which was purified by flash chromatogrphy in a 97:3 chloroform/methanol solvent system to 245 mg of purified product.

HPLC: 99% pure.
MS: M+ (14 ev) m/e 440
NMR: Consistent with title structure.
Anal. calc'd for $C_{26}H_{21}FN_4O_2.0.53H_2O$ N, 12.45; C, 69.39; H, 4.82; Found: N, 12.27; C, 69.32; H, 4.80.

EXAMPLE 124

1,3-Dihydro-5-(2-fluorophenyl)-3-(RS)-(2-indolylmethylamino)-2H-1,4-benzodiazepin-2-one 3-(RS)-Chloro-1,3-dihydro-5-(2-fluorophenyl)-2H-1,4-benzodiazepin-2-one (150 mg, 0.520 mmol) and 2-aminomethylindole (75.9 mg, 0.520 mmol) were combined in 1,2-dimethoxyethane (3 ml) and the mixture stirred 20 min. at 25° C. The mixture was evaporated to dryness in vacuo and the residue treated with $H_2O$ and extracted with EtOAc (3×). The combined extracts were washed with $H_2O$ (1×), dried over $MgSO_4$, filtered and stripped to dryness in vacuo to give an orange oil which, after chromatography on silica gel (4% MeOH in $CH_2Cl_2$) provided the title compound as a white solid from ether: (m.p. 200°–202°).

TLC: Silica GF (5% MeOH in $CH_2Cl_2$), $R_f=0.37$, single homogeneous component.
NMR: Consistent with title structure.
HPLC: Greater than 97.7% pure.
MS: Molecular ion at m/e=398.
Anal. calc'd for $C_{24}H_{19}FN_4O$: C, 72.35; H, 4.81; N, 14.06; Found: C, 72.48; H, 4.81; N, 13.69.

EXAMPLE 125

1,3-Dihydro-3-(RS)-(phenylaminomethylcarbonyl)amino-5-(2-fluorophenyl)-2H-1,4-benzodiazepin-2-one 1,3-Dihydro-3-(RS)-amino-5-(2-fluorophenyl)-2H-1,4-benzodiazepin-2-one (100 mg, 0.37 mmol) and N-phenyl glycine (64 mg, 0.42 mmol) were combined at room temperature in 5 ml of methlylene chloride. To this reaction mixture was added 1-ethyl-3-(3-dimethylaminopropyl)carbodiimide hydrochloride (81 mg, 0.42 mmole). The pH of the reaction mixture was then adjusted to 8.5 with triethylamine and stirring was continued at room temperature overnight. More N-phenylglycine and carbodiimide reagent were added (0.2 equivalents) and stirring was continued. The reaction mixture was partitioned between methylene chloride and 10% citric acid solution after 48 hours reaction time. The phases were separated and the organic layer was washed in succession with 20% citric acid solution (1×30 ml), saturated sodium bicarbonate solution (2×30 ml) and brine. The dried ($MgSO_4$) extracts were concentrated to yield 200 mg of crude product. Preparative thick layer chromatography (chloroform - ethanol - ammonia 92:8:0.8 v/v) afforded the analytical sample (100 mg), m.p. 145°–146°.

NMR ($CDCl_3$): Consistent with the title structure.
MS (14 ev): 402 (M+), 265.
Anal. calc'd for $C_{23}H_{19}FN_4O_2.0.55$ $CHCl_3$ N, 11.97; C, 60.43; H, 4.21; Found: N, 11.80; C, 60.37; H, 4.06.

EXAMPLE 126

1,3-Dihydro-3-(RS)-(5-methoxyindole-2-carbonylamino)-5-(2-fluorophenyl)-2H-1,4-benzodiazepin-2-one 3-(RS)-Amino-1,3-dihydro-5-(2-fluorophenyl)-2H-1,4-benzodiazepin-2-one (50 mg, 0.186 mmol) was suspended in 1 ml of methylene chloride. 5-Methoxyindole-2-carboxylic acid (36.9 mg, 0.207 mmol) was added to the suspension followed by the addition of 38.5 mg (0.2 mmol) of EDC. The mixture was brought to pH 8 with 60 μl of triethylamine. The solid which formed after 3 min. was filtered after 5 hours and washed with chloroform. The filtrate was applied to a 2000 μ preparative TLC plate and eluted with 90:10:1 chloroform:methanol:water (CMW). The product was extracted from silica with methanol and evaporated.

HPLC: 98% pure.
MS: M+ (14 ev) m/e 442
NMR: Consent with title structure.
Anal. calc'd for $C_{25}H_{19}FN_4O_3.0.1CHCl_3$ N, 12.33; C, 66.34; H, 4.24; Found N, 10.59; C, 66.19; H, 4.23.

EXAMPLE 127

1,3-Dihydro-3-(RS)-(1-methylindole-2-carbonylamino)-5-(2-fluorophenyl)-2H-1,4-benzodiazepine-2-one 3-(RS)-Amino-1,3-dihydro-5-(2-fluorophenyl)-2H-1,4-benzodiazepin-2-one (50 mg, 0.186 mmol) was suspended in 1 ml of methylene chloride. 1-Methylindole-2-carboxylic acid (36.2 mg, 0.2 mmol) was added to the solution followed by the addition of 38.5 mg (0.2 mmol) of EDC. The pH of the solution was brought to 8 with 60 μl of triethylamine. After stirring for 4 hours the product was purified by preparative TLC on a 2000 μ silica gel plate with a 95:5:0.5 chloroform/methanol/water solvent system. The product band was collected and isolated by washing the silica with 90:10:1 CMW. yield 16.5 mg.

HPLC: 99% pure
MS: M+ (14 ev) m/e 426
NMR: Consistent with title structure.
Analysis calc'd for $C_{25}H_{19}FN_4O_2$ $0.8CH_3OH$ N, 12.39; C, 68.54; H, 4.95; Found: N, 12.34; C, 68.29; H, 4.18.

EXAMPLE 128

1,3-Dihydro-5-(2-fluorophenyl)-3-(RS)-(2-benzofurancarbonylamino)-2H-1,4-benzodiazepin-2-one 3-(RS)-Amino-1,3-dihydro-5-(2-fluorophenyl)-2H-1,4-benzodiazepin-2-one (80 mg, 0.297 mmol), benzofuran-2-carboxylic acid (48 mg, 0.297 mmol), and EDC (56.9 mg, 0.297 mmol) were combined in $CH_2Cl_2$ (3 ml) and the pH adjusted to 9.5 with triethylamine (41 μl, 0.297 mmol). After stirring 30 minutes at 25° C., the reaction was concentrated and chromatographed on silica gel (3% MeOH in $CH_2Cl_2$) to give the title compound as a white solid from $CH_2Cl_2/Et_2O$: (m.p. 289°–291°).

TLC: Silica GF (5% MeOH in $CH_2Cl_2$), $R_f=0.48$, single homogeneous component.

NMR: Consistent with title structure and verified the presence of 0.15 $CH_2Cl_2$ and 0.1 $(C_2H_5)_2O$.

HPLC: Greater than 99.7% pure.

M.S.: Mol. ion=413 m/e (free base).

Anal. Calc'd for $C_{25}H_{16}FN_3O_3.0.15\ CH_2Cl_2.0.10\ (C_2H_5)_2O$: Calc'd: C, 68.01; H, 4.02; N, 9.69; Found: C, 68.22; H, 3.86; N, 9.36.

EXAMPLE 129

1-Ethoxycarbonylmethyl-1,3-dihydro-3(RS)-(4-chlorophenylcarbonyl)amino-5-(2-fluorophenyl)-2H-1,4-benzodiazepin-2-one To a suspension of sodium hydride (50%) (24.4 mg, 0.51 mmole) in 2 ml of dry dimethylformamide at 0° C. was added, under nitrogen, 1,3-dihydro-3(RS)-(4-chlorophenylcarbonyl)amino-5-(2-fluorophenyl)-2H-1,4-benzodiazepin-2-one (197.3 mg, 0.48 mmole). The resulting reaction mixture became homogeneous over a one-hour period, was stirred one hour more at 0° C. and then treated with ethylbromoacetate (55 μl, 0.50 mmole). The reaction mixture was warmed to room temperature and after one hour was quenched with brine. The aqueous mixture was extracted with ethyl acetate and the combined organic extracts were washed with brine. Rotoevaporation of the dried extracts ($MgSO_4$) gave a semi-solid which was chromatographed on silica gel (chloroform-methanol-ammonia 95:5:0.5 v/v elution) to afford 64 mg of the analytical sample. mp 172° (soften), 177°–178° C.

NMR ($CDCl_3$): Consistent with the title structure.

MS (14 ev): 493 (M+), 364, 354, 338, 327, 313

Analysis calc'd for $C_{26}H_{21}ClFN_3O_4.0.1\ C_4H_8O_2$ N, 8.35; C, 63.05; H, 4.32; Found: N, 8.16; C, 62.89; H, 4.44.

EXAMPLE 130

1,3-Dihydro-3-(RS)-(4-chlorophenylcarbonyl)amino-5-phenyl-2H-1,4-benzodiazepin-2-one 1,3-Dihydro-3-(RS)-amino-5-phenyl-2H-1,4-benzodiazepin-2-one (500 mg, 1.98 mmole) and p-chlorobenzoyl chloride (255 μl, 2.00 mmole) were combined at room temperature in 30 ml of methylene chloride. The resulting solution was protected from moisture and stirred at room temperature overnight. The reaction mixture was diluted with 70 ml of methylene chloride and washed with sodium bicarbonate solution (sat.) and brine. The organic extracts were dried ($MgSO_4$) and concentrated to give the crude product. Trituration with ether afforded the analytical sample as a white solid.

NMR ($CDCl_3$): Consistent with the title structure.

MS (14 ev): 389 (M+), 250, 234.

Analysis calc'd for: $C_{22}H_{16}ClN_2O_2$ N, 10.78; C, 67.78; H, 4.13; Found: N, 10.71; C, 67.79; H, 3.97.

EXAMPLE 131

1,3-Dihydro-1-methyl-3-(RS)-(4-chlorophenylcarbonyl)amino-5-phenyl-2H-1,4-benzodiazepin-2-one To a suspension of sodium hydride (50%) (10 mg, 0.21 mmole) in 1 ml of dry dimethylformamide at 0° C. was added, under a nitrogen, 1,3-dihydro-3-(RS)-(4-chlorophenylcarbonyl)amino-5-phenyl-2H-1,4-benzodiazepin-2-one (65.5 mg, 0.166 mmole). The resulting reaction mixture became homogeneous over a one-hour period, was stirred one hour more at 0° C. and then treated with iodomethane (10.8 μl, 0.17 mmole). The reaction mixture was warmed to room temperature and after one hour was quenched with brine. The aqueous mixture was extracted with ethyl acetate and the combined organic extracts were washed with brine. Rotoevaporation of the dried extracts ($MgSO_4$) gave a semisolid which was chromatographed on silica gel (chloroform-methanol-ammonia 95:5:0.5 v/v elution) to give the analytical sample.

NMR ($CDCl_3$): Consistent with the title structure;

MS (14 ev): 403 (M+)

Analysis calc'd for: $C_{23}H_{18}ClN_3O_2$: N, 10.40; C, 68.40; H, 4.49; Found: N, 10.11; C, 68.50; H, 4.57.

EXAMPLE 132

1-Carboxymethyl-1,3-dihydro-3-(RS)-(4-chlorophenylcarbonyl)amino-5-(2-fluorophenyl)-2H-1,4-benzodiazepin-2-one To a suspension of sodium hydride (50%) (14.0 mg, 0.30 mmole) in 2 ml of dry dimethylformamide at 0° C. was added, under nitrogen, 1,3-dihydro-3-(RS)-(4-chlorophenylcarbonyl)amino-5-(2-fluorophenyl)-2H-1,4-benzodiazepin-2-one (103.0 mg, 0.25 mmole). The resulting reaction mixture became homogeneous over a one-hour period, was stirred one hour more at 0° C. and then treated with 1 ml of dimethylformamide containing sodium iodoacetate (56 mg) (0.27 mmole). The reaction mixture was warmed to room temperature and after 12 hours was quenched with brine. The aqueous mixture was extracted with ethyl acetate and the combined organic extracts were washed with brine. Rotoevaporation of the dried extracts ($MgSO_4$) gave a semi-solid which was chromatographed on silica gel (chloroform-methanol-acetic acid, 93:6:1 v/v) to provide the analytical sample: (m.p. 225°–228° C., from methanol).

FABMS: m/e=466 (M+H), 245, 177

NMR (DMSO-$d_6$): consistent with title structure.

Anal. Calc'd for $C_{24}H_{17}ClFN_3O_4$ 0.45NaI 0.75 $H_2O$ C, 52.71; H, 3.41; N, 7.68. Found: C, 52.87; H, 3.64; N, 7.43.

EXAMPLE 133

1,3-Dihydro-3-(RS)-(2-indolinecarbonylamino)-5-phenyl-2-H-1,4-benzodiazepin-2-one 3-(RS)-Amino-1,3-dihydro-5-phenyl-2H-1,4-benzodiazepin-2-one (100 mg, 0.398 mmol), 1-indoline-2-carboxylic acid (64.9 mg, 0.398 mmol), 1-hydroxybenzotriazole hydrate (HBT, 53.8 mg, 0.398 mmol), and 1-ethyl-3-(3-dimethylaminopropyl)carbodiimide hydrochloride (EDC, 76.3 mg, 0.398 mmol) were combined in DMF (2 ml) and the pH of the solution was adjusted to 9.0–9.5 with triethylamine (TEA, 95 ξ1, 0.683 mmol). After stirring 15 minutes at 25° C., the DMF was removed in vacuo, the residue treated with $H_2O$ and extracted with EtOAc (3×). The combined organic extracts were washed with brine, dried over $MgSO_4$, filtered and stripped to dryness in vacuo to give a white solid (180 mg). Flash chromatography on silica gel (267/10/1 of $CH_2Cl_2$/MeOH/concentrated $NH_4OH$) gave a white solid (38 mg) from EtOAc/hexane. The product is a single stereoisomer whose absolute configuration is unknown; m.p. 252°–272° C. (slowly shrinks to a cloudy melt). TLC: Silica GF (190/10/1 of $CH_2Cl_2$/MeOH/concentrated $NH_4OH$), $R_f$=0.40, single, clean component.

NMR: Consistent with title structure and verifies the presence of EtOAc.

HPLC: Greater than 96% pure.

MS: Molecular ion at m/e=396.

Anal. calc'd for $C_{24}H_{20}N_4O_2 \cdot 0.45 C_4H_8O_2$ C, 71.06; H, 5.46; N, 12.85; Found: C, 70.71; H, 5.11; N, 13.20.

EXAMPLE 134

1,3-Dihydro-5-(2-fluorophenyl)-3-(RS)-(p-trifluoromethylbenzoylamino)-2H-1,4-benzodiazepin-2-one 1,3-Dihydro-3-(RS)-amino-5-(2-fluorophenyl)-2H-1,4-benzodiazepin-2-one (42 mg, 0.156 mmole) and p-trifluoromethylbenzoyl chloride (32.5 mg, 0.156 mmole) were combined in 3 ml of methylene chloride ($CH_2Cl_2$), treated with triethylamine (0.0157 g, 0.156 mmole) and stirred at room temperature 15 minutes. The mixture was diluted with $CH_2Cl_2$ (20 ml), washed with 10% citric acid (2×5 ml), dilute sodium bicarbonate (2×5 ml), and water (2×5 ml), dried over sodium sulfate, filtered, and evaporated to dryness in vacuo. The residue was crystallized from ethyl acetate (0.4 ml)/ether (1 ml) to give the title compound which was dried in vacuo at 90°: (m.p. 209°–211°).

TLC: Single spot, $R_f=0.62$, silica gel plate, 90:10:1:1 (v:v:v:v) $CH_2Cl_2$:MeOH:HOAc:$H_2O$.

NMR: The spectrum was consistent with the title structure and verified the presence of EtOAc.

HPLC: Greater than 98% pure.

MS: Molecular ion at m/e=441.

Anal. calc'd for $C_{23}H_{15}F_4N_3O_2 \cdot 0.2 EtOAc$: C, 62.27; H, 3.64; N, 9.16; Found: C, 62.25; H, 3.61; N, 9.11.

EXAMPLE 135

1,3-Dihydro-5-(2-fluorophenyl)-3-(RS)-(p-methylbenzoylamino)-2H-1,4-benzodiazepin-2-one The procedure of Example 134 was carried out using p-methylbenzoyl chloride (24 mg, 0.156 mmole) in place of p-trifluoromethylbenzoyl chloride. The title compound was crystallized from $CH_2Cl_2$ (3 ml)/$Et_2O$ (1 ml) and dried in vacuo at 90°: (m.p. 275°–276° (d)).

TLC: Single spot, $R_f=0.62$, silica gel plate, 90:10:1:1 (v:v:v:v) $CH_2Cl_2$:MeOH:HOAc:$H_2O$.

NMR: The spectrum was consistent with the title structure.

HPLC: Greater than 98% pure.

MS: Molecular ion at m/e=387.

Anal. calc'd for $C_{23}H_{18}FN_3O_2 \cdot 0.4 H_2O$: C, 70.00; H, 4.80; N, 10.65; Found: C, 70.04; H, 4.68; N, 10.56.

EXAMPLE 136

1,3-Dihydro-5-(2-fluorophenyl)-3-(RS)-(p-methoxybenzoylamino)-2H-1,4-benzodiazepin-2-one The procedure of Example 134 was carried out using p-methoxybenzoyl chloride (26.6 mg, 0.156 mmole) in place of p-trifluoromethylbenzoyl chloride. The title compound was crystallized from $CH_2Cl_2$ (2 ml)/$Et_2O$ (1 ml) and dried in vacuo at 90°: (m.p. 231°–233°).

TLC: Single spot, $R_f=0.47$, silica gel plate, 5% (v/v) MeOH/$CH_2Cl_2$.

NMR: The spectrum was consistent with the title structure.

HPLC: Greater than 97% pure.

MS: Molecular ion at m/e=403.

Anal. calc'd for $C_{23}H_{18}FN_3O_3$: C, 68.48; H, 4.50; N, 10.42; Found: C, 68.62; H, 4.60; N, 10.36.

EXAMPLE 137

3-(RS)-(o-Chlorobenzoylamino)-1,3-dihydro-5-phenyl-2H-1,4-benzodiazepin-2-one 3-(RS)-Amino-1,3-dihydro-5-phenyl-2H-1,4-benzodiazepine-2-one (250 mg, 0.93 mmol) was suspended in methylene chloride (10 ml) and treated with o-chlorobenzoylchloride (0.124 ml, 0.97 mmol) followed by triethylamine (0.143 ml, 0.97 mmol). The solution was stirred at room temperature overnight. The reaction solution was chromatographed on silica gel (chloroform followed by 97/3 chloroform/methanol) and the combined product fractions were evaporated to dryness in vacuo. TLC: Silica gel (90:10:1, $CHCl_3$:$CH_3OH$:$H_2O$), $R_f=0.85$.

NMR: Consistent with structure.

HPLC: 99% pure.

MS: Molecular ion at m/e=389.

Anal. calc'd for $C_{22}H_{16}ClN_3O_2$: C, 67.78; H, 4.14; N, 10.77; Found: C, 67.34; H, 4.00; N, 10.72.

EXAMPLE 138

3-(RS)-(N-(o-Chlorobenzoyl)-N-methylamino)-1,3-dihydro-1-methyl-5-phenyl-2H-1,4-benzodiazepin-2-one 3-(RS)-1,3-Dihydro-(o-Chlorobenzoylamino)-5-phenyl-2H-1,4-benzodiazepin-2-one (200 mg, 0.51 mmol) and sodium hydride (52 mg of a 50% suspension in mineral oil, 1.094 mmol) were stirred in 2 ml of dry, degassed dimethylformamide under nitrogen in an ice bath. The mixture was stirred until homogeneous. After 2 hours, methyl iodide (38 μl, 1.094 mmol) was added in one portion. The reaction was stirred for 1 hour at 0° C. and 1 hour at room temperature. The reaction was quenched with 3 ml of saturated sodium chloride solution. The mixture was extracted with ethyl acetate. The clear solution obtained when chloroform was added was evaporated to dryness then chromatographed on silica gel with chloroform as the elution solvent. The 7:1 mixture of the di and mono substituted compounds was further purified by preparative TLC. (Analtech silica gel 2000 μ prep TLC plates developed twice in a 98:2 chloroform/methanol solvent system).

TLC: Silica gel 97:2 $CHCl_3$:MeOH, $R_f=0.35$.

NMR: Consistent with structure.

MS: Molecular ion m/e=417

HPLC: 98%.

Anal. calc'd for $C_{24}H_{20}ClN_3O_2 \cdot 0.35 CHCl_3$: C, 63.62; H, 4.46; N, 9.14; Found: C, 63.40; H, 4.55; N, 8.97.

EXAMPLE 139

3-(RS)-(o-Chlorobenzoylamino)-1,3-dihydro-1-methyl-5-phenyl-2H-1,4-benzodiazepin-2-one 3-(RS)-1,3-Dihydro-(o-Chlorobenzoylamino)-5-phenyl-2H-1,4-benzodiazepin-2-one (207 mg, 0.53 mmol) and sodium hydride (26 mg of a 50% suspension in mineral oil, 0.54 mmol) were stirred in 2 ml of dry, degassed dimethylformamide under nitrogen in an ice bath. The mixture was stirred until homogeneous. After 2 hours, methyl iodide (34 μl, 0.547 mmol) was added in one portion. (The remainder of the experiment proceeds as described in Example 139).

NMR: Consistent with structure.

HPLC: 98%.

MS: Molecular ion m/e 403.

Anal. calc'd for $C_{23}H_{18}ClN_3O_2 \cdot 0.62 H_2O$ C, 66.56; H, 4.67; N, 10.12; Found: C, 66.71; H, 4.53; N, 9,90.

EXAMPLE 140

3-(RS)-(m-Chlorobenzoylamino)-1,3-dihydro-5-phenyl-2H-1,4-benzodiazepin-2-one

The procedure of Example 137 was carried out using m-chlorobenzoyl chloride in place of o-chlorobenzoyl-chloride. The reaction was chromatographed using chloroform as the elution solvent.

TLC: Silica gel 90:10:1 CMA; $R_f$=0.8.
NMR: Consistent with structure.
HPLC: 96%.
MS: Molecular ion at m/e 389.
Anal. calc'd for $C_{22}H_{16}N_3O_2$ 0.62$CHCl_3$: C, 59.86; H, 3.69; N, 9.30; Found: C, 59.99; H, 3.75; N, 9.18.

EXAMPLE 141

3-(RS)-(3,4-Dichlorobenzoylamino)-1,3-dihydro-5-phenyl-2H-1,4-benzodiazepin-2-one The EDC procedure in Example 126 was carried out using 3,4-dichlorobenzoic acid in place of 5-methoxyindole-2-carboxylic acid. The reaction product was dissolved in chloroform and chromatographed with chloroform followed by 99:1 $CHCl_3$:MeOH(CM).

TLC: Silica gel 97:3 CM, $R_f$=0.45.
HPLC: 100%.
NMR: Consistent with structure.
MS: Molecular ion at m/e 423.
Anal. calc'd for $C_{22}H_{15}Cl_2N_3O_2$ 0.08$CHCl_3$ C, 61.12; H, 3.50; N, 9.69; Found: C, 61.05; H, 3.50; N, 9.30.

EXAMPLE 142

3-(RS)-(p-Chlorobenzoylamino)-1,3-dihydro-5-(2'-fluorophenyl)-1-methyl-4-oxo-2H-1,4-benzodiazepin-2-one 3-(RS)-(p-Chlorobenzoylamino)1,3-Dihydro-5-(2'-fluorophenyl)-1-methyl-2H-1,4-benzodiazepin-2-one (50 mg, 0.118 mmol) was stirred in 3 ml of chloroform. m-Chloroperoxybenzoic acid (23.6 mg, 0.137 mmol) was added. After stirring overnight another 23.6 mg of MCPBA was added. The solution was stirred for 48 hours then diluted with chloroform and washed with cold saturated sodium bicarbonate. The chloroform solution was dried over sodium sulfate and evaporated. The residue obtained after evaporation was purified by preparative TLC with 98:2 $CHCl_3$:MeOH (CM) as the developing solvent.

TLC Silica gel 98:2 CM, $R_f$=0.4 CM.
NMR: Consistent with structure.
HPLC: 95%.
MS: Molecular ion at m/e=437.
Anal. calc'd for $C_{23}H_{17}ClFN_3O_3$ 0.05$CHCl_3$: C, 62.37; H, 3.87; N, 9.46; Found: C, 62.41; H, 3.80; H, 9.43.

EXAMPLE 143

30

1,3-Dihydro-5-Phenyl-3-(RS)-(4'-methylthiobenzoylamino)-2H-1,4-benzodiazepin-2-one The EDC procedure in Example 126 was carried out using 4-methyl thiobenzoic acid in place of 5-methoxyindole-2-carboxylic acid. The reaction solution was chromatographed on a silica gel column with chloroform followed by 99:1 $CHCl_3$:MeOH (CM).

TLC: Silica gel 97:3 CM, $R_f$=0.3
NMR: Consistent with structure.
HPLC: 97%.
MS: Molecular ion at m/e 401.

Anal. calc'd for $C_{23}H_{19}N_3O_2S$ 0.65$CHCl_3$: C, 59.28; H, 4.13; N, 8.77; Found: C, 59.33; H, 4.21; N, 8.57.

EXAMPLE 144

1-3-Dihydro-3-(RS)-(4'-fluorobenzoylamino)-5-phenyl-2H-1,4-benzodiazepin-2-one

The procedure of Example 137 was carried out using 4-fluorobenzoyl chloride in place of o-chlorobenzoyl chloride. The reaction was chromatographed on silica gel using chloroform as the elution solvent.

TLC: Silica gel 97:3 $CHCl_3$:MeOH (CM), $RF_f$=0.33.
NMR: Consistent with structure.
HPLC: 95%.
MS: Molecular ion at m/e 373.
Anal. calc'd for $C_{22}H_{16}FN_3O$ 0.2$H_2O$: C, 70.09; H, 4.39; N, 11.15; Found: C, 70.14; H, 4.36; N, 10.93.

EXAMPLE 145

1,3-Dihydro-5-Phenyl-3-(RS)-(4'-trifluoromethylbenzoylamino)-2H-1,4-benzodiazepin-2-one The procedure of Example 137 was carried out using 4-trifluoromethylbenzoyl chloride in place of o-chlorobenzoyl chloride. The reaction was chromatographed on silica gel using chloroform as the elution solvent.

TLC: Silica gel 97:3 $CHCl_3$:MeOH (CM), $R_f$=0.3.
NMR: Consistent with structure.
HPLC: 99%.
MS: Molecular ion at m/e 423.
Anal. calc'd for $C_{23}H_{16}F_3N_3O_2$: C, 65.24; H, 3.81; N, 9.92; Found: C, 65.14; H, 3.94; N, 9.69.

EXAMPLE 146

1,3-Dihydro-3-(RS)-(4-tert-butylbenzoylamino)-5-phenyl-2H-1,4-benzodiazepin-2-one The procedure of Example 137 was carried out using 4-tert-butylbenzoyl chloride in place of o-chlorobenzoyl chloride. The reaction was chromatographed on silica gel using chloroform as the elution solvent.

TLC: Silica 97:3, CHCl:MeOH, $R_f$=0.35.
NMR: Consistent with structure.
HPLC: 98%.
MS: Molecular ion at m/e 411.
Anal. calc'd for $C_{26}H_{25}N_3O_2$ 0.14$CHCl_3$: C, 73.31; H, 5.92; N, 9.81; Found: C, 73.69; H, 6.07; N, 9.78.

EXAMPLE 147

3-(RS)-(3,5-Dichlorobenzoylamino)1,3-dihydro-5-phenyl-2H-1,4-benzodiazepin-2-one The EDC procedure in Example 126 was carried out using 3,5-dichlorobenzoic acid in place of 5-methoxyindole-2-carboxylic acid. The reaction was diluted with chloroform and chromatographed on a silica gel column with chloroform as the elution solvent.

TLC: Silica gel 97:3 $CHCl_3$:MeOH (CM), $R_f$=0.5
NMR: Consistent with structure.
HPLC: 96%.
MS: Molecular ion at m/e 423.
Anal. calc'd for $C_{22}H_{15}Cl_2N_3O_2$: C, 62.27; H, 3.56; N, 9.90; Found: C, 62.65; H, 3.67; N, 9.80.

EXAMPLE 148

1-3-Dihydro-3-(RS)-(p-Hydroxybenzoylamino)-5-phenyl-2H-1,4-benzodiazepin-2-one

The EDC procedure in Example 126 was carried out using p-hydroxybenzoic acid in place of 5-methoxyindole-2-carboxylic acid. The reaction was chromatographed on silica gel with chloroform as the elution solvent.

TLC: Silica gel 97:3 CHCl$_3$:MeOH, R$_f$=0.50.
NMR: Consistent with structure.
HPLC: 99%.
MS: Molecular ion at 371.
Anal. calc'd for C$_{22}$H$_{17}$N$_3$O$_3$: C, 71.15; H, 4.61; N, 11.31; Found: C, 70.05; H, 4.63; H, 11.21.

EXAMPLE 149

3-(RS)-(4'-Cyanobenzoylamino)1,3-dihydro-5-phenyl-2H-1,4-benzodiazepin-2-one

The procedure in Example 137 was carried out using 4-cyanobenzoyl chloride in place of o-chlorobenzoyl chloride. The reaction was chromatographed on silica gel using chloroform followed by 98:2 CHCl$_3$:MeOH (CM) as the elution solvents.

TLC: Silica gel 97:3 CM, R$_f$=0.3.
NMR: Consistent with structure.
HPLC: 99.6%.
MS: Molecular ion at m/e=380.
Anal. calc'd for C$_{23}$H$_{16}$N$_4$O$_2$ 0.41H$_2$O C, 71.24; H, 4.37; N, 14.45; Found: C, 71.53; H, 4.37; N, 14.73.

EXAMPLE 150

3(S)-(−)-3-(2-Chlorobenzoylamino)-1,3-dihydro-1-methyl-5-phenyl-2H-1,4-benzodiazepin-2-one The procedure of Example 134 was carried out using 3(S)-(−)-3-amino-1,3-dihydro-5-phenyl-1-methyl-2H-1,4-benzodiazepin-2-one (41.4 mg, 0.156 mmole) in place of 1,3-dihydro-3(RS)-amino-5-(2-fluorophenyl)-2H-1,4-benzodiazepin-2-one and 2-chlorobenzoylchloride (27.3 mg, 0.156 mmole) in place of p-trifluoromethylbenzoyl chloride. The product was chromatographed on silica gel (5% (v/v) Et$_2$O in CH$_2$Cl$_2$ elution). The combined product fractions were evaporated to dryness in vacuo to give the title compound which was dried in vacuo at 78° C.: (m.p. 100°-118° C.).

TLC: Single spot, R$_f$=0.24, silica gel plate, 5% (v/v) Et$_2$O in CH$_2$Cl$_2$.
NMR: Consistent with structure.
HPLC: Greater than 99% pure.
MS: Molecular ion at m/e=403. [α]$_D^{25}$=−90.4° (1.15 mg/ml, CH$_2$Cl$_2$).
Anal. calc'd for C$_{23}$H$_{18}$ClN$_3$O: C, 68.40; H, 4.49; N, 10.41; Found: C, 68.20; H, 4.73; N, 10.07.

EXAMPLE 151

3(R)-(+)-3-(2-Chlorobenzoylamino)-1,3-dihydro-1-methyl-5-phenyl-2H-1,4-benzodiazepin-2-one The procedure of Example 134 was carried out using 3(R)-(+)-3-amino-1,3-dihydro-5-phenyl-1-methyl-2H-1,4-benzodiazepin-2-one (41.4 mg, 0.156 mmole) in place of 1,3-dihydro-3(RS)-amino-5-(2-fluorophenyl)-2H-1,4-benzodiazepin-2-one, and 2-chlorobenzoyl chloride (27.3 mg, 0.156 mmole) in place of p-trifluoromethylbenzoyl chloride. The product was chromatographed on silica gel (5% (v/v) Et$_2$O in CH$_2$Cl$_2$ elution). The combined product fractions were evaporated to dryness in vacuo to give the title compound which was dried in vacuo at 78° C.: (m.p. 102°-120° C.).

TLC: Single spot, R$_f$=0.24, silica gel plate, 5% (v/v) Et$_2$O in CH$_2$Cl$_2$.
NMR: Consistent with structure.
HPLC: Greater than 98% pure.
MS: Molecular ion at m/e=403.

[α]$_D^{25}$=+95.4° (1.75 mg/ml, CH$_2$Cl$_2$).
Anal. calc'd for C$_{23}$H$_{18}$ClN$_3$O: C, 68.40; H, 4.49; N, 10.41; Found: C, 68.74; H, 4.68; N, 10.16.

EXAMPLE 152

1,3-Dihydro-3(RS)-(p-dimethylaminobenzoylamino)-5-(2-fluorophenyl)-2H-1,4-benzodiazepin-2-one The procedure of Example 134 was carried out using p-dimethylaminobenzoyl chloride (28.6 mg, 0.156 mmole) in place of p-trifluoromethylbenzoyl chloride. The citric acid and sodium bicarbonate washes were omitted. The title compound was crystallized from CH$_2$Cl$_2$ (6 ml)/Et$_2$O (5 ml) and dried in vacuo at 90°: (m.p. 256°-258° C.).

TLC: Single spot, R$_f$=0.60, silica gel plate, 90:10:1:1 (v:v:v:v) CH$_2$Cl$_2$:MeOH:HOAc:H$_2$O.
NMR: The spectrum was consistent with the title structure and verified the presence of H$_2$O.
HPLC: Greater than 98% pure.
MS: Molecular ion at m/e=416.
Anal. calc'd for C$_{24}$H$_{21}$FN$_4$O$_2$.0.15H$_2$O: C, 68.77; H, 5.12; N, 13.37; Found: C, 68.73; H, 5.16; N, 13.27.

EXAMPLE 153

1,3-Dihydro-3(RS)-(3,4-dimethoxybenzoylamino)-5-(2-fluorophenyl)-2H-1,4-benzodiazepin-2-one The procedure of Example 134 was carried out using 3,4-dimethoxybenzoyl chloride (31.3 mg, 0.156 mmole) in place of p-trifluoromethylbenzoyl chloride. The title compound was crystallized from CH$_2$Cl$_2$ (1.5 ml)/Et$_2$O (3 ml) and dried in vacuo at 90°: (m.p. 206°-207.5° C.).

TLC: Single spot, R$_f$=0.64, silica gel plate, 90:10:1:1 (v:v:v:v) CH$_2$Cl$_2$:MeOH:HOAc:H$_2$O.
NMR: The spectrum was consistent with the title structure and verified the presence of Et$_2$O and CH$_2$Cl$_2$.
HPLC: Greater than 99% pure.
MS: Molecular ion at m/e=433.
Anal. calc'd for C$_{24}$H$_{20}$FN$_3$O$_4$.0.13C$_4$H$_{10}$O.0.13CH$_2$Cl$_2$: C, 65.24; H, 4.79; N, 9.26; Found: C, 65.22; H, 4.55; N, 9.14.

EXAMPLE 154

3(S)-(+)-3-(3-Bromobenzoylamino)-1,3-dihydro-5-(2-fluorophenyl)-1-methyl-2H-1,4-benzodiazepin-2-one The procedure of Example 134 was carried out using 3(S)-(−)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 3-bromobenzoyl chloride (34.2 mg, 0.156 mmole) in place of p-trifluoromethylbenzoyl chloride. The title compound was crystallized from Et$_2$O and dried in vacuo at 100° C.: (m.p. 172°-178° C).

TLC: Single spot, R$_f$=0.66, silica gel plate, 15% (v/v) Et$_2$O in CH$_2$Cl$_2$.
NMR: Consistent with structure.
HPLC: Greater than 99% pure.
MS: Molecular ion at m/e=465.
[α]$_D^{25}$=+16.7° (0.0025 g/ml, CH$_2$Cl$_2$).
Anal. calc'd for C$_{23}$H$_{17}$BrFN$_3$O$_2$: C, 59.24; H, 3.67; N, 9.01; Found: C, 59.45; H, 3.80; N, 8.97.

EXAMPLE 155

1,3-Dihydro-5-phenyl-3(RS)-(3-trifluoromethylthiobenzoylamino)-2H-1,4-benzodiazepin-2-one 3(RS)-Amino-1,3-dihydro-5-phenyl-2H-1,4-benzodiazepin-2-one (80.0 mg, 0.318 mmole), 3-trifluoromethylthiobenzoic acid (70.7 mg, 0.318 mmole), HBT (43.0 mg, 0.318 mmole) and EDC (61.0 mg, 0.318 mmole) were combined in dry DMF (2 ml) and stirred at room temperature. The pH of the mixture was adjusted to 9.0–9.5 with triethylamine (64.4 mg, 0.636 mmole) and the mixture stirred for 10 minutes. The DMF was removed in vacuo, and the residue was treated with 10% citric acid and extracted with EtOAc. The combined organic fractions were washed with sodium carbonate solution, dried over $Na_2SO_4$, filtered, and evaporated to dryness in vacuo. The residue was crystallized from EtOAc to give the title compound which was dried in vacuo at 100° C.: (m.p. 230°–232° C.).

TLC: Single spot, $R_f$=0.32, silica gel plate, 15% (v/v) $Et_2O$ in $CH_2Cl_2$.
NMR: Consistent with structure.
HPLC: Greater than 98% pure.
MS: Molecular ion at m/e=455.
Anal. calc'd for $C_{23}H_{16}F_3N_3O_2S$: C, 60.65; H, 3.54; N, 9.23; Found: C, 60.82; H, 3.51; N, 9.35.

EXAMPLE 156

3(S)-(+)-3-(4-Bromobenzoylamino)-1,3-dihydro-5-(2-fluorophenyl)-1-methyl-2H-1,4-benzodiazepin-2-one The procedure of Example 134 was carried out using 3(S)-(−)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 4-bromobenzoyl chloride (34.2 mg, 0.156 mmole) in place of p-trifluoromethylbenzoyl chloride. The title compound was chromatographed on silica gel (5% $Et_2O$ in $CH_2Cl_2$ elution) and the product fractions evaporated to dryness in vacuo. The title compound was dried in vacuo at 82° C.: (m.p. 123°–135° C.).

TLC: Single spot, $R_f$=0.46, silica gel plate, 10% (v/v) $Et_2O$ in $CH_3Cl_2$.
NMR: Consistent with structure.
HPLC: Greater than 99% pure.
MS: Molecular ion at m/e=465. $[\alpha]_D^{25}$=+9.6° (0.0023 g/ml, $CH_2Cl_2$).
Anal. calc'd for $C_{23}H_{17}BrFN_3O_2$: C, 59.24; H, 3.67; N, 9.01; Found: C, 59.12; H, 3.75; N, 8.77.

EXAMPLE 157

3(S)-(+)-3-(4-Butylbenzoylamino)-1,3-dihydro-5-(2-fluorophenyl)-1-methyl-2H-1,4-benzodiazepin-2-one The procedure of Example 134 was carried out using 3(S)-(−)-3-amino-1,3-dihydro-5-(2-fluorophenyl)-1-methyl-2H-1,4-benzodiazepin-2-one (44.2 mg, 0.156 mmole) in place of 1,3-dihdyro-3(RS)-amino-5-(2-fluorophenyl)-2H-1,4-benzodiazepin-2-one and 4-t-butylbenzoyl chloride (30.7 mg, 0.156 mmole) in place of p-trifluoromethylbenzoyl chloride. The product was chromatographed on silica gel (4% $Et_2O$ in $CH_2Cl_2$ elution), and the product fractions evaporated to dryness in vacuo. The title compound was dried in vacuo at 82° C.: (m.p. 184°–190° C.).

TLC: Single spot, $R_f$=0.37, silica gel plate, 5% (v/v) $Et_2O$ in $CH_2Cl_2$).
NMR: Consistent with structure.
HPLC: Greater than 99% pure.
MS: Molecular ion at m/e=443. $[\alpha]_D^{25}$=+6.7° (0.0021 g/ml, $CH_2Cl_2$).
Anal. calc'd for $C_{27}H_{26}FN_3O_2$: C, 73.12; H, 5.91; N, 9.48; Found: C, 73.03; H, 6.11; N, 9.44.

EXAMPLE 158

1,3-Dihydro-5-(2-fluorophenyl)-3(RS)-(pyrrole-2-carbonylamino)-2H-1,4-benzodiazepin-2-one The procedure of Example 134 was carried out using pyrrole-2-carbonyl chloride (20.2 mg, 0.156 mmole) in place of p-trifluoromethylbenzoyl chloride. Without washing, the reaction mixture was chromatographed on silica gel (225:10:1:1 (v:v:v:v) $CH_2Cl_2$:MeOH:HOAc:$H_2O$ elution). The combined product fractions were evaporated to dryness in vacuo and crystallized from EtOAc to give the title compound which was dried in vacuo at 82° C.: (m.p. 271°–274° C.).

TLC: Single spot, $R_f$=0.35, silica gel plate, 180:10:1:1 (v/v/v/v) $CH_2Cl_2$:MeOH:HOAc:$H_2O$.
NMR: Consistent with structure, verifies presence of 0.25 EtOAc.
HPLC: Greater than 95% pure.
MS: Molecular ion at m/e=362.
Anal. calc'd for $C_{20}H_{15}FN_4O_2 \cdot 0.25C_4H_{10}O$: C, 65.62; H, 4.46; N, 14.58; Found: C, 65.60; H, 4.55; N, 14.53.

EXAMPLE 159

3(S)-(+)-1,3-Dihydro-5-(2-fluorophenyl)-3-(4-iodobenzoylamino)-1-methyl-2H-1,4-benzodiazepin-2-one The procedure of Example 134 was carried out using 3(S)-(−)-3-amino-1,3-dihydro-5-(2-fluorophenyl)-1-methyl-2H-1,4-benzodiazepin-2-one (44.2 mg, 0.156 mmole) in place of 1,3-(dihydro-3(RS)-amino-5-(2-fluorophenyl)-2H-1,4-benzodiazepin-2-one and 4-iodobenzoyl chloride (41.6 mg, 0.156 mmole in place of p-trifluoromethylbenzoyl chloride. The product was chromatographed on silica gel (5% (v/v) $Et_2O$ in $CH_2Cl_2$ elution) and the product fractions evaporated to dryness in vacuo. The title compound was dried in vacuo at 82° C.: (m.p. 128°–140° C.).

TLC: Single spot, $R_f$=0.51, silica gel plate, 10% (v/v) $Et_2O$ in $CH_2Cl_2$.
NMR: Consistent with structure.
HPLC: Greater than 99% pure.
MS: Molecular ion at m/e=513. $[\alpha]_D^{25}$=+8.4° (0.0028 g/ml, $CH_2Cl_2$).
Anal. calc'd for $C_{23}H_{17}FIN_3O_2$: C, 53.82; H, 3.34; N, 8.19; Found: C, 53.72; H, 3.44; N, 8.00.

EXAMPLE 160

1,3-Dihydro-3(RS)-(2-naphthoylamino)-5-phenyl-2H-1,4-benzodiazepin-2-one

The procedure of Example 134 was carried out using 3(RS)-amino-1,3-dihydro-5-phenyl-2H-1,4-benzodiazepin-2-one (39.2 mg, 0.156 mmole) in place of 1,3-dihydro-3(RS)-amino-5-(2-fluorophenyl)-2H-1,4-benzodiazepin-2-one and 2-naphthoyl chloride (29.7 mg, 0.156 mmole) in place of p-trifluoromethylbenzoyl chloride. The product was chromatographed on silica gel (15% (v/v) $Et_2O$ in $CH_2Cl_2$ elution). The combined product fractions were evaporated to dryness in vacuo and crystallized from CH$_2$Cl$_2$/EtOAc to give the title compound which was dried in vacuo at 82° C.: (m.p. 293°–294° C.).

TLC: Single spot, R$_f$=0.28, silica gel plate, 15% (v/v) Et$_2$O in CH$_2$Cl$_2$.

NMR: Consistent with structure.

HPLC: Greater than 99% pure.

MS: Molecular ion at m/e=405.

Anal. calc'd for C$_{26}$H$_{19}$N$_3$O$_2$: C, 77.02; H, 4.72; N, 10.37; Found: C, 76.88; H, 4.85; N, 10.50.

EXAMPLE 161

3(S)-(−)-3-(2-Bromobenzoylamino)-1,3-dihydro-5-(2-fluorophenyl)-1-methyl-2H-1,4-benzodiazepin-2-one The procedure of Example 134 was carried out using 3(S)-(−)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 2-bromobenzoyl chloride (34.2 mg, 0.156 mmole) in place of p-trifluoromethylbenzoyl chloride. The product was chromatographed on silica gel (5% (v/v) Et$_2$O in CH$_2$Cl$_2$ elution). The combined product fractions were evaporated to dryness. The residue was crystallized from Et$_2$O to give the title compound which was dried in vacuo at 82° C.: (m.p. 165°–185° C.).

TLC: Single spot, R$_f$=0.38, silica gel plate, 10% (v/v) Et$_2$O in CH$_2$Cl$_2$.

NMR: Consistent with structure.

HPLC: Greater than 99% pure.

MS: Molecular ion at m/e=465. $[\alpha]_D^{25}$=−24.1° (0.0037 g/ml, CH$_2$Cl$_2$).

Anal. calc'd for C$_{23}$H$_{17}$BrFN$_3$O$_2$: C, 59.24; H, 3.67; N, 9.01; Found: C, 59.14; H, 3.61; N, 9.06.

EXAMPLE 162

3(S)-(+)-3-(4-Cyanobenzoylamino)-1,3-dihydro-5-(2-fluorophenyl)-1-methyl-2H-1,4-benzodiazepin-2-one The procedure of Example 134 was carried out using 3(S)-(−)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 4-cyanobenzoyl chloride (25.8 mg, 0.156 mmole) in place of p-trifluoromethylbenzoyl chloride. The product was chromatographed on silica gel (8% (v/v) Et$_2$O in CH$_2$Cl$_2$ elution). The combined product fractions were evaporated to dryness in vacuo to give the title compound which was dried in vacuo at 82° C.: (m.p. 130°–147° C.).

TLC: Single spot, R$_f$=0.29, silica gel plate, 10% (v/v) Et$_2$O in CH$_2$Cl$_2$.

NMR: Consistent with structure, verifies presence of 0.1 Et$_2$O.

HPLC: Greater than 98% pure.

MS: Molecular ion at m/e=412. $[\alpha]_D^{25}$=+13.0° (0.0027 g/ml, CH$_2$Cl$_2$).

Anal. calc'd for C$_{24}$H$_{17}$FN$_4$O$_2$. 0.1C$_4$H$_{10}$O: C, 69.80; H, 4.32; N, 13.34; Found: C, 69.50; H, 4.43; N, 13.44.

EXAMPLE 163

1,3-Dihydro-5-phenyl-3(RS)-(4-n-propylbenzoylamino)-2H-1,4-benzodiazepin-2-one

The procedure of Example 134 was carried out using 3(RS)-amino-1,3-dihydro-5-phenyl-2H-1,4-benzodiazepin-2-one (39.2 mg, 0.156 mmole) in place of 1,3-dihydro-3(RS)-amino-5-(2-fluorophenyl)-2H-1,4-benzodiazepin-2-one and 4-n-propylbenzoyl chloride (28.5 mg, 0.156 mmole) in place of p-trifluoromethylbenzoyl chloride. The product was chromatographed on silica gel (15% (v/v) Et$_2$O in CH$_2$Cl$_2$ elution). The combined product fractions were evaporated to dryness in vacuo and crystallized from Et$_2$O to give the title compound which was dried in vacuo at 82° C.: (m.p.. 158°–162° C.).

TLC: Single spot, R$_f$=0.24, silica gel plate, 15% (v/v) Et$_2$O in CH$_2$Cl$_2$.

NMR: Consistent with structure.

HPLC: Greater than 99% pure.

MS: Molecular ion at m/e=397.

Anal. calc'd for C$_{25}$H$_{23}$N$_3$O$_2$: C, 75.54; H, 5.83; N, 10.57; Found: C, 75.16; H, 5.98; N, 10.74.

EXAMPLE 164

1,3-Dihydro-5-phenyl-3(RS)-(4-phenylbenzoylamino)-2H-1,4-benzodiazepin-2-one

The procedure of Example 134 was carried out using 3(RS)-amino-1,3-dihydro-5-phenyl-2H-1,4-benzodiazepin-2-one (39.2 mg, 0.156 mmole) in place of 1,3-dihydro-3(RS)-amino-5-(2-fluorophenyl)-2H-1,4-benzodiazepin-2-one and 4-phenylbenzoyl chloride (33.8 mg, 0.156 mmole) in place of p-trifluoromethylbenzoyl chloride. The product was chromatographed on silica gel (15% (v/v) Et$_2$O in CH$_2$Cl$_2$ elution). The combined product fractions were evaporated to dryness in vacuo and crystallized from Et$_2$O to give the title compound which was dried in vacuo at 82° C.: (m.p. 274°–276° C.).

TLC: Single spot, R$_f$=0.24, silica gel plate, 15% (v/v) Et$_2$O in CH$_2$Cl$_2$.

NMR: Consistent with structure.

HPLC: Greater than 98% pure.

MS: Molecular ion at m/e=431.

Anal. calc'd for C$_{28}$H$_{21}$N$_3$O$_2$: C, 77.94; H, 4.91; N, 9.74; Found: C, 77.69; H, 5.17; N, 9.84.

EXAMPLE 165

1,3-Dihydro-3(RS)-(4-n-pentylbenzoylamino)-5-phenyl-2H-1,4-benzodiazepin-2-one

The procedure of Example 134 was carried out using 3(RS)-amino-1,3-dihydro-5-phenyl-2H-1,4-benzodiazepin-2-one (39.2 mg, 0.156 mmole) in place of 1,3-dihydro-3(RS)-amino-5-(2-fluorophenyl)-2H-1,4-benzodiazepin-2-one and 4-n-pentylbenzoyl chloride (32.9 mg, 0.156 mmole) in place of p-trifluorobenzoyl chloride. The product was chromatographed on silica gel (15%, (v/v) Et$_2$O in CH$_2$Cl$_2$ elution). The combined product fractions were evaporated to dryness in vacuo and crystallized from Et$_2$O to give the title compound which was dried in vacuo at 82° C.: (m.p. 203°–205° C.).

TLC: Single spot, R$_f$=0.28, silica gel plate, 15% (v/v) Et$_2$O in CH$_2$Cl$_2$.

NMR: Consistent with structure.

HPLC: Greater than 99% pure.

MS: Molecular ion at m/e=425.

Anal. calc'd for C$_{27}$H$_{27}$N$_3$O$_2$: C, 76.21; H, 6.40; N, 9.88; Found: C, 76.07; H, 6.53; N, 10.00.

EXAMPLE 166

1,3-Dihydro-3(RS)-(1-naphthoylamino)-5-phenyl-2H-1,4-benzodiazepin-2-one

The procedure of Example 134 was carried out using 3(RS)-amino-1,3-dihydro-5-phenyl-2H-1,4-benzodiazepin-2-one (39.2 mg, 0.156 mmole) in place of 1,3-dihydro-3(RS)-amino-5-(2-fluorophenyl)-2H-1,4-benzodiazepin-2-one and 1-naphthoyl chloride (29.7 mg, 0.156 mmole) in place of p-trifluoromethylbenzoyl chloride. The product was chromatographed on silica gel (15% (v/v) Et$_2$O in CH$_2$Cl$_2$ elution). The combined product fractions were evaporated to dryness in vacuo and crystallized from Et$_2$O to give the title compound which was dried in vacuo at 65° C.: (m.p. 162°–167° C.).

TLC: Single spot, R$_f$=0.22, silica gel plate, 15% (v/v) Et$_2$O in CH$_2$Cl$_2$.

NMR: Consistent with structure.

HPLC: Greater than 96% pure.

MS: Molecular ion at m/e=405.

Anal. calc'd for C$_{26}$H$_{19}$N$_3$O$_2$: C, 77.02; H, 4.72; N, 10.37; Found: C, 77.20; H, 4.91; N, 10.25.

EXAMPLE 167

3(S)-(+)-1,3-Dihydro-5-(2-fluorophenyl)-3-(3-iodobenzoylamino)-1-methyl-2H-1,4-benzodiazepin-2-one The procedure of Example 134 was carried out using 3(S)-(−)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 3-iodobenzoyl chloride (41.6 mg, 0.156 mmole) in place of p-trifluoromethylbenzoyl chloride. The product was chromatographed on silica gel (5% (v/v) Et$_2$O in CH$_2$Cl$_2$ elution). The combined product fractions were evaporated to dryness in vacuo to give the title compound which was dried in vacuo at 65° C.: (m.p. 105°–120° C.).

TLC: Single spot, R$_f$=0.34, silica gel plate, 5% (v/v) Et$_2$O in CH$_2$Cl$_2$.

NMR: Consistent with structure.

HPLC: Greater than 96% pure.

MS: Molecular ion at m/e=513. $[\alpha]_D^{25}$=+13.0° (0.0024 g/ml, CH$_2$Cl$_2$).

Anal. calc'd for C$_{23}$H$_{17}$FIN$_3$O$_2$: C, 53.82; H, 3.34; N, 8.19; Found: C, 54.10; H, 3.46; N, 8.18.

EXAMPLE 168

3(R)-(−)-1,3-Dihydro-5-(2-fluorophenyl)-3-(3-iodobenzoylamino)-1-methyl-2H-1,4-benzodiazepin-2-one The procedure of Example 134 was carried out using 3(R)-(+)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 3-iodobenzoyl chloride (41.6 mg, 0.156 mmole) in place of p-trifluoromethylbenzoyl chloride. The product was chromatographed on silica gel (5% (v/v) Et$_2$O in CH$_2$Cl$_2$ elution). The combined product fractions were evaporated to dryness in vacuo to give the title compound which was dried in vacuo at 65° C.: (m.p. 169°–172° C.).

TLC: Single spot, R$_f$=0.38, silica gel plate, 5% (v/v) Et$_2$O in CH$_2$Cl$_2$.

NMR: Consistent with structure.

HPLC: Greater than 97% pure.

MS: Molecular ion at m/e=513. $[\alpha]_D^{25}$=−10.2° (0.0026 g/ml, CH$_2$Cl$_2$).

Anal. calc'd for C$_{23}$H$_{17}$FIN$_3$O$_2$: C, 53.82; H, 3.34; N, 8.19; Found: C, 54.07; H, 3.42; N, 8.50.

EXAMPLE 169

3(R)-(+)-1,3-Dihydro-5-(2-fluorophenyl)-3-(2-iodobenzoylamino)-1-methyl-2H-1,4-benzodiazepin-2-one The procedure of Example 134 was carried out using 3(R)-(+)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one, and 2-iodobenzoyl chloride (41.6 mg, 0.156 mmole) in place of p-trifluoromethylbenzoyl chloride. The product was chromatographed on silica gel (5% (v/v) Et$_2$O in CH$_2$Cl$_2$ elution). The combined product fractions were evaporated to dryness in vacuo and crystallized from ether to give the title compound which was dried in vacuo at 65° C.: (m.p. 231°–235° C.).

TLC: Single spot, R$_f$=0.24, silica gel plate, 5% (v/v) Et$_2$O in CH$_2$Cl$_2$.

NMR: Consistent with structure.

HPLC: Greater than 99% pure.

MS: Molecular ion at m/e=513. $[\alpha]_D^{25}$=+26.1° (0.0028 g/ml, CH$_2$Cl$_2$).

Anal. calc'd for C$_{23}$H$_{17}$FIN$_3$O$_2$: C, 53.82; H, 3.34; N, 8.19; Found: C, 53.71; H, 3.38; N, 8.14.

EXAMPLE 170

3(S)-(−)-1,3-Dihydro-5-(2-fluorophenyl)-3-(2-iodobenzoylamino)-1-methyl-2H-1,4-benzodiazepin-2-one The procedure of Example 134 was carried out using 3(S)-(−)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 2-iodobenzoyl chloride (41.6 mg, 0.156 mmole) in place of p-trifluoromethylbenzoyl chloride. The product was chromatographed on silica gel (5% (v/v) Et$_2$O in CH$_2$Cl$_2$ elution). The combined product fractions were evaporated to dryness in vacuo and crystallized from Et$_2$O to give the title compound which was dried in vacuo at 65° C.: (m.p. 230°–232° C.).

TLC: Single spot, R$_f$=0.24, silica gel plate, 5% (v/v) Et$_2$O in CH$_2$Cl$_2$.

NMR: Consistent with structure.

HPLC: Greater than 98% pure.

MS: Molecular ion at m/e=513. $[\alpha]_D^{25}$=−25.6° (0.0029 g/ml, CH$_2$Cl$_2$).

Anal. calc'd for C$_{23}$H$_{17}$FIN$_3$O$_2$: C, 53.82; H, 3.34; N, 8.19; Found: C, 53,62; H, 3.25; N, 8.30.

EXAMPLE 171

3(R)-(+)-3-(2-Bromobenzoylamino)-1,3-dihydro-5-(2-fluorophenyl)-1-methyl-2H-1,4-benzodiazepin-2-one The procedure of Example 134 was carried out using 3(R)-(+)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 2-bromobenzoyl chloride (34.2 mg, 0.156 mmole) in place of p-trifluoromethylbenzoyl chloride. The product was chromatographed on silica gel (5% (v/v) Et$_2$O in CH$_2$Cl$_2$ elution). The combined product fractions were evaporated to dryness in vacuo and crystallized from Et$_2$O to give the title compound which was dried in vacuo at 65° C.: (m.p. 155°–160° C.).

TLC: Single spot, R$_f$=0.28, silica gel plate, 5% (v/v) Et$_2$O in CH$_2$Cl$_2$.

NMR: Consistent with structure.
HPLC: Greater than 99% pure.
MS: Molecular ion at m/e=465. $[\alpha]_D^{25}=+26.3°$ (0.0034 g/ml, $CH_2Cl_2$).
Anal. calc'd for $C_{23}H_{17}BrFN_3O_2$: C, 59,24; H, 3.67; N, 9.01; Found: C, 59.15; H, 3.70; N, 9.12.

EXAMPLE 172

3(R)-(+)-3-(2-Chlorobenzoylamino)-1,3-dihydro-5-(2-fluorophenyl)-1-methyl-2H-1,4-benzodiazepin-2-one The procedure of Example 134 was carried out using 3(R)-(+)-3-amino-1,3-dihydro-5-(2-fluorophenyl)-1-methyl-2H-1,4-benzodiazepin-2-one (44.2 mg, 0.156 mmole) in place of 1,3-dihydro-3(RS)-amino-5-(2-fluorophenyl)-2H-1,4-benzodiazepin-2-one and 2-chlorobenzoyl chloride (27.3 mg, 0.156 mmole) in place of p-trifluoromethylbenzoyl chloride. The product was chromatographed on silica gel (5% (v/v) $Et_2O$ in $CH_2Cl_2$ elution). The combined product fractions were evaporated to dryness in vacuo and crystallized from $CH_2Cl_2$ to give the title compound which was dried in vacuo at 65° C.: (m.p. 157°-165° C.).

TLC: Single spot, $R_f$=0.25, silica gel plate, 5% (v/v) $Et_2O$ in $CH_2Cl_2$.
NMR: Consistent with structure.
HPLC: Greater than 99% pure.
MS: Molecular ion at m/e=421. $[\alpha]_D^{25}=+16.7°$ (0.0032 g/ml, $CH_2Cl_2$).
Anal. calc'd for $C_{23}H_{17}ClFN_3O_2$: C, 65.48; H, 4.06; N, 9.96; Found: C, 65.63; H, 4.10; N, 10.03.

EXAMPLE 173

1,3-Dihydro-5-(2-fluorophenyl)-3(RS)-phenylcarbonylamino-2H-1,4-benzodiazepin-2-one The procedure of Example 134 was carried out using benzoyl chloride (21.9 mg, 0.156 mmole) in place of p-trifluoromethylbenzoyl chloride. The title compound was crystallized from ethyl acetate and dried in vacuo at 75° C.: (m.p. 243°-244° C.). TLC: Single spot, $R_f$=0.18, silica gel plate, (chloroform-methanol, 1:1 v/v).
NMR: The spectrum was consistent with the title structure.
HPLC: Greater than 98% pure.
MS: Molecular ion at m/e=373.
Anal. calc'd for $C_{22}H_{16}FN_3O_2$ C, 70.76; H, 4.32; N, 11.25; Found: C, 70.63; H, 4.35; N, 11.07.

EXAMPLE 174

1,3-Dihydro-5-(2-fluorophenyl)-3(RS)-(2-chlorophenyl)carbonylamino-2H-1,4-benzodiazepin-2-one The procedure of Example 134 was carried out using 2-chlorobenzoyl chloride (27.3 %g, 0.156 mmole) in place of p-trifluoromethylbenzoyl chloride. The title compound was crystallized from ethyl acetate and dried in vacuo at 75° C.: (m.p 224°-224.5° C.).
TLC: Single spot, $R_f$=0.27, silica gel plate, (chloroform-methanol, 97:3 v/v).
NMR: The spectrum was consistent with the title structure.
HPLC: Greater than 98% pure
MS: Molecular ion at m/e=407.
Anal. calc'd for $C_{22}H_{15}ClFN_3O_2$. $0.1C_4H_8O_2$: C, 64.57; H, 3.82; N, 10.08; Found: C, 64.30; H, 3.76; N, 9.99.

EXAMPLE 175

1,3-Dihydro-5-(2-fluorophenyl)-3(RS)-benzyloxycarbonylamino-2H-1,4-benzodiazepin-2-one The procedure of Example 134 was carried out using benzyl chloroformate (26.6 mg, 0.156 mmole) in place of p-trifluoromethylbenzoyl chloride. The title compound was crystallized from ethyl acetate and dried in vacuo at 75° C.: (m.p. 208° C.) TLC: Single spot, $R_f$=0.37, silica gel plate, (hexane-ethyl acetate, 1:1 v/v).
NMR: The spectrum was consistent with the title structure.
HPLC: Greater than 98% pure.
MS Molecular ion at m/e=403.
Anal. calc'd for $C_{23}H_{18}FN_3O_3$: C, 68.48; H, 4.50; N, 10.42; Found: C, 68.84; H, 4.62; N, 10.49.

EXAMPLE 176

1,3-Dihydro-5-(2-fluorophenyl)-3-(RS)-benzyloxycarbonylamino-2H-1,4-benzodiazepin-2-thione 1,3-Dihydro-5-(2-fluorophenyl)-3-(RS)-benzyloxycarbonylamino-2H-1,4-benzodiazepin-2-one (6.5 g, 16.1 mmole) and 2,4-bis-(4-methoxyphenyl)-2,4-dithioxo-1,3,2,4-dithiaphosphetane (4.9 g, 12.1 mmole) were combined in 500 ml of toluene and heated at reflux for 1.5 hours. The reaction mixture was cooled, diluted to 700 ml with ethyl acetate and washed with 10% sodium hydroxide solution (4×50 ml) and brine. The organic phase was dried ($Na_2SO_4$) and concentrated under reduced pressure to yield 12 g of crude product. Trituration with ethyl acetate gave 4.0 g of the analytical product as a yellow powder. Chromatography of the mother liquors on silica gel (hexane-ethyl acetate elution, 1:1 v/v) afforded an additional 2.2 g of pure product: m.p. 190°-191° C.

NMR ($CDCl_3$): Confirmed structure of the title compound.
MS (14 ev): 419 (M+), 311, 284, 256, 243, 224.
Anal. calc'd for $C_{23}H_{18}FN_3O_2S$: N, 10.02; C, 65.86; H, 4.33; Found: N, 9 79; C, 65.59; H, 4.44.

EXAMPLE 177

1-(4-Chlorophenyl)carbonyl-1,3-dihydro-5-(2-fluorophenyl)-3(RS)-(4-chlorophenyl)carbonylamino-2H-1,4-benzodiazepin-2-one To a solution of 1,3-dihydro-5-(2-fluorophenyl)-3-amino-2H-1,4-benzodiazepin-2-one (400 mg, 1.49 mmole) in 25 ml of methylene chloride was added p-chlorobenzoyl chloride (380 μl, 3.0 mmole). Triethylamine was added to bring the pH of the reaction mixture to approximately 6 (moist pH paper) followed by 4-dimethylamino pyridine (183 mg, 1.5 mmole). After stirring at room temperature overnight the reaction mixture was diluted with methylene chloride to 200 ml and washed in succession with 10% citric acid solution (3×50 ml), saturated sodium bicarbonate solution, and brine. The organic extracts were dried ($MgSO_4$) and concentrated to give 890 mg of crude product. Silica gel chromatography (hexane-ethyl acetate, 1:1 v/v) afforded the analytical product: m.p. 190°-191° C.

TLC Single spot, $R_f$=0.70, silica gel (hexane-ethyl acetate, 1:1 v/v).
NMR: The spectrum is consistent with the title structure.
HPLC: Greater than 97% pure.

MS: Molecular ion m/e=546.

Anal. calc'd for $C_{29}H_{18}Cl_2FN_3O_3$: N, 7.69; C, 63.74; H, 3.32; Found: N, 7.58; C, 63.88; H, 3.46.

EXAMPLE 178

1-(4-Chlorophenyl)carbonyl-1,3-dihydro-5-(2-fluorophenyl)-3(RS)-(4-chlorophenyl)carbonyloxy-2H-1,4-benzodiazepin-2-one A suspension of 1,3-dihydro-5-(2-fluorophenyl)-3-hydroxy-2H-1,4-benzodiazepin-2-one (610 mg, 2.25 mmole) in 25 ml of methylene chloride was treated with 4-chlorobenzoyl chloride (0.314 ml, 2.48 mmole) at room temperature. 4-Dimethylaminopyridine (303 mg, 2.48 mmole) was added and within minutes the reaction mixture became homogeneous. The reaction mixture was protected from moisture and stirred at room temperature overnight. An additional equivalent each of 4-chlorobenzoyl chloride and 4-dimethylaminopyridine were added and stirring was continued for 8 hours at 40°–45° C. The reaction mixture was diluted to 150 ml with methylene chloride and washed in succession with 10% citric acid solution (3×50 ml), saturated sodium bicarbonate solution (3×50 ml) and brine (50 ml). Rotoevaporation of the dried (MgSO4) organic phase gave a foam which on trituration with ether afforded a beige solid. Recrystallization from ethyl acetate afforded 612 mg of the title compound as a white powder in analytical purity: m.p. 198°–199° C.

NMR (DMSO-d6): The spectrum is consistent with the title structure.

MS (14 ev): 547 (M+), 407, 379, 374, 363, 224, 156.

Anal. calc'd for $C_{29}H_{17}Cl_2FN_2O_4$: N, 5.11; C, 63.63; H, 3.13; Found: N, 5.03; C, 63.68; H, 3.08.

EXAMPLE 179

1,3-Dihydro-5-(2-fluorophenyl)-3(RS)-(4-chlorobenzoyl)oxy-2H-1,4-benzodiazepin-2-one A suspension of 1,3-dihydro-5-(2-fluorophenyl)-3-hydroxy-2H-1,4-benzodiazepin-2-one (610 mg, 2.25 mmole) in 25 ml of methylene chloride was treated with 4-chlorobenzoyl chloride (0.314 ml, 2.48 mmole) at room temperature. 4-Dimethylaminopyridine (303 mg, 2.48 mmole) was added and within minutes the reaction mixture became homogeneous. The reaction mixture was protected from moisture and stirred at room temperature overnight. An additional equivalent each of 4-chlorobenzoyl chloride and 4-dimethylaminopyridine were added and stirring was continued for 8 hours at 40°–45° C. The reaction mixture was diluted to 150 ml with methylene chloride and washed in succession with 10% citric acid solution (3×50 ml), saturated sodium bicarbonate solution (3×50 ml) and brine (50 ml). Rotoevaporation of the dried (MgSO4) organic phase gave a foam which on trituration with ether afforded a beige solid. The mother liquors were concentrated and the residue chromatographed on silica gel (hexane-ethyl acetate, 1:1 v/v) to give the title compound.

NMR (CDCl3): The spectrum is consistent with the title structure.

Anal. calc'd for $C_{22}H_{14}ClFN_2O_3$: N, 6.85; C, 64.63; H, 3.45; Found: N, 6.68; C, 64.64; H, 3.60.

EXAMPLE 180

1,3-Dihydro-5-(2-fluorophenyl)-3-(RS)-(4-chlorophenyl)carbonylamino-2H-1,4-benzodiazepin-2-thione A mixture of 1,3-dihydro-5-(2-fluorophenyl)-3-(RS)-amino-2H-1,4-benzodiazepin-2-thione (200 mg, 0.70 mmole), 4-chlorobenzoic acid (120 mg, 0.77 mmole) and 1-ethyl-3-(3-dimethylaminopropyl) carbodiimide hydrochloride (150 mg, 0.77 mmole) were combined in 2 ml of dry N,N-dimethylformamide at room temperature. The pH of the homogeneous reaction mixture was then adjusted to 8 with triethylamine. The reaction mixture was protected from moisture and stirred at room temperature overnight (about 90% complete after 1 hour). The solvent was removed under reduced pressure and the residue dissolved in 100 ml of ethyl acetate. The organic phase was then washed in succession with 10% citric acid solution (2×20 ml), saturated sodium bicarbonate solution (20 ml), and brine. The dried (MgSO4) organic phase was rotoevaporated to dryness to yield 300 mg of crude product. Preparative thick layer chromatography on SiO2 (hexane-ethyl acetate, 2:1) gave the analytical sample as a solvate: m.p. 156°–158° C.

NMR (DMSO-d6): Confirmed structure of the title compound.

MS (14 ev): 423 (M+), 391, 284, 268, 236, 139.

Anal. calc'd for $C_{22}H_{15}ClFN_3OS$. $0.10C_4H_8O_2$: N, 9.71; C, 62.17; H, 3.68; Found: N, 9.39; C, 62.45; H, 4.01.

EXAMPLE 181

1,3-Dihydro-5-(2-fluorophenyl)-3-(RS)-(2-indole)carbonylamino-2H-1,4-benzodiazepin-2-thione A mixture of 1,3-dihydro-5-(2-fluorophenyl)-3-(RS)-amino-2H-1,4-benzodiazepin-2-thione (400 mg, 1.40 mmole), indole-2-carboxylic acid (248 mg, 1.54 mmole) and 1-ethyl-3-(3-dimethylaminopropyl) carbodiimide hydrochloride (295 mg, 1.54 mmole) were combined in 10 ml of dry N,N-dimethylformamide at room temperature. The pH of the homogeneous reaction mixture was then adjusted to 8 with triethylamine. The reaction mixture was protected from moisture and stirred at room temperature overnight (about 50% complete after 1 hour). The solvent was removed under reduced pressure and the residue dissolved in 200 ml of ethyl acetate. The organic phase was then washed in succession with 10% citric acid solution (2×25 ml), saturated sodium bicarbonate solution (25 ml), and brine. The dried (MgSO4) organic phase was rotoevaporated to dryness to yield 1.4 g of crude product. Preparative thick layer chromatography on SiO2 (hexane-ethyl acetate, 1:1) gave the analytical sample as a beige powder: m.p. 209°–211° C.

NMR (CDCl3): Confirmed structure of the title compound.

MS (14 ev): 428 (M+), 396, 394, 296, 293, 252, 249.

Anal. calc'd for $C_{24}H_{17}FN_4OS$. $0.15C_4H_8O_2$: N, 12.69; C, 66.89; H, 4.15; Found: N, 12.92; C, 66.69; H, 3.90.

EXAMPLE 182

1,3-Dihydro-3(RS)-(4-chlorophenyl)aminocarbonylamino-5-(2-fluorophenyl)-2H-1,4-benzodiazepin-2-one To a solution of 85 mg (0.315 mmole) of 1,3-dihydro-3(RS)-amino-5-(2-fluorophenyl)-2H-1,4-benzodiazepin-2-one in 8 ml of dry tetrahydrofuran was added 4-chlorophenylisocyanate (40 μl, 0.315 mmole) at room temperature. Within 15 minutes a flocculant, white precipitate formed. Stirring was continued for 8 hours more and the reaction mixture was filtered. The collected solids were washed with hot methanol and dried in vacuo to give the analytical product: m.p. 278° C.

NMR (DMSO-d6): Confirms structure assignment of product.

Anal. calc'd for $C_{22}H_{16}ClFN_4O_2$: N, 13.25; C, 62.48; H, 3.81; Found: N, 13.09; C, 62.33; H, 3.86.

EXAMPLE 183

1,3-Dihydro-1-methyl-3-oximino-5-phenyl(-2H-1,4-benzodiazepin-2-one

To a suspension of potassium tert-butoxide (24.9 g, 222 mmole) in 600 ml of dry tetrahydrofuran was added 200 ml of dry tert-butylalcohol at −20° C. under nitrogen. To this solution was then added via, addition funnel 1,3-dihydro-1-methyl-5-phenyl-2H-1,4-benzodiazepin-2-one (25 g, 99.9 mmole) in 260 ml of tetrahydrofuran. The resulting wine colored solution was stirred for 2 hours at −20° C. and treated with 17.4 ml (130 mmole) of isoamyl nitrite. The reaction mixture was warmed to 0° C. over 15 minutes and quenched with the addition of 60 ml of cold water and 20 ml of glacial acetic acid. All solvents were removed under reduced pressure and the residue was partitioned between ethyl acetate (600 ml) and brine (100 ml). The phases were separated and the organic extracts were dried ($Na_2SO_4$) and concentrated. The resulting semi-solid was triturated with ether to give 21 g of off-white solid. m.p 234°–235° C.; $R_f$=0.15 (ethylacetate-hexane, 1:1); $R_f$=0.28 chloroform-ethanol, 95:5); ir(KBr, partial): 3300, 1650, 1595, 1320, 1205, 1030, 975 cm$^{-1}$.

MS (14 ev.): 279 (M+), 262, 249, 236, 222.

$^1$HNMR (CDCl$_3$): 3.5 (3H, CH$_3$-N), confirms structure assignment.

Elemental Analysis Calc'd for $C_{16}H_{13}N_3O_2$: C, 4.69; H, 68.81; N, 15.04. Found: C, 4.62; H, 68.67; N, 15.08.

EXAMPLE 184

3(R,S)-Amino-1,3-dihydro-1-methyl-5-phenyl-2H-1,4-benzodiazepin-2-one

A solution of 150 ml of methanol containing 5 g (17.9 mmole) of 1,3-dihydro-1-methyl-3-oximino-5-phenyl-1,4-benzodiazepin-2-one was treated with a slurry of active Raney-nickel catalyst[1] (10 g wet weight). The resulting suspension was hydrogenated on a Parr apparatus at 60 psi and 23° C. for 30 hours. The catalyst was removed by filtration and the filtrate was concentrated to afford the title compound in 95% yield. $R_f$=0.23 (chloroform-ethanol, 95:5), $R_f$=0.23 (chloroform-methanol-acetic acid-water, 90:10:1:1)

$^1$HNMR (CDCl$_3$): spectrum confirms structure assignment.

Raney-Nickel catalyst was prepared according to Fieser & Fieser, Reagents for Organic Synthesis, Vol. I, John Wiley & Sons, Inc., New York 1967, p. 729.

EXAMPLE 185

4-Cyano-N-(2,3-dihydro-2-oxo-5-phenyl-1H-1,4-benzodiazepin-3-yl)-benzamide

The procedure of Example 134 was carried out employing equivalent amounts of 1,3-dihydro-3-(RS)-amino-5-phenyl-2H-1,4-benzodiazepin-2-one and 4-cyanobenzoylchloride. The product was purified by chromatography on silica gel (5% (v/v) Et$_2$O in CH$_2$Cl$_2$ elution). The combined product fractions were evaporated to dryness in vacuo and crystallized to give the title compound which was dried at 65° C.

NMR: Consistent with structure.
HPLC: Greater than 97% pure.
MS: Molecular ion at m/e=388.

Anal. Calc'd for $C_{23}H_{16}N_4O_2 \cdot 0.41H_2O$: C, 71.24; H, 4.37; N, 14.73. Found: C, 71.53; H, 4.37; N, 14.73.

EXAMPLE 186

(S)-α-Amino-N-(2,3-dihydro-2-oxo-5-phenyl-1H-1,4-benzodiazepin-benzodiazepin-3-yl)-benzenepropanamide A solution of 1.55 gm (3.11 mmol) α-t-butyloxycarbonylamino-N-(2,3-dihydro-2-oxo-5-phenyl-1H-1,4-benzodiazepin-3-yl)-benzenepropanamide in 10 ml EtoAc was cooled in an ice bath, saturated with HCl(g) and stirred 10 minutes. The solvent was removed in vacuo and the residue treated with saturated Na$_2$CO$_3$ and extracted (3× EtOAc). The organics were combined washed 1×H$_2$O, 1× brine, dried over Na$_2$SO$_4$, filtered and the solvent removed in vacuo. The residue was flash chromatographed on silica gel (90/10/1/1 of CH$_2$Cl$_2$/MeOH/H$_2$O/HOAc) and a clean higher R$_f$ component was isolated. After conversion to the free base (Na$_2$CO$_3$(aq)/EtOAc) the title compound crystallized from EtOAc: mp. 208°–210° C.

NMR: Confirms structure assignment of product and verifies presence of H$_2$O.
HPLC: Greater than 98.9% pure.
MS: Molecular ion at m/e=398 (free base).

Anal. Calc'd for $C_{24}H_{22}N_4O_2 \cdot 0.1 H_2O$: C, 72.02; H, 5.59; N, 14.00. Found: C, 72.01; H, 5.50; N, 14.01.

EXAMPLE 187

(S)-(2-Indolecarbonyl)amino-1,3-dihydro-5-phenyl-2H-1,4,-benzodiazepin-2-one

Equimolar amounts of 3(S)-amino-1,3-dihydro-5-phenyl-2H-1,4-benzodiazepin-2-one, indole-2-carbonyl chloride and triethylamine were mixed in CH$_2$Cl$_2$ at room temperature and stirred 10 minutes. Flash chromatography of the reaction solution on silica gel (25% Et$_2$O in CH$_2$Cl$_2$) provided the title compound as a white solid after removal of the solvent: m.p. 188°–95° C.

NMR: Confirms structure assignment of product and verifies presence of CH$_2$Cl$_2$.
HPLC: Greater than 98% pure.
MS: Molecular ion at m/e=394 (free base).

Anal Calc'd for $C_{24}H_{18}N_4O_2 \cdot 0.06$ CH$_2$Cl$_2$: C, 72.33; H, 4.57; N, 14.03. Found C, 72.32; H, 4.47; N, 14.08. $[\alpha]_D^{25}$=−88.1° (conc. 1.6 mg/ml CH$_2$Cl$_2$).

EXAMPLE 188

3-(2'-Chlorobenzoylamino)-1-ethoxycarbonylmethyl-5-(2'-fluorophenyl)-2H-1,4-benzodiazepine-2-one The procedure of Example 4 was employed using equimolar amounts of ethylbromoacetate and 1,3-dihydro-1-ethoxycarbonylmethyl-5-(2-fluorophenyl)-3-(RS)-(2-chlorophenylcarbonyl)amino-2H-1,4-benzodiazepin-2-one. The chromatographed product was dried in vacuo at room temperature.

NMR: Consistent with structure assignment.
HPLC: Greater than 95% pure.
MS: Molecular ion at m/e=494.

Anal. Calc'd for $C_{26}H_{21}ClFN_3L_4 \cdot 0.4H_2O$: C, 62.31; H, 4.39; N, 8.39. Found: C, 62.39; H, 4.39; N, 8.36.

EXAMPLE 189

(S)-N-(2,3-Dihydro-1-methyl-2-oxo-5-phenyl-1H-1,4-benzodiazepin-3-yl)-2-methylpropanamide Equimolar amounts of 3(S)-amino-1,3-dihydro-1-methyl-5-phenyl-2H-1,4-benzodiazepin-2-one, isobutyryl chloride, and triethylamine were mixed in $CH_2Cl_2$ at room temperature and stirred 10 minutes. Flash chromatography of the reaction solution on silica gel (10% $Et_2O$ in $CH_2Cl_2$) provided the title compound as a white foam upon removal of the solvent: m.p. 87°–107° C.

NMR: Confirms structure assignment of product and verifies presence of $H_2O$.
HPLC: Greater than 99.0% pure.
MS: Molecular ion at m/e=335 (free base).
Anal. Calc'd for $C_{20}H_{21}N_3O_2.0.2\ H_2O$: C, 70.86; H, 6.36; N, 12.40. Found: C, 70.71; H, 6.40; N, 12.40. $[\alpha]_D^{25} = -96.8°$ (conc.=2.2 mg/ml $CH_2Cl_2$).

EXAMPLE 190

(S)-N-(2,3-Dihydro-1-methyl-2-oxo-5-phenyl-1H-1,4-benzodiazepin-3-yl)-3-methylbutanamide Equimolar amounts of 3(S)-amino-1,3-dihydro-1-methyl-5-phenyl-2H-1,4-benzodiazepin-2-one, isovaleryl chloride and triethylamine were mixed in $CH_2Cl_2$ at room temperature and stirred 10 minutes. Flash chromatography of the reaction solution on silica gel (10% $Et_2O$ in $CH_2Cl_2$) provided the title compound as a white foam from $Et_2O$: m.p. 83°–102° C.

NMR: Confirms structure assignment of product.
HPLC Greater than 99.0% pure.
MS: Molecular ion at m/e=349.
Anal. Calc'd for $C_{21}H_{23}N_3O_2$: C, 72.18; H, 6.64; N, 12.03. Found: C, 71.92; H, 6.88; N, 12.05. $[\alpha]_D^{25} = -94.2°$ (conc.=3.1 mg/ml $CH_2Cl_2$).

EXAMPLE 191

(S)-N-(2,3-Dihydro-1-methyl-2-oxo-5-phenyl-1H-1,4-benzodiazepin-3-yl)-cyclohexanecarboxamide Equimolar amounts of 3(S)-amino-1,3-dihydro-1-methyl-5-phenyl-2H-1,4-benzodiazepin-2-one, cyclohexane carboxylic acid chloride and triethylamine were mixed in $CH_2Cl_2$ at room temperature and stirred 10 minutes. Flash chromatography of the reaction solution on silica gel (10% $Et_2O$ in $CH_2Cl_2$) provided the title compound as a white solid after removal of the solvent: m.p. 212°–214° C.

NMR: Confirms structure assignment of product and verifies presence of $H_2O$.
HPLC: Greater than 98.9% pure.
MS: Molecular ion at m/e=375 (free base).
Anal. Calc'd for $C_{23}H_{25}N_3O_2.0.25H_2O$: C, 72.70; H, 6.76; N, 11.06. Found: C, 72.73; H, 6.86; N, 11.25. $[\alpha]_D^{25} = -89.7°$ (conc.=3.2 mg/ml).

EXAMPLE 192

(S)-N-(2,3-Dihydro-1-methyl-2-oxo-5-phenyl-1H-1,4-benzodiazepin-3-yl)-3-phenyl-2-propenamide Equimolar amounts of 3(S)-amino-1,3-dihydro-1-methyl-5-phenyl-2H-1,4-benzodiazepin-2-one, cinnamoyl chloride, and triethylamine were mixed in $CH_2Cl_2$ at room temperature and stirred 10 minutes. Flash chromatography of the reaction solution on silica gel (10% $Et_2O$ in $CH_2Cl_2$) provided the title compound as a white solid after removal of the solvent: m.p. 126°–140° C.

NMR: Confirms structure assignment of product and verifies presence of $H_2O$.
HPLC: Greater than 94.6% pure.
MS: Molecular ion at 395 (Free base).
Anal. Calc'd for $C_{25}H_{21}N_3O_2.0.25H_2O$: C, 75.07; H, 5.42; N, 10.51. Found C, 75.02; H, 5.45; N, 10.39. $[\alpha]_D^{25} = -80.6°$ (conc.=2.13 mg/ml $CH_2Cl_2$).

EXAMPLE 193

(S)-N-(2,3-Dihydro-1-methyl-2-oxo-5-phenyl-1H-1,4-benzodiazepin-3-yl)-2,2-dimethylpropanamide Equimolar amounts of 3(S)-amino-1,3-dihydro-1-methyl-5-phenyl-2H-1,4-benzodiazepin-2-one, trimethylacetylchloride and triethylamine were mixed in $CH_2Cl_2$ at room temperature and stirred 10 minutes. Flash chromatography of the reaction solution on silica gel (10% $Et_2O$ in $CH_2Cl_2$) provided the title compound as a white foam after removal of the solvent: m.p. 85°–94° C.

NMR: Confirms structure assignment of product and verifies presence of trimethylacetic acid.
HPLC: Greater than 98.9% pure.
MS: Molecular ion at m/e=349 (free base).
Anal. Calc'd for $C_{21}H_{23}N_3O_2.0.15C_5H_{10}O_2$: C, 71.62; H, 6.77; N, 11.52. Found: C, 71.57; H, 6.85; N, 11.48. $[\alpha]_D^{25} = -97.1°$ (conc.=3.15 mg/ml $CH_2Cl_2$).

EXAMPLE 194

3-((((4-Chlorophenyl)amino)carbonyl)amino)-5-(2-fluorophenyl)-2,3-dihydro-2-oxo-1H-1,4-benzodiazepine-1-acetic acid ethyl ester Equimolar amounts of 3-(RS)-amino-1,3-dihydro-1-ethoxycarbonylmethyl-5-(2-fluorophenyl)-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 253°–254° C.

NMR: Confirms structure assignment of product.
HPLC: Greater than 99% pure.
MS: Molecular ion at m/e=509.
Anal. Calc'd for $C_{26}H_{22}ClFN_4O_4$: C, 61.36; H, 4.36; N, 11.01. Found: C, 61.33; H, 4.44; N, 10.90.

EXAMPLE 195

5-(2-Fluorophenyl)-2,3-dihydro-2-oxo-((((1-phenylethyl)
amino)carbonyl)amino)-1H-1,4-benzodiazepine-1-acetic acid ethyl ester Equimolar amounts of 3(R,S)-amino-1,3-dihydro-1-ethoxycarbonylmethyl-5-(2-fluorophenyl)-2H-1,4-benzodiazepin-2-one-and (+)-α-methylphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product as a 1:1 mixture of diastereomers: m.p 160°–162° C.

NMR: Confirms structure assignment of product.
HPLC: Greater than 98% pure.
MS: Molecular ion at m/e=503.
Anal. Calc'd for $C_{28}H_{27}FN_4O_4$: C, 66.92; H, 5.42; N, 11.15. Found: C, 66.57; H, 5.59; N, 10.82.

EXAMPLE 196

3-N-(2,3-Dihydro-1-methyl-2-oxo-5-phenyl-1H-1,4-benzodiazepine-3-yl)-2-amino-4-chlorobenzamide 3-(R,S)-Amino-1,3-dihydro-1-methyl-5-phenyl-2H-1,4-benzodiazepin-2-one (150 mg, 0.56 mmol) and 2-amino-4-chlorobenzoic acid were coupled according to the mixed anhydride method. Thus, the benzoic acid analogue was dissolved in 10 ml of 10:1 v/v methylene chloride-DMF at $-5°$ C. and treated with N-methylmorpholine (75 μl, 0.68 mmol) and i-butylchloroformate (90 μl, 0.68 mmol). After 15 minutes, the aminobenzodiazepine was added and stirring was continued at $0°$ C. for 1 hour, then at $23°$ for 12 hours. Extractive work-up afforded the crude product which was chromatographed on silica gel using hexane-ethyl acetate (2:1 v/v). The analytical product was a foam which melted at $146°$ C.

NMR: Confirms structure assignment.
HPLC: Greater than 99% pure.
MS: Molecular ion at m/e=419.
Anal. Calc'd for $C_{23}H_{19}ClN_4O_2 \cdot H_2O$: C, 63.22; H, 4.84; N, 12.82 Found: C, 63.49; H, 4.49; N, 12.79.

EXAMPLE 197

N-(4-Chlorphenyl)-2,3-dihydro-1-methyl-2-oxo-5-phenyl-1H-1,4-benzodiazepine-3-carboxamide Freshly distilled THF (3ml) was treated with 0.167 ml (1.20 mmol) diisopropylamine and cooled to $-75°$ C. under a $N_2$ atmosphere. n-Butyl lithium in hexane (1.20 mmol, 0.774 ml of 1.55M) was added, the solution stirred 5 minutes and then allowed to warm to room temperature. The solution was recooled to $-75°$ C. and 150 mg (0.60 mmol) of 1,3-dihydro-1-methyl-5-phenyl-2H-1,4-benzodiazepin-2-one was added in 25 mg increments as a solid. The red suspension was stirred 5 minutes and then warmed to room temperature. The solution was recooled to $-75°$ C, 76.8 ml (0.60 mmol) of p-chlorophenylisocyanate was added, stirred 5 minutes and then warmed to room temperature. After stirring 1 hour, brine was added and the mixture was extracted (3× EtOAc). The organics were combined, washed (2×$H_2O$, 1× brine), dried over $Na_2SO_4$, filtered and the solvent was removed in vacuo. The residue was flash chromatographed on silica gel (5% $Et_2O$ in $CH_2Cl_2$) to give the title compound which was crystallized from ether: m.p $159°-165°$ C.

NMR: Confirms structure assignment of product.
HPLC: Greater than 99.9% pure.
MS: Molecular ion at m/e=403.
Anal. Calc'd for $C_{23}H_{18}ClN_3O_2$: C, 68.40; H, 4.49; N, 10.41. Found: C, 68.33; H, 4.61; N, 10.35.

EXAMPLE 198

(R)-N-(2,3-Dihydro-1-methyl-2-oxo-5-phenyl-1H-1,4-benzodiazepin-3-yl)-cyclohexanecarboxamide The procedure of Example 134 was carried out using equivalent amounts of 3(R)-(+)-3-amino-1,3-dihydro-1-methyl-5-phenyl-2H-1,4-benzodiazepin-2-one and cyclohexane carboxylic acid chloride. The product was puridied by chromatography on silica gel (5% (v/v) $Et_2O$ in $CH_2Cl_2$ elution). The combined product fractions were evaporated to dryness in vacuo and crystallized to give the title compound which was dried at $65°$ C. m.p. $212°-214°$ C.

NMR: Consistent with structure.
HPLC: Greater than 97% pure.
MS: Molecular ion at m/e=375.
Anal. Calc'd for $C_{23}H_{25}N_3O_2$: C, 73.57; H, 6.71; N, 11.19. Found: C, 73.22; H, 6.81; N, 11.16.

EXAMPLE 199

3-((2,3-Dihydro-1H-indol-3-yl)methyl)-1,3-dihydro-5-phenyl-2H-1,4-benzodiazepin-2-one The procedure of Example 9 was followed in which 3(R)-[(1H-indol-3-yl)methyl]-5-phenyl-1,3-dihydro-2H-1,4-benzodiazepin-2-one was reduced to give the tile compound. The analytical sample was obtained after silica gel chromatography using hexane-ethyl acetate.

NMR: Consistent with structure.
HPLC: Greater than 95% pure.
MS: Molecular ion at m/e=367.
Anal. Calc'd for $C_{24}H_{21}N_3O$: C, 78.45; H, 5.76; N, 11.44. Found: C, 78.84; H, 5.75; N, 11.18.

EXAMPLE 200

1,3-Dihydro-1-methyl-3-((1-methyl-1H-indol-3-yl)methyl)-5-phenyl-2H-1,4-benzodiazepin-2-one The procedure of Example 4 was employed using equimolar amounts of iodomethane and 1,3-dihydro-5-phenyl-3(R)-(3'-indolyl)methyl-2H-1,4-benzodiazepin-2-one. The chromatographed product was dried in vacuo at room temperature as a foam.

NMR: Consistent with structure assignment.
HPLC: Greater than 99% pure.
MS: Molecular ion at m/e=393.
Anal. Calc'd for $C_{26}H_{23}N_3O$: C, 79.36; H, 5.89; N, 10.68. Found: C, 79.68; H, 6.02; N, 10.57.

EXAMPLE 201

(S)-N-2,3-Dihydro-1-methyl-2-oxo-5-phenyl-1H-1,4-benzodiazepin-3-yl)-4-pentylbenzamide The procedure of Example 134 was carried out using equivalent amounts of 3(S)-(−)-3-amino-1,3-dihydro-1-methyl-5-phenyl-2H-1,4-benzodiazepin-2-one and 4-n-pentylbenzoylchloride. The product was purified by chromatography on silica gel (5% (v/v) $Et_2O$ in $CH_2Cl_2$ elution). The combined product fractions were evaporated to dryness in vacuo and crystallized to give the title compound which was dried at $65°$ C.

$[\alpha]_D^{25} = -82°$ (conc.=3 mg/ml $CH_2Cl_2$).
NMR: Consistent with structure.
HPLC: Greater than 97% pure.
MS: Molecular ion at m/e=440.
Anal. Calc'd for $C_{28}H_{29}N_3O_2$: C, 76 51; H, 6.65; N, 9.56. Found: C, 76.34; H, 6.91; N, 9.21.

EXAMPLE 202

3-((((4-Chlorophenyl)amino)carbonyl)amino)-2,3-dihydro-2-oxo-5-phenyl-1H-1,4-benzodiazepine-1-acetic acid Equimolar amounts of 3(R,S)-amino-1,3-dihydro-1-carboxy-methyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p $178°-180°$ C.

NMR: Confirms structure assignment of product.
HPLC: Greater than 98% pure.
MS: Molecular ion at m/e=463.

Anal. Calc'd for $C_{24}H_{19}ClN_4O_4 \cdot \frac{1}{4}H_2O$: C, 61.67; H, 4.21; N, 11.99. Found: C, 61.61; H, 4.29; N, 11.79.

EXAMPLE 203

(S)-N-(2,3-Dihydro-1-methyl-2-oxo-5-phenyl-1H-1,4-benzodiazepin-3-yl)-4-(trifluoromethyl)-benzamide The procedure of Example 134 was carried out using equivalent amounts of 3(S)-(−)-3-amino-1,3-dihydro-1-methyl-5-phenyl-2H-1,4-benzodiazepin-2-one and 4-trifluoromethylbenzoylchloride. The product was purified by chromatography on silica gel (5% (v/v) $Et_2O$ in $CH_2Cl_2$ elution). The combined product fractions were evaporated to dryness in vacuo and crystallized to give the title compound which was dried at 65° C.: m.p. 125°-127° C.;

$[\alpha]_D^{25} = -65°$ (conc. = 3 mg/ml $CH_2Cl_2$).
NMR: Consistent with structure.
HPLC: Greater than 97% pure.
MS: Molecular ion at m/e=437.
Anal. Calc'd for $C_{24}H_{18}F_3N_3O_2 \cdot 0.25C_6H_{14}$: C, 66 73; H, 4.72; N, 9.15. Found: C, 66.95; H, 4.67; N, 9.18.

EXAMPLE 204

3-((((4-Chlorophenyl)amino)carbonyl)amino)-2,3-dihydro-2-oxo-5-phenyl-1H-1,4-benzodiazepine-1-acetic acid ethyl ester Equimolar amounts of 3(R,S)-amino-1,3-dihydro-1-ethoxycarbonylmethyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 228°-229° C.

NMR: Confirms structure assignment of product.
HPLC: Greater than 98% pure.
MS: Molecular ion at m/e=491.
Anal Calc'd for $C_{26}H_{23}ClN_4O_4$: C, 63.61; H, 4.72; N, 11.41. Found: C, 63.54; H, 4.88; N, 11.08.

EXAMPLE 205

5-(2-Fluorophenyl)-2,5-dihydro-3-((((1-methylethyl)amino)carbonyl)amino)-2-oxo-1H-1,4-benzodiazepine-1-acetic acid ethyl ester Equimolar amounts of 3(R,S)-amino-1,3-dihydro-1-ethoxycarbonylmethyl-5-(2-fluorophenyl)-2H-1,4-benzodiazepin-2-one and isoproplylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 155°-157° C.

NMR: Confirms structure assignment of product.
HPLC: Greater than 98% pure.
MS: Molecular ion at m/e=449.
Anal. Calc'd for $C_{23}H_{25}FN_4O_4 \cdot \frac{1}{2}H_2O$: C, 61.45; H, 5.83; N, 12.46. Found: C, 61.18; H, 5.52; N, 12.37.

EXAMPLE 206

(R)-N-(2,3-Dihydro-1-methyl-2-oxo-5-phenyl-1H-1,4-benzodiazepin-3-yl)-4-pentylbenzamide The procedure of Example 134 was carried out using equivalent amounts of 3(R)-(+)-3-amino-1,3-dihydro-1-methyl-5-phenyl-2H-1,4-benzodiazepin-2-one and 4-n-pentylbenzoylchloride. The product was purified by chromatography on silica gel (5% (v/v) $Et_2O$ in $CH_2Cl_2$ elution). The combined product fractions were evaporated to dryness in vacuo and dried at 65° C.

NMR: Consistent with structure.
HPLC: Greater than 97% pure.
MS: Molecular ion at m/e=440.
Anal. Calc'd for $C_{28}H_{29}N_3O_2 \cdot \frac{1}{4}H_2O$: C, 75.73; H, 6.69; N, 9.46. Found: C, 75.69; H, 6.85; N, 9.45.

EXAMPLE 207

(R)-N-(2,3-Dihydro-1-methyl-2-oxo-5-phenyl-1H-1,4-benzodiazepin-3-yl)-4-(trifluoromethyl)-benzamide The procedure of Example 134 was carried out using equivalent amounts of 3(R)-(+)-3-amino-1,3-dihydro-1-methyl-5-phenyl-2H-1,4-benzodiazepin-2-one and 4-trifluoromethylbenzoylchloride. The product was purified by chromatography on silica gel (5% (v/v) $Et_2O$ in $CH_2Cl_2$ elution). The combined product fractions were evaporated to dryness in vacuo and dried at 65° C.

NMR: Consistent with structure.
HPLC: Greater than 98% pure.
MS: Molecular ion at m/e=437.
Anal. Calc'd for $C_{24}H_{18}F_3N_3O_2 \cdot \frac{1}{4}C_6H_{14}$: C, 66.95; H, 4.67; N, 9.18. Found: C, 66.92; H, 4.57; N, 9.54.

EXAMPLE 208

3-((((4-Chlorophenyl)amino)carbonyl)amino)-2,3-dihydro-2-oxo-5-phenyl-1H-1,4-benzodiazepine-1-acetic acid phenylmethyl ester Equimolar amounts of 3(RS)-amino-1,3-dihydro-1-phenylmethyloxycarbonylmethyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 220°-222° C.

NMR: Confirms structure assignment of product.
HPLC: Greater than 98% pure.
MS: Molecular ion at m/e=553.
Anal. Calc'd for $C_{31}H_{25}ClN_4O_4 \cdot 0.3H_2O$: C, 66.67; H, 4.62; N, 10.03. Found: C, 66.52; H, 4.42; N, 9.87.

EXAMPLE 209

2,3-Dihydro-2-oxo-5-phenyl-3-(((phenylmethoxy)carbonyl)amino)-1H-1,4-benzodiazepine-1-acetic acid ethyl ester The procedure of Example 4 was employed using equimolar amounts of ethylbromoacetate and 1,3-dihydro-3(R,S)-(phenylmethyloxycarbonyl)amino-5-phenyl-2H-1,4-benzodiazepin-2-one. The chromatographed product (ethyl acetate-hexane) was dried in vacuo at room temperature over $P_2O_5$: m.p. 65°-66° C.

NMR: Consistent with structure assignment and shows approximately 10% of the 3,4-double bond isomer.
HPLC: Greater than 98% pure.
MS: Molecular ion at m/e=472.
Anal. Calc'd for $C_{27}H_{25}N_3O_5$: C, 68.78; H, 5.34; N, 8.91. Found: C, 68.85; H, 5.55; N, 8.60.

EXAMPLE 210

(R)-1,3-Dihydro-3-(1H-indol-3-ylmethyl)-1-methyl-5-phenyl-2H-1,4-benzodiazepin-2-one The procedure of Example 4 was employed using equimolar amounts of iodomethane and 1,3-dihydro-5-phenyl-3(R)-(3'-indolyl)methyl-2H-1,4-benzodiazepin- 2-one. The chromatographed product was dried in vacuo at room temperature as a foam.

NMR: Consistent with structure assignment.
HPLC: Greater than 99% pure.
MS: Molecular ion at m/e=379.
Anal. Calc'd for $C_{25}H_{21}N_3O$: C, 79.13; H, 5.58; N, 11.08. Found: C, 78.99; H, 5.60; N, 11.03.

EXAMPLE 211

3-((2,3-Dihydro-1-methyl-1H-indol-3-yl)methyl)-1,3-dihydro-1-methyl-5-phenyl-2H-1,4-benzodiazepin-2-one The procedure of Example 9 was followed in which 1-methyl-3(R)-[(N-methyl-1H-indol-3-yl)methyl]-5-phenyl-1,3-dihydro-2H-1,4-benzodiazepin-2-one was reduced to give the title compound. The analytical sample was obtained after silica gel chromatography using methylene chloride - ethyl ether (2%).

NMR: Consistent with structure.
HPLC: Greater than 99% pure.
MS: Molecular ion at m/e=395.
Anal Calc'd for $C_{26}H_{25}N_3O$: C, 78.96; H, 6.37; N, 10.63. Found: C, 78.45; H, 6.36; N, 10.46.

EXAMPLE 212

(2,3-Dihydro-2-oxo-1-(2-oxo-2-((phenylmethyl)amino)ethyl)-5-phenyl-1H-1,4-benzodiazepin-3-yl)-carbamic acid phenylmethyl ester The procedure of Example 134 was carried out using equivalent amounts of 1,3-dihydro-1-chlorocarbonylmethyl-3-(phenylmethyloxycarbonyl)amino-5-phenyl-2H-1,4-benzodiazepin-2-one and aniline. The product was purified by chromatography on silica gel (hexane-ethyl acetate elution). The combined product fractions were evaporated to dryness in vacuo and crystallized to give the title compound which was dried at 65° C.: m.p. 204°-205° C.

NMR: Consistent with structure.
HPLC: Greater than 98% pure.
MS: Molecular ion at m/e=533.
Anal. Calc'd for $C_{32}H_{28}N_4O_4$: C, 72.16; H, 5.30; N, 10.52. Found: C, 72.14; H, 5.51; N, 10.73.

EXAMPLE 213

{2,3-Dihydro-2-oxo-1-[2-oxo-2-(butylamino)ethyl]-5-phenyl-1H-1,4-benzodiazepin-3-yl}-carbamic acid phenylmethyl ester The procedure of Example 134 was carried out using equivalent amounts of 1,3-dihydro-1-chlorocarbonylmethyl-3-(phenylmethyloxycarbonyl)amino-5-phenyl-2H-1,4-benzodiazepin-2-one and n-butylamine. The product was purified by chromatography on silica gel (hexane-ethyl acetate elution). The combined product fractions were evaporated to dryness in vacuo and crystallized to give the title compound which was dried at 65° C.: m.p. 127°-129° C.

NMR: Consistent with structure.
HPLC: Greater than 98% pure.
MS: Molecular ion at m/e=499.
Anal. Calc'd for $C_{29}H_{30}N_4O_4.0.2H_2O$: C, 69.36; H, 6.10; N, 11.16. Found: C, 69.31; H, 5.89; N, 11.24.

EXAMPLE 214

5-(2-Fluorophenyl)-2,3-dihydro-3-((1H-indol-2-ylcarbonyl)amino)-2-oxo-1H-1,4-benzodiazepine-1-acetic acid ethyl ester The procedure of Example 4 was employed using equimolar amounts of ethylbromoacetate and 1,3-dihydro-1-ethoxycarbonylmethyl-5-(2-fluorophenyl)-3(RS)-(2-indolecarbonyl)amino-2H-1,4-benzodiazepin-2-one. The chromatographed product was dried in vacuo at room temperature, and triturated with ether.

NMR: Consistent with structure assignment and confirms ether solvate.
HPLC: Greater than 98% pure.
MS: Molecular ion at m/e=498.
Anal. Calc'd for $C_{28}H_{23}N_4O_4.0.15C_4H_{10}O$: C, 67.40; H, 4.85; N, 11.00. Found: C, 67.48; H, 5.00; N, 11.23.

EXAMPLE 215

(1(2-(Ethylamino)-2-oxoethyl)-2,3-dihydro-5-phenyl-2-oxo-1H-1,4-benzodiazepin-3-yl)-carbamic acid phenylmethyl ester The products of Example 134 was carried out using equivalent amounts of 1,3-dihydro-1-chlorocarbonylmethyl-3(phenylmethyloxycarbonyl)amino-5-phenyl-2H-1,4-benzodiazepin-2-one and ethylamine. The product was purified by chromatography on silica gel (hexane-ethyl acetate elution). The combined product fractions were evaporated to dryness in vacuo and crystallized to give the title compound which was dried at 65° : m.p. 149° C.

NMR: Consistent with structure.
HPLC: Greater than 99% pure.
MS: Molecular ion at m/e=471.
Anal. Calc'd for $C_{27}H_{26}N_4O_4$: C, 68.92; H, 5.57; N, 11.91. Found: C, 68.92; H, 5.62; N, 12.17.

EXAMPLE 216

4-Bromo-N-(2,3-dihydro-1-methyl-2-oxo-5-phenyl-1H-1,4-benzodiazepin-3-yl)-benzamide The procedure of Example 134 was carried out employing equivalent amounts of 1,3-dihydro-1-methyl-3(RS)-amino-5-phenyl-2H-1,4-benzodiazepin-2-one and 4-bromobenzoyl chloride. The product was purified by chromatography on silica gel (5% (v/v) Et₂O in CH₂Cl₂ elution). The combined product fractions were evaporated to dryness in vacuo and crystallized to give the title compound which was dried at 65° C.

NMR: Consistent with structure.
HPLC: Greater than 99% pure.
MS: Molecular ion at m/e=448.
Anal. Calc'd for $C_{23}H_{18}BrN_3O_2$: C, 61.62; H, 4.05; N, 9.37. Found: C, 61.77; H, 3.96; N, 9.12.

EXAMPLE 217

N-(4-Chlorophenyl-N'-(2,3-dihydro-1-methyl-2-oxo-5-phenyl-1H-1,4-benzodiazepin-3-yl)-urea Equimolar amounts of 1,3-dihydro-1-methyl-3(RS)-amino-5-phenyl-2H-1,4-benzodiazepin-2-one and 4-chlorophenyl isocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product.

NMR: Confirms structure assignment of product.

HPLC: Greater than 99% pure.
MS: Molecular ion at m/e=419.
Anal Calc'd for $C_{23}H_{19}ClN_4O$: C, 65.94; H, 4.52; N, 13.38. Found: C, 65.57; H, 4.76; N, 13.50.

EXAMPLE 218

N-(5-(2-Fluorophenyl)-2,3-dihydro-1-methyl-2-oxo-1H-1,4-benzodiazepin-3-yl)-4-(trifluoromethyl)-benzamide The procedure of Example 134 was carried out using equivalent amounts of 3(R,S)-3-amino-1,3-dihydro-1-methyl-5-(2-fluorophenyl)-2H-1,4-benzodiazepin-2-one and 4-trifluoromethylbenzoylchloride. The product was purified by chromatography on silica gel (5% (v/v) $Et_2O$ in $CH_2Cl_2$ elution). The combined product fractions were evaporated to dryness in vacuo to give the title compound which was dried at 65° C.
NMR: Consistent with structure.
HPLC: Greater than 98% pure.
MS: Molecular ion at m/e=455.
Anal. Calc'd for $C_{24}H_{17}F_4N_3O_2$: C, 63.30; H, 3.76; N, 9.23. Found: C, 63.48; H, 3.71; N, 9.22.

EXAMPLE 219

(S)-N-(5-(2-Fluorophenyl)-2,3-dihydro-1-methyl-2-oxo-1H-1,4-benzodiazepin-3-yl)-4-(trifluoromethyl)benzamide The procedure of Example 134 was carried out using equivalent amounts of 3(S)-(−)-3-amino-1,3-dihydro-1-methyl-5-(2-fluorophenyl)-2H-1,4-benzodiazepin-2-one and 4-trifluoromethylbenzoylchloride. The product was purified by chromatography on silica gel (5% (v/v) $Et_2O$ in $CH_2Cl_2$ elution). The combined product fractions were evaporated to dryness in vacuo to give the title compound which was dried at 65° C.
NMR: Consistent with structure.
HPLC: Greater than 98% pure.
MS: Molecular ion at m/e=455.
Anal. Calc'd for $C_{24}H_{17}F_4N_3O_2$: C, 63.30; H, 3.76; N, 9.23. Found: C, 63.25; H, 3.87; N, 8.99.

EXAMPLE 220

3-((((4-Chlorophenyl)amino)carbonyl)amino)2,3-dihydro-2-oxo-5-phenyl-N-(phenylmethyl)1H-1,4-benzodiazepine-1-acetamide Equimolar amounts of 3(R,S)-amino-1,3-dihydro-1-phenylmethylaminocarbonylmethyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 260°–262° C.
NMR: Confirms structure assignment of product.
HPLC: Greater than 99% pure.
MS: Molecular ion at m/e=552.
Anal. Calc'd for $C_{31}H_{26}ClN_5O_3$: C, 67.45; H, 4.75; N, 12.69. Found: C, 67.30; H, 4.58; N, 12.63.

EXAMPLE 221

3-((((4-Chlorophenyl)amino)carbonyl)amino)-N,N-diethyl-2,3-dihydro-2-oxo-5-phenyl-1H-1,4-benzodiazepine-1-acetamide Equimolar amounts of 3(R,S)-amino-1,3-dihydro-1-diethylaminocarbonylmethyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 284°–285° C.
NMR: Confirms structure with assignment of product.
HPLC: Greater than 99% pure.
MS: Molecular ion at m/e=518.
Anal. Calc'd for $C_{28}H_{28}ClN_5O_3$: C, 64.92; H, 5.48; N, 13.52. Found: C, 64.88; H, 5.26; N, 13.54.

EXAMPLE 222

(1-(2-Diethylamino)-2-oxoethyl)-2,3-dihydro-2-oxo-5-phenyl-1H-1,4-benzodiazepin-3-yl)carbamic acid phenylmethyl ester The procedure of Example 134 was carried out using equivalent amounts of 1,3-dihydro-1-chlorocarbonylmethyl-3-(phenylmethyloxycarbonyl)amino-5-phenyl-2H-1,4-benzodiazepin-2-one and diethylamine. The product was purified by chromatography on silica gel (hexane-ethyl acetate elution). The combined product fractions were evaporated to dryness in vacuo to give the title compound which was dried at 65° C.: m.p. 153°–154° C.
NMR: Consistent with structure.
HPLC: Greater than 99% pure.
MS: Molecular ion at m/e=499.
Anal. Calc'd for $C_{29}H_{30}N_4O_4 \cdot \frac{1}{2}H_2O$: C, 68.62; H, 6.15; N, 11.04. Found: C, 68.76; H, 5.94; N, 10.88.

EXAMPLE 223

N-(5-(2-Fluorophenyl)-2,3-dihydro-1-methyl-2-oxo-1H-1,4-benzodiazepin-3-yl)-4-pentylbenzamide The procedure of Example 134 was carried out using equivalent amounts of 3(R,S)-amino-1,3-dihydro-1-methyl-5-(2-fluorophenyl)-2H-1,4-benzodiazepin-2-one and 4-n-pentylbenzoyl chloride. The product was purified by chromatography on silica gel (5% (v/v) $Et_2O$ in $CH_2Cl_2$ elution). The combined product fractions were evaporated to dryness in vacuo to give the title compound which was dried at 65° C.
NMR: Consistent with structure.
HPLC: Greater than 97% pure.
MS: Molecular ion at m/e=458.
Anal. Calc'd for $C_{28}H_{28}FN_3O_2 \cdot \frac{1}{4}H_2O$: C, 72.94; H, 6.01; N, 9.11. Found: C, 73.08; H, 6.37; N, 9.43.

EXAMPLE 224

3-((((4-Chlorophenyl)amino)carbonyl)amino)-N-ethyl-2,3-dihydro-2-oxo-5-phenyl-1H-1,4-benzodiazepine-1-acetamide Equimolar amounts of 3(R,S)-amino-1,3-dihydro-1-ethylaminocarbonylmethyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 293° C. (d).
NMR: Confirms structure assignment of product
HPLC: Greater than 98% pure.
MS: Molecular ion at m/e=490.
Anal. Calc'd for $C_{26}H_{24}ClN_5O_3$: C, 63.73; H, 4.94; N, 14.29. Found: C, 63.37; H, 5.15; N, 14.22.

EXAMPLE 225

(1-((3-((2,3-Dihydro-2-oxo-5-phenyl-1H-1,4-benzodiazepin-3-yl)methyl)-2,3-dihydro-1H-indol-1-yl)carbonyl)-3-methylbutyl)-carbamic acid-1,1-dimethylethyl ester The procedure of Example 21 was carried out using the same reagents and amounts except that 1,3-dihydro-5-phenyl-3(R)-3'-α,β-indolenyl)methyl-2H-1,4-benzodiazepin-2-one was substituted for the 5-(2-fluorophenyl) analog. The purified product (silica gel chromatography) was dried at 65° C. in vacuo.

NMR: Structure assignment is consistent with spectrum.
HPLC: Greater than 99% pure.
MS: Molecular ion at m/e=581.
Anal. Calc'd for $C_{35}H_{40}N_4O_4$: C, 72.39; H, 6.94; N, 9.65. Found: C, 72.49; H, 6.68; N, 9.58.

EXAMPLE 226

4-(1,1-Dimethylethyl)-N-(5-(2-fluorophenyl)-2,3-dihydro-1-methyl-2-oxo-1H-1,4-benzodiazepin-3-yl)benzamide The procedure of Example 134 was carried out using equivalent amounts of 1,3-dihydro-3(R,S)-amino-5-(2-fluorophenyl)-2H-1,4-benzodiazepin-2-one and 4-t-butylbenzoylchloride. The product was purified by chromatography on silica gel (5% (v/v) $Et_2O$ in $CH_2Cl_2$ elution). The combined product fractions were evaporated to dryness in vacuo and crystallized to give the title compound which was dried at 65° C.

NMR: Consistent with structure.
HPLC: Greater than 96% pure.
MS: Molecular ion at m/e=444.
Anal. Calc'd for $C_{27}H_{26}FN_3O_2$: C, 73.12; H, 5.91; N, 9.47. Found: C, 73.17; H, 6.28; N, 9.27.

EXAMPLE 227

1-(2-Amino-4-methyl-1-oxopentyl)-3-((2,3-dihydro-2-oxo-5-phenyl-1H-1,4-benzodiazepin-3-yl)methyl)-2,3-dihydro-1H-indole hydrochloride The procedure of Example 2 was carried out in which (1-[(3-[(2,3-dihydro-2-oxo-5-phenyl-1,4-benzodiazepin-3-yl)methyl]-2,3-dihydro-1H-indol-1-yl)carbonyl]-3-methylbutyl]-carbamic acid-1,1-dimethylethyl ester was reacted with excess HCl gas in ethyl acetate at 0° C. to give the title compound as a foam.

NMR: Consistent with structure assignment.
HPLC: Greater than 96% pure.
Anal. Calc'd for $C_{30}H_{32}N_4O_2 \cdot 1.5HCl$: C, 67.31; H, 6.31; N, 10.47; Cl, 9.94. Found: C, 66.95; H, 6.63; N, 9.97; Cl, 9.73.

EXAMPLE 228

(S)-N-(5-(2-Fluorophenyl)-2,3-dihydro-1-methyl-2-oxo-1H-1,4-benzodiazepin-3-yl)-4-pentylbenzamide The procedure of Example 134 was carried out using equivalent amounts of 3(S)-(−)-3-amino-1,3-dihydro-1-methyl-5-(2-fluorophenyl)-2H-1,4-benzodiazepin-2-one and 4-n-pentylbenzoylchloride. The product was purified by chromatography on silica gel (5% (v/v) $Et_2O$ in $CH_2Cl_2$ elution). The combined product fractions were evaporated to dryness in vacuo to give the title compound which was dried at 65° C.

NMR: Consistent with structure.
HPLC: Greater than 97% pure.
MS: Molecular ion at m/e=457.
Anal. Calc'd for $C_{28}H_{28}FN_3O_2$: C, 73.66; H, 5.98; N, 9.20. Found: C, 73.29; H, 6.09; N, 9.25.

EXAMPLE 229

2,3-Dihydro-2-oxo-5-phenyl-3-(((phenylmethoxy)carbonyl)amino)-1H-1,4-benzodiazepine-1-propanoic acid ethyl ester The procedure of Example 134 was carried out using equivalent amounts of 1,3-dihydro-3-phenylmethyloxycarbonylamino-5-phenyl-2H-1,4-benzodiazepin-2one and ethyl bromopropionate. The product was purified by chromatography on silica gel (hexane-ethyl acetate elution). The combined product fractions were evaporated to dryness in vacuo and crystallized to give the title compound which was dried at 65° C.: m.p. 57°–59° C.

NMR: Consistent with structure.
HPLC: Greater than 99% pure.
MS: Molecular ion at m/e=486.
Anal. Calc'd for $C_{28}H_{27}N_3O_5$: C, 69.26; H, 5.60; N, 8.65. Found: C, 69.11; H, 5.60; N, 8.54.

EXAMPLE 230

3-((((4-Chlorophenyl)amino)carbonyl)amino)-2,3-dihydro-2-oxo-5-phenyl-1H-1,4-benzodiazepine-1-propanoic acid ethyl ester Equimolar amounts of 3(R,S)-amino-1,3-dihydro-1-ethoxycarbonylethyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 251°–253° C.

NMR: Confirms structure assignment of product.
HPLC: Greater than 99% pure.
MS: Molecular ion at m/e=505.
Anal. Calc'd for $C_{27}H_{25}ClN_4O_4$: C, 64.22; H, 4.99; N, 11.10. Found: C, 64.02; H, 5.11; N, 10.91.

EXAMPLE 231

(2-((5-(2-Fluorophenyl)-2,3-dihydro-1-methyl-2-oxo-1H-1,4-benzodiazepin-3-yl)amino)-2-oxo-1-(phenylmethyl) ethyl)-carbamic acid 1,1-dimethylethyl ester The procedure of Example 77 was carried out in which Boc-D-phenylalanine was coupled to 3(R,S)-amino-1,3-dihydro-1-methyl-5-(2-fluorophenyl)-2H-1,4-benzodiazepin-2-one using dicyclohexylcarbodiimide. Following the identical work-up and purification procedure of Example 77 gave the analytical product.

NMR: Confirms structure assignment.
HPLC: Greater than 98% pure.
Anal. Calc'd for $C_{30}H_{31}FN_4O_4$: C, 67.91; H, 5.89; N, 10.56. Found: C, 67.69; H, 6.21; N, 10.85.

EXAMPLE 232

(S-(R*,S*))-(2-((5-(2-Fluorophenyl)-2,3-dihydro-1-methyl-2-oxo-1H-1,4-benzodiazepin-3-yl)amino)-2-oxo-1-(phenylmethyl)ethyl)-carbamic acid 1,1-dimethylethyl ester The procedure of Example 77 was carried out in which Boc-D-phenylalanine was coupled to 3(S)-(−)-amino-1,3-dihydro-1-methyl-5-(2-fluorophenyl)-2H-1,4-benzodiazepin-2-one with dicyclohexylcarbodiimide.

Following the identical work-up and purification procedure of Example 77 gave the analytical product.
NMR: Spectrum confirms structure assignment.
HPLC: Greater than 98% pure.
MS: Molecular ion at m/e=505.
Anal. Calc'd for $C_{30}H_{31}FN_4O_4$: C, 67.91; H, 5.89; N, 10.56. Found: C, 67.83; H, 6.08; N, 10.25.

EXAMPLE 233

(S)-N-(4-Chlorophenyl)-N'-(2,3-dihydro-1-methyl-2-oxo-5-phenyl-1H-1,4-benzodiazepin-3-yl)-Urea Equimolar amounts of 1,3-dihydro-1-methyl-3(S)-amino-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product.
NMR: Confirms structure assignment of product.
HPLC: Greater than 95% pure.
MS: Molecular ion at m/e=419.
Anal. Calc'd for $C_{23}H_{19}ClN_4O_2$: C, 65.94; H, 4.57; N, 13.38. Found: C, 65.78; H, 4.82; N, 13.34.

EXAMPLE 234

(R)-N-(4-Chlorophenyl)-N'-(2,3-dihydro-1-methyl-2-oxo-5-phenyl-1H-1,4-benzodiazepin-3-yl)-Urea Equimolar amounts of 1,3-dihydro-1-methyl-3(R)-amino-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product
NMR: Confirms structure assignment of product.
HPLC: Greater than 99% pure.
MS: Molecular ion at m/e=419.
Anal. Calc'd for $C_{23}H_{19}ClN_4O_2$: C, 65.94; H, 4.57; N, 13.38. Found: C, 66.24; H, 4.57; N, 13.74.

EXAMPLE 235

(2,3-Dihydro-1-(2-(4-methyl-1-piperazinyl)-2-oxoethyl)-2-oxo-5-phenyl-1H-1,4-benzodiazepin-3-yl)carbamic acid phenylmethyl ester The procedure of Example 134 was carried out using equivalent amounts of 1,3-dihydro-1-chlorocarbonylmethyl-3-(phenylmethyloxycarbonyl)-5-phenyl-2H-1,4-benzodiazepin-2-one and 1-methylpiperazine. The product was purified by chromatography on silica gel (hexane-ethyl acetate elution) The combined product fractions were evaporated to dryness in vacuo and crystallized to give the title compound which was dried at 65° C.: m.p. 200°-202° C.
NMR: Consistent with structure.
HPLC: Greater than 99% pure.
MS: Molecular ion at m/e=526.
Anal. Calc'd for $C_{30}H_{31}N_5O_4$: C, 68.55; H, 5.94; N, 13.32. Found: C, 68.29; H, 5.72; N, 13.21.

EXAMPLE 236

1-((3-((((4-Chlorophenyl)amino)carbonyl)amino)-2,3-dihydro-2-oxo-5-phenyl-1H-1,4-benzodiazepin-1-yl)acetyl)pyrrolidine Equimolar amounts of 3(R,S)-amino-1,3-dihydro-1-pyrrolidinecarbonylmethyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product m.p. 264°-266° C.
NMR: Confirms structure assignment of product.
HPLC: Greater than 99% pure.
MS: Molecular ion at m/e=516.
Anal. Calc'd for $C_{28}H_{26}ClN_5O_3$: C, 65 18; H, 5.08; N, 13.57. Found: C, 64.94; H, 5.01; N, 13.50.

EXAMPLE 237

1-((3-((((4-Chlorophenyl)amino)carbonyl)amino)-2,3-dihydro-2-oxo-5-phenyl-1H-1,4-benzodiazepin-1-yl)acetyl)-4-methylpiperazine Equimolar amounts of 3(R,S)-amino-1,3-dihydro-1-(4-methylpiperazinecarbonylmethyl-5-phenyl-2H-1,4-benzodiazepin-2-one and 4-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 278°-280° C.
NMR: Confirms structure assignment of product.
HPLC: Greater than 99% pure.
MS: Molecular ion at m/e=545.
Anal. Calc'd for $C_{29}H_{29}ClN_6O_3$: C, 63 91; H, 5.36; N, 15.42. Found: C, 63.72; H, 5.66; N, 15.32.

EXAMPLE 238

N-(5-(2-Fluorophenyl)-2,3-dihydro-1-methyl-2-oxo-1H-1,4-benzodiazepin-3-yl)-3-thiophenecarboxamide The procedure of Example 134 was carried out using equivalent amounts of 3(R,S)-amino-1,3-dihydro-1-methyl-5-(2-fluorophenyl)-2H-1,4-benzodiazepin-2-one and 3-thiophenecarbonyl chloride. The product was purified by chromatography on silica gel (5% (v/v) $Et_2O$ in $CH_2Cl_2$ elution). The combined product fractions were evaporated to dryness in vacuo to give the title compound which was dried at 65° C.
NMR: Consistent with structure.
HPLC: Greater than 97% pure.
MS: Molecular ion at m/e=393.
Anal. Calc'd for $C_{21}H_{16}FN_3O_2S$: C, 64.11; H, 4.10; N, 10.68. Found: C, 63.87; H, 4.44; N, 10.96.

EXAMPLE 239

3-(((4-Chlorophenyl)acetyl)amino)-2,3-dihydro-2-oxo-5-phenyl-1H-1,4-benzodiazepine-1-acetic acid ethyl ester The procedure of Example 134 was carried out using equivalent amounts of 3(R,S)-amino-1,3-dihydro-1-ethoxycarbonylmethyl-5-phenyl-2H-1,4-benzodiazepin-2-one and 4-chlorophenylacetyl chloride. The product was purified by chromatography on silica gel (hexane-ethyl acetate elution). The combined product fractions were evaporated to dryness in vacuo and crystallized to give the title compound which was dried at 65° C.: m.p. 205°-207° C.
NMR: Consistent with structure.
HPLC: Greater than 98% pure.
MS: Molecular ion at m/e=490.
Anal. Calc'd for $C_{27}H_{24}ClN_3O_4$: C, 66.19; H, 4.94; N, 8.58. Found: C, 66.18; H, 4.96; N, 8.55.

EXAMPLE 240

4-Chloro-N-(2,3-dihydro-2-oxo-5-phenyl-1,4-benzodiazepin-3-yl)-benzeneacetamide

The procedure of Example 134 was carried out using equivalent amounts of 3(R,S)-amino-1,3-dihydro-5-phenyl-2H-1,4-benzodiazepin-2-one and 4-chlorophenylacetyl chloride. The product was purified by chromatography on silica gel (hexane-ethyl acetate elution). The combined product fractions were evaporated to dryness in vacuo and crystallized to give the title compound which was dried at 65° C.: m.p. 238°–240° C.

NMR: Consistent with structure.
HPLC: Greater than 98% pure.
MS: Molecular ion at m/e=404.
Anal. Calc'd for $C_{23}H_{18}ClN_3O_2O$: $H_2O$: C, 67.20; H, 4.61; N, 10.22. Found: C, 67.33; H, 4.63; N, 9.95.

EXAMPLE 241

2,3-Dihydro-alpha-methyl-2-oxo-5-phenyl-3-((phenylmethoxy)
carbonyl)amino-1H-1,4-benzodiazepine-1-acetic acid ethyl ester A mixture of 72.9 mg (1.51 mmol) NaH (50% oil dispersion) in 30 ml DMF was stirred at 0° C. for 10 minutes and then treated with a 10 ml DMF solution containing 530 mg (1.38 mmol) 3-benzyloxycarbonylamino-1,3-dihydro-2-oxo-5-phenyl-2H-1,4-benzodiazepin-2-one. After stirring 2 hours at 0° C., 0.194 ml (1.49 mmol) of ethyl-2-bromopropionate was added and the reaction allowed to warm to room temperature while stirring overnight DMF was removed in vacuo and the residue treated with $H_2O$ and extracted 3×$CH_2Cl_2$. The organics were combined, washed 1×$H_2O$, 1× brine, dried over $Na_2SO_4$, filtered and stripped to dryness. The crude, oily residue was flash chromatographed on silica gel (4% $Et_2O$ in $CH_2Cl$) to give the individual diastereomers. α-Diastereomer: The title compound was crystallized from ether m.p. 147°–148° C.

TLC: Rf=0.39 Silica gel (5% $Et_2O$ in $CH_2Cl_2$);
NMR: Confirms structure assignment of product
HPLC: 99.4% single diastereomer (contains 0.6% of opposite diastereomer).
MS: Molecular ion at M+H=486 (FAB).
Anal. Calc'd for $C_{20}H_{27}N_3O_5$: C, 69.26; H, 5.61; N, 8.66. Found: C, 69.35; H, 5.65; N, 8.45.

EXAMPLE 242

2,3-Dihydro-beta-methyl-2-oxo-5-phenyl-3-((phenylmethoxy)
carbonyl)amino-1H-1,4-benzodiazepine-1-acetic acid ethyl ester For the synthesis and isolation of the title compound refer to the procedure of Example 241.

β-diastereomer: The title compound was provided by flash chromatography and obtained as a white foam after removal of the solvent: m.p. 65°–75° C.

TLC: Rf=0.33 Silica gel (5% $Et_2O$ in $CH_2Cl_2$);
NMR: Confirms structure assignment of product plus 5% of α-diastereomer.
HPLC: 100% chemically pure; 5.2%/94.8%=α/β Diastereomeric purity.
MS: Molecular ion at M+H=486 (FAB).
Anal. Calc'd for $C_{28}H_{27}N_3O_5$: C, 69.26; H, 5.61; N, 8.66. Found: C, 69.14; H, 5.81; N, 8.42.

EXAMPLE 243

2,3-Dihydro-alpha-methyl-2-oxo-5-phenyl-3-((phenylmethoxy)
carbonyl)amino-1H-1,4-benzodiazepine-1-acetic acid 470 mg (0.968 mmol) of 2,3-dihydro-alpha-methyl-2-oxo-5-phenyl-3-((phenylmethoxy)carbonyl)amino-1H-1,4-benzodiazepine-1-acetic acid ethyl ester was dissolved in 10 ml THF and 1.94 ml (1.94 mmol) of 1M NaOH was added. The turbid mixture was stirred overnight at room temperature. The pH was adjusted to 3.0 with 6N HCl. THF was removed in vacuo and the residue was dissolved in $H_2O$ and extracted (3×EtOAc). The combined organics were washed (1×$H_2O$, 1× brine), dried over $Na_2SO_4$, filtered and then stripped to dryness in vacuo. The title compound was crystallized from $Et_2O$: m.p. 223°–225° C.

NMR: Confirms structure assignment of product and verifies presence of ether solvate.
HPLC: 100% pure.
MS: Molecular ion at M+H=458 (FAB).
Anal. Calc'd for $C_{26}H_{23}N_3O_5 \cdot \frac{1}{2}C_4H_{10}O$: C, 68.08; H, 5.50; N, 8.72. Found: C, 68.00.; H, 5.40; N, 8.98.

Note: The title compound is a mixture of diastereomers.

EXAMPLE 244

(1-(2-(Diethylamino)-1-methyl-2-oxoethyl)-2,3-dihydro-2-oxo-5-phenyl-1H-1,4-benzodiazepin-3-yl)-carbamic acid phenylmethyl ester 390 mg (0.853 mmol) of 2,3-dihydro-alpha-methyl-2-oxo-5-phenyl-3-((phenylmethoxy)carbonyl)-amino-1H-1,4-benzodiazepine-1-acetic acid was suspended in 28 ml toluene, treated with 1.07 ml (14.6 mmol) thionyl chloride, and stirred at 90° C. for 2 hours. The solvent was removed in vacuo and the residue treated with fresh toluene. The cycle was repeated 4 times. The resulting brown oil was dissolved in 5 ml THF, treated with 185 μl (1.79 mmol) of diethylamine and stirred at room temperature for 1 hour. The solvent was removed in vacuo, treated with 10% $Na_2CO_3$ solution and extracted (3×EtOAc). The extracts were combined, washed (1× $H_2O$, 1× brine), dried over $Na_2SO_4$, filtered and stripped to dryness in vacuo. Flash chromatography of the crude product on silica gel (10% $Et_2O$ in $CH_2Cl_2$) gave the title compound which was crystallized from $Et_2O$: m.p. 170°–171° C.

NMR: Confirms structure assignment of product.
HPLC: 98.5% pure.
MS Molecular ion at M+H=513 (FAB).
Anal. Calc'd for $C_{30}H_{32}N_4O_4$: C, 70.29; H, 6.29; N, 10.93. Found: C, 70.17; H, 6.24; N, 10.94.

Note: The only evidence of diastereomers is observed in the NMR, which indicates a 1:1 mixture.

EXAMPLE 245

(5-(2-Fluorophenyl)-2,3-dihydro-1-methyl-2-oxo-1H-1,4-benzodiazepin-3-yl)-carbamic acid-4-nitrophenyl ester The procedure of Example 134 was carried out using equivalent amounts of 3(R,S)-amino-1,3-dihydro-1-methyl-5-(2-fluorophenyl)-2H-1,4-benzodiazepin-2-one and 4-nitrophenylchloroformate. The product was purified by chromatography on silica gel (5% (v/v) $Et_2O$ in $CH_2Cl_2$ elution). The combined product fractions were evaporated to dryness in vacuo and crystallized to give the title compound which was dried at 65° C.: m.p. 202°-204° C.
NMR: Consistent with structure.
HPLC: Greater than 99% pure.
MS: Molecular ion at m/e=448.
Anal Calc'd for $C_{23}H_{17}FN_4O_5$: C, 61.61; H, 3.82; N, 12.50. Found: C, 61.80; H, 4.07; N, 12.26.

EXAMPLE 246

N-(5-(2-Fluorophenyl)-2,3-dihydro-1-methyl-2-oxo-1H-1,4-benzodiazepin-3-yl)-N'-(3-methoxyphenyl)-urea Equimolar amounts of 3(R,S)-amino-1,3-dihydro-1-methyl-5-(2-fluorophenyl)-2H-1,4-benzodiazepi n-2-one and 3-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 271°-273° C.
NMR: Confirms structure assignment of product.
HPLC: Greater than 99% pure.
MS: Molecular ion at m/e=432.
Anal. Calc'd for $C_{24}H_{21}FN_4O_3$: C, 66.66; H, 4.89; N, 12.96. Found: C, 66.54; H, 5.00; N, 12.79.

EXAMPLE 247

N-(2,3-Dihydro-1-methyl-2-oxo-5-phenyl-1H-1,4-benzodiazepin-3-yl)-N'-(3-methoxyphenyl)-urea Equimolar amounts of 3(R,S)-amino-1,3-dihydro-1-methyl-5-phenyl-2H-1,4-benzodiazepin-2-one and 3-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 245°-246° C.
NMR: Confirms structure assignment of product.
HPLC: Greater than 99% pure.
MS: Molecular ion at m/e=414.
Anal. Calc'd for $C_{24}H_{22}N_4O_3$: C, 69.55; H, 5.35; N, 13.52. Found: C, 69.23; H, 5.23; N, 13.66.

EXAMPLE 248

N-(((2,3-Dihydro-1-methyl-2-oxo-5-phenyl-1H-1,4-benzodiazepin-3-yl)amino)carbonyl)-4-methylbenzenesulfonamide Equimolar amounts of 3(R,S)-amino-1,3-dihydro-1-methyl-5-phenyl-2H-1,4-benzodiazepin-2-one and p-toluenesulfonylchloride were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 244°-246° C.
NMR: Confirms structure assignment of product.
HPLC: Greater than 97% pure.
MS: Molecular ion at m/e=463.
Anal. Calc'd for $C_{24}H_{22}N_4O_4S$: C, 62.32; H, 4.79; N, 12.11. Found: C, 62.44; H, 5.11; N, 12.11.

EXAMPLE 249

3-((((4-Chlorophenyl)amino)carbonyl)amino)-N,N,-diethyl-2,3-dihydro-alpha-methyl-2-oxo-5-phenyl-1H-1,4-benzodiazepine-1-acetamide Under a nitrogen atmosphere, 93.1 mg of 10% Pd on activated carbon was added to a 3 ml solution of 4.5% $HCO_2H$ in MeOH followed by 200 mg (0.390 mmol) of (1-(2-(diethylamino)-1-methyl-2-oxoethyl)-2,3-dihydro-2-oxo-5-phenyl-1H-1,4-benzodiazepin-3-yl)-carbamic acid phenyl methyl ester dissolved in 4 ml of 4.5% $HCO_2H$ in MeOH. The mixture was stirred 1 hour at room temperature. The solvent was removed in vacuo and the residue was treated with toluene. The solvent was again removed in vacuo and this cycle was repeated with toluene, 1:1 toluene-tetrahydrofuran and finally, with tetrahydrofuran. The crude amine-formate salt was suspended in 5 ml THF, cooled to 0° C., treated with 104 μl (0.746 mmol) of triethylamine followed by 58.4 mg (0.380 mmol) of p-chlorophenylisocyanate and allowed to warm to room temperature with stirring overnight. The solvent was removed in vacuo and the residue was dissolved in $CH_2Cl_2$ and flash chromatographed on silica gel (20% EtoAc in $CH_2Cl_2$) to give the title compound as a white solid after trituration with $Et_2O$: m.p. 280°-282° C.
NMR: Confirms structure assignment of product.
HPLC: Greater than 98.4% pure.
MS: Molecular ion at M+H=532 (FAB).
Anal. Calc'd for $C_{29}H_{30}ClN_5O_3$: C, 65.46; H, 5.68; N, 13.17. Found: C, 65.21; H, 5.28; N, 12.89.
Note: NMR appears to show a single diastereomer. HPLC shows a single peak.

EXAMPLE 250

N-(2,3-Dihydro-1-methyl-2-oxo-5-phenyl-1H-1,4-benzodiazepin-3-yl)-N'-phenylurea

Equimolar amounts of 3(R,S)-amino-1,3-dihydro-1-methyl-5-phenyl-2H-1,4-benzodiazepin-2-one and phenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 260°-261° C.
NMR: Confirms structure assignment of product
HPLC: Greater than 98% pure.
MS: Molecular ion at m/e=384.
Anal. Calc'd for $C_{23}H_{20}N_4O_2$: C, 71.86; H, 5.24; N, 14.57. Found: C, 71.65; H, 5.54; N, 14.76.

EXAMPLE 251

N-(2,3-Dihydro-1-methyl-2-oxo-5-phenyl-1H-1,4-benzodiazepin-3-yl)-N'-phenylmethylurea Equimolar amounts of 3(R,S)-amino-1,3-dihydro-1-methyl-5-phenyl-2H-1,4-benzodiazepin-2-one and phenylmethylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: 240°-242° C.
NMR: Confirms structure assignment of product
HPLC: Greater than 98% pure.
MS: Molecular ion at m/e=398.
Anal. Calc'd for $C_{24}H_{22}N_4O_2$: C, 72.34; H, 5.56; N, 14.06. Found: C, 71.94; H, 5.88; N, 14.12.

EXAMPLE 252

N-(2,3-Dihydro-1-methyl-2-oxo-5-phenyl-1H-1,4-benzodiazepin-3-yl)-N'-(4-methylphenyl)-urea Equimolar amounts of 3(R,S)-amino-1,3-dihydro-1-methyl-5-phenyl-2H-1,4-benzodiazepin-2-one and 4-methyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 274°–277° C.

NMR: Confirms structure assignment of product.
HPLC: Greater than 98% pure.
MS: Molecular ion at m/e=398.
Anal. Calc'd for $C_{24}H_{22}N_4O_2$: C, 72.34; H, 5.57; N, 14.06. Found: C, 72.17; H, 5.28; N, 14.26.

EXAMPLE 253

N-(2,3-Dihydro-1-methyl-2-oxo-5-phenyl-1H-1,4-benzodiazepin-3-yl)-N'-(4-methoxyphenyl)-urea Equimolar amounts of 3(R,S)-amino-1,3-dihydro-1-methyl-5-phenyl-2H-1,4-benzodiazepin-2-one and 4-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 261°–263° C.

NMR: Confirms structure assignment of product.
HPLC: Greater than 98% pure.
MS: Molecular ion at m/e=414.
Anal Calc'd for $C_{24}H_{22}N_4O_3$: C, 69.55; H, 5.35; N, 13.52. Found: C, 69.31; H, 4.98; N, 13.56.

EXAMPLE 254

N-(2-Chlorophenyl)-N'-(2,3-dihydro-1-methyl-2-oxo-5-phenyl-1H-1,4-benzodiazepin-3-yl)-urea Equimolar amounts of 3(R,S)-amino-1,3-dihydro-1-methyl-5-phenyl-2H-1,4-benzodiazepin-2-one and 2-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 263°–265° C.

NMR: Confirms structure assignment of product.
HPLC: Greater than 98% pure.
MS: Molecular ion at m/e=419.
Anal. Calc'd for $C_{23}H_{19}ClN_4O_2$: C, 65.95; H, 4.57; N, 13.38. Found: C, 65.65; H, 4.74; N, 13.46.

EXAMPLE 255

N-(4-Bromophenyl-N'-(2,3-dihydro-1-methyl-2-oxo-5-phenyl-1H-1,4-benzodiazepin-3-yl)-urea Equimolar amounts of 3(R,S)-amino-1,3-dihydro-1-methyl-5-phenyl-2H-1,4-benzodiazepin-2-one and 2-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 286°–287° C.

NMR: Confirms structure assignment of product.
HPLC: Greater than 99% pure.
MS: Molecular ion at m/e=463.
Anal. Calc'd for $C_{23}H_{19}BrN_4O_2$: C, 59.62; H, 4.13; N, 12.09. Found: C, 59.74; H, 4.32; N, 12.14.

EXAMPLE 256

N-(4-Nitrophenyl)-N'-(2,3-dihydro-1-methyl-2-oxo-5-phenyl-1H-1,4-benzodiazepin-3-yl)-urea Equimolar amounts of 3(R,S)-amino-1,3-dihydro-1-methyl-5-phenyl-2H-1,4-benzodiazepin-2-one and 4-nitrophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 292°–293° C.

NMR: Confirms structure assignment of product.
HPLC: Greater than 99% pure.
MS: Molecular ion at m/e=429.
Anal. Calc'd for $C_{23}H_{19}N_5O_4$: C, 64.33; H, 4.46; N, 16.31. Found: C, 64.05; H, 4.39; N, 16.38.

EXAMPLE 257

N-(3,4-Dichlorophenyl)-N'-(2,3-dihydro-1-methyl-2-oxo-5-phenyl-1H-1,4-benzodiazepin-3-yl)-urea Equimolar amounts of 3(R,S)-amino-1,3-dihydro-1-methyl-5-phenyl-2H-1,4-benzodiazepin-2-one and 3,4-dichlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 274°–276° C.

NMR: Confirms structure assignment of product.
HPLC: Greater than 99% pure.
MS: Molecular ion at m/e=453.
Anal. Calc'd for $C_{23}H_{18}Cl_2N_4O_2$: C, 60.94; H, 4.00; N, 12.36. Found: C, 61.01; H, 4.22; N, 12.48.

EXAMPLE 258

N-(2,4-Dichlorophenyl)-N'-(2,3-dihydro-1-methyl-2-oxo-5-phenyl-1H-1,4-benzodiazepin-3-yl)-urea Equimolar amounts of 3(R,S)-amino-1,3-dihydro-1-methyl-5-phenyl-2H-1,4-benzodiazepin-2-one and 2,4-dichlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 285°–287° C. (d).

NMR: Confirms structure assignment of product.
HPLC: Greater than 98% pure.
MS: Molecular ion at m/e=453.
Anal. Calc'd for $C_{23}H_{18}Cl_2N_4O_2$: C, 60.94; H, 4.00; N, 12.36. Found: C, 61.30; H, 4.29; N, 12.35.

EXAMPLE 259

N-(2,3-Dihydro-1-methyl-2-oxo-5-phenyl-1H-1,4-benzodiazepin-3-yl)-N'-(4-fluorophenyl)-urea Equimolar amounts of 3(R,S)-amino-1,3-dihydro-1-methyl-5-phenyl-2H-1,4-benzodiazepin-2-one and 4-fluorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 269°–270° C.

NMR: Confirms structure assignment of product.
HPLC: Greater than 99% pure.
MS: Molecular ion at m/e=402.
Anal. Calc'd for $C_{23}H_{19}FN_4O_2$: C, 68.65; H, 4.76; N, 13.92. Found: C, 68.48; H, 4.71; N, 13.98.

EXAMPLE 260

N-(2,3-Dihydro-1-methyl-2-oxo-5-phenyl-1H-1,4-benzodiazepin-3-yl)-N'-(1,1-dimethylethyl)-urea Equimolar amounts of 3(R,S)-amino-1,3-dihydro-1-methyl-5-phenyl-2H-1,4-benzodiazepin-2-one and t-butylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 281°–282° C.

NMR: Confirms structure assignment of product.
HPLC: Greater than 99% pure.
MS: Molecular ion at m/e=364.
Anal Calc'd for $C_{21}H_{24}N_4O_2$: C, 69.21; H, 6.64; N, 15.37. Found: C, 69.11; H, 6.40; N, 15.44.

EXAMPLE 261

(N-(2,3-Dihydro-1-methyl-2-oxo-5-phenyl-1H-1,4-benzodiazepin-3-yl)-N'-((R)1-phenylethyl)-urea Equimolar amounts of 3(R,S)-amino-1,3-dihydro-1-methyl-5-phenyl-2H-1,4-benzodiazepin-2-one and (R)-(+)-α-methylbenzylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product as a mixture of diastereomers: m.p. 146°–150° C.

NMR: Confirms structure assignment of product.
HPLC: Greater than 99% pure.
MS: Molecular ion at m/e=412.
Anal. Calc'd for $C_{25}H_{24}N_4O_2.0.2C_4H_8O$: C, 72.58; H, 6.04; N, 13.12. Found: C, 72.20; H, 5.75; N, 13.36.

EXAMPLE 262

N-Cyclohexyl-N'-(2,3-dihydro-1-methyl-2-oxo-5-phenyl-1H-1,4-benzodiazepin-3-yl)-urea Equimolar amounts of 3(R,S)-amino-1,3-dihydro-1-methyl-5-phenyl-2H-1,4-benzodiazepin-2-one and cyclohexylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p 287°–288° C.

NMR: Confirms structure assignment of product.
HPLC: Greater than 98% pure.
MS: Molecular ion at m/e=390.
Anal. Calc'd for $C_{23}H_{26}N_4O_2$: C, 70 75; H, 6.71; N, 14.35. Found: C, 70.39; H, 6.43; N, 14.44.

EXAMPLE 263

N-(2,3-Dihydro-1-methyl-2-oxo-5-phenyl-1H-1,4-benzodiazepin-3-yl)-N'-(3-methylphenyl)-urea Equimolar amounts of 3(R,S)-amino-1,3-dihydro-1-methyl-5-phenyl-2H-1,4-benzodiazepin-2-one and 3-methylphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 207°–209° C.

NMR: Confirms structure assignment of product
HPLC: Greater than 99% pure.
MS: Molecular ion at m/e=398.
Anal. Calc'd for $C_{23}H_{22}N_4O_2$: C, 72.34; H, 5.56; N, 14.06. Found: C, 72.26; H, 5.22; N, 14.23.

EXAMPLE 264

N-(2,3-Dihydro-1-methyl-2-oxo-5-phenyl-1H-1,4-benzodiazepin-3-yl)-N'-(3-nitrophenyl)-urea Equimolar amounts of 3(R,S)-amino-1,3-dihydro-1-methyl-5-phenyl-2H-1,4-benzodiazepin-2-one and 3-nitrophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 288°–289° C.

NMR: Confirms structure assignment of product.
HPLC: Greater than 98% pure.
MS: Molecular ion at m/e=429.
Anal. Calc'd for $C_{23}H_{19}N_5O_4$: C, 64.33; H, 4.46; N, 16.31. Found: C, 64.49; H, 4.22; N, 15.94.

EXAMPLE 265

N-(3-Chlorophenyl)-N'-(2,3-dihydro-1-methyl-2-oxo-5-phenyl-1H-1,4-benzodiazepin-3-yl)urea Equimolar amounts of 3(R,S)-amino-1,3-dihydro-1-methyl-5-phenyl-2H-1,4-benzodiazepin-2-one and 3-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 233°–234° C.

NMR Confirms structure assignment of product.
HPLC: Greater than 99% pure.
MS: Molecular ion at m/e=419.
Anal. Calc'd for $C_{23}H_{19}ClN_4O_2$: C, 65.95; H, 4.57; N, 13.38. Found: C, 65.93; H, 4.65; N, 13.14.

EXAMPLE 266

(R)-N-(2,3-Dihydro-1-methyl-2-oxo-5-phenyl-1H-1,4-benzodiazepin-3-yl)-N'-(3-methoxyphenyl)-urea Equimolar amounts of 3-(R)-amino-1,3-dihydro-1-methyl-5-phenyl-2H-1,4-benzodiazepin-2-one and 3-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 216°–219° C.

NMR: Confirms structure assignment of product.
HPLC: Greater than 99% pure.
MS: Molecular ion at m/e=414.
Anal. Calc'd for $C_{24}H_{22}N_4O_3$: C, 69.55; H, 5.35; N, 13.52. Found: C, 69.61; H, 5.62; N, 13.57.

EXAMPLE 267

(S)-N-(2,3-Dihydro-1-methyl-2-oxo-5-phenyl-1H-1,4-benzodiazepin-3-yl)-N'-(3-methoxyphenyl)-urea Equimolar amounts of 3-(S)-amino-1,3-dihydro-1-methyl-5-phenyl-2H-1,4-benzodiazepin-2-one and 3-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 216°–219° C.

NMR: Confirms structure assignment of product.
HPLC: Greater than 99% pure.
MS: Molecular ion at m/e=414.
Anal. Calc'd for $C_{24}H_{22}N_4O_3$: C, 69.55; H, 5.35; N, 13.52. Found: C, 69.90; H, 5.79; N, 13.53.

EXAMPLE 268

(S)-N-(2,3-Dihydro-1-methyl-2-oxo-5-phenyl-1H-1,4-benzodiazepin-3-yl)-3-methoxybenzeneacetamide The procedure of Example 134 was carried out using equivalent amounts of 3-(S)-amino-1,3-dihydro-1-methyl-5-phenyl-2H-1,4-benzodiazepin-2-one and 3-methoxyphenylacetylchloride. The product was purified by chromatography on silica gel (hexane-ethyl acetate elution). The combined product fractions were evaporated to dryness in vacuo and crystallized to give the title compound which was dried at 65° C.: m.p. 198°–199° C.

NMR: Consistent with structure.
HPLC: Greater than 98% pure.
MS: Molecular ion at m/e=413.
Anal. Calc'd for $C_{25}H_{23}N_3O_3$: C, 72.62; H, 5.61; N, 10.16. Found: C, 73.00; H, 5.70; N, 10.25.

EXAMPLE 269

(R)-N-(2,3-Dihydro-1-methyl-2-oxo-5-phenyl-1H-1,4-benzodiazepin-3-yl)-3-methoxybenzenacetamide The procedure of Example 134 was carried out using equivalent amounts of 3-(R)-amino-1,3-dihydro-1-methyl-5-phenyl-2H-1,4-benzodiazepin-2-one and 3-methoxyphenylacetyl chloride. The product was purified by chromatography on silica gel (hexane-ethyl acetate elution). The combined product fractions were evaporated to dryness in vacuo and crystallized to give the title compound which was dried at 65° C.: m.p 198°–199° C.

NMR: Consistent with structure.
HPLC: Greater than 98% pure.
MS: molecular ion at m/e =413.
Anal. Calc'd for $C_{25}H_{23}N_3O_3$: C, 72.62: H, 5.61; N, 10.16. Found: C, 72.29: H, 5.60; N, 10.15.

EXAMPLE 270

N-(2,3-Dihydro-1-methyl-2-oxo-5-phenyl-1H-1,4-benzodiazepin-3-yl)-N'-(2-nitrophenyl)-urea Equimolar amounts of 3(R,S)-amino-1,3-dihydro-1-methyl-5-phenyl-2H-1,4-benzodiazepin-2-one and 2-nitrophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p 260°–261° C.

NMR Confirms structure assignment of product.
HPLC: Greater than 99% pure.
MS: Molecular ion at m/e=429.
Anal. Calc'd for $C_{23}H_{19}N_5O_4$: C, 64.33; H, 4.46; N, 16.31. Found: C, 64.16; H, 4.37; N, 16.40.

EXAMPLE 271

N-(2,3-Dihydro-1-methyl-2-oxo-5-phenyl-1H-1,4-benzodiazepin-3-yl)-N'-(3-fluorophenyl)-urea Equimolar amounts of 3(R,S)-amino-1,3-dihydro-1-methyl-5-phenyl-2H-1,4-benzodiazepin-2-one and 2-fluorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 252°–254° C.

NMR: Confirms structure assignment of product.
HPLC: Greater than 99% pure.
MS: Molecular ion at m/e=402.
Anal Calc'd for $C_{23}H_{19}FN_4O_2$: C, 68.65; H, 4.76; N, 13.92. Found: C, 69.00; H, 5.00; N, 13.78.

EXAMPLE 272

N-(3-Bromophenyl)-N'-(2,3-dihydro-1-methyl-2-oxo-5-phenyl-1H-1,4-benzodiazepin-3-yl)-urea Equimolar amounts of 3(R,S)-amino-1,3-dihydro-1-methyl-5-phenyl-2H-1,4-benzodiazepin-2-one and 2-bromophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 219°–221° C.

NMR: Confirms structure assignment of product.
HPLC: Greater than 99% pure.
MS: Molecular ion at m/e=463.
Anal. Calc'd for $C_{23}H_{19}BrN_4O_2$: C, 59.62; H, 4.13; N, 12.09. Found: C, 59.78; H, 4.26; N, 12.01.

EXAMPLE 273

N-(2,3-Dihydro-1-methyl-2-oxo-5-phenyl-1H-1,4-benzodiazepin-3-yl)-N'-1-naphthalenyl-urea Equimolar amounts of 3(R,S)-amino-1,3-dihydro-1-methyl-5-phenyl-2H-1,4-benzodiazepin-2-one and 1-naphthylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 234°–235° C.

NMR: Confirms structure assignment of product.
HPLC: Greater than 99% pure.
MS: Molecular ion at m/e=434.
Anal. Calc'd for $C_{27}H_{22}N_4O_2$: C, 74.64; H, 5.10; N, 12.89. Found: C, 74.64; H, 5.03; N, 12.69.

EXAMPLE 274

N-(2,3-Dihydro-1-methyl-2-oxo-5-phenyl-1H-1,4-benzodiazepin-3-yl)-N'-(3,5-dimethylphenyl)-urea Equimolar amounts of 3(R,S)-amino-1,3-dihydro-1-methyl-5-phenyl-2H-1,4-benzodiazepin-2-one and 3,5-dimethoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 267°–269° C.

NMR: Confirms structure assignment of product.
HPLC: Greater than 99% pure.
MS: Molecular ion at m/e=444.
Anal. Calc'd for $C_{25}H_{24}N_4O_4 \cdot \frac{1}{4}H_2O$: C, 66.88; H, 5.50; N, 12.48. Found: C, 66.77; H, 5.43; N, 12.12.

EXAMPLE 275

N-(2,3-Dihydro-2-oxo-5-phenyl-1H-1,4-benzodiazepin-3-yl)-N'-(3-methoxyphenyl)-urea Equimolar amounts of 3(R,S)-amino-1,3-dihydro-5-phenyl-2H-1,4-benzodiazepin-2-one and 3-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 254°–255° C.

NMR: Confirms structure assignment of product.
HPLC: Greater than 99% pure; $R_f=0.42$ (5% $CH_3OH$ in $CH_2Cl_2$).
MS: Molecular ion at m/e=400.
Anal. Calc'd for $C_{22}H_{26}N_4O_3.0.15(C_2H_5)_2O$: C, 68.87; H, 5.27; N, 13.62. Found: C, 68.50; H, 5.09; N, 13.63.

EXAMPLE 276

(S)-N-(2,3-Dihydro-1-methyl-2-oxo-5-phenyl-1H-1,4-benzodiazepin-3-yl)-N'-(2-chlorophenyl)-urea Equimolar amounts of 3(S)-(−)-amino-1,3-dihydro-1-methyl-5-phenyl-2H-1,4-benzodiazepin-2-one and 2-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 212°–214° C.

NMR: Confirms structure assignment of product.
HPLC: Greater than 99% pure.
MS Molecular ion at m/e=419.
Anal. Calc'd for $C_{23}H_{19}ClN_4O_2$: C, 65.95; H, 4.57; N, 13.38. Found: C, 66.17; H, 4.86; N, 13.23.

EXAMPLE 277

N-(2,3-Dihydro-1-methyl-2-oxo-5-phenyl-1H-1,4-benzodiazepin-3-yl)-N'-phenylthiourea Equimolar amounts of 3(R,S)-amino-1,3-dihydro-1-methyl-5-phenyl-2H-1,4-benzodiazepin-2-one and phenylisothiocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 209°–211° C.

NMR: Confirms structure assignment of product.
HPLC: Greater than 99% pure.
MS: Molecular ion at m/e=401.
Anal. Calc'd for $C_{23}H_{20}N_4OS$: C, 68.98; H, 5.03; N, 13.99. Found: C, 68.97; H, 5.25; N, 14.07.

EXAMPLE 278

N-(2,3-Dihydro-1-methyl-2-oxo-5-phenyl-1H-1,4-benzodiazepin-3-yl)-N'-(2-methoxyphenyl)-urea Equimolar amounts of 3(R,S)-amino-1,3-dihydro-1-methyl-5-phenyl-2H-1,4-benzodiazepin-2-one and 2-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 258°–260° C.

NMR: Confirms structure assignment of product.
HPLC: Greater than 99% pure.
MS: Molecular ion at m/e=414.
Anal. Calc'd for $C_{24}H_{22}N_4O_3.\frac{1}{2}H_2O$: C, 68.08; H, 5.47; N, 13.23. Found: C, 68.18; H, 5.33; N, 13.05.

EXAMPLE 279

1-Pivaloyloxymethyloxycarbonylmethyl-1,3-dihydro-3-(2-indolecarbonylamino)-5-phenyl-2H-1,4-benzodiazepin-2-one A mixture of 1-carboxymethyl-1,3-dihydro-3-(2-indolecarbonylamino)-5-phenyl-2H-1,4-benzodiazepin-2-one (85 mg, 0.20 mmol), pivaloyloxymethylchloride (32 μl, 0.22 mmol) and triethylamine (28 μl, 0.20 mmol) was combined in 2 ml of dry dimethylformamide and allowed to stand at room temperature for 48 hours. Solvent was removed under reduced pressure and the residue partitioned between ethyl acetate and water. Extractive work-up gave 100 mg of crude product which was chromatographed on silica gel ($CH_3OH$—$CHCl_3$, 3:97 v/v elution) to give a white solid after trituration with ether: m.p. 225°–226° C.

NMR: Spectrum confirms structure assignment.
HPLC: Greater than 98% pure.
S: Molecular ion at m/e=567.
Anal. Calc'd for $C_{32}H_{30}N_4O_6$: C, 67.83; H, 5.34; N, 9.89. Found: C, 67.61; H, 5.42; N, 9.63.

EXAMPLE 280

N-(2,3-Dihydro-5-phenyl-2-thioxo-1H-1,4-benzodiazepin-3-yl)-N'-(3-methoxyphenyl)-urea Equimolar amounts of 3(R,S)-amino-1,3-dihydro-5-phenyl-2H-1,4-benzodiazepin-2-thione and 3-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 229°–231° C. (d).

NMR: Confirms structure assignment of product.
HPLC: Greater than 98% pure.
MS: Molecular ion at m/e=417 (FAB).
Anal. Calc'd for $C_{23}H_{20}N_4O_2S$: C, 66.33; H, 4.84; N, 13.45. Found: C, 65.99; H, 4.90; N, 13.34.

EXAMPLE 281

(R)-N-(2,3-Dihydro-1-methyl-2-oxo-5-phenyl-1H-1,4-benzodiazepin-3-yl)-N'-(3-methylphenyl)-urea Equimolar amounts of 3(R)-amino-1,3-dihydro-1-methyl-5-phenyl-2H-1,4-benzodiazepin-2-one and 3-methylphenyl-isocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 208°–210° C.

NMR: Confirms structure assignment of product.
HPLC: Greater than 99% pure.
MS: Molecular ion at m/e=399 (FAB).
Anal. Calc'd for $C_{24}H_{22}N_4O_2$: C, 72.34; H, 5.56; N, 14.06. Found: C, 72.12; H, 5.84; N, 14.04.

EXAMPLE 282

(R)-N-(2,3-Dihydro-1-methyl-2-oxo-5-phenyl-1H-1,4-benzodiazepin-3-yl)-N'-(3-bromophenyl)-urea Equimolar amounts of 3(R)-amino-1,3-dihydro-1-methyl-5-phenyl-2H-1,4-benzodiazepin-2-one and 3- bromophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 194°–196° C.
NMR: Confirms structure assignment of product.
HPLC: Greater than 99% pure.
MS: Molecular ion at m/e=463.
Anal. Calc'd for $C_{23}H_{19}BrN_4O_2$: C, 59.62; H, 4.13; N, 12.09. Found: C, 59.67; H, 4.17; N, 11.72.

EXAMPLE 283

(S)-N-(2,3-Dihydro-1-methyl-2-oxo-5-phenyl-1H-1,4-benzodiazepin-3-yl)-2-iodobenzamide Equimolar amounts of 3(S)-amino-1,3-dihydro-1-methyl-5-phenyl-2H-1,4-benzodiazepin-2-one, o-iodobenzoylchloride and triethylamine were mixed at room temperature and stirred 1 hour. Flash chromatography of the reaction solution on silica gel (5% $Et_2O$ in $CH_2Cl_2$) provided the title compound as a crystalline solid from EtOAc: m.p. 115°–120° C. (physical change), 173°–175° C. (melt).
NMR: Confirms structure assignment of product and verifies presence of EtOAc solvate.
HPLC: Greater than 99.6% pure.
MS: Molecular ion at m/e=496 (FAB).
Anal. Calc'd for $C_{23}H_{18}IN_3O_2 \cdot 0.3C_4H_8O_2$: C, 55.71; H, 3.94; N, 8.05. Found: C, 55.56; H, 3.81; N, 8.37. $[\alpha]_D^{25}=-85.5°$ (conc.=2.9 mg/ml $CH_2Cl_2$).

EXAMPLE 284

1-{[3-[(((3-Methoxyphenyl)amino)carbonyl)amino]-2,3-dihydro-2-oxo-5-phenyl-1H-1,4-benzodiazepin-1-yl]acetyl}pyrrolidine Equimolar amounts of 1-{[(3-amino)-2,3-dihydro-2-oxo-5-phenyl-1H-1,4-benzodiazepin-1-yl]acetyl}pyrrolidine and 3-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 193°–194° C.
NMR: Confirms structure assignment of product.
HPLC: Greater than 99% pure.
MS: Molecular ion at m/e=512.
Anal. Calc'd for $C_{29}H_{29}N_5O_4$: C, 68.09; H, 5.71; N, 13.69. Found: C, 68.14; H, 5.65; N, 13.24.

EXAMPLE 285

3-{[((3-Methoxyphenyl)amino)carbonyl)amino]-N,N-diethyl-2,3-dihydro-2-oxo-5-phenyl-1H-1,4-benzodiazepin-1-acetamide Equimolar amounts of 3-amino-N,N-diethyl-2,3-dihydro-2-oxo-5-phenyl-1H-1,4-benzodiazepine-1-acetamide and 3-methoxyphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 222°–224° C.
NMR: Confirms structure assignment of product.
HPLC: Greater than 99% pure.
MS Molecular ion at m/e=514.
Anal Calc'd for $C_{29}H_{31}N_5O_4 \cdot \frac{1}{4}H_2O$: C, 67.26; H, 6.13; N, 13.52. Found: C, 67.22; H, 6.04; N, 13.30.

EXAMPLE 286

3-{[((2-Chlorophenyl)amino)carbonyl]amino}-N,N-diethyl-2,3-dihydro-2-oxo-5-phenyl-1H-1,4-benzodiazepine-1-acetamide Equimolar amounts of 3-amino-N,N-diethyl-2,3-dihydro-2-oxo-5-phenyl-1H-1,4-benzodiazepine-1-acetamide and 2-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 173°–175° C.
NMR: Confirms structure assignment of product.
HPLC: Greater than 99% pure.
MS: Molecular ion at m/e=518.
Anal. Calc'd for $C_{28}H_{28}ClN_5O_3 \cdot \frac{1}{4}H_2O$: C, 64.35; H, 5.49; N, 13.40. Found: C, 64.31; H, 5.41; N, 13.22.

EXAMPLE 287

3-N-(2,3-Dihydro-9-methyl-2-oxo-5-phenyl-1H-1,4-benzodiazepin-3-yl)-1H-indole-2-carboxamide Equimolar amounts of 3-(R,S)-amino-1,3-dihydro-9-methyl-5-phenyl-2H-1,4-benzodiazepin-2-one, indole-2-carbonyl chloride, and triethylamine were mixed at room temperature and stirred for 30 minutes. Flash chromatography of the reaction solution on silica gel (20% $Et_2O$ in $CH_2Cl_2$) provided the title compound as a crystalline solid from $Et_2O$: m.p. 229°–232° C.
NMR: Confirms structure assignment of product.
HPLC: Greater than 99.7% pure.
MS: Molecular ion at m/e=408.
Anal. Calc'd for $C_{25}H_{20}N_4O_2$: C, 73.51; H, 4.94; N, 13.72. Found: C, 73.44; H, 5.18; N, 13.35.

EXAMPLE 288

N-(3-Methoxyphenyl)-N'-(2,3-dihydro-9-methyl-2-oxo-5-phenyl-1H-1,4-benzodiazepin-3-yl)-urea Equimolar amounts of 3-(R,S)-amino-1,3-dihydro-9-methyl-5-phenyl-2H-1,4-benzodiazepin-2-one, 3-methoxy-phenylisocyanate and triethylamine were mixed in THF at 0° C. and stirred 40 minutes. Removal of THF in vacuo gave a residue which was crystallized from MeOH: m.p. 250°–252° C.
NMR: Confirms structure assignment of product and verifies presence of $CH_3OH$ solvate.
HPLC: Greater than 96.9% pure.
MS: Molecular ion at m/e=415 (FAB).
Anal Calc'd for $C_{24}H_{22}N_4O_3 \cdot 0.1CH_4O$: C, 69.30; H, 5.41; N, 13.42. Found: C, 69.00; H, 5.57; N, 13.31.

EXAMPLE 289

3-N-(2,3-Dihydro-1,9-dimethyl-2-oxo-5-phenyl-1H-1,4-benzodiazepin-3-yl)-1H-indole-2-carboxamide Equimolar amounts of 3-(R,S)-amino-1,3-dihydro-1,9-dimethyl-5-phenyl-2H-1,4-benzodiazepin-2-one, indole-2-carbonyl chloride and triethylamine were mixed at room temperature and stirred 30 minutes. Flash chromatography of the reaction solution on silica gel (7% $Et_2O$ in $CH_2Cl_2$) provided the title compound as a crystalline solid from $Et_2O$: m.p. 286°–289° C.
NMR: Confirms structure assignment of product and verifies presence of $Et_2O$ solvate.
HPLC: Greater than 96.2% pure.
MS: Molecular ion at m/e=422.

EXAMPLE 290

N-(3-Methoxyphenyl)-N'-(2,3-dihydro-1,9-dimethyl-2-oxo-5-phenyl-1H-1,4-benzodiazepin-3-yl)-urea Equimolar amounts of 3-(R,S)-amino-1,3-dihydro-1,9-dimethyl-5-phenyl-2H-1,4-benzodiazepin-2-one, 3-methoxyphenylisocyanate and triethylamine were mixed in THF at 0° C. and stirred 20 minutes. Removal of THF in vacuo, dissolution of the residue in $CH_2Cl_2$ and flash chromatography on silica gel (12% $Et_2O$ in $CH_2Cl_2$) gave the title compound which was crystalized as a white fluffy solid from $Et_2O$: m.p. 215°–217° C.

NMR: Confirms structure assignment of product.
HPLC: Greater than 98.8% pure.
MS: Molecular ion at m/e=429.
Anal. Calc'd for $C_{22}H_{25}N_4O_3$: C, 70.07; H, 5.65; N, 13.08. Found: C, 70.08; H, 5.88; N, 13.07.

EXAMPLE 291

3-N-(2,3-Dihydro-1-methyl-2-oxo-5-(p-tolyl)-1H-1,4-benzodiazepin-3-yl)-1H-indole-2-carboxamide Equimolar amounts of 3-(R,S)-amino-1,3-dihydro-1-methyl-5-(p-tolyl)-2H-1,4-benzodiazepin-2-one, indole-2-carbonyl chloride, and triethylamine were mixed at room temperature and stirred 30 minutes. Flash chromatography of the reaction solution on silica gel (5% $Et_2O$ in $CH_2Cl_2$) provided the title compound as a crystalline solid from $Et_2O$: m.p. 280°–282° C.

NMR: Confirms structure assignment of product and verifies presence of $Et_2O$ solvate.
HPLC: Greater than 99.2% pure.
MS: Molecular ion at m/e=422.
Anal. Calc'd for $C_{26}H_{22}N_4O_2 \cdot 0.15C_4H_{10}O$: C, 73.68; H, 5.46; N, 12.92. Found: C, 73.97; H, 5.44; N, 13.09.

EXAMPLE 292

N-(3-Methoxyphenyl)-N'-(2,3-dihydro-1-methyl-2-oxo-5-(p-tolyl)-1H-1,4-benzodiazepin-3-yl)-urea Equimolar amounts of 3-(R,S)-amino-1,3-dihydro-1-methyl-5-(p-tolyl)-2H-1,4-benzodiazepin-2-one, 3-methoxyphenylisocyanate, and triethylamine were mixed in THF at 0° C. and stirred 20 minutes. Removal of THF in vacuo and crystallization from MeOH gave the title compound: m.p. 240°–242° C.

NMR: Confirms structure assignment of product.
HPLC: Greater than 99.9% pure.
MS: Molecular ion at m/e=428.
Anal. Calc'd for $C_{25}H_{24}N_4O_3$: C, 70.07; H, 5.65; N, 13.08. Found C, 69.86; H, 5.62; N, 12.83.

EXAMPLE 293

(R)-N-(2,3-Dihydro-1-methyl-2-oxo-5-phenyl-1H-1,4-benzodiazepin-3-yl)-N'-(4-methylphenyl)-urea Equimolar amounts of 3(R)-amino-1,3-dihydro-1-methyl-5-phenyl-2H-1,4-benzodiazepin-2-one and 4-methylphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 233°–235° C.

NMR: Confirms structure assignment of product.
HPLC: Greater than 98% pure.
MS: Molecular ion at m/e=399 (FAB).
Anal. Calc'd for $C_{24}H_{22}N_4O_2$: C, 72.34; H, 5.57; N, 14.06. Found: C, 72.62; H, 5.76; N, 14.24.

EXAMPLE 294

3N-(2,3-Dihydro-1,8-dimethyl-2-oxo-5-phenyl-1H-1,4-benzodiazepin-3-yl)-1H-indole-2-carboxamide Equimolar amounts of 3-(R,S)-amino-1,3-dihydro-1,8-dimethyl-5-phenyl-2H-1,4-benzodiazepin-2-one, indole-2-carbonyl chloride, and triethylamine were mixed at room temperature and stirred 30 minutes. Flash chromatography of the reaction solution on silica gel (7% $Et_2O$ in $CH_2Cl_2$) provided the title compound as a crystalline solid from $Et_2O$: m.p. 291°–294° C.

NMR: Confirms structure assignment of product and verifies presence of $Et_2O$ solvate.
HPLC: Greater than 99.5% pure.
MS: Molecular ion at m/e=422.
Anal. Calc'd for $C_{26}H_{22}N_4O_2 \cdot 0.25C_4H_{10}O$: C, 73.53; H, 5.60; N, 12.71. Found: C, 73.56; H, 5.71; N, 12.87.

EXAMPLE 295

N-(3-Methoxyphenyl)-N'-(2,3-dihydro-1,8-dimethyl-2-oxo-5-phenyl-1H-1,4-benzodiazepin-3-yl)-urea Equimolar amounts of 3-(R,S)-amino-1,3-dihydro-1,8-dimethyl-5-phenyl-2H-1,4-benzodiazepin-2-one, 3-methoxyphenylisocyanate, and triethylamine were mixed in THF at 0° C. and stirred 20 minutes. Removal of THF in vacuo and crystallization from MeOH gave the title compound: m.p. 184°–188° C.

NMR: Confirms structure assignment of product.
HPLC: Greater than 99.9% pure.
MS: Molecular ion at m/e=428.
Anal. Calc'd for $C_{25}H_{24}N_4O_3$: C, 70.07; H, 5.65; N, 13.08. Found: C, 70.36; H, 6.01; N, 13.08.

EXAMPLE 296

(R)-N-(2,3-Dihydro-1-methyl-2-oxo-5-phenyl-1H-1,4-benzodiazepin-3-yl)-N'-(3-chlorophenyl)-urea Equimolar amounts of 3(R)-amino-1,3-dihydro-1-methyl-5-phenyl-2H-1,4-benzodiazepin-2-one and 3-chlorophenylisocyanate were mixed in 8 ml of dry tetrahydrofuran at room temperature. The reaction mixture was allowed to stand for 8 hours and was then filtered. The collected solids were washed with tetrahydrofuran and dried in vacuo over $P_2O_5$ to give the analytical product: m.p. 178°–180° C.

NMR: Confirms structure assignment of product.
HPLC: Greater than 98% pure.
MS: Molecular ion at m/e=419 (FAB).
Anal. Calc'd for $C_{23}H_{19}ClN_4O_2 \cdot 0.2H_2O$: C, 65.39; H, 4.63; N, 13.26. Found: C, 65.20; H, 4.67; N, 13.17.

EXAMPLE 297

N-(4-Chlorophenyl)-2,3-dihydro-1-methyl-2-oxo-5-phenyl-1H-1,4-Benzodiazepine-3-acetamide The lithium salt of 1,3-dihydro-1-methyl-5-phenyl-2H-1,4-benzodiazepin-2-one (0.5 g, 2 mmole) was made according to the procedure of Example 47. To the anion solution was added ethyl bromoacetate (0.33 g, 2 mmole). After stirring at room temperature for ½ hour, the reaction was worked up as described in Example 47 to give the 3-ethoxycarbonylmethylbenzodiazepine.

This compound (120 mg, 0.36 mmole) was combined with aqueous sodium hydroxide solution (0.4 ml/1M solution, 0.4 mmole) in 2 ml of methanol plus 1.5 ml of tetrahydrofuran and stirred at room temperature for 18 hours. The mixture was adjusted to pH 5 with 1N HCl and filtered to provide the 3-carboxymethylbenzodiazepine. The entire lot of this material was stirred in DMF (4 ml) in an ice bath. N-Methylmorpholine (55 mg, 0.5 mmole) was added, followed by isobutylchlorocarbonate (70 mg, 0.5 mmole). The mixture was stirred ½ hour in the cold, then treated with a solution of 4-chloroaniline (76 mg, 0.6 mmole) in DMF (3 ml). The mixture was stirred at room temperature for 3 days, then evaporated in vacuo. The residue was combined with water and extracted with $CH_2Cl_2$ (3×10 ml). The $CH_2Cl_2$ extracts were combined, washed with dilute citric acid, then sodium bicarbonate solution, dried over sodium sulfate, filtered, and evaporated to dryness in vacuo. The residue was chromatographed on silica gel (eluted with 2% (v/v) methanol in $CH_2Cl_2$) to give the title compound which was dried at 90° C.: m.p. 238°–240° C.

HPLC: Greater than 99% pure.

MS: Molecular ion at m/e=417.

Anal. Calc'd for $C_{24}H_{20}ClN_3O_2$: C, 68.98: H, 4.82; N, 10.06. Found: C, 68.82: H, 4.78; N, 9.86.

What is claimed is:

1. A method of antagonizing the binding of cholecystokinins to cholecystokinin receptors or antagonizing the binding of gastrin to gastrin receptors which comprises contacting said cholecystokinin receptors or said gastrin receptors, respectively, with a compound represented by the formula:

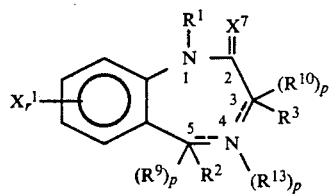

wherein
$R^1$ is H, $C_1$-$C_6$ linear or branched alkyl, loweralkenyl, lower alkynyl, $-X^{12}COOR^6$, $-X^{11}$-cycloloweralkyl, $-X^{12}NR^4R^5$, $X^{12}CONR^4R^5$, $-X^{12}CN$, or $-X^{11}CX_3^{10}$;

$R^2$ is H, loweralkyl, substituted or unsubstituted phenyl (wherein the substituents may be 1 or 2 or halo, loweralkyl, loweralkoxy, loweralkylthio, carboxyl, carboxyloweralkyl, nitro, $-CF_3$, or hydroxy), 2-, 3-, 4-pyridyl

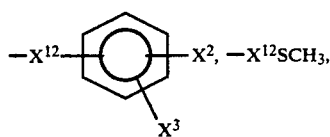

$-X^{12}SOCH_3$, $-X^{12}SO_2CH_3$, or $-X^{12}COOR^6$;

$R^3$ is $-X^{11}NR^{18}(CH_2)_qR^{16}$,

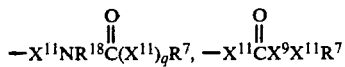

$NH(CH_2)_{2-3}NHR^7$, $-NH(CH_2)_{2-3}NHCOR^7$,

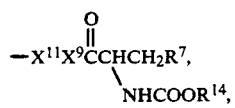

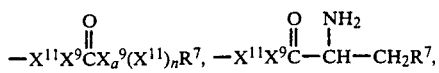

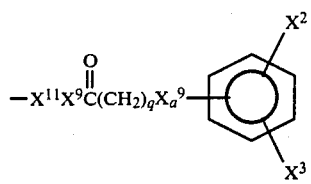

$-X^{11}NR^{18}SO_2(CH_2)_qR^7$ or

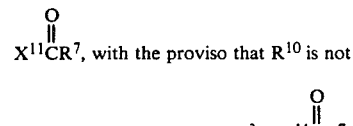

H or $-CH_3$ when $R^3$ is $X^{11}\overset{O}{\overset{\|}{C}}R^7$;

$R^4$ and $R^5$ are independently $R^6$ or in combination with the N of the $NR^4R^5$ group form an unsubstituted or mono or disubstituted, saturated or unsaturated, 4–7 membered heterocyclic ring or benzofused 4–7 membered heterocyclic ring, wherein said heterocyclic ring or said benzofused heterocyclic ring may contain a second heteroatom selected from O and $NCH_3$ and the substituent(s) is/are independently selected from $C_{1-4}$ alkyl;

$R^6$ is H, loweralkyl, cycloloweralkyl, substituted or unsubstituted phenyl, or substituted or unsubstituted phenylloweralkyl wherein the phenyl or phenyloweralkyl substituents may be 1 or 2 of halo, loweralkyl, loweralkoxy, nitro, or $CF_3$;

$R^7$ is α- or β-naphthyl, substituted or unsubstituted phenyl (wherein the substituents may be 1 or 2 of halo, $-NO_2-$ $-OH$, $-X^{11}NR^4R^5$, loweralkyl, $CF_3$, CN, $SCF_3$, C≡CH, $CH_2SCF_3$, O $OCCH_3$, $OCHF_2$, SH, SPh, $PO_3H$, loweralkoxy, or loweralkylthio, COOH); 2-, 3-, 4-pyridyl,

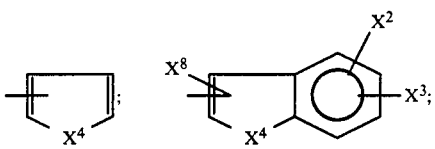

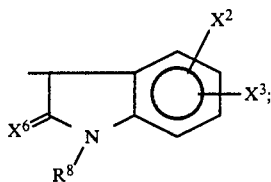

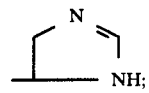

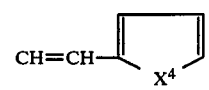

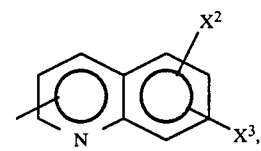

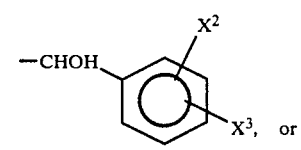

-continued

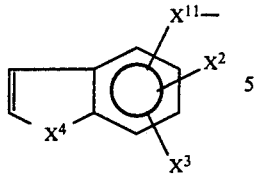

$R^8$ is H, loweralkyl, cyclololoweralkyl, $-X^{12}CONH_2$, $-X^{12}COOR^6$, $-X^{12}$-cyclololoweralkyl, $-X^{12}NR^4R^5$,

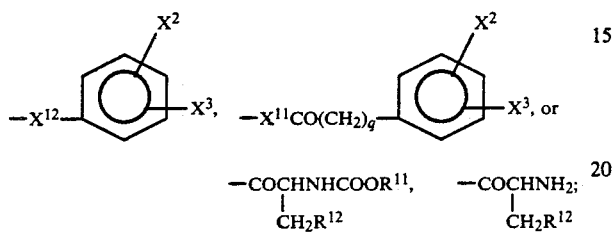

$R^9$ and $R^{10}$ are independently H, —OH, or —CH$_3$;
$R^{11}$ and $R^{12}$ are independently loweralkyl or cyclo-loweralkyl;
$R^{13}$ is H, loweralkyl, acyl, O, or cyclololoweralkyl;
$R^{14}$ is loweralkyl or phenylloweralkyl;
$R^{15}$ is H, loweralkyl,

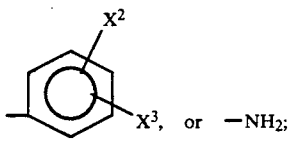

$R^{16}$ is alpha and beta napthyl or 2-indolyl;
$R^{18}$ is H, or loweralkyl;
p is 0 when its adjacent --- is unsaturated and 1 when its adjacent --- is saturated except that when $R^{13}$ is O, p=1 and is unsaturated;
q is 0-4;
r is 1 or 2;
$X^1$ is H, —NO$_2$, CF$_3$, CN, OH, loweralkyl, halo, loweralkylthio, loweralkoxy, —$X^{11}$COOR$^6$, or —$X^{11}$NR$^4$R$^5$;
$X^2$ and $X^3$ are independently H, —OH, —NO$_2$, halo, loweralkylthio, loweralkyl, or loweralkoxy;
$X^4$ is S, O, CH$_2$, or NR$^8$;
$X^5$ is H, CF$_3$, CN, —COOR$^6$, NO$_2$, or halo;
$X^6$ is O or HH; $X^7$ is O, S, HH, or NR$^{15}$ with the proviso that
$X^7$ can be NR$^{15}$ only when R$^1$ is not H;
$X^8$ is H, loweralkyl; $X^9$ and $X_a^9$ are independently NR$^{18}$ or O;
$X^{10}$ is F, Cl, or Br;
$X^{11}$ is absent or C$_{1-4}$ linear or branched alkylidene;
$X^{12}$ is C$_{1-4}$ linear or branched alkylidene; --- is a saturated or unsaturated bond; with the proviso that when X$^1$ is Cl in the seven position, R$^1$ is H and R$^2$ is unsubstituted phenyl, then R$^3$ is not NHCO(CH$_2$)$_2$C$_6$H$_5$ or NHCOC$_6$H$_5$ and the pharmaceutically acceptable salts thereof.

2. The method of claim 1 wherein:
$R^1$ is H, C$_1$-C$_6$ linear or branched alkyl, —X$^{12}$COOR$^6$, —X$^{11}$-cyclololoweralkyl, X$^{12}$CONR$^4$R$^5$ or X$^{12}$CONR$^4$R$^5$;

$R^2$ is substituted or unsubstituted phenyl (wherein the substituents may be 1 or 2 of halo, loweralkyl, loweralkoxy, loweralkylthio, carboxyl, carboxyloweralkyl, nitro, —CF$_3$, or hydroxy), 2-, 3-, or 4-pyridyl,

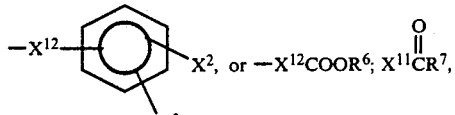

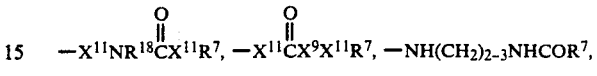

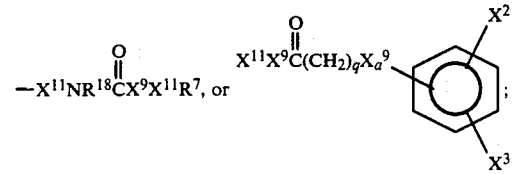

$R^4$ and $R^5$ are independently $R^6$ or in combination with the N of the NR$^4$R$^5$ group form an unsubstituted or mono or disubstituted saturated or unsaturated, 4–7 membered heterocyclic ring, or benzofused 4–7 membered heterocyclic ring wherein said heterocyclic ring or said benzofused heterocyclic ring may contain a second heteroatom selected from O and NCH$_3$ and the substitutent(s) is/are independently selected from C$_{1-4}$alkyl;
$R^6$ is H, C$_1$-C$_4$ straight or branched-chain alkyl or C$_3$-C$_6$-cycloalkyl
$R^7$ is $\alpha$- or $\beta$-naphthyl, substituted or unsubstituted phenyl (wherein the substituents may be 1 to 2 of halo, —NO$_2$, —OH, —X$^{11}$NR$^4$R$^5$, loweralkyl, CF$_3$, CN, SCF$_3$,

SH, SPh, loweralkoxy, loweralkylthio, or carboxy), 2-, 3-, 4-pyridyl,

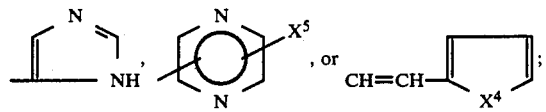

$R^8$ is H, loweralkyl or cyclololoweralkyl;
$R^9$ and $R^{10}$ are independently H, —OH, or —CH$_3$;
$R^{13}$ is H, loweralkyl, acyl, O, or cyclololoweralkyl;
$R^{18}$ is H or loweralkyl;
p is 0 when its adjacent --- is unsaturated and 1 when its adjacent --- is saturated except that when R$^{13}$ is O, p=1 and --- is unsaturated;
q is 0-2;

r is 1 or 2;

$X^1$ is H, —$NO_2$, $CF_3$, CN, loweralkyl, halo, loweralkylthio or —$X^{11}COOR^6$;

$X^2$ and $X^3$ are independently H, —$NO_2$, halo, loweralkylthio, loweralkyl, or loweralkoxy;

$X^4$ is S, O, or $NR^8$;

$X^5$ is H, $CF_3$, CN, —$COOR^6$, $NO_2$, or halo;

$X^6$ is O or HH;

$X^7$ is O, S;

$X^9$ and $X_a^9$ are independently $NR^{18}$, or O;

$X^{11}$ is absent or $C_{1-4}$ linear alkylidene;

$X^{12}$ is $C_{1-4}$ linear or branched alkylidene; --- is a saturated or unsaturated bond and the pharmaceutically acceptable salts thereof.

3. The method of claim 2 wherein:

$R^1$ is H, $C_1$-$C_3$ linear or branched alkyl, —$X^{12}COOR^6$, —$X^{12}CONR^4R^5$, $R^2$ is substituted or unsubstituted phenyl (wherein the substituents may be 1 or 2 of halo, loweralkyl, carboxyl, nitro or —$CF_3$); —$X^{12}COOR^6$; 2-, 3-, 4-pyridyl;

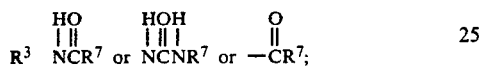

$R^4$ and $R^5$ are independently $R^6$ or in combination with the N of the $NR^4R^5$ group form an unsubstituted or mono or disubstituted, saturated or unsaturated, 4–7 membered heterocyclic ring, or benzofused 4–7 membered heterocyclic ring wherein said heterocyclic ring or said benzofused heterocyclic ring may contain a second heteroatom selected from O and $NCH_3$ and the substituent(s) is/are independently selected from $C_{1-4}$alkyl;

$R^6$ is H, $C_1$-$C_4$ straight or branched-chain alkyl;

$R^7$ is α- or β-naphthyl, substituted or unsubstituted phenyl (wherein the substituents may be 1 to 2 of halo, —$NO_2$, —OH, —$NR^4R^5$, loweralkyl, $CF_3$, CN, or loweralkoxy), 2-, 3-, 4-pyridyl,

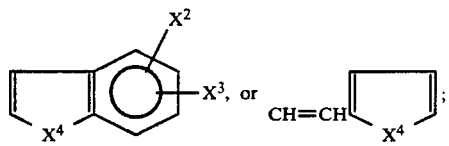

$R^9$ and $R^{10}$ are independently H, or —OH;

p is 0 when its adjacent --- is unsaturated and 1 when its adjacent --- is saturated, the p of $(R^{13})_p$ is 0;

r is 1 or 2;

$X^1$ is H, —$NO_2$, $CF_3$, loweralkyl or halo;

$X^2$ and $X^3$ are independently H, —$NO_2$, halo, loweralkyl, or loweralkoxy;

$X^4$ is O or $NR^8$;

$X^7$ is O or S, $X^{12}$ is $C_{1-2}$ linear or branched alkylidene;

--- is a saturated or unsaturated bond; and the pharmaceutically acceptable salts thereof.

4. The method of claim 3 wherein:

$R^1$ is H, $C_1$-$C_2$ linear alkyl, —$X^{12}COOR^6$, —$X^{12}CONR^4R^5$;

$R^2$ is substituted or unsubstituted phenyl (wherein the substituent may be halo, loweralkyl, nitro, —$CF_3$), 2-, 3-, 4-pyridyl, or $X^{12}COOR^6$;

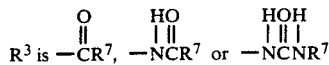

$R^4$ and $R^5$ are independently $R^6$ or in combination with the N of the $NR^4R^5$ group form an unsubstituted or mono or disubstituted, saturated or unsaturated, 4–7 membered heterocyclic ring, or benzofused 4–7 membered heterocyclic ring wherein said heterocyclic ring or said benzofused heterocyclic ring may contain a second heteroatom selected from O and $NCH_3$ and the substituent(s) is/are independently selected from $C_{1-4}$alkyl;

$R^6$ is H, $C_1$-$C_3$ straight chain alkyl;

$R^7$ is α- or β-naphthyl, substituted or unsubstituted phenyl (wherein the substituents may be 1 or 2 of halo, —$NO_2$, $NH_2$, methyl, ethyl, $CF_3$, CN, or loweralkoxy), 2-, 3-, 4-pyridyl,

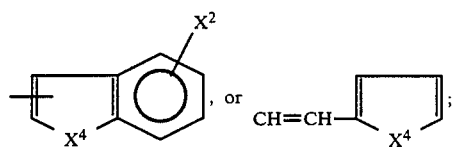

$R^{10}$ is H, or OH;

p is 1 of $(R^{10})_p$ and 0 of $(R^9)_p$ and $(R^{13})_p$, --- at 4,5 is unsaturated and --- at 3,4 is saturated;

r is 1 or 2;

$X^1$ is H, —$NO_2$, $CF_3$, loweralkyl or halo;

$X^2$ is H, —$NO_2$, halo or loweralkyl;

$X^4$ is O, NH, $NCH_3$;

$X^7$ is O or S;

$X^{12}$ is $C_{1-2}$ linear alkylidene; and the pharmaceutically acceptable salts thereof.

5. The method of claim 4 wherein:

$R^1$ is H, $CH_3$, $CH_2CH_3$, $CH_2COOH$, $CH_2COOEt$,

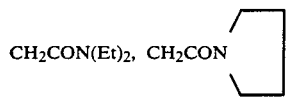

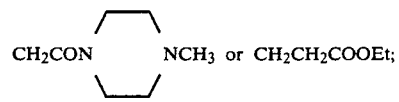

$R^2$ is phenyl, 2-F-phenyl, 4-$CH_3$-phenyl 2-, 3, 4-pyridyl;

$R^3$ is

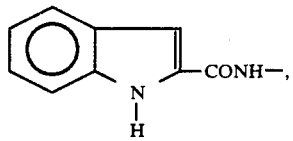

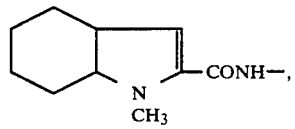

$R^{10}$ is H or —OH;

p is 1 of $(R^{10})_p$ and O of $(R^9)_p$ and $(R^{13})_p$;

- - - at 4, 5 is unsaturated and - - - at 3, 4 is saturated;

r is 1;

$X^1$ is H, 7-Cl, 8-CH$_3$, 9-CH$_3$;

$X^7$ is O or S; and the pharmaceutically acceptable salts thereof.

6. The method of claim 1 wherein said compound is selected from the group consisting of:

3(R)-N-(4-Chlorophenyl)-N'-(2,3-dihydro-1-methyl-5-phenyl-2-oxo-1H-1,4-benzodiazepin-3-yl)urea, 3-Benzoyl-1,3-dihydroxy-3-hydroxy-1-methyl-5-phenyl-2H-1,4-benzodiazepin-2-one, 5-(2-Fluorophenyl)-1,3-dihydroxy-3-hydroxy-3-(4-methoxybenzoyl)-1-methyl-2H-1,4-benzodiazepin-2-one, N-(2,3-Dihydro-1-methyl-2-oxo-5(3-methylphenyl)-1-H-1,4-benzodiazepin-3-yl)-N'-(phenylmethyl)urea, N-(2,3-Dihydro-1-ethyl-2-oxo-5-phenyl-1H-1,4-benzodiazepin-3-yl)-N'-(3-methoxyphenyl)urea, 3-(S-)-N-(2,3-Dihydro-1-methyl-2-oxo-5-phenyl-1H-1,4-benzodiazepin-3-yl)-3-(3-methoxyphenyl)-2-propenamide, 3-((((4-Chlorophenyl)amino)carbonyl)amino-2,3-dihydro-2-oxo-5-phenyl-1H-1,4-benzodiazepin-1-propanoic acid ethyl ester, 3(RS)-1,3-Dihydro-(2-indolecarbonylamino)-5-phenyl-2H-1,4-benzodiazepin-2-one, 1-Carboxymethyl-1,3-dihydro-3(RS)-(2-indolecarbonylamino)-5-phenyl-2H-1,4-benzodiazepin-2-one, 1,3-Dihydro-3(RS)-(2-indolecarbonylamino)-1-methyl-5-phenyl-2H-1,4-benzodiazepin-2-one, 1,3-Dihydro-1-methyl-3(RS)-[2-(1-methylindole)carbonylamino]-5-phenyl-2H-1,4-benzodiazepin-2-one, 1,3-Dihydro-1-methyl-3(RS)-(4-chlorophenylcarbonyl)-amino-5-(2-fluorophenyl)-2H-1,4-benzodiazepin-2-one, 1,3-Dihydro-5-(2-fluorophenyl)-3(RS)-(2-indolecarbonylamino)-1-methyl-2H-1,4-benzodiazepin-2-one, 1,3-Dihydro-5-(2-fluorophenyl)-1-methyl-3(RS)-[2'-(1'-methylindole)carbonylamino]-2H-1,4-benzodiazepin-2-one, 3(S)-(—)-1,3-Dihydro-3-(2-indolecarbonylamino)-1-methyl-5-phenyl-2H-1,4-benzodiazepin-2-one, 3(S)-(+)-1,3-Dihydro-5-(2-fluorophenyl)-3-(2-indolecarbonylamino)-1-methyl-2H-1,4-benzodiazepin-2-one, 3(S)-(+)-1,3-Dihydro-3-(4-chlorobenzoylamino)-5-(2-fluorophenyl)-1-methyl-2H-1,4-benzodiazepin-2-one, 3(S)-(—)-1,3-Dihydro-3-(4-bromobenzoylamino)-1-methyl-5-phenyl-2H-1,4-benzodiazepin-2-one, 1,3-Dihydro-5-(2-fluorophenyl)-3-(RS)-(2-indolecarbonylamino)-2H-1,4-benzodiazepin-2-one, 1,3-Dihydro-3-(RS)-(4-chlorophenylcarbonyl)amino-5-(2-fluorophenyl)-2H-1,4-benzodiazepin-2-one,
1-Carboxymethyl-1,3-dihydro-5-(2-fluorophenyl)-3(RS)-(2-indolecarbonylamino)-2H-1,4-benzodiazepin-2-one,
1,3-Dihydro-3-(RS)-(5-fluoroindole-2-carbonylamino)-5(2-fluorophenyl)-2H-1,4-benzodiazepin-2-one,
1,3-Dihydro-3-(RS)-(1-methylindole-2-carbonylamino)-5-(2-fluorophenyl)-2H-1,4-benzodiazepine-2-one,
1,3-Dihydro-5-(2-fluorophenyl)-3-(RS)-(2-benzofurancarbonylamino)-2H-1,4-benzodiazepin-2-one,
1,3-Dihydro-1-methyl-3-(RS)-(4-chlorophenylcarbonyl)-amino-5-phenyl-2H-1,4-benzodiazepin-2-one,
3(S)-(+)-3-(3-Bromobenzoylamino)-1,3-dihydro-5-(2-fluorophenyl)-1-methyl-2H-1,4-benzodiazepin-2-one,
3(S)-(+)-3-(4-Bromobenzoylamino)-1,3-dihydro-5-(2-fluorophenyl)-1-methyl-2H-1,4-benzodiazepin-2-one,
3(S)-(+)-1,3-Dihydro-5-(2-fluorophenyl)-3-(4-iodobenzoylamino)-1-methyl-2H-1,4-benzodiazepin-2-one,
3(S)-(+)-1,3-Dihydro-5-(2-fluorophenyl)-3-(3-iodobenzoylamino)-1-methyl-2H-1,4-benzodiazepin-2-one,
1,3-Dihydro-5-(2-fluorophenyl)-3-(RS)-(2-indole)carbonylamino-2H-1,4-benzodiazepin-2-thione,
3(S)-(2-Indolecarbonyl)amino-1,3-dihydro-5-phenyl-2H-1,4,-benzodiazepin-2-one,
(S)-N-(2,3-Dihydro-1-methyl-2-oxo-5-phenyl-1H-1,4-benzodiazepin-3-yl)-3-phenyl-2-propenamide,
3-((((4-Chlorophenyl)amino)carbonyl)amino)-5-(2-fluorophenyl)-2,3-dihydro-2-oxo-1H-1,4-benzodiazepine-1-acetic acid ethyl ester,
(S)-N-(2,3-Dihydro-1-methyl-2-oxo-5-phenyl-1H-1,4-benzodiazepin-3-yl)-4-(trifluoromethyl)-benzamide,
3-((((4-Chlorophenyl)amino)carbonyl)amino)-2,3-dihydro-2-oxo-5-phenyl-1H-1,4-benzodiazepine-1-acetic acid ethyl ester,
5-(2-Fluorophenyl)-2,3-dihydro-3-((1H-indol-2-ylcarbonyl)amino)-2-oxo-1H-1,4-benzodiazepine-1-acetic acid ethyl ester,
4-Bromo-N-(2,3-dihydro-1-methyl-2-oxo-5-phenyl-1H-1,4-benzodiazepin-3-yl)-benzamide,
N-(5-(2-Fluorophenyl)-2,3-dihydro-1-methyl-2-oxo-1H1,4-benzodiazepin-3-yl)-4-(trifluoromethyl)-benzamide,
(S)-N-(5-(2-Fluorophenyl)-2,3-dihydro-1-methyl-2-oxo-1H-1,4-benzodiazepin-3-yl)-4-(trifluoromethyl)benzamide,
3-((((4-Chlorophenyl)amino)carbonyl)amino-N,N-diethyl-2,3-dihydro-2-oxo-5-phenyl-1H-1,4-benzodiazepine-1-acetamide,
1-((3-((((4-Chlorophenyl)amino)carbonyl)amino-2,3-dihydro-2-oxo-5-phenyl-1H-1,4-benzodiazepin-1-yl)-acetyl)pyrrolidine,
1-((3-((((4-Chlorophenyl)amino)carbonyl)amino)-2,3-dihydro-2-oxo-5-phenyl-1H-1,4-benzodiazepin-1-yl)acetyl)-4-methylpiperazine,
3-(((4-Chlorophenyl)acetyl)amino)-2,3-dihydro-2-oxo-5-phenyl-1H-1,4-benzodiazepine-1-acetic acid ethyl ester,
N-(5-(2-Fluorophenyl)-2,3-dihydro-1-methyl-2-oxo-(1H-1,4-benzodiazepin-3-yl)-N'-(3-methoxyphenyl)-urea,
N-(2,3-Dihydro-1-methyl-2-oxo-5-phenyl-1H-1,4-benzodiazepin-3-yl)-N'-(3-methoxyphenyl)-urea,
N-(2,3-Dihydro-1-methyl-2-oxo-5-phenyl-1H-1,4-benzodiazepin-3-yl)-N'-phenylurea,
N-(2,3-Dihydro-1-methyl-2-oxo-5-phenyl-1H-1,4-benzodiazepin-3-yl)-N'-(4-methylphenyl)-urea,
N-(2-Chlorophenyl)-N'-(2,3-dihydro-1-methyl-2-oxo-5-phenyl-1H-1,4-benzodiazepin-3-yl)-urea,
N-(4-Nitrophenyl)-N'-(2,3-dihydro-1-methyl-2-oxo-5-phenyl-1H-1,4-benzodiazepin-3-yl)-urea,
N-(2,4-Dichlorophenyl)-N'-(2,3-dihydro-1-methyl-2-oxo-5-phenyl-1H-1,4-benzodiazepin-3-yl)-urea,
N-(2,3-Dihydro-1-methyl-2-oxo-5-phenyl-1H-1,4-benzodiazepin-3-yl)-N'-(3-methoxyphenyl)-urea,
N-(2,3-Dihydro-1-methyl-2-oxo-5-phenyl-1H-1,4-benzodiazepin-3-yl)-N'-(2-nitrophenyl)-urea,
N-(3-Chlorophenyl)-N'-(2,3-dihydro-1-methyl-2-oxo-5-phenyl-1H-1,4-benzodiazepin-3-yl)urea,
(R)-N-(2,3-Dihydro-1-methyl-2-oxo-5-phenyl-1H-1,4-benzodiazepin-3-yl)-N'-(3-methoxyphenyl)-urea,
(S)-N-(2,3-Dihydro-1-methyl-2-oxo-5-phenyl-1H-1,4-benzodiazepin-3-yl)-N'-(2-methoxyphenyl)-urea,
N-(2,3-Dihydro-1-methyl-2-oxo-5-phenyl-1H-1,4-benzodiazepin-3-yl)-N'-(2-nitrophenyl)-urea,
N-(2,3-Dihydro-1-methyl-2-oxo-5-phenyl-1H-1,4-benzodiazepin-3-yl)-N'-(3-fluorophenyl)-urea,
N-(3-Bromophenyl)-N'-(2,3-dihydro-1-methyl-2-oxo-5-phenyl-1H-1,4-benzodiazepin-3-yl)-urea,
N-(2,3-Dihydro-1-methyl-2-oxo-5-phenyl-1H-1,4-benzodiazepin-3-yl)-N'-1-naphthalenyl-urea,
(S)-N-(2,3-Dihydro-1-methyl-2-oxo-5-phenyl-1H-1,4-benzodiazepin-3-yl)-N'-(2-chlorophenyl)-urea,
(R)-N-(2,3-Dihydro-1-methyl-2-oxo-5-phenyl-1H-1,4-benzodiazepin-3-yl)-N'-(3-methylphenyl)-urea,
(R)-N-(2,3-Dihydro-1-methyl-2-oxo-5-phenyl-1H-1,4-benzodiazepin-3-yl)-N'-(3-bromophenyl)-urea,
1-{[3-[(((3-Methoxyphenyl)amino)carbonyl)amino]-2,3-dihydro-2-oxo-5-phenyl-1H-1,4-benzodiazepin-1-yl]acetyl}pyrrolidine,
3-{[((3-Methoxyphenyl)amino)carbonyl]amino}-N,N-diethyl-2,3-dihydro-2-oxo-5-phenyl-1H-1,4-benzodiazepin-1-acetamide,
3-{[((2-Chlorophenyl)amino)carbonyl]amino}-N,N-diethyl-2,3-dihydro-2-oxo-5-phenyl-1H-1,4-benzodiazepine-1-acetamide,
3-N-(2,3-Dihydro-9-methyl-2-oxo-5-phenyl-1H-1,4-benzodiazepin-3-yl)-1H-indole-2-carboxamide,
3-N-(2,3-Dihydro-1,9-dimethyl-2-oxo-5-phenyl-1H-1,4-benzodiazepin-3-yl)-1H-indole-2-carboxamide,
N-(3-Methoxyphenyl)-N'-(2,3-dihydro-1,9-dimethyl-2-oxo-5-phenyl-1H-1,4-benzodiazepin-3-yl)-urea,
3-N-(2,3-Dihydro-1-methyl-2-oxo-5-(p-tolyl)-1H-1,4-benzodiazepin-3-yl)-1H-indole-2-carboxamide,
N-(3-Methoxyphenyl)-N'-(2,3-dihydro-1-methyl-2-oxo-5-(p-tolyl)-1H-1,4-benzodiazepin-3-yl)-urea,
(R)-N-(2,3-Dihydro-1-methyl-2-oxo-5-phenyl-1H-1,4-benzodiazepin-3-yl)-N'-(4-methylphenyl)-urea,
3-N-(2,3-Dihydro-1,8-dimethyl-2-oxo-5-phenyl-1H-1,4-benzodiazepin-3-yl)-1H-indole-2-carboxamide,
N-(3-Methoxyphenyl)-N'-(2,3-dihydro-1,8-dimethyl-2-oxo-5-phenyl-1H-1,4-benzodiazepin-3-yl)-urea or
(R)-N-(2,3-Dihydro-1-methyl-2-oxo-5-phenyl-1H-1,4-benzodiazepin-3-yl)-N'-(3-chlorophenyl)-urea,
(R)-N-(2,3-Dihydro-1-methyl-2-oxo-5-phenyl-1H-1,4-benzodiazepin-3-yl)-N'-(3-chlorophenyl)urea.

7. The method of claim 1 wherein said method is for antagonizing the binding of cholecystokinins to cholecystokin receptors and said compound is selected from the group consisting of:
3-(RS)-1,3-dihydro-(2-indolecarbonylamino)-5-phenyl-2H-1,4-benzodiazepin-2-one,
1-Carboxymethyl-1,3-dihydro-3(RS)-(2-indolecarbonylamino)-5-phenyl-2H-1,4-benzodiazepin-2-one, 1,3-Dihydro-3-(RS)-(2-indolecarbonylamino)-1-methyl-5-phenyl-2H-1,4-benzodiazepin-2-one,
1,3-dihydro-1-methyl-3(RS)-[2-(1-methylindole)carbonylamino]-5-phenyl-2H-1,4-benzodiazepin-2-one,
1,3-Dihydro-1-methyl-3(RS)-(4-chlorophenylcarbonyl)amino-5-(2-fluorophenyl)-2H-1,4-benzodiazepin-2-one,
1,3-Dihydro-5-(2-fluorophenyl)-3-(RS)-(2-indolecarbonylamino)-1-methyl-2H-1,4-benzodiazepin-2-one,
1,3-Dihydro-5-(2-fluorophenyl)-1-methyl-3(RS)-[2'-(1'-methylindole)carbonylamino]-2H-1,4-benzodiazepin-2-one,
3(S)-(−)-1,3-Dihydro-3-(2-indolecarbonylamino)-1-methyl-5-phenyl-2H-1,4-benzodiazepin-2-one,
3(S)-(+)-1,3-Dihydro-5-(2-fluorophenyl)-3-(2-indolecarbonylamino)-1-methyl-2H-1,4-benzodiazepin-2-one,
3(S)-(+)-1,3-Dihydro-3-(4-chlorobenzoylamino)-5-(2-fluorophenyl)-1-methyl-2H-1,4-benzodiazepin-2-one,
3(S)-(−)-1,3-Dihydro-3-(4-bromobenzoylamino)-1-methyl-5-phenyl-2H-1,4-benzodiazepin-2-one,
1,3-Dihydro-5-(2-fluorophenyl)-3-(RS)-(2-indolecarbonylamino)-2H-1,4-benzodiazepin-2-one,
1,3-Dihydro-3-(RS)-(4-chlorophenylcarbonyl)amino-5-(2-fluorophenyl)-2H-1,4-benzodiazepin-2-one,
1-Carboxymethyl-1,3-dihydro-5-(2-fluorophenyl)-3-(RS)-(2-indolecarbonylamino)-2H-1,4-benzodiazepin-2-one,
1,3-Dihydro-3-(RS)-(5-fluoroindole-2-carbonylamino)-5-(2-fluorophenyl)-2H-1,4-benzodiazepin-2-one,
1,3-Dihydro-3-(RS)-(1-methylindole-2-carbonylamino)-5-(2-fluorophenyl)-2H-1,4-benzodiazepine-2-one,
1,3-Dihydro-5-(2-fluorophenyl)-3-(RS)-(2-benzofurancarbonylamino)-2H-1,4-benzodiazepin-2-one,
1,3-Dihydro-1-methyl-3(RS)-(4-chlorophenylcarbonyl)amino-5-phenyl-2H-1,4-benzodiazepin-2-one,
3(S)-(+)-3-(3-Bromobenzoylamino)-1,3-dihydro-5-(2-fluorophenyl)-1-methyl-2H-1,4-benzodiazepin-2-one,
3(S)-(+)-3-(4-Bromobenzoylamino)-1,3-dihydro-5-(2-fluorophenyl)-1-methyl-2H-1,4-benzodiazepin-2-one,
3(S)-(+)-1,3-Dihydro-5-(2-fluorophenyl)-3-(4-iodobenzoylamino)-1-methyl-2H-1,4-benzodiazepin-2-one,
3(S)-(+)-1,3-Dihydro-5-(2-fluorophenyl)-3-(3-iodobenzoylamino)-1-methyl-2H-1,4-benzodiazepin-2-one,
1,3-Dihydro-5-(2-fluorophenyl)-3-(RS)-(2-indole) carbonylamino-2H-1,4-benzodiazepin-2-thione,
3(S)-(2-Indolecarbonyl)amino-1,3-dihydro-5-phenyl-2H-1,4,-benzodiazepin-2-one,
(S)-N-(2,3-Dihydro-1-methyl-2-oxo-5-phenyl-1H-1,4-benzodiazepin-3-yl)-3-phenyl-2-propenamide,
3-N-(2,3-Dihydro-1-methyl-2-oxo-5-phenyl-1H-1,4-benzodiazepin-3-yl)-2-amino-4-chlorobenzamide,
(S)-N-(2,3-Dihydro-1-methyl-2-oxo-5-phenyl-1H-1,4-benzodiazepin-3-yl)-4-(trifluoromethyl)-benzamide,
5-(2-Fluorophenyl)-2,3-dihydro-3-((1H-indol-2-ylcarbonyl)amino)-2-oxo-1H-1,4-benzodiazepine-1-acetic acid ethyl ester,
4-Bromo-N-(2,3-dihydro-1-methyl-2-oxo-5-phenyl-1H-1,4-benzodiazepin-3-yl)-benzamide,
N-(5-(2-Fluorophenyl)-2,3-dihydro-1-methyl-2-oxo-1H-1,4-benzodiazepin-3-yl)-4-(trifluoromethyl)-benzamide,
(S)-N-(5-(2-Fluorophenyl)-2,3-dihydro-1-methyl-2-oxo-1H-1,4-benzodiazepin-3-yl)-4-(trifluoromethyl)benzamide,
N-(2-Chlorophenyl)-N'-(2,3-dihydro-1-methyl-2-oxo-5-phenyl-1H-1,4-benzodiazepin-3-yl)-urea,
N-(2,4-Dichlorophenyl)-N'-(2,3-dihydro-1-methyl-2-oxo-5-phenyl-1H-1,4-benzodiazepin-3-yl)-urea,
(S)-N-(2,3-Dihydro-1-methyl-2-oxo-5-phenyl-1H-1,4-benzodiazepin-3-yl)-N'-(3-methoxyphenyl)-urea,
N-(2,3-Dihydro-1-methyl-2-oxo-5-phenyl-1H-1,4-benzodiazepin-3-yl)-N'-(2-nitrophenyl)-urea,
(S)-N-(2,3-Dihydro-1-methyl-2-oxo-5-phenyl-1H-1,4-benzodiazepin-3-yl)-N'-(2-chlorophenyl)-urea
3-N-(2,3-Dihydro-9-methyl-2-oxo-5-phenyl-1H-1,4-benzodiazepin-3-yl)-1H-indole-2-carboxamide,
3-N-(2,3-Dihydro-1,9-dimethyl-2-oxo-5-phenyl-1H-1,4-benzodiazepin-3-yl)-1H-indole-2-carboxamide,
3-N-(2,3-Dihydro-1-methyl-2-oxo-5-(p-tolyl)-1H-1,4-benzodiazepin-3-yl)-1H-indole-2-carboxamide,
N-(3-Methoxyphenyl)-N'-(2,3-dihydro-1-methyl-2-oxo-5-(p-tolyl)-1H-1,4-benzodiazepin-3-yl)-urea,
3-N-(2,3-Dihydro-1,8-dimethyl-2-oxo-5-phenyl-1H-1,4-benzodiazepin-3-yl)-1H-indole-2-carboxamide, and
N-(3-Methoxyphenyl)-N'-(2,3-dihydro-1,8-dimethyl-2-oxo-5-phenyl-1H-1,4-benzodiazepin-3-yl)-urea.

8. The method of claim 1 wherein said method is for antagonizing the binding of gastrin to gastrin receptors and said compound is selected from the group consisting of:
3-((((4-Chlorophenyl)amino)carbonyl)amino)-5-(2-fluorophenyl)-2,3-dihydro-2-oxo-1H-1,4-benzodiazepine-1-acetic acid ethyl ester,
3-((((4-Chlorophenyl)amino)carbonyl)amino)-2,3-dihydro-2-oxo-5-phenyl-1H-1,4-benzodiazepine-1-acetic acid ethyl ester,
3-((((4-Chlorophenyl)amino)carbonyl)amino)-N,N-diethyl-2,3-dihydro-2-oxo-5-phenyl-1H-1,4-benzodiazepine-1-acetamide,
1-((3-((((4-Chlorophenyl)amino)carbonyl)amino)-2,3-dihydro-2-oxo-5-phenyl-1H-1,4-benzodiazepin-1-yl)acetyl)pyrrolidine,
1-((3-((((4-Chlorophenyl)amino)carbonyl)amino)-2,3-dihydro-2-oxo-5-phenyl-1H-1,4-benzodiazepin-1-yl)acetyl)-4-methylpiperazine,
3-(((4-Chlorophenyl)acetyl)amino)-2,3-dihydro-2-oxo-5-phenyl-1H-1,4-benzodiazepine-1-acetic acid ethyl ester,
N-(2,3-Dihydro-1-methyl-2-oxo-5-phenyl-1H-1,4-benzodiazepin-3-yl)-N'-phenylurea,
N-(4-Nitrophenyl)-N'-(2,3-dihydro-1-methyl-2-oxo-5-phenyl-1H-1,4-benzodiazepin-3-yl)-urea,
(R)-N-(2,3-Dihydro-1-methyl-2-oxo-5-phenyl-1H-1,4-benzodiazepin-3-yl)N'-(3-methoxyphenyl)-urea,
(R)-N-(2,3-Dihydro-1-methyl-2-oxo-5-phenyl-1H-1,4-benzodiazepin-3-yl)-N'-(3-methylphenyl)-urea,
(R)-N-(2,3-Dihydro-1-methyl-2-oxo-5-phenyl-1H-1,4-benzodiazepin-3-yl)-N'-(3-bromophenyl)-urea,
1-{[3-[(((3-Methoxyphenyl)amino)carbonyl)amino]-2,3-dihydro-2-oxo-5-phenyl-1H-1,4-benzodiazepin-1-yl]acetyl}pyrrolidine,
3-{[((3-Methoxyphenyl)amino)carbonyl)amino]-N,N-diethyl-2,3-dihydro-2-oxo-5-phenyl-1H-1,4-benzodiazepin-1-acetamide,
3-{[((2-Chlorophenyl)amino)carbonyl]amino}-N,N-diethyl-2,3-dihydro-2-oxo-5-phenyl-1H-1,4-benzodiazepine-1-acetamide,
(R)-N-(2,3-Dihydro-1-methyl-2-oxo-5-phenyl-1H-1,4-benzodiazepin-3-yl)-N'-(4-methylphenyl)-urea,
(R)-N-(2,3-Dihydro-1-methyl-2oxo-5-phenyl-1H-1,4-benzodiazepin-3-yl)-N'-(3chlorophenyl)-urea.

9. The method of claim 1 wherein a therapeutically effective amount of said compound is utilized for treating gastrointestinal disorders, central nervous system disorders or regulating appetite in animals.

10. A pharmaceutical composition useful for antagonizing the binding of cholecystokinins to cholecystokinin receptors or antagonizing the binding of gastrin to gastrin receptors which comprises contacting said cholecystokinin receptors or said gastrin receptors, respectively, comprising a therapeutically effective amount of a compound of claim 1 and an acceptable pharmaceutical carrier.

11. The method of claim 1 wherein said compound is selected from the group consisting of:
3-(N-(2,3-Dihydro-1-methyl-2-oxo-5-(p-toly)-1H-1,4-benzodiazepin-3-yl)-1H-indole-2-carboxamide,
3-N-(2,3-Dihydro-1,9-dimethyl-2-oxo-5-phenyl-1H-1,4-benzodiazepin-3-yl)-1H-indole-2-carboxamide,
3-N-(2,3-Dihydro-1,8-dimethyl-2-oxo-5-phenyl-1H-1,4-benzodiazepin-3-yl)-1H-indole-2-carboxamide,
(S)-N-(2,3-Dihydro-1-methyl-2-oxo-5-phenyl-1H-1,4-benzodiazepin-3-yl)-3-phenyl-2-propenamide,
(S)-N-(2,3-Dihydro-1-methyl-2-oxo-5-phenyl-1H-1,4-benzodiazepin-3-yl)-N'-(2-chlorophenyl)-urea,
(S)-N-(5-(2-Fluorophenyl)-2,3-dihydro-1-methyl-2-oxo-1H-1,4-benzodiazepin-3-yl)-4-(trifluoromethyl)benzamide,
3(S)-(+)-1,3-Dihydro-5-(2-fluorophenyl)-3-(2-indolecarbonylamino)-1-methyl-2H-1,4-benzodiazepin-2-one,
3(S)-(+)-1,3-Dihydro-5-(2-fluorophenyl)-3-(3-iodobenzoylamino)-1-methyl-2H-1,4-benzodiazepin-2-one,
3(S)-(−)-1,3-Dihydro-3-(2-indolecarbonylamino)-1-methyl-5-phenyl-2H-1,4-benzodiazepin-2-one,
3-N-(2,3-Dihydro-1-methyl-2-oxo-5-phenyl-1H-1,4-benzodiazepin-3-yl)-2-amino-4-chlorobenzamide,
4-bromo-N-(2,3-Dihydro-1-methyl-2-oxo-5-phenyl-1H-1,4-benzodiazepin-3-yl)-benzamide,
1,3-Dihydro-5-(2-fluorophenyl)-1-methyl-3(RS)-[2'-(1'-methylindole)carbonylamino]-2H-1,4-benzodiazepin-2-one,
(S)-N-(2,3-Dihydro-1-methyl-2-oxo-5-phenyl-1H-1,4-benzodiazepin-3-yl)-N'-(3-methoxyphenyl)-urea,
1,3-dihydro-1-methyl-3(RS)-[2-(1-methylindole)carbonylamino]-5-phenyl-2H-1,4-benzodiazepin-2-one,
1-Carboxymethyl-1,3-dihydro-3(RS)-(2-indolecarbonylamino)-5-phenyl-2H-1,4-benzodiazepin-2-one, or
3(S)-(+)-1,3-Dihydro-3-(4-chlorobenzolyamino)-5-(2-fluorophenyl)-1-methyl-2H-1,4-benzodiazepin-2-one,
or a pharmaceutically acceptable salt thereof.

12. The method of claim 1 wherein said compound is selected from the group consisting of:
3{[((3-Methoxyphenyl)amino)carbonyl]amino}-N,N-diethyl-2,3-dihydro-2-oxo-5-phenyl-1H-1,4-benzodiazepin-1-acetamide,
1-((3-((((4-Chlorophenyl)amino)carbonyl)amino-2,3-dihydro-2-oxo-5-phenyl-1H-1,4-benzodiazepin-1-yl)acetyl)pyrrolidine,
(R)-N-(2,3-Dihydro-1-methyl-2-oxo-5-phenyl-1H-1,4-benzodiazepin-3-yl)-N'-(3-bromophenyl)-urea,
3-{((2-Chlorophenyl)amino)carbonyl]amino{-N,N-diethyl-2,3-dihydro-2-oxo-5-phenyl-1H-1,4-benzodiazepin-1-acetamide,
(R)-N-(2,3-Dihydro-1-methyl-2-oxo-5-phenyl-1H-1,4-benzodiazepin-3-yl)-N'-(3-bromophenyl)-urea, or
(R)-N-(2,3-Dihydro-1-methyl-2-oxo-5-phenyl-1H-1,4-benzodiazepin-3-yl)-N'-(4-methylphenyl)-urea,
or pharmaceutically acceptable salt thereof.

13. The method of claim 1 wherein said compound is selected from the group consisting of:
3(S)-(−)-1,3-dihydro-3-(2-indolecarbonylamino)-1-methyl-5-phenyl-2H-1,4-benzodiazepin-2-one, or
(R)-N-(2,3-dihydro-1-methyl-2-oxo-5-phenyl-1H-1,4-benzodiazepin-3-yl)-N'-(3-methylphenyl)urea,
or pharmaceutically acceptable salt thereof.

14. The method of claim 1 wherein said compound is selected from the group consisting of:
3(S)-(−)-1,3,-dihydro-3-(2-indolecarbonyl amino)-1-methyl-5-phenyl-2H-1,4-benzodiazepin-2-one,
or pharmaceutically acceptable salt thereof.

15. The method of claim 1 wherein said compound is selected from the group consisting of:
(R)-N-(2,3-dihydro-1-methyl-2-oxo-5-phenyl-1H-1,4-benzodiazepin-3-yl)-N'-(3-methyl-phenyl)urea,
or pharmaceutically acceptable salt thereof.

* * * * *